(12) United States Patent
Norville et al.

(10) Patent No.: US 11,826,385 B2
(45) Date of Patent: Nov. 28, 2023

(54) MAJOR HISTOCOMPATIBILITY COMPLEX-BASED CHIMERIC RECEPTORS AND USES THEREOF FOR TREATING AUTOIMMUNE DISEASES

(71) Applicant: Jura Bio, Inc., Somerville, MA (US)

(72) Inventors: Julie Norville, Somerville, MA (US); Elizabeth Wood, Somerville, MA (US)

(73) Assignee: Jura Bio, Inc., Somerville, MA (US)

(*) Notice: Subject to any disclaimer, the term of this patent is extended or adjusted under 35 U.S.C. 154(b) by 370 days.

(21) Appl. No.: 16/762,723

(22) PCT Filed: Nov. 10, 2018

(86) PCT No.: PCT/US2018/060227
§ 371 (c)(1),
(2) Date: May 8, 2020

(87) PCT Pub. No.: WO2019/094847
PCT Pub. Date: May 16, 2019

(65) Prior Publication Data
US 2021/0169929 A1  Jun. 10, 2021

Related U.S. Application Data

(60) Provisional application No. 62/584,449, filed on Nov. 10, 2017.

(51) Int. Cl.
| | | |
|---|---|---|
| C12N 5/0783 | (2010.01) | |
| A61K 38/17 | (2006.01) | |
| A61K 39/395 | (2006.01) | |
| C07K 16/02 | (2006.01) | |
| A61K 35/17 | (2015.01) | |
| C07K 14/725 | (2006.01) | |
| C07K 14/705 | (2006.01) | |
| C07K 14/74 | (2006.01) | |
| C12N 15/85 | (2006.01) | |

(52) U.S. Cl.
CPC .......... *A61K 35/17* (2013.01); *C07K 14/7051* (2013.01); *C07K 14/70521* (2013.01); *C07K 14/70539* (2013.01); *C07K 14/70596* (2013.01); *C12N 15/85* (2013.01)

(58) Field of Classification Search
CPC ............... A61K 35/17; C07K 14/7051; C07K 14/70521; C07K 14/70539; C07K 14/70596; C12N 15/85
See application file for complete search history.

(56) References Cited

U.S. PATENT DOCUMENTS

| | | |
|---|---|---|
| 2012/0148552 A1 | 6/2012 | Jensen |
| 2015/0139943 A1 | 5/2015 | Campano et al. |
| 2016/0129133 A1 | 5/2016 | McCreedy et al. |

FOREIGN PATENT DOCUMENTS

| | | |
|---|---|---|
| CN | 106535925 A | 3/2017 |
| CN | 106574272 A | 4/2017 |
| CN | 107074969 A | 8/2017 |
| WO | WO 2012/056407 A1 | 5/2012 |
| WO | WO 2016/033570 A1 | 3/2016 |

OTHER PUBLICATIONS

Carpenito et al., Control of large, established tumor xenografts with genetically retargeted human T cells containing CD28 and CD137 domains. Proc Natl Acad Sci U S A. Mar. 3, 2009;106(9):3360-5. Epub Feb. 11, 2009.

Till et al., CD20-specific adoptive immunotherapy for lymphoma using a chimeric antigen receptor with both CD28 and 4-1BB domains: pilot clinical trial results. Blood. Apr. 26, 2012;119(17):3940-50. Epub Feb. 3, 2012.

Moisini, Ioana, et al. "Redirecting therapeutic T cells against myelin-specific T lymphocytes using a humanized myelin basic protein-HLA-DR2-ζ chimeric receptor" The Journal of Immunology, vol. 180, No. 5, pp. 3601-3611, Mar. 1, 2008.

*Primary Examiner* — Jeanette M Lieb
*Assistant Examiner* — Kristina M Hellman
(74) *Attorney, Agent, or Firm* — McDermott Will & Emery LLP

(57) ABSTRACT

Major histocompatibility complex-based chimeric receptors (MHC-CAR) for use in targeting autoreactive immune cells. Also provided herewith are genetically engineered immune cells expressing the MHC-CAR for use in treating autoimmune diseases such as multiple sclerosis.

9 Claims, 10 Drawing Sheets
Specification includes a Sequence Listing.

Single chain - Class II

Single chain - Class I

Multi-chain: Class II

Multi-chain: Class I

MAJOR HISTOCOMPATIBILITY COMPLEX-BASED CHIMERIC RECEPTORS AND USES THEREOF FOR TREATING AUTOIMMUNE DISEASES

RELATED APPLICATIONS

This application is a national stage filing under 35 U.S.C. § 371 of International Application No. PCT/US2018/060227, filed on Nov. 10, 2018, which claims the benefit of filing date of U.S. Provisional Application Ser. No. 62/584,449, filed on Nov. 10, 2017. The entire contents of each of the prior applications are incorporated by reference herein.

BACKGROUND OF THE INVENTION

Autoimmune diseases are characterized by abnormal immune responses against self-antigens, leading to damage or disruption of tissues. Multiple sclerosis (MS) is a central nervous system autoimmune disease, in which activated autoreactive T cells invade the blood brain barrier, initiating an inflammatory response that leads to myelin destruction and axonal loss. Although the etiology of MS, the mechanisms associated with its onset and progression, and determination of its outcome remains unelucidated, all available evidence suggests that therapies specifically targeting the pathologic immune cells responsible for MS would have improved therapeutic outcomes over available therapies. Reinhard et al., *Proceedings of the National Academy of Sciences*, 101 (suppl 2):14599-14606; 2004. This strategy could be extended to other immune disorders with similar mechanisms, including rheumatoid arthritis. Carol et al., *Nature Reviews Immunology*, 2(2):85-95, 2002.

The major histocompatibility complex (WIC), known as human leukocytes (HLA) in humans, is a set of cell surface proteins essential for the immune system to recognize foreign agents. MHC complexes bind to antigens derived from pathogens and display such to T cells, which are then activated, leading to elimination of cells displaying foreign antigens. MHC complexes may also display intact, and in some cases misfolded, host-derived proteins to B cells thereby inducing the autoantibody responses characteristic of autoimmune disorders. Jiang et al., *International immunology*, 25(4):235-246 (2013), and Busch et al., *The EMBO journal*, 15(2):418, (1996).

SUMMARY OF THE INVENTION

In aspect, the disclosure features a major histocompatibility complex (MHC)-based chimeric receptor (CAR), comprising: (i) an extracellular domain of a MHC molecule conjugated to an antigenic peptide from an antigen involved in an autoimmune disease; and (ii) a cytoplasmic signaling domain, at least one co-stimulatory domain, or a combination thereof. The MHC-based CAR may further comprises a hinge domain located between (i) and (ii). The antigenic peptide is dependent on the autoimmune disorder and may be from myelin basic protein (MBP), proteolipid protein (PLP), insulin, glutamate decarboxylase, or the additional exemplary self-antigens as described in Table 1.

In some examples, the MHC-based chimeric receptor comprises at least one co-stimulatory domain, which may be a co-stimulatory domain from 4-1BB (CD137), a co-stimulatory domain from CD28, or a combination thereof. In other examples, the MHC-based chimeric receptor as described herein may be free of a cytoplasmic signaling domain. Alternatively or in addition, the MHC-CAR comprises a cytoplasmic signaling domain of CD3ζ.

In some embodiments, the MHC molecule in the MHC-CAR is a class I MHC, for example, a human class I MHC. In some instances, the extracellular domain of the chimeric receptor comprises an extracellular domain of the alpha chain of the class I MHC, which is fused to the antigenic peptide. For example, the chimeric receptor may be a fusion polypeptide comprising (i) the extracellular domain of the class I MHC molecule, and (ii) the cytoplasmic domain, the at least one co-stimulatory domain, or the combination thereof. In one example, the chimeric receptor is a fusion polypeptide, which comprises, from N-terminus to C-terminus, a signal peptide, a first peptide linker, the antigenic peptide, a second peptide linker, an extracellular domain of macroglobulin, a third peptide linker, the class I MHC molecule, a transmembrane domain, the at least one co-stimulatory domain, and CD3ζ.

In other embodiments, the MHC-based chimeric receptor as described herein comprises a class II MHC (e.g., a human MHC II) or a portion thereof. Such a chimeric receptor may comprise a first polypeptide, which comprises an extracellular domain of a first MHC class II, and a second polypeptide, which comprises an extracellular domain of a beta chain of a second MHC class II, and wherein the antigenic peptide is fused to either the first polypeptide or the second polypeptide, and wherein either the first polypeptide or the second polypeptide further comprises the cytoplasmic signaling domain, the at least one co-stimulatory domain, or the combination thereof, in some examples, the chimeric receptor can be a fusion polypeptide comprising (i) an extracellular domain of the alpha chain of a first MHC class II molecule, (ii) an extracellular domain of the beta chain of a second MHC class II molecule, (iii) the antigenic peptide, and (iv) the cytoplasmic signaling domain, the at least one co-stimulatory domain, or the combination thereof. In some examples the antigenic protein may not be linked to the MHC class II and may instead be expressed as a separate fusion polypeptide with an alternative signal peptide (such as that from CD150, i.e., MDPKGLLSLTFVLFLSLAFG (SEQ ID NO: 388)). In some examples, the first MHC class II is HLA-DRA*1010. Alternatively or in addition, the second MHC class II is HLA-DRB1*1501.

In another aspect, the present disclosure features a nucleic acid or a nucleic acid set, which collectively encodes any of the MHC-based chimeric receptors described herein. In some instances, the nucleic acid or nucleic acid set can be located in one or more vectors, for example, viral vector(s).

Further, the present disclosure provides a genetically modified immune cell (e.g., a T cell), which expresses any of the MHC-based chimeric receptors described herein. In some instances, the activity of the endogenous T cell receptor (TCR) can be suppressed, which may be achieved by mutating or deleting the alpha chain of the endogenous TCR, the beta chain of the endogenous TCR, or both to disrupt surface expression of the endogenous TCR. Alternatively or in addition, the expression of the endogenous CD52 can be disrupted.

In some embodiments, the genetically modified immune cell as described herein may further express a suicide gene (e.g., RQR8), a marker gene (e.g., GFP), or both. When necessary, the immune cell can be further modified for lymph node or tertiary lymphoid organ delivery and retention. For example, the immune cell can be further engineered to overexpress VAP-1, L-selectin, CCR7, CXCR5, or a combination thereof. In some instances, the expression of endogenous sphingosine-1-phosphate receptor 1 can be disrupted in the genetically modified immune cell.

In some embodiments, the immune cell can be engineered to travel to the site of inflammation, for instance using a chemokine receptor such as CCR6 (e.g., to the site of Th17 cells), CXCR3 or CXCR4 (e.g., to the site of plasma cells), or through a membrane linked, antigen targeted antibody. Alternatively or in addition, the genetically modified immune cell may further comprise a genetic modification that results in blockade of PD-1 signaling. If needed and the disorder is especially severe the MHC-CAR cells can also be designed to remove or inactive bystander B cells (with a CD19 or CD20-CAR) or plasma cells (with a CS1-CAR and/or CS1 knockout).

In some embodiments, the genetically modified immune cell as described herein may be a regulatory T cell, which can be CD25+, and optionally CD4+. In some instances, the regulatory T cell can be derived from CD25++CD45R+ T cells isolated from peripheral blood mononuclear cells or from cord blood. In other instance, the regulatory T cell may comprise a transgene coding for CD25. Any of the Treg cells disclosed herein may further express a chimeric receptor specific to CD19, a chimeric receptor specific to CS-1, or both. Alternatively or in addition, the regulatory cell may further express CCR6, CXCR5, PD-1, or a combination thereof. In some examples, the regulatory cell may display an antibody specific to MOG.

In yet another aspect, the present disclosure provides a method for suppressing autoreactive immune cells in a subject having an autoimmune disease (e.g., multiple sclerosis). The method may comprise administering to the subject an effective amount of genetically modified immune cells as described herein, which can be T cells.

In some embodiments, the genetically modified immune cells are autologous. In other embodiments, the genetically modified immune cells are allogeneic. Any of the genetically modified immune cells may be administered to a lymph node of the subject. In some instances, the subject is undergoing a therapy comprising an antibody specific to CD52.

In some embodiments, the subject is a human patient having or at risk for multiple sclerosis and the genetically modified T cells are Treg cells or cytotoxic lymphocytes (CTLS) as described herein.

In some examples, the human patient is an early-stage MS patient and the Treg cells express the MHC-CAR and have one or more of the following genetic modifications: (i) PD-L1 and/or PD-1 knockout; (ii) surface expression of CCR6 and/or CXCR5; (iii) surface display of an antibody or an antigen-binding fragment thereof that is specific to MOG; and (iv) surface expression of a chimeric receptor targeting CD19. In some examples the patient may first, simultaneously, or alternatively be treated with cytotoxic CTLs with modifications of the same type.

In some examples, the human patient has relapsing-remitting MS or early-stage progressive MS and the Treg cells express the MHC-CAR and have one or more of the following modifications: (i) surface display of an antibody or antigen binding fragment that is specific to MOG; and (ii) surface expression of CCR6. In some examples the patient may first, simultaneously, or alternatively be treated with cytotoxic CTLs with modifications of the same type.

In some examples, the human patient has relapsing-remitting MS or early-stage progressive MS and the Treg cells express the MHC-CAR and have one or more of the following modifications: (i) surface expression of a chimeric receptor targeting CD19; and (ii) surface expression of CXCR5. In some examples the patient may first, simultaneously, or alternatively be treated with CTLs with the same modifications.

In some examples, the human patient has MS in chronic progressive form and the Treg cells express the MHC-CAR and have one or more of the following modifications: surface expression of a chimeric receptor targeting CS-1; and (ii) surface expression of an agent CXCR4, CCR6, and/or CXCR5. In some examples the patient may first, simultaneously, or alternatively be treated with CTLs with the same modifications.

In some embodiments, the subject is a human patient having or at risk for systemic lupus erythematosus, rheumatoid arthritis, juvenile idiopathic arthritis (also known as juvenile idiopathic arthritis), Sjögren's syndrome, systemic sclerosis, ankylosing spondylitis. Type 1 diabetes, autoimmune thyroid diseases (Grave's and Hashimoto's), multiple sclerosis myasthenia gravis, inflammatory bowel disease (Crohn's or ulcerative colitis), Psoriasis, or a diseases mentioned in Table 1 and the genetically modified T cells are Treg cells and/or CTLs as described herein.

In some examples, the human patient is an early-stage patient of any of the autoimmune disorders described herein (e.g., those listed in Table 1) and the Treg cells express the MHC-CAR and have one or more of the following genetic modifications: (i) PD-L and/or PD-1 knockout; (ii) surface expression of CCR6 and/or CXCR5; (iii) surface display of an antibody or an antigen-binding fragment thereof that is specific to a relevant protein described as an autoantigen in Table 1 for that autoimmune disorder; and (iv) surface expression of a chimeric receptor targeting CD19. In some examples the patient may first, simultaneously, or alternatively be treated with CTLs with the same modifications.

In some examples, the human patient has moderately severe disease state of any of the autoimmune disorders as described herein (e.g., those listed in Table 1) and the Treg cells express the MHC-CAR and have one or more of the following modifications: (i) surface display of an antibody or antigen binding fragment that is specific to a relevant protein described as an autoantigen in Table 1 for that autoimmune disorder; and (ii) surface expression of CCR6. In some examples the patient may first, simultaneously, or alternatively be treated with CTLs with the same modifications.

In some examples, the human patient has moderately severe disease state of any of the autoimmune disorders as described herein (e.g., those listed in Table 1) and the Treg cells express the MHC-CAR and have one or more of the following modifications: (i) surface expression of a chimeric receptor targeting CD19; and (ii) surface expression of CXCR5. In some examples the patient may first, simultaneously, or alternatively be treated with CTLs with the same modifications.

In some examples, the human patient has severe disease state of any of the autoimmune disorders described herein (e.g., those listed in Table 1) and the Treg cells express the MHC-CAR and have one or more of the following modifications: (i) surface expression of a chimeric receptor targeting CS-1; and (ii) surface expression of an agent targeting CXCR4, CCR6, and/or CXCR5. In some examples the patient may first, simultaneously, or alternatively be treated with CTLs with the same modifications.

Also within the scope of the present disclosure are pharmaceutical compositions for use in treating an autoimmune disease, the composition comprising genetically modified immune cells expression MHC-CAR as described herein such as Treg cells and a pharmaceutically acceptable carrier, and uses of such genetically modified immune cells for manufacturing a medicament for use in treating the target autoimmune disease.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 1 is a schematic illustration of an exemplary design of a lentiviral expression vector for expression of an antigen-specific T cell receptor (TCR). mRNA and multicistronic mRNA designs are similar.

FIG. 8A depicts exemplary designs of MHC Class I moieties linked to antigenic peptides. "N" refers to the N-terminus of a polypeptide. Circled black dots refer to the antigenic peptides. FIG. 8B depicts an exemplary expression cassette for a MHC Class I CAR construct.

DETAILED DESCRIPTION OF THE INVENTION

Figure 1:
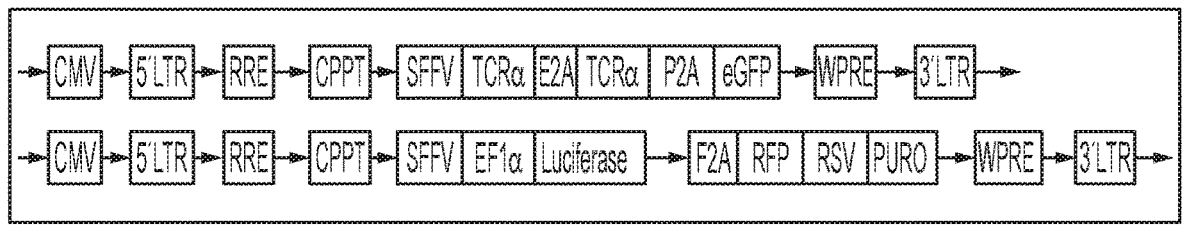

Autoreactive T cells, (e.g., those for myelin components involved in multiple sclerosis) exist in normal individuals. The majority of determinant of disease induction is in the class of immune response that occurs when these autoreactive T cells are triggered in autoimmune patients (e.g., in MS patients). Generation of pathologic autoreactive T cells is favored both by specific major histocompatibility complex (MHC) and non-MHC genes, which determine the protein sequences an individual reacts against and the class of the immune response.

Once an immune attack begins on an initial autoantigen (for example, a myelin antigen in MS), there is a spreading of reactivity to other autoantigens; that is, if a T cell attacks one autoantigen (for example, a brain protein in MS), other structures are damaged and they can sensitize additional T cells to attack other targets in a process called "epitope-spreading", a process that is shared by all autoimmune disorders and common to disease response in general.

B cells are ordinary components of the immune reaction in the early disease lesion caused by initial autoreactive attacks, for example, active MS lesion as well. B cell accumulation occurs as packed aggregates or ectopic B cell follicles. Serafini et al., Brain Pathol. 14: 164-144 (2004); Wekerle, Autoimmunity, 50:1, 57-60 (2017); and Pröbstel, et al., International journal of molecular sciences, 16(7), pp. 16576-16592 (2015). In MS, B cells were reported to be found in the brain and spinal cord of RR-, SP-, and P-stage MS patients. Therapeutic treatments that target B cells either directly or indirectly have proven beneficial in treatment of autoimmune diseases such as MS. Wekerle, 2017.

Both CD4+ and CD8+ T cells are present in MS lesions and are believed to play a central role in disease development. Increased frequencies of myelin-reactive (MBP, PLP, and MOG) CD4 and CD8 cells are found in MS patients compared to healthy controls. Cao, et al., Sci. Transl. Med. 7 (287), 287ra74 (2014); Martin, et al., J. Exp. Med. 173 (Jan. 1, 1991); Ota, et al., Nature 346, 183 (Jul. 12, 1990); Pette, et al., Neurology 40, 1770 (1990); and Raddassi, et al., J. Immunol. 187, 1039 (2011).

Th1 cells producing IFN-gamma and Th17 cells are uniquely pathogenic. Factors that favor the development of Th1 cells are elevated in MS patients and are also triggered by viral infections: gamma interferon; IL-12—in almost all treatments that affect the immune system and help MS, almost all decrease Th1 response and increase Th2 and TH3 response. Th17 cells are present at sites of tissue inflammation and are implicated in autoimmune/chronic inflammatory conditions. Th17 producing CD4 and CD8 cells are increased in the lesions, blood, and CSF of patients. [Tzartos 2008; Matusevicius 1999; Bruchlacher-Waldert 2009]. The CCR6 and CD161 on Th17 cells are hypothesized to be homing molecules to inflamed tissues [Cosmi, 2008].

Th17 cells are also implicated in a number of other autoimmune diseases such as sytemic lupus erythematosus, rheumatoid arthritis, juvenile idiopathic arthritis (also known as juvenile idiopathic arthritis), Sjögren's syndrome, systemic sclerosis, ankylosing spondylitis, Type 1 diabetes, autoimmune thyroid diseases (Grave's and Hashimoto's), myasthenia gravis, inflammatory bowel disease (Crohn's or ulcerative colitis), and psoriasis. Tabarkiewicz et al., Archivum immunologiae et therapiae experimentalis, 63(6): 435-449 (2015).

The ultimate goal of any treatment for autoimmune disease is a complete suppression of pathology. In the case of multiple sclerosis and other autoimmune disorders, pathologic lymphocytes (both B and T cells, and if necessary plasma cells for very severe cases) are expected to be eliminated or controlled to halt the disease course, and interventions at different stages of disease progression require different cellular targets and therefore therapeutic cells.

Disclosed herein are major histocompatibility complex (MHC)-based chimeric receptors (MHC-CAR) for targeting autoreactive immune cells such as autoreactive T cells. A MHC-CAR as described herein comprises one or more MHC polypeptides or an extracellular domain thereof and one or more cell signaling domains, for example, a cytoplasmic signaling domain (e.g., that from CD3ζ), at least one co-stimulatory domain (e.g., that from 4-1BB or CD28), or both. The MHC-CAR may further comprise an antigenic peptide from an autoantigen or a foreign antigen that mimics an autoantigen in eliciting autoimmune responses. Also herein are nucleic acids encoding the MHC-CAR, vectors carrying such, and genetically engineered immune cells such as T cell and natural killer (NK) cells expressing the MHC-CAR. Such genetically engineered immune cells can be used to target autoreactive immune cells, thereby benefiting treatment of autoimmune diseases involving the autoreactive immune cells.

Also disclosed herein are genetically modified regulatory T (Treg) cells expressing an MHC-based chimeric receptor as disclosed herein. Such Treg cells may be further modified with chimeric receptor(s) targeting T cell and/or B cell surface markers, as well as additional genetic engineering for, e.g., targeting specific tissue sites (e.g., lymph nodes or inflammation sites) or modulating immune responses e.g., checkpoint modulation). The genetically modified Treg cells may be used to inhibit pathogenicity at an early stage of a target disease, to control disease progression at a middle stage of the disease (e.g., relapsing or remitting MS), or to suppress pathology via, e.g., inducing cytotoxicity of pathologic CD8+ T cells at a late stage of the disease chronic progressive MS).

I. Major Histocompatibility Complex (MHC)-Based Chimeric Receptors (MHC-CARS)

The MHC based chimeric receptor (MHC-CAR) described herein comprises an MHC moiety, which is conjugated to an antigenic peptide (e.g., a misfolded one), and at least one cell signaling moiety, which can be a cytoplasmic signaling domain (e.g., that of CD3ζ), one or more co-stimulatory domains (e.g., that of 4-1BB or CD28), or a combination thereof. In some instances, the antigenic peptide can be part of a fusion polypeptide of the MHC-CAR. In other instances, the antigenic peptide does not form a fusion polypeptide with the MHC-CAR but forms a complex with the MHC-CAR. As used herein, the term "conjugated" means that at least two components are physically associated, either Via covalent bonds or Via non-covalent interactions.

In some examples, the MHC-CAR can be a single fusion polypeptide containing the MHC moiety, the antigenic peptide, and the at least one cell signaling moiety. Such a single fusion polypeptide may form complexes with endogenous cell membrane proteins (e.g., β-microglobulin) when expressed in a suitable immune cells.

In other examples, the MHC-CAR described herein may be a multi-chain protein complex, for example, a heterodimer, comprising one polypeptide that comprises the antigenic peptide. In some instances, the antigenic peptide or polypeptide may be expressed as a separate polypeptide, which may form a complex (e.g., a trimer) with the MHC components. The antigenic polypeptide can be a misfolded antigenic protein that binds to the MHC. Optionally, the MHC-CAR may further comprise a hinge domain, which may be adjacent to the antigenic peptide and/or the MHC moiety, a signal peptide at the N-terminus, and/or one or more tagging sites, for example, a histidine protein tag and/or an RQR domain that additionally acts as a kill-switch site.

(i) Components of MHC-CARs (a) MHC Moiety

The MHC-CAR constructs disclosed herein comprise an MHC moiety, which may comprise one or more MHC polypeptides or an extracellular domain thereof. The MHC moiety may be derived from a suitable source, for example, human or a non-human mammal (e.g., monkey, mouse, rat, rabbit, pig, etc.) In some instances, the MHC moiety is from a human MHC molecule (also known as HLA). In some instances the domains that interact with molecules from other cells (TCR or BCR) are from a human MHC molecule. There are primarily two classes of MHC molecules, MHC class I molecules and WIC class II molecules, both of which can be used for constructing the MHC-CARs described herein. Sequences of MHC class I and class II molecules of various species (e.g., human, non-human primates, canids, fish, ovids, bovines, equids, suids, murids, and gallus) are available from public gene datasets, for example, the IPD-MHC database and the IMGT/HLA database provided by EMBL-EBI and the dbMHC database provided by National Center for Biotechnology Information (NCBI).

MHC class I molecules are heterodimers containing an alpha chain and β-microglobulin. The extracellular domain of an alpha chain includes three subdomains, α1, α2, and α3. In some embodiments, the MHC moiety may include the alpha chain of a MHC class I molecule, or an extracellular domain thereof, for example, the α1 domain, the α2 domain, the α3 domain, or a combination thereof. The MHC class I molecule may be a human HLA-A molecule, a human HLA-B molecule, or a human HLA-C molecule. In some instances, the alpha chain of the MHC class I molecule may be fused with β-microglobulin to produce a single chain fusion protein. In some examples, the MHC Class I moiety is from HLA A3, which can be co-used with a PLP peptide. Honma et al., J. Neuroimmunol. 73:7-14 (1997). In other examples, the MHC Class I is from HLA A2, which can be used with the same PLP peptide and display of a viral peptide such as TAX. TAX is from the protein tax or p40 (Genhank accession no. BAB20130.1) that is a molecular mimic of a human neuronal protein and from the HTLV-1 virus, which is implicated in diseases such as rheumatoid arthritis, system lupus erythematosus, and Sjogren's syndrome. Garboczi, et al. The Journal of Immunology, 157 (12):5403-5410, 1996. Quaresma, et al., 2015. Viruses, 8(1):5 2015. The class I protein and peptide may additionally contain modifications to enable more robust peptide loading such replacement of the invariant tyrosine at position 84 of the heavy chain with alanine; or alternatively the position 84 tyrosine can be replaced with cysteine as can the second position of the peptide-β2m linker to create a disulfide trap. Hansen et al. *Trends in immunology*, 31(10):363 (2010).

Like MHC class I molecules, MHC class II molecules are also heterodimers consisting of two homogenous peptides, an α-chain and a β-chain. The extracellular domain of each of the α-chain and the β-chain contains two subdomains α1/α2, and β1/β2. When a MHC class II molecule is used for constructing a MHC-CAR, the MHC moiety may include two subunits, one including the α-chain or a portion thereof, for example, an extracellular domain thereof (e.g., α1, α2, or both), the other including the b-chain or a portion thereof, for example, an extracellular domain thereof (e.g., β1, β2, or both). In cases where only the region that interacts with other cell types is used (i.e., α1 and β1), specific amino acid modifications may be required to enhance the folding of the mini-MHC, see mini-sequence with shaded regions and Birnbaum et al. The MHC class II molecule may be a human HLA DP molecule, a human HLA DM molecule, a human HLA DOA molecule, a human HLA DOB molecule, a human HLA DQ molecule, or a human HLA DR molecule. In some examples, the MHC class II molecule is a human HLA DR molecule, for example HLA DR*1501.

(b) Antigenic Peptides

The antigenic peptides of the MHC-CAR described herein are an antigenic peptide that is recognizable by pathogenic immune cells (e.g., autoreactive T cells or B cells) involved in an autoimmune disease. When presented by a suitable MHC molecule, such an antigenic peptide would interact with the antigen-specific T cell receptors of pathogenic T cells, leading to downstream immune responses.

In some instances, a specific antigenic peptide can be designed for a specific autoimmune disease patient such as an MS patient, using methods known in the art. Programs like NetMHC enable personalized design of antigenic peptides that are specific to the patients MHC, and have been used to develop personalized cancer vaccines. Hacohen et al., Cancer immunology research, 1(1):11-15 (2013). Also within the scope of the present disclosure are personalized CAR T and Treg therapies for autoimmune disorders. For disorders with very strong MHC associations (such as MS), a personalized therapy can be utilized to treat a large patient class at different stages of the disease. Recent studies have also demonstrated that Class II MHCs and specifically the HLAs implicated in autoimmune disorders can display entire antigenic proteins rather than just processed peptides. Jiang et al., International immunology, 25(4):235-246, (2013). These MHC-protein complexes appear to induce autoantibody production in autoimmune disorders, including antibodies that do not bind to properly folded proteins as well as autoantibodies that are specific to those with specific autoimmune disorders. The inventors impute that display of antigenic proteins in MHC-CAR can provide a specific route to remove or deactivate autoimmune specific B cells, such as those in MS which produce oligoclonal bands whose specificity to proteins has not been unraveled, despite many rigorous attempts. Owens et al., Annals of neurology, 65(60):639-649, 2009; Chastre et al., New England Journal of Medicine, 374(15):1495-1496, 2016; Housley et al., Clinical immunology, 161(1):51-58, 2015; Larman et al., 2013. Journal of autoimmunity, 43:1-9, 2013. In the event that the antigenic protein does not bind the MHC, then that specific MHC-CAR will not be expressed, but as a Treg or CTL it can still play a bystander role in modifying the immune response depending upon its other characteristics and as part of a patient specific population of MHC-CAR and Treg cells with different specificities.

The antigenic peptides used herein may be fragments of autoantigens involved in autoimmune diseases, for example, myelin basic protein (MBP), myelin oligodendrocyte glycoprotein (MOG), and proteolipid protein (PLP) involved in multiple sclerosis, insulin and glutamate decarboxylase (GAD) involved in type I diabetes, tryptase involved in rheumatoid arthritis (RA), and the proteins included in Table 1 below. Alternatively, the antigenic peptide can be a fragment of a pathogen protein such as a viral or a bacterial protein that is highly homologous to a self-antigen involved in an autoimmune disease. Such an antigenic peptide also can target pathogenic T cells. If needed, the antigenic peptide can be a (typically misfolded) antigenic protein or protein fragment that can be expressed separately and binds directly to the MHC moiety of a MHC-CAR described herein. In their natural state (attached to an MHC rather than an MHC moiety of a MHC-CAR), such antigenic protein/MHC complexes stimulate pathogenic B cells to produce autoantibodies. For proteins such as IgGH or rheumatoid factor in rheumatoid arthritis (Jin et al., *Proceedings of the National Academy of Sciences*, 111(10):3787-3792, 2014), β2-glycoprotein I in antiphospholipid syndrome (Tanimura et al., *Blood*, 25(142835-2844, 2015) and recurrent miscarriage (Tanimura et al., *Placenta*, 46:108, 2016), GM-CSF in autoimmune pulmonary alveolar proteinosis (Hamano et al., *ALVEOLAR MACROPHAGE BIOLOGY* B32: A3147-A3147, 2016), tyrosinase in vitiligo (Arase et al. *Journal of Dermatological Science*, 84(1):e87, 2016), and myeloperoxidase in microscopic polyangiitis (Hiwa et al., *Arthritis & Rheumatology*, 69(10):2069-2080, 2017), HLA mediated surface display and in some cases autoantibody binding of misfolded variant/HLA complex can occur.

The antigenic peptides for use in the MHC-CAR described herein may contain up to 20 amino acid residues, the extracellular domain of the antigenic protein, or the full length antigenic protein. When co-used with a MHC class I moiety, the antigenic peptide may be 8-10 amino acid-long. Such antigenic peptides would fit well into the peptide binding site of a MHC class I molecule. Antigenic peptides to be co-used with MHC class II moieties can be longer, for example, containing 15-24 amino acid residues or up to the full length of the antigenic protein, since the antigen-binding groove of MHC class II molecules is open at both ends, while the corresponding antigen-binding groove on class I molecules is usually closed at each end. The open antigen-binding groove of MHC class II molecules implicated in autoimmune disorders can also frequently display intact (e.g., yet misfolded) antigenic proteins or splice variants. Jiang et al., *International immunology*, 25(4):235-246, 2013.

In some examples, a fragment of human MBP is used for constructing the MHC-CARs described herein. An exemplary amino acid sequence of a human MBP is provided below:

```
                                         (SEQ ID NO: 1)
MASQKRPSQRHGSKYLATASTMDHARHGFLPRHRDTGILDSIGRFFGGDR

GAPKRGSGKVPWLKPGRSPLPSHARSQPGLCNMYKDSHHPARTAHYGSLP

QKSHGRTQDENPVVHFFKNIVTPRTPPPSQGKGRGLSLSRFSWGAEGQRP

GFGYGGRASDYKSAHKGFKGVDAQGTLSKIFKLGGRDSRSGSPMARRHHH

HHH
```

Exemplary MBP antigenic peptides include, but are not limited to:

GSKYLATASTMDHARHGFLPRHRDTGILDSIGRFFGGDRG, (SEQ ID NO: 2)

KYLATASTMDHARHGFLPRH, (SEQ ID NO: 3)

ATASTMDHARHGFLPRHRDTGIL, (SEQ ID NO: 4)

RDTGILDSIGRFFGGDRGAP, (SEQ ID NO: 5)

IGRFFGGDRGAPKRGSGKDSHHPARTAHY, (SEQ ID NO: 6)

APKRGSGKDSHHAARTAHY, (SEQ ID NO: 7)

GSGKDSHHPARTAHYGSLPQ, (SEQ ID NO: 8)

HHPARTAHYGSLPQKSHGR, (SEQ ID NO: 9)

HAARTAHYGSLPQKSQGHR, (SEQ ID NO: 10)

SLPQSHGRTQDENPVVHF, (SEQ ID NO: 11)

PQDENPVVHFFKNIVTPRTP, (SEQ ID NO: 12)

TQDENPVVHFFKNIVTPRTP, (SEQ ID NO: 13)

QDENPVVHFFKNIVTPRTP, (SEQ ID NO: 14)

DENPVVHFFKNIVTPRTPP, (SEQ ID NO: 15)

ENPVVHFFKNIVTPR, (SEQ ID NO: 16)

ENPVVHFFKNIVTPRTP, (SEQ ID NO: 17)

ENPVVHFFKNIVTP, (SEQ ID NO: 18)

NPVVHFFKNIVTPRTPPPSQ, (SEQ ID NO: 19)

VVHFFKNIVTPRT, (SEQ ID NO: 20)

VVHFFKNIVTPRTPPPSQGK, (SEQ ID NO: 21)

KNIVTPRTPPPSQGKGRGL, (SEQ ID NO: 22)

PSQGKGRGLSLSRFSWGAE, (SEQ ID NO: 23)

GKGRGLSLSRFSWGAEGQRP, (SEQ ID NO: 24)

LSRFSWGAEGQRPGFGYGG, (SEQ ID NO: 25)

QRPGFGYGGRASDYKSAHK, (SEQ ID NO: 26)

ASDYKSAHKGFKGVDAQGT, (SEQ ID NO: 27)

FKGVDAQGTLSKIFKLGGR, (SEQ ID NO: 28)

VDAQGTLSKIFKLGGRDSRS, (SEQ ID NO: 29)
and

SKIFKLGGRDSRSGSPMARR. (SEQ ID NO: 30)

An example nucleic acid sequence encoding the MBP antigenic peptide of SEQ ID NO: 15 is provided below:

(SEQ ID NO: 411)
GATGAGAATCCCGTGGTTCATTTTTTTAAGAACATCGTCACACCGCGCAC

CCCACCTG

Specific examples include MBP13-32, MBP89-101, MBP83-99, MBP111-129, or MBP146-170.

Exemplary amino acid sequences for human myelin oligodendrocyte glycoprotein, proteolipid protein, and myelin associated glycoprotein are provided below:

>CAA52617.1 myelin oligodendrocyte glycoprotein
[Homo sapiens]
(SEQ ID NO: 31)
MASLSRPSLPSCLCSFLLLLLLQVSSSYAGQFRVIGPRHPIRALVGDEVE

LPCRISPGKNATGMEVGWYPRRFSRVVHLYRNGKDQDGDQAPEYRGRTEL

LKDAIGEGKVTLRIRNVRFSDEGGFTCFFRDHSYQEEAAMELKVEDPFYW

VSPGVLVLLAVLPVLLLQITVGLVFLCLQYRLRGKLRAEIENLHRTFDPH

FLRVPCWKITLFVIVPVLGPLVALIICYNWLHRRLAGQFLEELRNPF

Exemplary MOG antigenic peptides include MOG1-20 or MOG35-55.

AAA60117.1 proteolipid protein [Homo sapiens]
(SEQ ID NO: 32)
MGLLECCARCLVGAPFASLVATGLCFFGVALFCGCGHEALTGTEKLIETY

FSKNYQDYEYLINVIHAFQYVIYGTASFFFLYGALLLAEGFYTTGAVRQI

FGDYKTTICGKGLSATVTGGQKGRGSRGQHQAHSLERVCTCLGKWLGHPD

KFVGITYALTVVWLLVFACSAVPVYIYFNTWTTCQSIAFPSKTSASIGSL

CADARMYGVLPWNAFPGKVCGSNLLSICKTAEFQMTFHLFIAAFVGAAAT

LVSLLTFMIAATYNFAVLKLMGRGTKF

An exemplary antigenic fragment of PLP is underlined and in boldface. Other examples include PLP139-151(4) or PLP78-191.

>AAH93045.1 Myelin associated glycoprotein
[Homo sapiens]
(SEQ ID NO: 33)
MIFLTALPLFWIMISASRGGHWGAWMPSSISAFEGTCVSIPCRFDFPDEL

RPAVVHGVWYFNSPYPKNYPPVVFKSRTQVVHESFQGRSRLLGDLGLRNC

TLLLSNVSPELGGKYYFRGDLGGYNQYTFSEHSVLDIVNTPNIVVPPEVV

AGTEVEVSCMVPDNCPELRPELSWLGHEGLGEPAVLGRLREDEGTWVQVS

LLHFVPTREANGHRLGCQASFPNTTLQFEGYASMDVKYPPVIVEMNSSVE

AIEGSHVSLLCGADSNPPPLLTWMRDGTVLREAVAESLLLELEEVTPAED

-continued

GVYACLAENAYGQDNRTVGLSVMYAPWKPTVNGTMVAVEGETVSILCSTQ

SNPDPILTIFKEKQILSTVIYESELQLELPAVSPEDDGEYWCVAENQYGQ

RATAFNLSVEFAPVLLLESHCAAARDTVQCLCVVKSNPEPSVAFELPSRN

-continued

VTVNESEREFVYSERSGLVLTSILTLRGQAQAPPRVICTARNLYGAKSLE

LPFQGAHRLMWAKIGPVGAVVAFAILIAIVCYITQTRRKKNVTESPSFSA

GDNPPVLFSSDFRISGAPEKYESKEVSTLESH

Table 1 below provides additional exemplary autoantigens associated with other autoimmune diseases.

TABLE 1

Autoantigens of Various Autoimmune Disorders

| Autoantigen | GenBank Accession No. | Associated Autoimmune Disease |
| --- | --- | --- |
| Dopachrome tautomerase | AAH28311.1 | Alopecia areata |
| Melanoma antigen gp100 | AAC60634.1 | Alopecia areata |
| Melanocyte protein Pmel | NP_001186983.1 | Alopecia areata |
| Melanocyte-stimulating hormone receptor | NP_002377.4 | Alopecia areata |
| Trichohyalin | AAA65582.1 | Alopecia areata |
| Tyrosine 3-monooxygenase | NP_954986.2 | Alopecia areata |
| Amyloid beta A4 protein | NP_000475.1 | Alzheimer's |
| Vasoactive intestinal polypeptide receptor 1 | NP_004615.2 | Ankylosing spondylitis |
| Latent membrane protein 2 | CAA57360.1 | Ankylosing spondylitis |
| Nitrogenase iron protein | ART03999.1 | Ankylosing spondylitis |
| Aggrecan core protein | NP_001126.3 | Ankylosing spondylitis |
| Beta-2-glycoprotein 1 | NP_000033.2 | Antiphospholipid syndrome |
| M protein precursor | AAA26918.1 | Antiphospholipid syndrome |
| Large tegument protein | ACL51127.1 | Antiphospholipid syndrome |
| Steroid 21-hydroxylase | NP_000491.4 | Autoimmune adrenalitis |
| Steroid 17-alpha-hydroxylase/17,20 lyase | NP_000093.1 | Autoimmune adrenalitis |
| Potassium-transporting ATPase alpha chain | AAB50172.1 | Autoimmune gastritis |
| Potassium-transporting ATPase beta chain | AAA35987.1 | Autoimmune gastritis |
| Cytochrome P450 2D6 | ABB77909.1 | Autoimmune hepatitis |
| Genome polyprotein | S35630 | Autoimmune hepatitis |
| O-phosphoseryl-tRNA(Sec) selenium transferase | NP_058651.3 | Autoimmune hepatitis |
| Asialoglycoprotein receptor | AAB58308.1 | Autoimmune hepatitis |
| Glutathione S-transferase | CAA48637.1 | Autoimmune hepatitis |
| Cytokeratin 8 | AAB18966.1 | Autoimmune hepatitis |
| M protein | AAA26918.1 | Autoimmune myocarditis |
| Myosin-7 | NP_000248.2 | Autoimmune myocarditis |
| Cardiac myosin light chain 1 | AAF91089.1 | Autoimmune myocarditis |
| Cardiac myosin light chain 2 | AAA91832.1 | Autoimmune myocarditis |
| Cardiac actin | NP_005150.1 | Autoimmune myocarditis |
| Troponin I | AC14461.1 | Autoimmune myocarditis |
| Thyroid peroxidase | AAA61217.2 | Autoimmune thyroiditis |
| Thyrotropin receptor | AAB23390.2 | Autoimmune thyroiditis |
| Thyroglobulin | NP_003226.4 | Autoimmune thyroiditis |
| S-arrestin | NP_000532.2 | Autoimmune uveitis |
| LAMP2 | AAB67314.1 | Autoimmune vasculitis |
| Myeloperoxidase | AAA59863.1 | Autoimmune vasculitis |
| Myeloblastin | NP_002768.3 | Autoimmune vasculitis |
| Alpha-gliadin | AFX69628.1 | Coeliac disease |
| Protein-glutamine gamma-glutamyltransferase 2 | NP_004604.2 | Coeliac disease |
| 75k gamma secalin | ADP95479.1 | Coeliac disease |
| Gamma 1 hordein | AFM77738.1 | Coeliac disease |
| Avenin-3-like | ADA62372.1 | Coeliac disease |
| Glycosyltransferase | ANR93567.1 | Crohn's disease |
| 60 kDa heat shock protein, mitochondrial | NP_002147.2 | Crohn's disease |
| Transmembrane protein UO-44D | NP_002147.2 | Crohn's disease |
| GM-CSF | AAA52578.1 | Crohn's disease |
| Sucrase-isomaltase, intestinal | NP_001032.2 | Crohn's disease |
| Glutathione peroxidase 2 | NP_002074.2 | Crohn's disease |
| 60 kDa chaperonin 2 | ARX70571.1 | Crohn's disease |
| Pancreatic secretory glycoprotein 2 | NP_001493.2 | Crohn's disease |
| 60 kDa chaperonin 2 | OMH58317.1 | Crohn's disease |
| Cytoskeleton-associated protein 5 | EAW67976.1 | Crohn's disease |
| AhpC | ETZ42359.1 | Crohn's disease |
| Leukotriene B4 receptor 2 | NP_062813.2 | Crohn's disease |

TABLE 1-continued

Autoantigens of Various Autoimmune Disorders

| Autoantigen | GenBank Accession No. | Associated Autoimmune Disease |
|---|---|---|
| Chromodomain-helicase-DNA-binding protein 4 | NP_001264.2 | Dermatomyositis |
| Chromodomain-helicase-DNA-binding protein 3 | NP_001005273.1 | Dermatomyositis |
| Beta-1 adrenergic receptor | NP_000675.1 | Dialated cardiomyopathy |
| Muscarinic acetylcholine receptor M2 | NP_001006633.1 | Dialated cardiomyopathy |
| Collagen alpha-3(IV) chain | CAA56335.1 | Goodpasture's syndrome |
| Thyrotropin receptor | AAB23390.2 | Grave's disease |
| Thyroid peroxidase | AAA61217.2 | Grave's disease |
| Thyroglobulin | CAA29104.1 | Grave's disease |
| Glutamate decarboxylase 2 | NP_000809.1 | Grave's disease |
| TSHR protein | AAI27629.1 | Grave's disease |
| Thyroid peroxidase | AAA61217.2 | Hashimoto's thyroiditis |
| Thyroglobin | CAA29104.1 | Hashimoto's thyroiditis |
| Thyroid stimulating hormone receptor | AAI41971.1 | Hashimoto's thyroiditis |
| Insulin | AAA59172.1 | Hypogycemia |
| Insulin receptor | AAA59452.1 | Hypogycemia |
| Integrin beta-3 | NP_000203.2 | Immune thrombocytopenic purpura |
| Integrin alpha-IIb | NP_000410.2 | Immune thrombocytopenic purpura |
| Platelet glycoprotein Ib alpha chain | NP_000164.5 | Immune thrombocytopenic purpura |
| Platelet glycoprotein IIIa | AAA52600.1 | Immune thrombocytopenic purpura |
| Thrombopoietin | AAB03393.1 | Immune thrombocytopenic purpura |
| Insulin receptor | AAA59452.1 | Insulin resistant diabetes |
| Phospholipase A2 | NP_000919.1 | Membranous nephritis |
| Myelin basic protein | AAC41944.1 | Multiple sclerosis |
| Myelin proteolipid protein | AAA59565.1 | Multiple sclerosis |
| Myelin-oligodendrocyte glycoprotein | CAA52617.1 | Multiple sclerosis |
| Epstein-Barr nuclear antigen 1 | Q1HVF7.1 | Multiple sclerosis |
| DNA polymerase catalytic subunit | AMD82168.1 | Multiple sclerosis |
| 2',3'-cyclic-nucleotide 3'-phosphodiesterase | AAB24298.2 | Multiple sclerosis |
| Oligodendrocyte-myelin glycoprotein | AAA59970.1 | Multiple sclerosis |
| Aquaporin-4 | AAH22286.1 | Multiple sclerosis |
| Actin, cytoplasmic 1 | NP_001092.1 | Multiple sclerosis |
| Transposase, mutator family protein | EUA40098.1 | Multiple sclerosis |
| E4 gene product | YP_002640224.1 | Multiple sclerosis |
| Protein BOLF1 | AIE89051.1 | Multiple sclerosis |
| Myelin-associated glycoprotein | AAH93045.1 | Multiple sclerosis |
| Transaldolase | NP_006746.1 | Multiple sclerosis |
| Possible transposase | CCP46656.1 | Multiple sclerosis |
| Claudin-11 | NP_005593.2 | Multiple sclerosis |
| Interferon beta | AAC41702.1 | Multiple sclerosis |
| Alpha-crystallin B chain | ACA05949.1 | Multiple sclerosis |
| Apolipoprotein E | AAB59518.1 | Multiple sclerosis |
| Epstein-Barr nuclear antigen 6 | AAA45895.1 | Multiple sclerosis |
| Trans-activator protein BZLF1 | BAP94413.1 | Multiple sclerosis |
| Hemagglutinin | ALB07770.1 | Multiple sclerosis |
| Protein S100-B | NP_006263.1 | Multiple sclerosis |
| DNA polymerase catalytic subunit | SCL76875.1 | Multiple sclerosis |
| Tripartite terminase subunit UL15 | SCL76864.1 | Multiple sclerosis |
| Glyceraldehyde-3-phosphate dehydrogenase | CAA25833.1 | Multiple sclerosis |
| Alpha-enolase | CAA34360.1 | Multiple sclerosis |
| Neurofilament light polypeptide | NP_006149.2 | Multiple sclerosis |
| Connexin 43 | AAA52131.1 | Multiple sclerosis |
| Neurofilament medium polypeptide | NP_005373.2 | Multiple sclerosis |
| POTE ankyrin domain family member I | NP_001264335.1 | Multiple sclerosis |
| 60 kDa heat shock protein, mitochondrial | NP_002147.2 | Multiple sclerosis |
| Epstein-Barr nuclear antigen 3 | BAP94411.1 | Multiple sclerosis |
| Putative HTLV-1-related endogenous sequence | CAA34646.1 | Multiple sclerosis |
| Glial fibrillary acidic protein | AAB22581.1 | Multiple sclerosis |
| Phosphomannomutase/phosphoglucomutase | OPA62825.1 | Multiple sclerosis |
| Minor capsid protein L2 | P36745.1 | Multiple sclerosis |
| N-acetylmuramoyl-L-alanine amidase CwlH | KIX84070.1 | Multiple sclerosis |

TABLE 1-continued

Autoantigens of Various Autoimmune Disorders

| Autoantigen | GenBank Accession No. | Associated Autoimmune Disease |
|---|---|---|
| ATP-sensitive inward rectifier potassium channel 10 | NP_002232.2 | Multiple sclerosis |
| mRNA export factor ICP27 homolog | YP_401659.1 | Multiple sclerosis |
| Acetylcholine receptor subunit alpha | NP_001034612.1 | Myasthenia gravis |
| Acetylcholine receptor subunit gamma | NP_005190.4 | Myasthenia gravis |
| Acetylcholine receptor subunit delta | NP_000742.1 | Myasthenia gravis |
| Acetylcholine receptor subunit epsilon | NP_000071.1 | Myasthenia gravis |
| Muscarinic receptor | AAB95158.1 | Myasthenia gravis-MUSC |
| Aquaporin 4 | AAH22286.1 | Neuromyelitis optica |
| Alpha-synuclein | NP_000336.1 | Parkinson's disease |
| DNA polymerase processivity factor | SBO07788.1 | Parkinson's disease |
| Desmoglein-3 | NP_001935.2 | Phemphigus |
| Collagen alpha-1(XVII) chain | NP_000485.3 | Phemphigus |
| Desmoglein-1 | NP_001933.2 | Phemphigus |
| Glutamate decarboxylase 2 | NP_000809.1 | Prediabetes |
| 60 kDa heat shock protein, mitochondrial | NP_002147.2 | Prediabetes |
| Insulin | AAA59172.1 | Prediabetes |
| Insulin, isoform 2 | NP_001035835.1 | Prediabetes |
| Islet cell antigen | NP_002837.1 | Prediabetes |
| Dihydrolipoyllysine-residue acetyltransferase component of pyruvate dehydrogenase complex | NP_001922.2 | Primary biliary cirrhosis |
| Dihydrolipoyllysine-residue acetyltransferase component of pyruvate dehydrogenase complex | OAF98393.1 | Primary biliary cirrhosis |
| Dihydrolipoyllysine-residue succinyltransferase component of 2-oxoglutarate dehydrogenase complex | WP_032229692.1 | Primary biliary cirrhosis |
| Glycogen phosphorylase | AAC18079.1 | Primary biliary cirrhosis |
| Nuclear pore glycoprotein 210 | NP_079199.2 | Primary biliary cirrhosis |
| Sarcosine dehydrogenase | AAD32214.1 | Primary biliary cirrhosis |
| Sulfite oxidase | AAA74886.1 | Primary biliary cirrhosis |
| Transglutaminase | BAA14329.1 | Primary biliary cirrhosis |
| Nuclear autoantigen Sp-100 | NP_001073860.1 | Primary biliary cirrhosis |
| Dihydrolipoyllysine-residue succinyltransferase component of 2-oxoglutarate dehydrogenase complex, mitochondrial | NP_001924.2 | Primary biliary cirrhosis |
| Nuclear pore p62 | AAA59990.1 | Primary biliary cirrhosis |
| M protein precursor | AAA26918.1 | Psoriasis |
| Keratin, type I cytoskeletal 16 | NP_005548.2 | Psoriasis |
| Keratin, type I cytoskeletal 17 | NP_000413.1 | Psoriasis |
| ADAMTS-like protein 5 | NP_998769.2 | Psoriasrs |
| Transcriptional activator | AHF70996.1 | Psoriatic arthritis |
| Fibrinogen alpha chain | AAI01936.1 | Psoriatic arthritis |
| Vimentin | NP_003371.2 | Psoriatic arthritis |
| Nebulin-related-anchoring protein | AI26408.1 | Psoriatic arthritis |
| M protein | CAM31002.1 | Rheumatic fever |
| Myosin-2 | NP_060004.3 | Rheumatic fever |
| Fibrinogen beta chain | AAI06761.1 | Rheumatoid arthritis |
| Vimentin | NP_003371.2 | Rheumatoid arthritis |
| Rheumatoid factor (IgG) | AAH73766.1 | Rheumatoid arthritis |
| Glucose-6-phosphate isomerase | ARJ36701.1 | Rheumatoid arthritis |
| Collagen alpha-1(II) chain | NP_001835.3 | Rheumatoid arthritis |
| Fibrinogen alpha chain | AAI01936.1 | Rheumatoid arthritis |
| Alpha-enolase | CAA34360.1 | Rheumatoid arthritis |
| Tryptase precursor | AAA86934.1 | Rheumatoid arthritis |
| Filaggrin | NP_002007.1 | Rheumatoid arthritis |
| Aggrecan core protein | NP_001126.3 | Rheumatoid arthritis |
| Small nuclear ribonucleoprotein Sm D1 | NP_008869.1 | Rheumatoid arthritis |
| Ribosomal protein L23a | AAB17510.1 | Rheumatoid arthritis |
| 60 kDa chaperonin 2 | OMH58317.1 | Rheumatoid arthritis |
| Trans-activator protein BZLF1 | BAP94413.1 | Rheumatoid arthritis |
| Epstein-Barr nuclear antigen 1 | YP_401677.1 | Rheumatoid arthritis |
| Chaperone protein DnaJ | EDV64758.1 | Rheumatoid arthritis |
| 60 kDa heat shock protein, mitochondrial | NP_002147.2 | Rheumatoid arthritis |
| Chitinase-3-like protein 1 | NP_001267.2 | Rheumatoid arthritis |
| mRNA export factor ICP27 homolog | YP_401659.1 | Rheumatoid arthritis |
| Arrestin | AAC50992.1 | Rheumatoid arthritis, iritis |
| Protein BOLF1 | AIE89051.1 | Rheumatoid arthritis, juvenile |

TABLE 1-continued

Autoantigens of Various Autoimmune Disorders

| Autoantigen | GenBank Accession No. | Associated Autoimmune Disease |
| --- | --- | --- |
| 60 kDa heat shock protein, mitochondrial | NP_002147.2 | Rheumatoid arthritis, juvenile |
| Major DNA-binding protein | BAX36606.1 | Rheumatoid arthritis, juvenile |
| Keratin, type II cytoskeletal 3 | NP_476429.2 | Rheumatoid arthritis, juvenile |
| Fibrillin 1 | BAD16739.1 | Rheumatoid arthritis, juvenile |
| Tenascin precursor | NP_002151.2 | Rheumatoid arthritis, juvenile |
| Stromelysin-1 preproprotein | NP_002413.1 | Rheumatoid arthritis, juvenile |
| Interstitial collagenase | NP_002412.1 | Rheumatoid arthritis, juvenile |
| OspA | CAA32579.1 | Rheumatoid arthritis, Lyme |
| Integrin alpha-L | NP_002200.2 | Rheumatoid arthritis, Lyme |
| DNA topoisomerase 1 | NP_003277.1 | Scleroderma/Systemic sclerosis |
| Histone H3-like centromeric protein A | NP_001800.1 | Scleroderma/Systemic sclerosis |
| Small nuclear ribonucleoprotein Sm D1 | NP_008869.1 | Scleroderma/Systemic sclerosis |
| Major centromere autoantigen B | NP_001801.1 | Scleroderma/Systemic sclerosis |
| E3 ubiquitin-protein ligase TRIM21 | NP_003132.2 | Scleroderma/Systemic sclerosis |
| Epstein-Barr nuclear antigen 1 | YP_401677.1 | Scleroderma/Systemic sclerosis |
| U11/U12 snRNP | Q6IEG0 | Scleroderma/Systemic sclerosis |
| rRNA 2'-O-methyltransferase fibrillarin | NP_001427.2 | Scleroderma/Systemic sclerosis |
| Ribonuclease P protein subunit p25 | NP_060263.2 | Scleroderma/Systemic sclerosis |
| 60 kDa SS-A/Ro ribonucleoprotein | NP_001166995.1 | Sjogren's syndrome |
| Lupus La protein | NP_003133.1 | Sjogren's syndrome |
| E3 ubiquitin-protein ligase TRIM21 | NP_003132.2 | Sjogren's syndrome |
| Muscarinic acetylcholine receptor M3 | NP_000731.1 | Sjogren's syndrome |
| Small nuclear ribonucleoprotein Sm D1 | NP_008869.1 | Sjogren's syndrome |
| U1 small nuclear ribonucleoprotein A | NP_004587.1 | Sjogren's syndrome |
| Putative HTLV-1-related endogenous sequence | CAA34646.1 | Sjogren's syndrome |
| Calreticulin | AAB51176.1 | Sjogren's syndrome |
| Spectrin alpha chain, non-erythrocytic 1 | NP_001123910.1 | Sjogren's syndrome |
| Beta-tubulin | AAB59507.1 | Sydenham's chorea |
| Dopamine receptor 1 | NP_000785.1 | Sydenham's chorea |
| Dopamine receptor 2 | NP_000786.1 | Sydenham's chorea |
| 60 kDa SS-A/Ro ribonucleoprotein | NP_001166995.1 | Systemic lupus erythematosis |
| Small nuclear ribonucleoprotein Sm D1 | NP_008869.1 | Systemic lupus erythematosis |
| U1 small nuclear ribonucleoprotein 70 kDa | NP_003080.2 | Systemic lupus erythematosis |
| Natural killer group protein 2-A | AAC17488.1 | Systemic lupus erythematosis |
| Small nuclear ribonucleoprotein-associated proteins B and B' | NP_937859.1 | Systemic lupus erythematosis |
| Small nuclear ribonucleoprotein-associated protein N | NP_001336393.1 | Systemic lupus erythematosis |
| E3 ubiquitin-protein ligase TRIM21 | NP_003132.2 | Systemic lupus erythematosis |
| Epstein-Barr nuclear antigen 1 | YP_401677.1 | Systemic lupus erythematosis |
| U1 small nuclear ribonucleoprotein C | NP_003084.1 | Systemic lupus erythematosis |
| NHP2-like protein 1 | NP_001003796 | Systemic lupus erythematosis |
| 60S acidic ribosomal protein P2 | XP_805182.1 | Systemic lupus erythematosis |
| Histone H1.4 | NP_005312.1 | Systemic lupus erythematosis |
| Glutamate decarboxylase 2 | NP_000809.1 | Type 1 diabetes |
| Insulin | AAA59172.1 | Type 1 diabetes |
| Islet cell antigen | NP_002837.1 | Type 1 diabetes |
| Glucose-6-phosphatase 2 | NP_066999.1 | Type 1 diabetes |
| 60 kDa heat shock protein, mitochondrial | AAH02676.1 | Type 1 diabetes |
| Zinc transporter 8 | AAP44332.1 | Type 1 diabetes |
| Insulin, isoform 2 | NP_001035835.1 | Type 1 diabetes |
| Genome polyprotein | AAX23962.1 | Type 1 diabetes |
| Islet amyloid polypeptide | NP_000406.1 | Type 1 diabetes |
| Hemagglutinin | ALB07770.1 | Type 1 diabetes |
| Islet amyloid polypeptide | NP_000406.1 | Type 2 diabetes |
| Zinc transporter 8 | AAP44332.1 | Type 2 diabetes |
| Pancreatic secretory glycoprotein 2 | NP_001493.2 | Ulcerative colitis |
| GM-CSF | AAA52578.1 | Ulcerative colitis |

TABLE 1-continued

Autoantigens of Various Autoimmune Disorders

| Autoantigen | GenBank Accession No. | Associated Autoimmune Disease |
|---|---|---|
| Myeloblastin | NP_002768.3 | Ulcerative colitis |
| Type VII collagen | AAA96439.1 | Ulcerative colitis |
| Melanocyte protein PMEL | NP_001186983.1 | Vitiligo |
| Melanin-concentrating hormone receptor 1 | NP_05288.3 | Vitiligo |
| Tyrosine 3-monooxygenase | NP_954986.2 | Vitiligo |
| Tyrosinase | NP_000363.1 | Vitiligo |
| L-dopachrome tautomerase | NP_001913.2 | Vitiligo |
| TrpC1 | NP_001238774.1 | Vitiligo |
| Myeloblastin | NP_02768.3 | Wegener's granulomatosis |
| Collagen alpha-1(II) chain | NP_001835.3 | Wegener's granulomatosis |

Table 2 below provides HLA and classes commonly associated with autoimmune disorders though in the exemplary case the HLA or a portion of the HLA will be patient specific and derived from high resolution sequence of the patient suffering from the disorder or a serological equivalent.

TABLE 2

HLA types and classes commonly associated with autoimmune disease

| Common HLA Class II Serotypes | Common Class II Variants | Common HLA Class I Serotypes | Common Class I Variants | Associated Autoimmune Disease |
|---|---|---|---|---|
| DR4 (e,g,, DRB1*04); and DR5 (e.g., DRB1*11 and DRB1*12) | DRB1*04:01; DRB1*11; and DRB1*11:04 | A2 (e.g., A*02) | A*02; A*02:01 and B*07:02 | Alopecia areata |
| | | A2 | | Alzheimer's |
| | | B27 (e.g., B*2701-2759); B40 (e,g,, B*40); B27-B40; and B7 (e.g., B*07) | B*27:02; B*27:05; B*40:01; B*52; and B*38 | Ankylosing spondylitis |
| DR7 (e.g., DRB1*0701-0705); DR4; DR5; and DR12 (e.g., DRB1*1201-3 and DRB1*1206) | DRB1*09; DRB1*09:01; DRB1*04; DRB1*04:05; and DRB1*14 | | | Antiphospholipid syndrome |
| DR17 (e.g., DRB1*0301 and DRB1*0304); DR4; DR4/DR3; DQ2 (e.g., DQB1*02); and DQ8 (e.g., DQB1*0302) | DRB1*03:01; DRB1*04; and DRB1*04:04 | | | Autoimmune adrenalitis |
| DR2 (e.g., DRB1*15 and DRB1 DR4; DR5; DR2/DR4; and DR4/DR5 | | | | Autoimmune gastritis |
| | DRB1*03:01: DRB3*01:01; DRB1*04:01; DRB1*04:05; DRB1*07; and DRB1*13:01 | | | Autoimmune hepatitis |
| DR7; DR4; DR11 (e.g., DRB1*1101 to DRB1*1110); DR3 (e.g., DRB1*03); and DR11-DQ7.5 | DRB1*04:09; DRB1*07; and DRB1*04 | | | Autoimmune myocarditis |
| | | B27; A29 (e.g., | A*29:02; and B*57:01 | Autoimmune uveitis |

TABLE 2-continued

HLA types and classes commonly associated with autoimmune disease

| Common HLA Class II Serotypes | Common Class II Variants | Common HLA Class I Serotypes | Common Class I Variants | Associated Autoimmune Disease |
|---|---|---|---|---|
| | | A*29); and B51 (e.g., B*51) | | |
| DQ2; DQ8; DR12-DQ7.5; and DR7-DQ2.2 | DQA1*05:01/ DQB1*02:01; DQA1*03/ DQB1*03:02; and DQA1*0505/ DQBA1*0301 | | | Coeliac disease |
| DR1 (e.g., DRB1*01); and DR3 | DRB1*07; DRB1*01:03; DRB1*0301; DRB1*0302; and DRB3*0301/ DRB1*1302 | B27 | | Crohn's disease |
| | DRB1*0301; and DRB1*0302 | | | Dermatomyositis |
| DR4 | DRB1*0302 | | | Dilated cardiomyopathy |
| DR2 | | B8 (e.g., B*08) | | Goodpasture's syndrome |
| DR17; DR52 (e.g., DRB3*); and DR7 | DRB1*03:01; DRB1*04:01; DRB3*01; and DRB3*0202 | | | Grave's disease |
| DR3; and DR5 | | | | Hashimoto's thyroiditis |
| DR4 | | | | Immune thrombocytopenic purpura |
| DR3; DR4; and DR3/DR4 | | | | Insulin resistant diabetes |
| DR3 | DRB1*01:02 | | | Membranous nephritis |
| DR2; DR15 (e.g., DRB1*1505-5 and DRB1*1507); and DR53 (DRB4*) | DRB1*15:01; DRB1*15:01/ DRB1*15:01; DRB1*15:01/ DRB5*01:01; DRB1*15; DRB5*01:01; DPw2; DRB1*04:01; DRB1*04:04; DPA1*01:03/ DPB1*02:01; DPA1*01:03/ DPB1*04:01; DQA1*01:02/ DQB1*05:02; DQB1*06; and DQB1*06:02 | A3 (A*03); and B7 | | Multiple sclerosis |
| DR17; DR3; and DR7 | DRB1*03:01 | | | Myasthenia gravis |
| DR14-DQ5 | | | | Myasthenia gravis-MUSC |
| DR3 | | | | Neuromyelitis optica |
| DR patient specific | | | | Parkinson's disease |
| DR4; and DR6 | DRB1*01:01; and DRB1*04:02 | | | Phemphigus |
| DR3; DR4; and DR3/DR4 | DRB1*03:01; DRB1*04:01; and DRB1*03:01/ *04:01 | | | Prediabetes |
| DR8 (e.g., DRB1*0801-*0807 and DRB1*0810-*0812) | DRB1*0801; and DRB1*0803 | | | Primary biliary cirrhosis |
| DR7 | DRB1*0102 | B27; and Cw6 (C*06:02 and C*06:05) | | Psoriasis |
| | | B16 (e.g., B38 and B39); B17 (e.g., B57 and B58); B27; B39 (e.g., B*39); and Cw6 | | Psoriatic arthritis |
| DR7 | | | | Rheumatic fever |
| DR4; DR4-DQ8; DR1; DR12; and DR18 (e.g., | DRB1*01:01; DRB1*01:02; DRB1*04:01; | | | Rheumatoid arthritis |

TABLE 2-continued

HLA types and classes commonly associated with autoimmune disease

| Common HLA Class II Serotypes | Common Class II Variants | Common HLA Class I Serotypes | Common Class I Variants | Associated Autoimmune Disease |
|---|---|---|---|---|
| DRB1*0302 and DRB1*0303) | DRB1*04:02; DRB1*04:03; DRB1*04:04; DRB1*04:05; DRB1*04:06; DRB1*04:07; DRB1*04:08; DRB1*04:09; DRB1*04:10; DRB1*04:11; DRB1*04:12; DRB1*04:13; homozygous for the above;; DRB1*01:01/*04:04; and DRB1*01:01/*04:01 | | | |
| DR4; DR5; DR14 (e.g., DRB1*1401-*1408 and DRB1*1410-*1408); and DR15 | DRB1*04:01; DRB1*04:04; DRB1*04:05; DRB1*14:02; and DRB1*12:01 | | | Rheumatoid arthritis, juvenile |
| DR5; and DR11 | DRB1*04:01; DRBl*10:01: and DRB1*11:02 | | | Rheumatoid arthritis, Lyme |
| DR11; and DR8 | DRB1*11:04 | | | Rheumatoid arthritis, pauciarticular (juvenile) |
| DR5 | DRB1*12:01 | B35 | | Rheumatoid arthritis, iritis |
| DR5 | DQB1*05:01; DRB1*11; DRB1*11:04; DRB1*15:02; DRB1*13:02; DRB1*04:06; DRB1*03 DRB1*15; DRB1*03:01/ DRB1*15:01 | | | Scleroderma/Systemic sclerosis Sjogren's syndrome |
| DR1 | | B49 (e.g., B*49) | | Sydenham's chorea |
| DR11; and DR53-DR7 | DRB1*03:01; DRB1*15:01; DRB1*04:02; DRB1*04:03; DRB1*04:06; DRB1*11:01; and DRB3*03:01 | | | Systemic lupus erythematosis |
| DR3 | DRB1*03:02; DRB1*04; DRB1*04:01; DRB1*04:02; DRB1*04:05; DRB1*03:01; and DRB1*03:01/ DRB1*04:01 | | | Type 1 diabetes |
| DR4 | | | | Type 2 diabetes |
| DR1 | DRB1*01:03; and DRB1*15:02 DRB1*07:01 DPB1*04 | B27 | A*02:01 | Ulcerative colitis Vitiligo
Wegener's granulomatosis |

In some embodiments, the antigenic peptides used herein are associated with HLA-DR*1501, for example, GAD peptide TYEIAPVFVLLFYVTLKKMR (SEQ ID NO: 34) (involved in Type 1 diabetes), the MBP peptides listed above, the following MPP peptides (involved in MS) LLEC-CARCLVGAPFASLVATGLCFFGVALFC (SEQ ID NO: 35), LVGAPFASLVATGLCFFGVA (SEQ ID NO: 36), FGVALFCGCEVEALTGTEKLIETYFSKNYQD (SEQ ID NO: 37), LFCGCGHEALTGTEKLIETY (SEQ ID NO: 38), TGTEKLIETYFSKNYQDYEY (SEQ ID NO: 39), TGTEKHETYFSKNYQDYEYL (SEQ NO: 40), YFSKNYQDYEYLINVIHAFQYVIYGTASFFFL (SEQ ID NO: 41), GTASFFFLYGALLLAYGYTTGAVRQIFGDYK (SEQ ID NO: 42), LYGALLLAEGFYTTGAVRQI (SEQ ID NO: 43), FYYTTGAVRQIFGDYKTTICG (SEQ ID NO: 44), AVRQIFGDYKTTICGKGLSATV (SEQ ID NO: 45), RQIFGDYKTTCGKGLSATVTGGQKGRGSRGQ (SEQ ID NO: 46), KGLSATVTGGQKGRGYRGQH (SEQ ID NO: 47), QKGRGSRGQHQAHSLERVCH (SEQ ID NO: 48), KGRGSRGQHQAHSLERVCHCLGCWLGHPDKFV (SEQ ID NO: 49), LGHPDKFVGITYALTVVWLL-VFACSAVPVYIY (SEQ ID NO: 50), SAVPVYIYFNTWTTCQSIAAPCKTSASIGTLC (SEQ ID NO: 51), AVPVYIYFNTWTTCQSIAFP (SEQ ID NO: 52), WTTCQSIAFPSKTSASIGSL (SEQ ID NO: 53), SASIGTLCADARMYGVLPWNAFFGKVCGSNLL (SEQ ID NO: 54), KVCGSNLLSICKTAEFQMTFHLFIAAF-VGAAA (SEQ ID NO: 55), AAFVGAAATLVSLLTFMI-AATYNFAVLKLMGR (SEQ ID NO: 56), MIAATYN-FAVLKLMGRGTKF (SEQ ID NO: 57), and MAATYNFAVLKLMGRFTKF (SEQ ID NO: 58).

In some embodiments, the antigenic peptides or antigenic polypeptides are patient specific and designed for the patient's MHC. For example, a physician can diagnose the patient with an autoimmune disorder and determine the severity of the disease. The patient's Class I (HLA-A, B, and C) and II (HLA-DR, DQ, DP) regions can be typed, which can now be performed at high resolution using DNA sequencing and with comparison to a reference database (www.ebi.ac.uk/ipd/imgt/hla/). The patient's Class I and II MHC with the strongest evidence of autoimmune involvement can be identified for the disorder. Those known to be associated with a particular autoimmune disorder can be used as references. See, e.g., Tables 1 and 2. The strongest evidence based antigens are identified for the disorder (iedb.org/) and Table 1. A set of personalized peptide (cbs.dtu.dk/services/NetMHC/ or cbs.dtu.dk/services/NetMHCII/) and protein targets (for Class II) that are expected to bind the patient autoimmune implicated MHC can be identified.

Personalized MHC-CABs lentivirus or mRNA can be prepared for the patient to enable targeting of pathogenic immune cells. The personalized lentivirus is used to prepare autologous or allogeneic T cells (CTL and/or Tregs) that can be combined with receptor or cellular modifications to allow co-treatment with additional therapeutics, desired interactions with pathogenic cells, routing to a desired location (for interaction with pathogenic inflammatory or inflammation generating cells), or secretion of cytokines (to reduce inflammation).

(c) Co-Stimulatory Signaling Domains

Many immune cells require co-stimulation, in addition to stimulation of an antigen-specific signal, to promote cell proliferation, differentiation and survival, as well as to activate effector functions of the cell. The WIC-CAR described herein may comprise one or more co-stimulatory signaling domain. The term "co-stimulatory signaling domain," as used herein, refers to at least a portion of a protein that mediates signal transduction within a cell to induce an immune response such as an effector function. The co-stimulatory signaling domain of the MHC-CAR described herein can be a cytoplasmic signaling domain from a co-stimulatory protein, which transduces a signal and modulates responses mediated by immune cells, such as T cells, NK cells, macrophages, neutrophils, or eosinophils.

Activation of a co-stimulatory signaling domain in a host cell (e.g., an immune cell) may induce the cell to increase or decrease the production and secretion of cytokines, phagocytic properties, proliferation, differentiation, survival, and/ or cytotoxicity. The co-stimulatory signaling domain of any co-stimulatory molecule may be compatible for use in the MHC-CAR described herein. Examples of co-stimulatory signaling domains for use in the chimeric receptors can be the cytoplasmic signaling domain of co-stimulatory proteins, including, without limitation, members of the B7/CD28 family (e.g., B7-1/CD80, B7-2/CD86, B7-H1/PD-L1, B7-H2, CD28, CTLA-4, ICOS/CD278, or PD-1); members of the TNF superfamily (e.g., 4-1BB/TNFSF9/CD137, 4-1BB Ligand/TNFSF9, CD40/TNFRSF5, CD40 Ligand/TNFSF5, DR3/TNFRSF25, OX40/TNFRSF4, OX40 Ligand/TNFSF4, or TNF-alpha); and other molecules, such as FRB, and FKBF, that allow co-stimulation to be induced only in the presence of a specific drug molecule (but here in association with a the unique heterodimeric MHC-CAR). Wu et al., *Science,* 350(6258):aab4077, 2015. In some embodiments, any of the cytoplasmic signaling domains of co-stimulatory proteins may be used in receptors targeting inactive bystander B cells (e.g., with a CD19 or CD20-CAR) or plasma cells (e.g., with a CS1-CAR and/or CS1 knockout).

Figure 9:
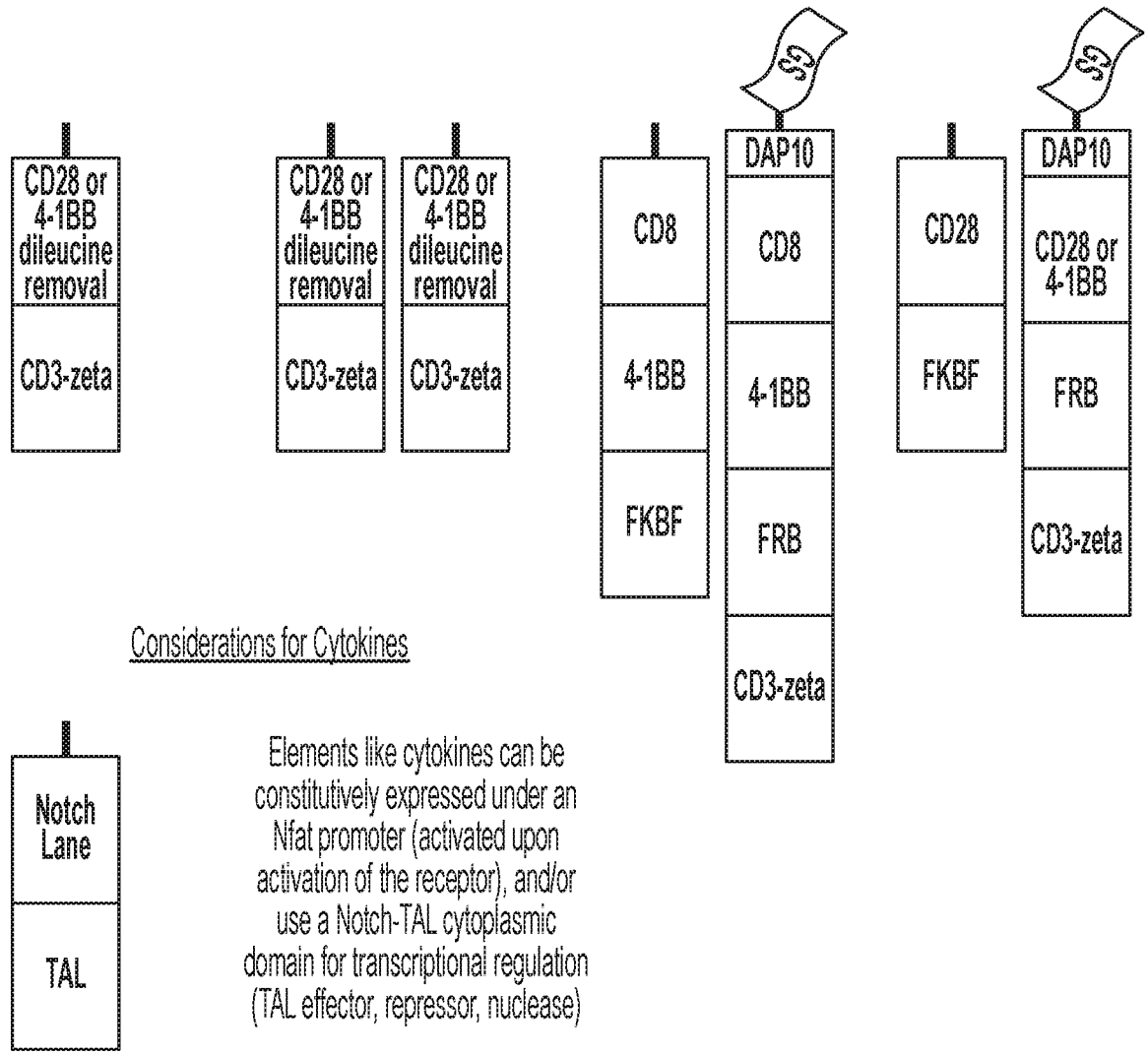
FIG. 9 depicts exemplary co-stimulatory domains and combinations thereof for constructing the MHC-CAR and considerations for co-expression of cytokines.

In some instances, the MHC-CAR may comprise a combination (e.g., 2 or 3) co-stimulatory domains, which may be from the same co-stimulatory receptor or from different co-stimulatory receptors. Examples include: CD28+4-1BB, CD28+FRB, CD28+FKBF, or 4-1BB+FRB. See also FIG. 9. In some examples, the MHC-CAR comprises a co-stimulatory domain from CD28, a co-stimulatory domain from 4-1BB, or both. In some embodiments, the co-stimulatory domain is preceded by a short linker. For example, for a class H MHC-CAR, the short linker may be TS (i.e., a MHC internal Linker); for a class I MHC-CAR, the short linker may be PG.

In some instances, the MHC-CAR constructs described herein may include no co-stimulatory domain. Alternatively, it may contain a non-traditional element such as a TALEN nuclease, activators, or repressors which may now be implemented in a clinically applicable lentiviral form using a recoded or non-repeat containing TAL domain and would be linked to a single chain MHC-CAR through a membrane domain derived from Notch.

Exemplary co-stimulatory domains for use in the MHC-CAR described herein include, but are not limited to:

41BB intracellular domain:
(SEQ ID NO: 59)
KRGRKKLLYIFKQPFMRPVQTTQEEDGCSCRFPEEEEGGCEL 41BBe intracellular domain:
(SEQ ID NO: 60)
pgKRGRKKLLYIFKQPFMRPVQTTQEEDGCSCRFPEEEEGGCELaha CD28 intracellular domain:
(SEQ ID NO: 61)
RSKRSRGGHSDYMNMTPRRPGPTRKHYQPYAPPRDFAAYRS CD28e intracellular domain:
(SEQ ID NO: 62)
pgRSKRSRGGHSDYMNMTPRRPGPTRKHYQPYAPPRDFAAYRSaha FRB:
(SEQ ID NO: 63)
EMWHEGLEEASRLYFGERNVKGMFEVLEPLHAMMERGPQTLKETSFNQAY
GRDLMEAQEWDRKYMKSGNVKDLLQAWDLYYHVFRRI FBP-with linkers
(SEQ ID NO: 64)
(GSSS)$_4$-EMWHEGLEEASRLYFGERNVKGMFEVLEPLHAMMERGPQTLK

ETSFNQAYGRDLMEAQEWCRKYMKSGNVKDLLQAWDLYYHVFRRI- (GSSS)₃

FKRB (SEQ ID NO: 65)
GVQVETISPGDGRTFPKRGQTCVVHYTGMLEDGKKFDSSRDRNKPFKFML

GKQEVIRGWEEGVAQMSVGQRAKLTISPDYAYGATGHPGIIPPHATLVFD

VELLKLE

FKBP-with linkers (SEQ ID NO: 66)
GVQVETISPGDGRTFPKRGQTCVVHYTGMLEDGKKFDSSRDRNKPFKFML

GKQEVIRGWEEGVAQMSVGQRAKLTISPDYAYGATGHPGIIPPHATLVFD

VELLKLE-(GSSS)₃

(d) Cytoplasmic Signaling Domain

Any cytoplasmic signaling domain comprising an immunoreceptor tyrosine-based activation motif (ITAM) can be used to construct the chimeric receptors described herein. An "ITAM," as used herein, is a conserved protein motif that is generally present in the tail portion of signaling molecules expressed in many immune cells. The motif may comprises two repeats of the amino acid sequence YxxL/I separated by 6-8 amino acids, wherein each x is independently any amino acid, producing the conserved motif YxxL/Ix(6-8)YxxL/I. In some examples, the cytoplasmic signaling domain comprising an ITAM is of CD3ζ. In some examples, the MHC-CAR does not comprise a co-stimulatory domain and the cytoplasmic signaling domain is preceded by a short linker. For example, for a class II MHC-CAR, the short linker may be TS (i.e., a MHC internal Linker). For example for a class I MHC-CAR, the short linker may be PG. In some cases the linker may be AHA or absent, such as certain instances when a co-stimulatory domain occurs before a signaling domain.

In some embodiments, the MHC-CAR may include no cytoplasmic signaling domain, for example, that of CD3ζ. Such CD3ζ-free MHC-CAR would have suppressive effects against target cells or induce target cell death. Moisini, et al., The Journal of Immunology, 180(5), pp. 3601-3611.

Provided below is an exemplary cytoplasmic signaling domain from CD3ζ:

(SEQ ID NO: 67)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

Provided below are exemplary nucleic acid sequences encoding a cytoplasmic signaling domain from CD3ζ:

(SEQ ID NO: 410)
AGAGTAAAGTTTTCCCGAAGTGCGGACGCTCCCGCGTATCAGCAAGGTCA

AAACCAGCTTTACAACGAACTGAACTTGGGACGACGCGAAGAGTACGATG

TTCTTGATAAGCGGAGAGGGCGCGATCCCGAAATGGGGGAAAGCCTCGG

AGGAAGAACCCACAAGAAGGCCTTTATAATGAACTGCAGAAGGACAAGAT

GGCCGGAGGCGTATTCCGAAATAGGCATGAAGGGTGAACGGAGGAGAGGAA

AGGGACATGACGGACTTTATCAAGGATTGTCTACCGCAACTAAAGAaACC

TATGACGCGTTGCACATGCAGGCTCTCCCTCCGAGA (SEQ ID NO: 422)
CGGGTCAAATTTAGCAGATCCGCTGACGCACCGGCCTACCAGCAGGGCCA

GAACCAACTCTACAACGAGCTGAATCTCGGCCGACGGGAAGAGTATGACG

TACTCGACAAGCGGAGAGGTCGAGACCCTGAGATGGGCGGTAAACCGAGA

CGGAAAAATCCCCAAGAGGGTCTTTATAATGAACTCCAGAAGGATAAGAT

GGCTGAAGCCTATTCTGAGATAGGGATGAAAGGCGAGCGGCGGAGGGGTA

AGGGCCATGATGGCCTTTACCAGGGACTCTCCACGGCAACCAAAGATACT

TACGACGCCCTTCACATGCAAGCCCTCCCGCCACGC (e) Additional Components

The MHC-CAR described herein may optionally further include one or more of the following components: a hinge domain, a transmembrane domain, a signal (leader) peptide, and a peptide linker.

In some instances, the antigenic peptide may be linked to a hinge peptide to enhance immune targeting activity of the resultant MHC-CAR and/or to reduce antibody responses by the target cell to the MHC-TCR complex. In some examples, a MHC-CAR containing a hinge peptide may not include a cytoplasmic domain (for example, free of a CD3ζ domain). A MHC-CAR construct that contains a hinge peptide may also include a MHC class I moiety. The hinge domain may contain about 10-100 amino acids, e.g., 15-75 amino acids, 20-50 amino acids, or 30-60 amino acids. In some embodiments, the hinge domain may be of 10, 11, 12, 13, 14, 15, 16, 17, 18, 19, 20, 21, 22, 23, 24, 25, 26, 27, 28, 29, 30, 35, 40, 45, 50, 55, 60, 65, 70, or 75 amino acids in length.

In some examples, the following peptide linkers can be used in a class I MHC-CAR:

MHCILinker 1:

(SEQ ID NO: 68)
GGGGSGGGGSGGGGS

MHCILinker 2:

(SEQ ID NO: 69)
GGGGGGSGGSGGSGG

MHCILinker 3:

(SEQ ID NO: 70)
GGGGSGGGGSGGGGSGGGGS

MHCILinker 4:

(SEQ ID NO: 68)
GGGGSGGGGSGGGGS

Exemplary peptide linkers for a class II MHC-CAR can be GSGSGSGS (MHCII Linker1; SEQ ID NO: 72), GGGGSGGGGSGGGGS (MHC II LinkerII, SEQ ID NO: 68), GGGGSGGGGSGGS (SEQ ID NO: 400), or those described herein as MHCI Linkers (i.e., MHO Linkers 1-4). An exemplary pre-peptide linker for a class II MHC-CAR can be AS or GS or one or two copies of either AS or GS.

An example nucleic acid sequence encoding the peptide linker provided by SED ID NO: 400 is provided below (SEQ ID NO: 401)
GGGGGAGGCGGATCTGGCGGAGGCGGGAGTGGAGGCTCA A hinge peptide for use in the MHC-CAR described herein may be derived from a naturally-occurring receptor. Hinge domains of any protein known in the art to comprise a hinge domain are compatible for use in the chimeric receptors described herein. In some embodiments, the hinge domain is a portion of the hinge domain of CD8α, e.g., a fragment containing at least 15 (e.g., 20, 25, 30, 35, or 40) consecutive amino acids of the hinge domain of CD8a. Alternatively, it may be a synthetic peptide.

Exemplary hinge domains include: IYIWAPLAGTCGVLLLSLVIT (SEQ ID NO: 73), and IWAPLAGICVALLLSLIITLI (SEQ ID NO: 74). Additional examples are provided below:

FKBP/FRB-CD8 hinge:
(SEQ ID NO: 75)
GVQVETISPGDGRTFPKRGQTCVVHYTGMLEDGKKFDSSRDRNKPFKFML

GKQEVIRGWEEGVAQMSVGQRAKLTISPDYAYGATGHPGIIPPHATLVFD

VELLKLEEAAAREAAAREAAAREAAARGRVAILWHEMWHEGLEEASRLYF

GERNVKGMFEVLEPLHAMMERGPQTLKETSFNQAYGRDLMEAQEWCRKYH

KSGNVKDLLQAWDLYYHVFRRITTTPAPRPPTPAPTIASQPLSLRPEACR

PAAGGAVHTRGLDFACD

GS short hinge:
(SEQ ID NO: 68)
GGGGSGGGGSGGGGS

GS long hinge:
(SEQ ID NO: 76)
GGGGSGGGGSGGGGSGGGGSGGGGSGGGGSGGGGSGGGGSGGGGS

H2-Kb hinge:
(SEQ ID NO: 77)
LRWEPPPSTVSNM

HLA-A2 hinge:
(SEQ ID NO: 78)
LRWEPSSQPTIPI

HLA-A3 hinge:
(SEQ ID NO: 79)
LRWELSSQPTIPI

DAP10 hinge:
(SEQ ID NO: 80)
QTTPGERSSLPAFYPGTSGSCSGCGSLSL

DAP10 hinge with linker:
(SEQ ID NO: 81)
(GSSS)₄QTTPGERSSLPAFYPGTSGSCSGCGSLSLP

DAP12 hinge:
(SEQ ID NO: 82)
LRPVQAQAQSDCSCSTVS

DAP12 hinge with linker:
(SEQ ID NO: 83)
(GSSS)₄LRPVQAQAQSDCSCSTVSP

FcIgGIIIa hinge:
(SEQ ID NO: 84)
GLAVSTISSFFPPGYQ

CD8α hinge:
(SEQ ID NO: 85)
TTTPAPRPPTPAPTIASQPLSLRPEACRPAAGGAVHTRGLDFACD

IgG1 hinge:
(SEQ ID NO: 86)
EPKSPDKTHTCPPCPAPPVAGPSVFLFPPKPKDTLMIARTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK

DRA*0101 hinge:
(SEQ ID NO: 87)
EFDAPSPLPETTE

DRB1*1501 hinge:
(SEQ ID NO: 88)
VEWRARSESAQSK

An example nucleic acid sequence encoding a DRA*0101 hinge is provided below.

(SEQ ID NO: 417)
GAGTTCGACGCCCCATCACCGCTTCCAGAAACGACTGAA

An example nucleic acid sequence encoding a DRB1*1.501 hinge is provided below.

(SEQ ID NO: 404)
GTTGAGTGGAGGGCGCGGTCAGAGAGCGCACAATCTAAA

In some embodiments, the MHC-CAR constructs described herein further comprise a transmembrane domain. Any transmembrane domain for use in the MHC-CAR can be in any form known in the art. As used herein, a "transmembrane domain" refers to any protein structure that is thermodynamically stable in a cell membrane, preferably a eukaryotic cell membrane. Transmembrane domains compatible for use in the chimeric receptors used herein may be obtained from a naturally-occurring protein. Alternatively, it can be a synthetic, non-naturally occurring protein segment, e.g., a hydrophobic protein segment that is thermodynamically stable in a cell membrane.

Transmembrane domains are classified based on the three dimensional structure of the transmembrane domain. For example, transmembrane domains may form an alpha helix, a complex of more than one alpha helix, a beta-barrel, or any other stable structure capable of spanning the phospholipid bilayer of a cell. Furthermore, transmembrane domains may also or alternatively be classified based on the transmembrane domain topology, including the number of passes that the transmembrane domain makes across the membrane and the orientation of the protein. For example, single-pass membrane proteins cross the cell membrane once, and multi-pass membrane proteins cross the cell membrane at least twice (e.g., 3, 4, 5, 6, 7 or more times).

Membrane proteins may be defined as Type I, Type II or Type III depending upon the topology of their termini and membrane-passing segment(s) relative to the inside and outside of the cell. Type I membrane proteins have a single membrane-spanning region and are oriented such that the N-terminus of the protein is present on the extracellular side of the lipid bilayer of the cell and the C-terminus of the protein is present on the cytoplasmic side. Type II membrane proteins also have a single membrane-spanning region but are oriented such that the C-terminus of the protein is present on the extracellular side of the lipid bilayer of the cell and the N-terminus of the protein is present on the cytoplasmic side. Type III membrane proteins have multiple membrane-spanning segments and may be further sub-classified based on the number of transmembrane segments and the location of N- and C-termini.

In some embodiments, the transmembrane domain of the MHC-CAR described herein is derived from a Type I single-pass membrane protein, e.g., CD8α, CD8β, 4-1BB/CD137, or CD28. Transmembrane domains from multi-pass membrane proteins may also be compatible for use in the chimeric receptors described herein. Multi-pass membrane proteins may comprise a complex (at least 2, 3, 4, 5, 6, 7 or more) alpha helices or a beta sheet structure. Preferably, the N-terminus and the C-terminus of a multi-pass membrane protein are present on opposing sides of the lipid bilayer, e.g., the N-terminus of the protein is present on the cytoplasmic side of the lipid bilayer and the C-terminus of the protein is present on the extracellular side. Either one or multiple helix passes from a multi-pass membrane protein can be used for constructing the chimeric receptor variant described herein.

Exemplary transmembrane domains for use in constructing the MHC-CAR constructs described herein are provided below:

```
CD8a transmembrane domain:
                                     (SEQ ID NO: 89)
IYIKAFLAGTCGVLLLSLVITLYC HLA-A2 transmembrane domain:
                                     (SEQ ID NO: 90)
VGIIAGLVLFGAVITGAVVAAVMW HLA-A3 transmembrane domain:
                                     (SEQ ID NO: 91)
VGIIAGLVLLGAVITGAVVAAVMW Cd3zeta transmembrane domain:
                                     (SEQ ID NO: 92)
LCYLLDGILFIYGVILTALFL DR*1501 transmembrane domain:
                                     (SEQ ID NO: 93)
MLSGVGGFVLGLLFLGAGLFI DR*1501e transmembrane domain:
                                     (SEQ ID NO: 94)
MLSGVGGFVLGLLFLGAGLFIYFRNQ DRA*0101 transmembrane domain:
                                     (SEQ ID NO: 416)
NVVCALGLTVGLVGIIIGTIFII DRA*0101e transmembrane domain:
                                     (SEQ ID NO: 418)
NVVCALGLTVGLVGIIIGTIFIIKGL
```

An example nucleic acid sequence encoding the DR*1501e transmembrane domain is provided below:

```
                                     (SEQ ID NO: 406)
ATGCTGTCAGGAGTAGGCGGATTTGTACTCGGACTCCTTTTTGGGCGCTG

GGTTGTTTATCTACTTTAGAAACCAA
```

An example nucleic acid sequence encoding the DRA*0101e transmembrane domain is provided below:

```
                                     (SEQ ID NO: 419)
AACGTTGTCTGCGCTCTTGGCCTGACAGTGGGCCTGGTAGGCATTATTAT

CGGGACCATCTTTATCATCAAAGGTTTG
```

```
Notch transmembrane domain:
                                     (SEQ ID NO: 95)
ILDYSFTGGAGRDIPPPQIEEACSLPECQVDAGNKVCNLQCNNHACGWDG

GDCSLNFNDPWKNCTQSLQCWKYFSDGHCDSQCNSAGCLFDGFDCQLTEG

QCNPLYDQYCKDHFSDGHCDQGCNSAECEWDGLDCAEHVPERLAAGTLVL

VVLLPPDQLRNNSFHFLRELSHVLHTNVVFKRDAQGQQMIFPYYGHEEEL

RKHPIKRSTVGWATSSLLPGTSGGRQRRELDPMDIRGSIVYLEIDNRQCV

QSSSQCFQSATDVAAFLGALASLGSLNIPYKIEAVKSEPVEPPLPSQLHL

MYVAAAAFVLLBTVGCGVLLSRKRRR

Notch 2 transmembrane domain:
                                     (SEQ ID NO: 96)
PCVGSNPCYNQGTCEPTSENPFYRCLCPAKFNGLLCHILDYSFTGGAGRD

IPPPQIEEACELPECQVDAGNKVCNLQCNNHACGWDGGDCSLNFNDPWKN

CTQSLQCWKYFSDGHCDSQCNSAGCLFDGFDCQLTEGQCNPLYDQYCKDH

FSDGHCDQGCNSAECEWDGLDCAEHVPESLAAGTLVLVVLLPPDQLRNNS

FHFLRELSHVLHTNVVFKRDAQGQQMIFPYYGHEEELRKHPIKRSTVGWA

TSSLLPGTSGGRQRRELDPMDIRGSIVYLEIDNRQCVQSSSQCFQSATDV

AAFLGALASLGSLNIPYKIEAVKSEPVEPPLPSQLHLMYVAAAAFVLLFF

VGCGVLLSRKRRR
```

In some embodiments, the MHC-CAR may also comprise a signal peptide (also known as a signal sequence or a leader peptide) at the N-terminus of the polypeptide. In general, signal sequences are peptide sequences that target a polypeptide to the desired site in a cell. In some embodiments, the signal sequence targets the MHC-CAR to the secretory pathway of the cell and will allow for integration and anchoring of the MHC-CAR into the lipid bilayer. Signal sequences including signal sequences of naturally occurring proteins or synthetic, non-naturally occurring signal sequences, that are compatible for use in the chimeric receptors described herein will be evident to one of skill in the art. In some embodiments, the signal sequence from CD8α. In some embodiments, the signal sequence is from CD28 (e.g., MLRLLLALNLFPSIQVTG (SEQ ID NO: 97)).

Exemplary signal peptides include, but are not limited to, Beta-2-microglobulin signal peptide (e.g., MSRSVALAVLALLSLSGLEA (SEQ ID NO: 98)), HLA A3 signal peptide (e.g., MAVMAPRTLLLLLSGALALTQTWA (SEQ ID NO: 99) or), DRA*0101 signal peptide (e.g., MAISGVPVLGFFIIAVLMSAQESWA (SEQ ID NO: 100)), DRB1*1501 signal peptide (e.g., MVCLKLPGGSCMTALTVTLMVLSSPLAL (SEQ ID NO: 101)), and DRB5 signal peptide (e.g., MVCLKLPGGSYMAKLTVTLMVLSSPLALA (SEQ ID NO: 102)). Exemplary signal peptides may be followed by flexible pre-peptide linkers such as AS, GS, ASAS, GSGS. In some embodiments, a flexible pre-peptide linker is used when the signal peptide is class II and followed by an introduced peptide. Any of the constructs encoding the MHC-CARs described herein may comprise a nucleic acid sequence encoding any of the pre-peptide linkers above, e.g. AS may be encoded by the nucleic acid sequence GCATCT, TS may be encoded by the nucleic acid sequence ACAAGT. Example nucleic acid sequence encoding beta-2-microglobulin signal peptides are provided below:

```
                                     (SEQ ID NO: 397)
ATGGTATGCTTGAAGCTCCCGGGCGGGTCCTGCATGACCGCTCTCACTGT

TACTCTTATGGTCCTTAGTTCACCGCTTGCCCTG (SEQ ID NO: 414)
ATGGCAATATCTGGTGTTCCTGTCCTCGGGTTTTTTATCATAGCCGTACT

GATGTCAGCACAGGAATCATGGGCG
```

In some embodiments, the MHC-CAR described herein may include one or more peptide linkers between the other components as described herein. Examples include a $(Gly_xSer)_n$ linker, wherein x and n, independently can be an integer between 3 and 12, including 3, 4, 5, 6, 7, 8, 9, 10, 11, 12, or more. In some examples, the peptide linker can be $(Gly_4Ser)_n$ (SEQ ID NO: 103), wherein n can be an integer between 3 and 20. Specific examples include $(Gly_4Ser)_3$ (SEQ If) NO: 68), $(Gly_4Ser)_6$ (SEQ ID NO: 69), $(Gly_4Ser)_9$ (SEQ ID NO: 76), $(Gly_4Ser)_{12}$ (SEQ ID NO: 105), and $(Gly_4Ser)_{15}$ (SEQ ID NO: 106).

(ii) Configuration of MHC-CARs

The MHC-CAR constructs disclosed herein, comprising one or more components described herein, may be configured in any suitable format. Exemplary WIC class I constructs and MHC class II constructs are provided in FIGS. 7 and 8.

A MHC-CAR construct containing a MHC class I moiety as described herein may be a single fusion polypeptide that comprise the MHC class I moiety, the antigenic peptide, and a signaling domain (e.g., a co-stimulatory domain, a cytoplasmic signaling domain, or a combination thereof), and optionally one or more of the additional components described herein. See, e.g., FIG. 8. In some examples, a MHC Class I CAR construct contains a hinge domain adjacent to the antigenic peptide. A MHC class I CAR may not contain β2-microglobulin (b2m). When expressed on cell surface, such a MHC-CAR may form a heterodimer with endogenous b2m. Alternatively, a MHC class I CAR may also include b2m, which may be fused with the alpha chain to produce a single polypeptide. In some instances, a MHC class I CAR may contain two subunits, one including the alpha chain or a portion thereof (e.g., an extracellular domain), and the other including b2m or a portion thereof (e.g., an extracellular domain). In some examples, the antigenic peptide may be fused to the alpha chain. In other examples, the antigenic peptide may be fused to b2m. Optionally, a MHC class I CAR may contain peptide linkers between two components. One example is provided in FIG. 8B.

In some examples, the MHC-CAR comprises a class I molecule or a portion thereof, for example, HLA A3 or HLA A2, and a antigenic peptide suitable for presentation by the class I molecule (e.g., the PLP fragment KLIETYFSK (SEQ ID NO: 107) or the TAX fragment LLFGYPVYV (SEQ ID NO: 108)). Optionally, the MHC-CAR may further comprise b2m. Alternatively, the b2m molecule may be expressed separately from the class I MHC-CAR. Examples of the class I molecules and b2m sequences are provided below:

```
HLA A2:
                                    (SEQ ID NO: 109)
GSHSMRYFFTSVSRPGRGEPRFIAVGYVDDTQFVRFDSDAASQRMEPRAP

WIEQSGPEYWDGETRKVKAHSQTHRVDLGTLRGYYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRTDAPKTHMTHHAVSDHEAT

LRCWALSFYPAEITLTWQRDGSDQTQDTELVETRPAGDGTFQKWAAVVVP

SGQEQRYTCHVQHEGLPKPLT

HLA A3:
                                    (SEQ ID NO: 110)
GSHSMRYFFTSVSRPGRGEPRFIAVGYVDDTQFVRFDSDAASQRMEPRAP
```

```
-continued
WIEQEGPEYWDQSTRNVKAQSQTDRVDLGTLRGYYNQSSAGSHTIQIMYG

CDVGSDGRFLRGYRQDAYDGKDYIALNEDLRSWTAADMAAQITKRKWEAA

HEAEQLPAYLDGTCVEWLRRYLENGKETLQRTDPPKTHMTHHPISDHEAT

LRCWALGFYPAEITLTWQRDGEDQTQDTELVETRPAGDGTFQKWAAVVVP

SGEEQRYTCHVQHEGLPKPLT

Microextension for above:
                                    (SEQ ID NO: 111)
LRWE HLA A2 with H-2K$^b$ alpha3 domain
(underlined/italicized)
                                    (SEQ ID NO: 112)
GSHSMRYFFTSVSRPGRGEPRFIAVGYVDDTQFVRFDSDAASQRMSPRAP

WIEQSGPEYWDGETRKVKAHSQTHRVDLGTLRGYYNQSEAGSHTVQRMYG

CDVGSDWRFLRGYHQYAYDGKDYIALKEDLRSWTAADMAAQTTKHKWEAA

HVAEQLRAYLEGTCVEWLRRYLENGKETLQRT*DSPKAHVTHHSRPEDKVT*

*LRCWALGFYPADITLTWQLNGEELIQDMELVETRPAGDGTFQKWASVVVP*

*LGKEQYYTCHVYHQGLPEPLT*

HLA A3 with H-2K$^b$ alpha3 domain
(underlined/italicized)
                                    (SEQ ID NO: 113)
GSHSMRYFFTSVSRPGRGEPRFIAVGYVDDTQFVRFDSDAASQRMEPRAP

WIEQEGPEYWDQETRNVKAQSQTDRVDLGTLRGYYNQSSAGSHTIQIMYG

CDVGSDGRFLRGYRQDAYDGKDYIALNEDLRSWTAADMAAQITKRKWEAA

HEASQLRAYLDGTCVEWLRRYLENGKETLQRT*DSPKAHVTHHSRPEDKVT*

*LRCWALGFYPADITLTWQLNGEELIQDMELVETRPAGDGTFQKWASVVVP*

*LGKEQYYTCHVYHQGLPEPLT*

Microextension for above:
                                    (SEQ ID NO: 111)
LRWE Beta-2-microglobulin (human):
                                    (SEQ ID NO: 114)
IQRTPKIQVYSRHPAENGKSNFLNCYVSGFHPSDIEVDLLKNGERISKVE

HSDLSFSKDWSFYLLYYTEFTPTEKDEYACRVNHVTLSQPKIVKWDRDM

Beta-2-microglobuiin (mouse):
                                    (SEQ ID NO: 115)
IQKTPQIQVYSRHPPENGKPNILNCYVTQFHPPHIEIQMLKNGKKIPKVE

MSDMSFSKDWSFYILAHTEFTPTETDTYACRVKHASMAEPKTVYWDRDM
```

Figure 7:
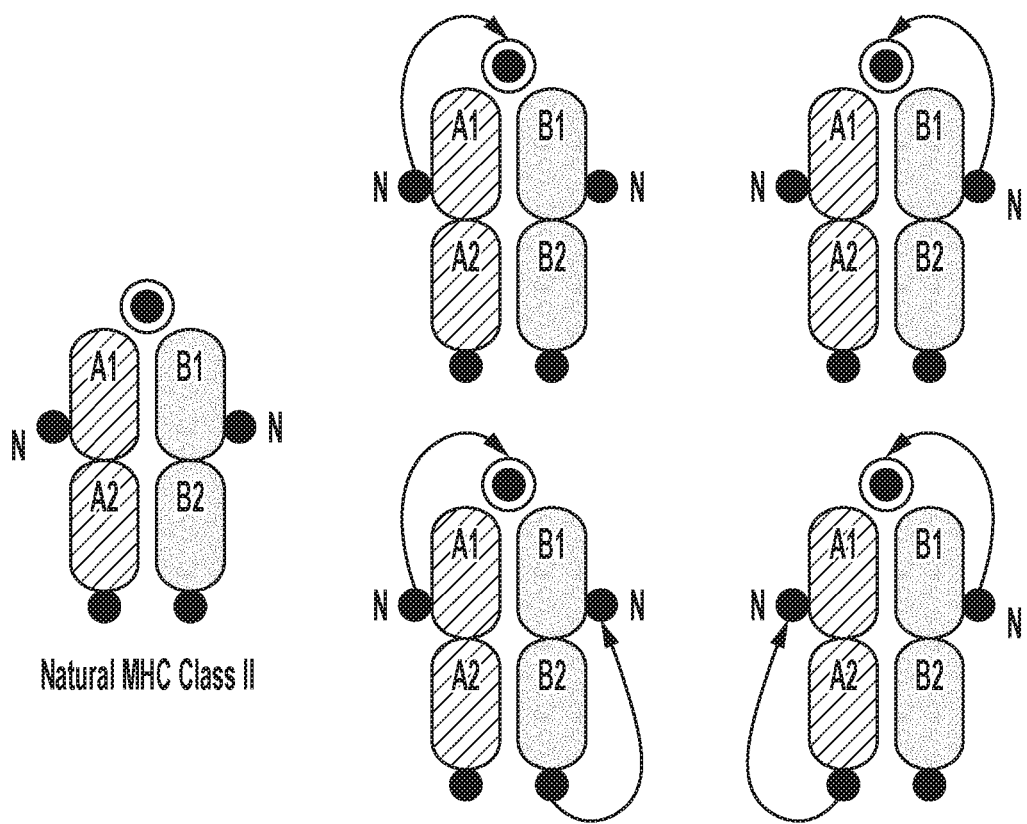
FIG. 7 is a schematic illustration of exemplary designs of MHC Class II moieties linked to antigenic peptides. "N" refers to the N-terminus of a polypeptide. Circled black dots refer to the antigenic peptides.
Figure 8A:
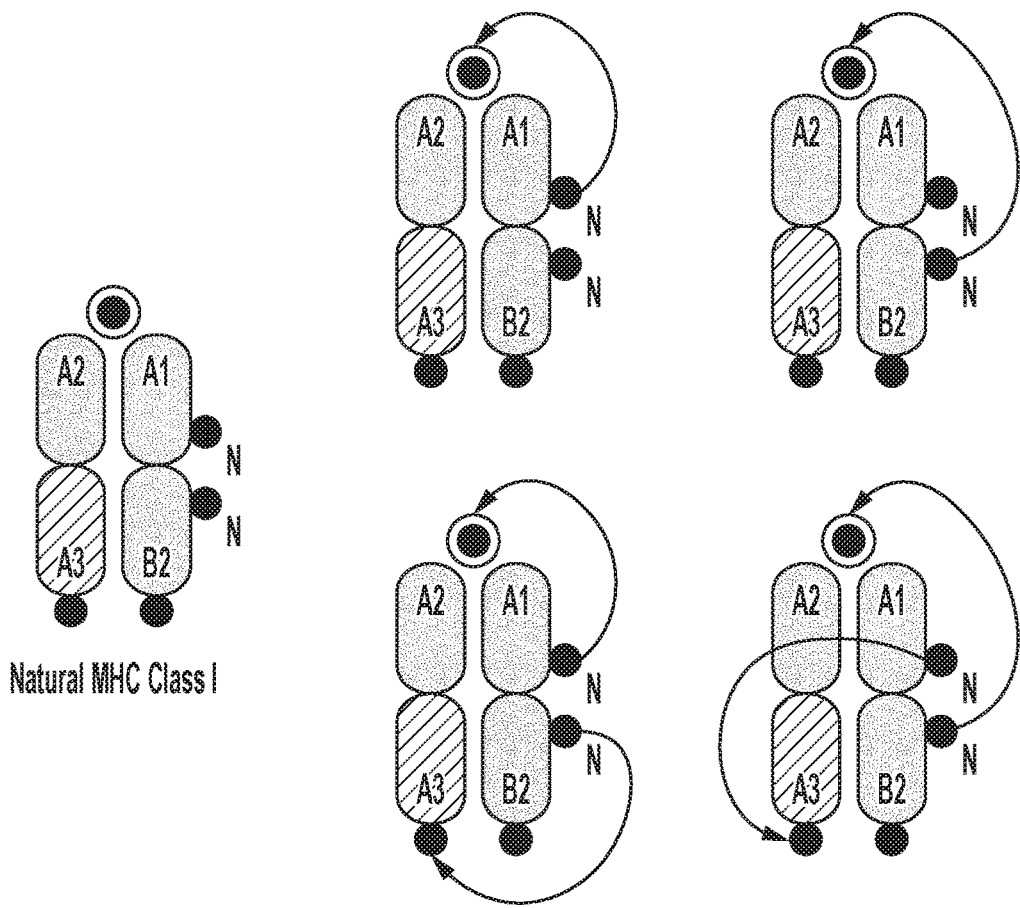
FIG. 8A and FIG. 8B are schematic illustrations of MHC Class I exemplary constructs.
Figure 8B:
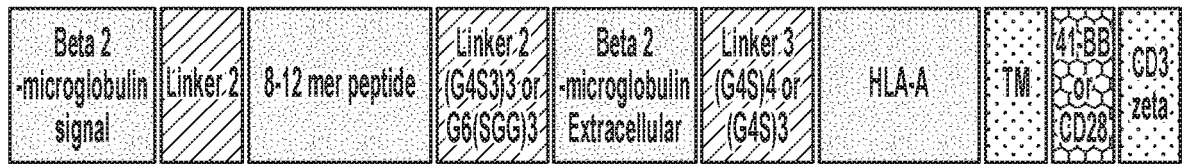

FIG. 7 provides a number of exemplary designs of MHC class II CAR constructs. Typically, a MHC class II CAR construct contains two subunits, one including the alpha chain or a portion thereof (e.g., an extracellular domain) and the other including the beta chain or a portion thereof (e.g., an extracellular domain). The antigenic peptide can be fused to either the alpha chain or the beta chain. In some instances, a MHC class II CAR can also be in a single fusion polypeptide format, in which the alpha and beta chains are fused to form a single polypeptide. The alpha chain and beta chain of a MHC class II CAR may be derived from the same MHC class II molecule. Alternatively, they may be from different WIC class II molecules. For example, a MHC class II CAR may contain an alpha chain from HLA DRA*1010 and a beta chain from HLA DRB1*1501, which may be fused with an antigenic peptide, such as an MBP peptide.

In some examples, the MHC-CAR comprises a class II molecule or a portion thereof, for example, DRB1*1501 or DRA*0101, and a antigenic peptide suitable for presentation by the class II molecule (e.g., the MBP fragment DENPVVHFFKNIVTPRTPP (SEQ ID NO: 15)). Examples of the class II molecule sequences are provided below;

DRB1*1501:
(SEQ ID NO: 117)
GDTRPRFLWQPKRSCHFFNGTERVRFLDRYFYNQEESVRFDSDVGSFRAV

TELGRPDAEYWNSQKDILEQARAAVDTYCRHNYGVVESFTVQRRVQPKVT

VYPSKTQPLQHHNLLVCSVSGFYPGSIEVRWFLNGQEEKAGMVSTGLIQN

GDWTFQTLVMLETVPRSGEVYTCQVEHPSVTSPLT

DRA*0101
(SEQ ID NO: 118)
IKEEHVIIQAEFYLNPDQSGEFMFDFDGDEIFHVDMAKKETVWRLESFGR

FASFEAQGALANIAVDKANLEIMTKRSNYTPITNVPPEVTVLTNSPVELR

EPNVLICFIDKFTPPVVNVTWLRNGKPVTTGVSETVFLPREDHLFRKFHY

LPFLPSTEDVYDCRVEHWGLDSPLLKHW

DRB1*1501 human/IA-Dbeta mouse (mutated
residues in boldface and underlined)
(SEQ ID NO: 119)
IKEEHVIIQAESYLNPDQSGEFKFDFDGDEIFHVDMAKKETVWRLEEFGR

FASFEAQGALANIAVDKANLEIMTKRSNYTPIEETEVPTSLRRLEQPNVA

ISLSRTEALNHHNTLVCSVTDFYPAKIKVRWFRNGQEETVGVSSTQLIRN

GDWTFQVLVMLEMTPHQGEVYTCHVEWPSLKSPIT

DRA*0101 human/IA-Dalpha mouse (mutated
residues in boldface and underlined)
(SEQ ID NO: 120)
IKEEHVIIQAESYLNPDQSGEFKFDFDGDEIFHVDMAKKETVWRLESFGR

FASFEAQGALANIAVDKANLEIMTKRSNYTPIATNEAPQATVFPKSPVLL

GQPHTLICFVDNIFPPVINITWLRNSKSVTDGVYETSFLVNRDHSFHKLS

YLTFIPSDDDIYDCKVEHWGLEEPVLKHWEPEI

DR-2$_{beta}$ mini (mutated residue in boldface
and underlined)
(SEQ ID NO: 121)
RPRFLWQSKRECHFFNGTERVRFLDRYFYNQEESVRFDSDVGEFRAVTEL

GRPDAEYWNSQKDILEQARAAVDTYCRHNYGVVESFTVQR

DR-2$_{alpha}$ mini
(SEQ ID NO: 122)
IKEEHVIIQAESYLNPDQSGEFKFDFDGDEIFHVDMAKKETVWRLEEFGR

FASFEAQGALANIAVDKANLSIMTKRSNYTPI

An example nucleic acid sequence encoding DRB1*1501 is provided below:

(SEQ ID NO: 402)
GGAGACACAAGACCCCGATTCTTGTGGCAGCCCAAAAGGGAGTGCCATTT

TTTCAATGGGACGGAACGAGTTCGCTTCCTTGATCGGTACTTTTACAACC

AAGAAGAGAGTGTACGGTTCGACTCAGATGTCGGCGAGTTCCGAGCGGTT

ACGGAATTGGGGCGACCTGACGCGGAGTACTGGAACTCCCAAAAGGATAT

TTTGGAGCAGGCACGAGCAGCTGTGGACACCTATTGTCGACATAATTATG

GTGTGGTGGAATCCTTTACAGTTCAGCGGCGGGTGCAACCTAAAGTGACC

GTGTATCCATCTAAAACGCAACCCCTCCAACACCATAACCTCCTGGTGTG

TTCCGTAAGCGGCTTCTATCCCGGGTCAATTGAGGTCAGGTGGTTCCTCA

ACGGTCAGGAGGAGAAGGCCGGAATGGTAAGTACTGGTCTTATCCAGAAC

GGAGACTGGACCTTCCAAACTTTGGTAATGTTGGAAACGGTGCCGCGATC

CGGGGAGGTGTATACATGCCAAGTTGAACACCCGAGTGTTACGAGCCCCC

TGACG

An example nucleic acid sequence encoding DRA*0101 is provided below:

(SEQ ID NO: 415)
ATAAAAGAAGAGCACGTGATAATACAGGCGGAGTTTTATTTGAACCCGGA

CCAGAGCGGTGAGTTCATGTTCGATTTTGATGGCGACGAGATATTTCACG

TTGACATGGCAAAAAAGGAAACGGTGTGGAGACTTGAGGAGTTTGGACGA

TTCGCATCATTTGAGGCACAAGGAGCACTCGCCAATATCGCGGTGGACAA

GGCCAACCTGGAGATCATGACAAAACGCTCCAATTATACGCCTATCACTA

ATGTGCCCCCTGAGGTTACTGTGCTCACAAATTCTCCCGTAGAACTTAGG

GAACCTAACGTCCTCATATGTTTCATCGACAAGTTCACTCCTCCGGTGGT

CAATGTAACGTGGCTTCGGAATGGTAAGCCGGTCACCACGGGTGTCTCAG

AGACCGTATTTCTGCCCAGAGAAGACCACCTCTTCCGCAAATTTCATTAC

CTTCCCTTTCTTCCTTCAACGaAAGACGTTTACGACTGCAGGGTCGAACA

TTGGGGGCTTGACGAGCCACTTCTCAAGCATTGG

Any of MHC class I and MHC class II constructs described herein can be further fused to one or more signaling domains and optionally one or more of the additional components. In some instances, the MHC-CAR constructs described herein are free of singling domains.

Preferably, a MHC-CAR as described herein contains matched MHC moiety and antigenic peptide, e.g., a MHC molecule that would present the antigenic peptide or homologous analogs in natural state. In some instances, a MHC-CAR described herein may contain an alpha chain or a beta chain from HLA DRB1*1501 and an antigenic peptide associated with this HLA allele, e.g., those MBP peptides described herein and others as well. The association between antigenic peptides involved in an autoimmune disease and a specific HLA allele is well known in the art or can be identified via routine practice, for example, library screening.

One exemplary MHC-CAR may have the following formula (+/− means that the specific component is optional):

> Single chain (MHC Class I or II+peptide) (+/−hinge)+single chain CD28/4-1BB (+/−dileucine motifs) (+/−cd3zeta)). (Additional short peptide linkers can be added between components as described previously.)

Figure 10:
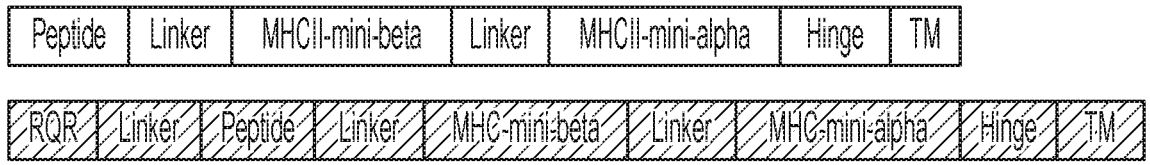
FIG. 10 depicts exemplary single-chain and multi-chain MHC Class I and Class II MHC-CAR constructs, including multi-chain MHC-CAR constructs containing both MHC Class I and Class II components.
Figure 10:
Figure 10:
Figure 10:
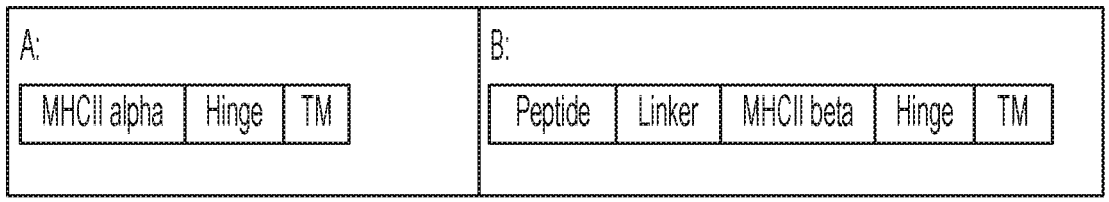
Figure 10:
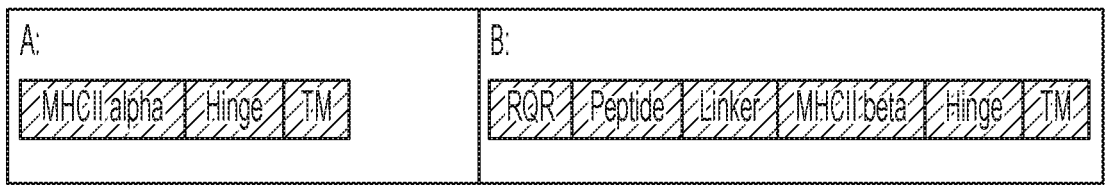
Figure 10:
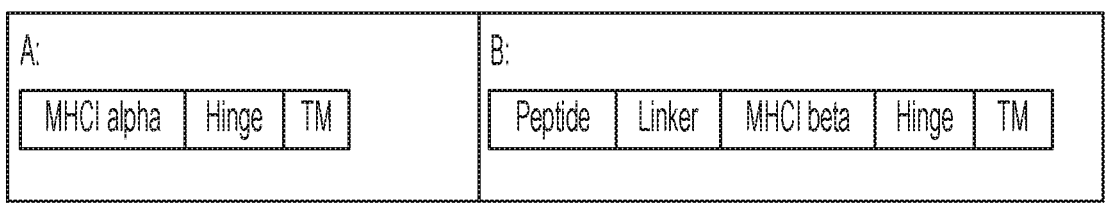
Figure 10:
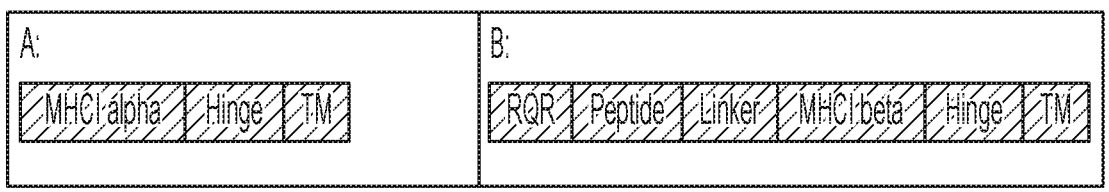
Figure 10:
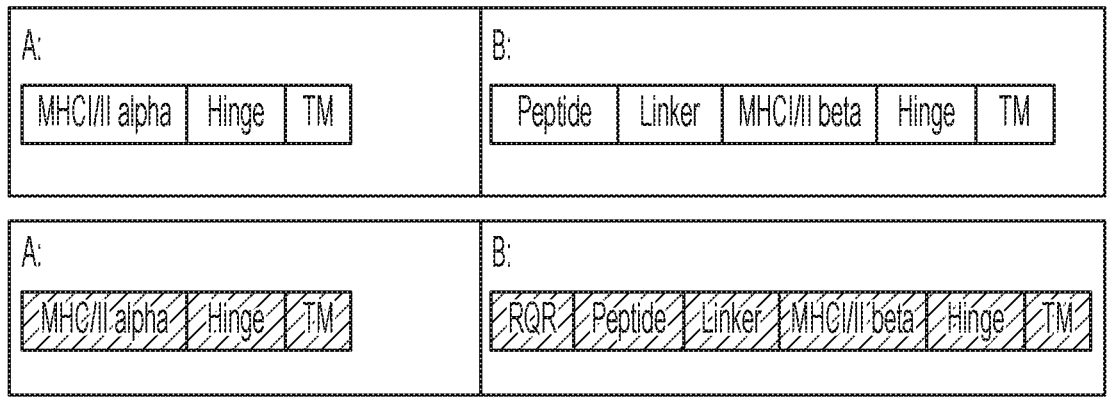

Other exemplary MHC-CAR designs (single chain and multi-chain) are illustrated in FIG. 10. In the case of multi-chain constructs, one or more short hinges may be used to enhance successful expression of the MHC-CAR. Further, it may be desirable to replace a portion of the structure with conserved domains from mice domains to prevent cross-reactivity. Note that in some cases, the internal domain may only be attached to one of the chains.

The amino acid sequence of a MHC-CAR binding (that displays MBP) TCR is provided below:

TCR alpha MBP:
(SEQ ID NO: 123)
METLLGVSLVILWLQLARVNSQQGEEDPQALSIQEGENATMNCSYKTSIN

NLQWYRQNSGRGLVHLILIRSNEREKHSGRLRVTLDTSKKSSSLLITASR

AADTASYFCATAAVGGFKTIFGAGTRLFVKANIQNPDPAVYQLRDSKSSD

KSVCLFTDFDSQTNVSQSKDSDVYITDKTVLDMRSMDFKSNSAVAWSNKS

DFACANAFNNSIIPEDTFFPSPESSCDVKLVEKSFETDTNLNFQNLSVIG

FRILLLKVAGFNLLMTLRLWSS

TCR beta MBP
(SEQ ID NO: 124)
MLLLLLLLGLAGSGLGAWSQHPSWVISKSGTSVKIECRSLDSFQATTMFW

YRQFPKQSLMLMATSNEGSKATYEQGVEKDKFLINHASLTLSTLTVTSAH

PEDSSFYICSARDLTSGANNEQFFGPGTRLTVLSDLKNVFPPEVAVFEPS

EAEISHTQKATLVCLATGFYPDHVELSWWVNGKEVHSGVSTDPQPLKEQP

ALNDSRYSLSSRLRVSATFWQNPRNHFRCQVQFYGLSENDEWTQDRAKPV

TQIVSAEAWGRADCGFTSESYQQGVLSATILYEILLGKATLYAVLVSALV

LMAMVKRKDSRG

TCR alpha class I
(SEQ ID NO: 125)
mamllgasvl ilwlqpdwvn sqqkndd

QQVKQNSPSLSVQEGRISILNCDYTNSMFDYFLWYKKYPAEGPTFLISIS

SIKDKNADGRFTVFLNKSAKHLSLHIVPSQPGDSAVYFCAAMEGAQKLVF

GQGTRLTINPNIQNPDPAVYQLRDSKSSDKSVCLFTDFDSQTNVSQSKDS

DVYITDKTVLDMRSMDFKSNSAVAWSNKSDFACANAFNNSIIPSDTFFPS

PESS

Cdvklve ksfetdtnln fqnlsvigfr illlkvagfn llmclrlwss

TCR beta class I:
(SEQ ID NO: 126)
msigllccaa lsllwagpv

NAGVTQTPKFQVLKTGQSMTLQCAQDMNHEYMSWYRQDPGMGLRLIHYSV

GAGITDQGEVPNGYNVSRSTTEDFPLRLLSAAPSQTSVYFCASSYPGGGF

YEQYFGPGTRLTVTEDLKNVFPPEVAVFEPSEASISHTQKATLVCLATGF

YPDHVELSWWVNGKEVHSGVSTDPQPLKEQPALNDSRYALSSRLRVSATF

WQDPRNHFRCQVQFYGLSENDEWTQDRAKPVTQIVSAEAWGRAD cgftse syqqgvlsat ilyeillgka tlyavlvsal vlmamvkrkd srg The amino acid sequences of exemplary CD19 targeting CAR constructs are provided below (note that these designs contain a 4-1BB domain which may be replaced with a cd28 domain):

4G7-CAR version 1:
(SEQ ID NO: 127)
MALPVTALLLPLALLLHAARPEVQLQQSGPELIKPGASVKMSCKASGYTF

TSYVMHWVKQPGQGLEWIGYINPYNDGTKYNEKFKGKATLTDKSSSTA

YMELSSLTSEDSAVYYCARGTYYYGSRVFDYWGQGTTLTVSSGGGGSGGG

GSGGGGSDIVMTQAAPSIPVTPGESVSISCRSSKSLLNSNGNGSGSGTAF

TLRISRVEAEDVGVYYCMQHLEYPFTAGTKLELKRSDPTTTPAPRPPTPA

PTIASQPLSLRPEACRPAAGGAVHTRGLDFACDIYIWAPLAGTCGVLLLS

LVITLYCKRGRKKLLYIFKQPFMRPVQTTQEEDGCSCRFPEEEEGGCELR

VKFSRSADAPAYQQGQNQLYNELNLGRREEYDVLDKRRGRDPEMGGKPRR

KNPQEGLYNELQKDKMAEAYSEIGMKGERRRGKGHDGLYQGLSTATKDTY

DALHMQALPPR

4G7-CAR version 2:
(SEQ ID NO: 128)
METDTLLLWV LLLWVPGSTG EVQLQQSGPE LIKPGASVKM

SCKASGYTFT SYVMHWVKQK PGOGLEWIGY INPYNDGTKY

NEKFKGKATL TSDKSSSTAY MELSSLTSED SAVYYCARGT

YYYGSRVEDY WGQGTTLTVS SGGGGSGGGG SGGGGSDIVM

TQAAPSIPVT PGESVSISCR SSKSLLNSNG NTYLYWFLQR

PGQSPQLLIY RMSNLABGVP DRFSGSGSGT AFTLRISRVE

AEDVGVYYCM QHLEYPFTFG AGTKLELKRS DPTTTPAPRP

PTPAPTIASQ PLSLRPEACR PAAGGAVHTR GLDEACDIY<u>I</u>

<u>WAPLAGTCGV LLLSLVITLY</u> CKRGRKKLLY IFKOPFMRPV

QTTQEEDGCS CRFPEEEEGG CE<u>LRVKFSRS ADAPAYQQGQ</u>

<u>NQLYNELNLG RREEYDVLDK RRGRDPEMGG KPRRKNPQEG</u>

<u>LYNELQKDKM ALAYSEIGMK GEPPRGKGHD GLYQGLSTAT</u>

<u>KDTYDALHMQ ALPPR</u>

The nucleic acid sequences of exemplary CD19 targeting CAR constructs are provided below, 4G7-CAR version 2:
(SEQ ID NO: 390)
atggagacagacactcttctcctttgggtcttgctgctgtgggtt cccggaagcacaggagaagtacagttgcaacagtctgggccagaa ctcatcaaacccggagcttctgtaaaaatgtcatgcaaagctagt ggatatacatttacttcttacgtgatgcactgggtaaaacagaaa cctggtcaggggcttgagtggatcgggcacattaacccatataat gacggcaccaaatataacgagaaattcaagggaaaggctacgctt acascagataagtccagtagcaccgcttatatggaacccagcagc cttacttccgaagattccgcggtgcactactgcgcgagagggact tactactacgggagtcgagtattcgattattggggtcaaggcacg acgctcacggtgagctcaggtggtggagggtctgggggtggcggc agtggtgggggggctcagacatcgtgatgacccaggcagcacct tctatcccggtaaccccaggcgagtctgtatctatcagstgtcgg tccagcaagcctcttctcaacagtaacggcaatacatatctccac tggttcctccaaaggcctgggcaaagtcctcaacttcttatatat cggatgtccaatcttgcgagtggcgtacccgacaggttttcaggg tctgggagcggaacagcttttacgttgagaatccagggtagaa

```
gctgaggacgtcggtgtatattattgcatgcaacatctcgaatac cccttacccttcggcgctggtacaaagctcgaattgaaacgcagc gatccaaccacgacgccagcgccacgaccacctacgcccgctcca actattgcctcccagccctgagtcttcggccagaagcgtgtaga cctgctgccggcggggccgttcacacgcggggccttgactttgca tgtgatatctatatatgggctcctttggcgggaacttgcggagtg cttcttttgtcactcgtgataacgttgtattgtaaaaggggtcga aagaaactcctctatatatttaagcagcccctttatgaggcccgtg caaacaacacaagaagaggacggatgctcttgtcgattcccggaa gaggaggagggggggtgtgagctcagggtcaagttttctcgctct gccgacgcgccagcctatcaacagggccaaaaccagctgtataac gaactcaacctcgggcgccgggaagagtatgacgtccttgacaaa cggcgcggtcgcgaccctgaaatgggtggaaaaccgaggcgaaag aaccccaggagggactttacaacgaattgcaaaaagacaagatg gccgaagcctattccgaaattggaatgaaaggcgagcggagacga ggtaaggggcatgacggcctgtatcaagggctctctacggccacg aaggatacttacgacgcccttcatatgcaagctcttccaccacgg
```

MHC-CAR1 containing MHC-CART part B (MHC-DRB CAR)-HLA DRB1*1501 (signal peptide), MBP peptide, HLA DRB1*1501 (external, hinge, transmembrane) CD3ζ (cytoplasmic signaling domain) is provided below:

```
                                    (SEQ ID NO 412)
MVCLKLPGGSCMTALTVTLMVLSSPLALASDENPVVH

FFKNIVTPRTPPGGGSGGGGSGGSGDTRPRFLWQPK

RECHFFNGTERVRFLDRYFYNQSESVRFDSDVGEFRA

VTSLGRPDASYWNSQKDILEQARAAVDTYCRHNYGVV

ESFTVQRRVQPKVTVYPSKTQPLQHHNLLVCSVSGFY

PGSIEVRWFLNGQEEKAGMVSTGLIQNGDWTFQTLVM

LETVPRSGSVYTCQVEHPSVTSPLTVEWRARSSSAQS

KMLSGVGGFVLGLLFLGAGLFIYFRNQTSRVKFSRSA

DAPAYQQGQNQLYNELNLGRREEYDVLDKRRGRDPEM

GGKPRRKNPQEGLYNELQKDKMAEAYSEIGMKGERRR

GKGHDGLYQGLSTATKDTYDALHMQALPPR
```

An example nucleic acid sequence encoding a MHC_CAR1 containing MHC-CAR1 part B (MHC-DRB CAR)-HLA DRB1*1501 (signal peptide), MBP peptide, HLA DRB1*1501 (external, hinge, transmembrane) CD3ζ (cytoplasmic signaling domain) is provided below:

```
                                    (SEQ ID NO: 413)
ATGGTATGCTTGAAGCTCCCGGGCGGGTCCTGCATGA

CCGCTCTCACTGTTACTCTTATGGTCCTTAGTTCACC

GCTTGCCCTGGCATCTGATGAGAATCCCGTGGTTCAT

TTTTTTAAGAACATCGTCACACCGCGCACCCCACCTG

GGGGAGGCGGATCTGGCGGAGGCGGGAGTGGAGGCTC

AGGAGACACAAGACCCCGATTCTTGTGGCAGCCCAAA

AGGGAGTGCCATTTTTTCAATGGGACGGAACGAGTTC

GCTTCCTTGATCGGTACTTTTACAACCAAGAAGAGAG

TGTACGGTTCGACTCAGATGTCGGCGAGTTCCGAGCG

GTTACGGAATTGGGGCGACCTGACGCGAGTACTGGA

ACTCCCAAAAGGATATTTTGGAGCAGGCACGAGCAGC

TGTGGACACCTATTGTCGACATAATTATGGTGTGGTG

GAATCCTTTACAGTTCAGCGGCGGGTGCAACCTAAAG

TGACCGTGTATCCATCTAAAACGCAACCCCTCCAACA

CCATAACCTCCTGGTGTGTTCCGTAAGCGGCTTCTAT

CCCGGGTCAATTGAGGTCAGGTGGTTCCTCAACGGTC

AGGAGGAGAAGGCCGGAATGGTAAGTACTGGTCTTAT

CCAGAACGGAGACTGGACCTTCCAAACTTTGGTAATG

TTGGAAACGGTGCCGCGATCCGGGGAGGTGTATACAT

GCCAAGTTGAACACCCGAGTGTTACGAGCCCCCTGAC

GGTTGAGTGGAGGGCGCGGTCAGAGAGCGCACAATCT

AAAATGCTGTCAGGAGTAGGCGGATTTGTACTCGGAC

TCCTCTTTTTGGGCGCTGGGTTGTTTATCTACTTTAG

AAACCAAACAAGTAGAGTAAAGTTTTCCCGAAGTGCG

GACGCTCCCGCGTATCAGCAAGGTCAAAACCAGCTTT

ACAACGAACTGAACTTGGGACGACGCGAAGAGTACGA

TGTTCTTGATAAGCGGAGAGGGCGCGATCCCGAAATG

GGGGGAAAGCCTCGGAGGAAGAACCCACAAGAAGGCC

TTTATAATGAACTGCAGAAGGACAAGATGGCGGAGGC

GTATTCCGAAATAGGCATGAAGGGTGAACGGAGGAGA

GGAAAGGGACATGACGGACTTTATCAAGGATTGTCTA

CCGCAACTAAAGACACCTATGACGCGTTGCACATGCA

GGCTCTCCCTCCGAGA
```

MHC-CAR containing MHC-CAR1 part A (MHC-DRA CAR) HLA-DRA*1010 (signal peptide, external, hinge, transmembrane), CD3ζ (cytoplasmic signaling domain) is provided below:

```
                                    (SEQ ID NO: 423)
MAISGVPVLGFFIIAVLMSAQESWAIKEEHVIIQAEFYLNPDQS

GSFMFDEDGDEIFHVDMAKKETVWRLEEFGRFASFEAQGALANI

AVDKANLEIMTKRSNYTPITNVPPEVTVLiTNSPVELREPNVLI

CFIDKFTPPWNVTWLRNGKPVTTGVSETVFLPREDHLFRKFHYL

PFLPSTEDVYDCRVEHWGLDEPLLKHVJEFDAPSPLPETTENWC

ALGLTVGLVGIIIGTIFIIKGLTSRVKFSRSADAPAYQQGQKQL

YNELNLGRREEYDVLDKRRGRDPEMGGKPRRKNPQEGLYNELQK
```

DKMAEAYSEIGMKGERRRGKGHDGLYQGLSTATKDTYDALHMQA

LPPR

An example nucleic acid sequence encoding a MHC-CAR1 part A (MHC-DRA CAR) HLA-DRA*1010 (signal peptide, external, hinge, transmembrane), CD3ζ (cytoplasmic signaling domain) is provided below:

(SEQ ID NO: 424)
ATGGCAATATCTGGTGTTCCTGTCCTCGGGTTTTTTATCATAGC

CGTACTGATGTCAGCACAGGAATCATGGGCGATAAAGAAGAGC

ACGTGATAATACAGGCGGAGTTTTATTTGAACCCGGACCAGAGC

GGTGAGTTCATGTTCGATTTTGATGGCGACGAGATATTTCACGT

TGACATGGCAAAAAAGGAAACGGTGTGGAGACTTGAGGAGTTTG

GACGATTCGCATCATTTGAGGCACAAGGAGCACTCGCCAATATC

GCGGTGGACAAGGCCAACCTGGAGATCATGACAAAACGCTCCAA

TTATACGCCTATCACTAATGTGCCCCCTGAGGTTACTGTGCTCA

CAAATTCTCCCGTAGAACTTAGGGAACCTAACGTCCTCATATGT

TTCATCGACAAGTTCACTCCTCCGGTGGTCAATGTAACGTGGCT

TCGGAATGGTAAGCCGGTCACCACGGGTGTCTCAGAGACCGTAT

TTCTGCCCAGAGAAGACCACCTCTTCCGCAAATTTCATTACCTT

CCCTTTCTTCCTTCAACGGAAGACGTTTACGACTGCAGGGTCGA

ACATTGGGGGCTTGACGAGCCACTTCTCAAGCATTGGGAGTTCG

ACGCCCCATCACCGCTTCCAGAAACGACTGAAAACGTTGTCTGC

GCTCTTGGCCTGACAGTGGGCCTGGTAGGCATTATTATCGGGAC

CATCTTTATCATCAAAGGTTTGACTTCCCGGGTCAAATTTAGCA

GATCCGCTGACGCACCGGCCTACCAGCAGGGCCAGAACCAACTC

TACAACGAGCTGAATCTCGGCCGACGGGAAGAGTATGACGTACT

CGACAAGCGGAGAGGTCGAGACCCTGAGATGGGCGGTAAACCGA

GACGGAAAAATCCCCAAGAGGGTCTTTATAATGAACTCCAGAAG

GATAAGATGGCTGAAGCCTATTCTGAGATAGGGATGAAAGGCGA

GCGGCGGAGGGGTAAGGGCCATGATGGCCTTTACCAGGGACTCT

CCACGGCAACCAAAGATACTTACGACGCCCTTCACATGCAAGCC

CTCCCGCGACGC

Construct 1 (CD19 CAR and CCR6 region) is provided below:

(SEQ ID NO: 425)
METDTLLLWVLLLWVPGSTGEVQLQQSGPELIKPGASVKMSCKA

SGYTFTSYVMHWVKQKPGQGLEWIGYINPYNDGTKYNEKFKGKA

TLTSDKSSSTAYMELSSLTSEDSAVYYCARGTYYYGSRVFDYWG

QGTTLTVSSGGGGSGGGGSGGGGSDIVMTQAAPSIPVTPGESVS

ISCRSSKSLLNSNGNTYLYWFLQRPGQSPQLLIYRMSNLASGVP

DRFSGSGSGTAFTLRISRVEAEDVGVYYCMQHLEYPFTFGAGTK

LELKRSDPTTTPAPRPPTPAPTIASQPLSLRPEACRPAAGGAVH

TRGLDFACDIYIWAPLAGTCGVLLLSLVITLYCKRGRKKLLYIF

KQPFMRPVQTTQEEDGCSCSFPEEEEGGCELRVKFSRSADAPAY

QQGQNQLYNELNLGRREEYDVLDKRRGRDPEMGGKPRRKNPQSG

LYNELQKDKMAEAYSEIGMKGERRRGKGHDGLYQGLSTATKDTY

DALHMQALPPRGSSGSGEGRGSLLTCGDVSENPGPMSGESMNFS

DVFDSSEDYFVSVNTSYYSVDSEMLLCSLQEVRQFSRLFVPIAY

SLICVFGLLGNILVVITFAFYKKARSMTDVYLLNMAIADILFVL

TLPFWAVSHATGAWVFSNATCKLLKGIYAINFNCGMLLLTCISM

DRYIAIVQATKSFRLRSRTLPRSKIICLVVWGLSVIXSSSTFVF

NQKYNTQGSDVCEPKYQTVSEPIRWKLLMLGLELLFGFFIPLMF

MIFCYTFIVKTLVQAQNSKRHKAIRVIIAVVLVFLACQIPHNMV

LLVTAANLGKMNRSCQSEKLIGYTKTVTEVLAFLHCCLNPVLYA

FIGQKFRNYFLKILKDLWCVRRKYKSSGFSCAGRYSENISRQTS

ETADNDNASSFTM

Construct 1 (CD19 CAR, CCR6, GYP region is provided below:

(SEQ ID NO: 429)
METDTLLLWVLLLWVPGSTGEVQLQQSGPELIKPGASVKMSCKASGYT

FTSYVMHWVKQKPGQGLEWIGYINPYNDGTKYNEKFKGKATLTSDKSS

STAYMELSSLTSEDSAVYYCARGTYYYGSRVFDYWGQGTTLTVSSGGG

GSGGGGSGGGGSDIVMTQAAPSIPVTPGESVSISCRSSKSLLNSNGNT

YLYWFLQRPGQSPQLLIYRMSNLASGVPDRFSGSGSGTAFTLRISRVE

AEDVGVYYCMQHLEYPFTFGAGTKLELKRSDPTTTPAPRPFTPAPTIA

SQPLSLRPEACRPAAGGAVHTRGLDFACDIYIWAPLAGTCGVLLLSLV

ITLYCKRGRKKLLYIFKQPFMRPVQTTQEEDGCSCRFPEEEEGGCELR

VKFSRSADAPAYQQGQNQLYNSLNLGRRESYDVLDKRRGRDPEMGGKP

RRKNPQEGLYNELQKDKMAEAYSEIGMKGERRRGKGHDGLYQGLSTAT

KDTYDALHMQALPPRGSSGSGEGRGSLLTCGDVEENPGPMSGESMNFS

DVFDSSEDYFVSVNTSYYSVDSEMLLCSLQEVRQFSRLFVPIAYSLIC

VFGLLGNILVVITFAFYKKARSMTDVYLLNMAIADILFVLTLPFWAVS

HATGAWVFSNATCKLLKGIYAINFNCGMLLLTCISMDRYIAIVQATKS

FRLRSRTLPRSKIICLVVWGLSVIISSSTFVFNQKYNTQGSDVCSPKY

QTVSEPIRWKLLMLGLELLFGFFIPLMFMIFCYTFIVKTLVQAQNSKR

HKAIRVIIAVVLVFLACQIPHNMVLLVTAANLGKMNRSCQSEKLIGYT

KTVTEVLAFLHCCLNPVLYAFIGQKFRNYFLKILKDLWCVRRKYKSSG

FSCAGRYSENISRQTSETADNDNASSFTMGSGATNFSLLKQAGDVEEN

PGPVSKGEELFTGVVPILVELDGDVNGHKFSVSGEGEGDATYGKLTLK

FICTTGKLPVPWPTLVTTLTYGVQCFSRYPDHMKQHDFFKSAMPSGYV

QERTIFFKDDGNYKTRAEVKFEGDTLVNRIELKGIDFKEDGNILGHKL

EYNYNSHNVYIMADKQKNGIKANFKIRHNIEDGSVQLADHYQQNTPIG

DGPVLLPDNHYLSTQSALSKDPNEKRDHMVLLEFVTAAGITLGMDELY

K

An example nucleic acid sequence encoding Construct 1 (CD19 CAR, CCR6, GFP region) provided below:

(SEQ ID NO: 430)
atggagacagacactcttctcctttgggtcttgctgctgtgggttccc ggaagcacaggagaagtacagttgcaacagtctgggccagaacccatc aaacccggagcccctgtaaaaatgtcacgcaaagctagtggatacaca tttacttcttacgtgatgcactgggtaaaacagaaacctggtcagggg cttgagtggatcgggcacattaacccatataatgacggcaccaaatat aacgagaaattcaagggaaaggctacgcttacatcagataagtccagt agcaccgcttatatggaacttagcagccttacttccgaagattccgcg gtgtattactgcgcgagagggacttactactacgggagtcgagtaccc gattattggggtcaaggcacgacgctcacggcgagctcaggtggtgga gggtctgggggtggcggcagtggtggggggggctcagacatcgtgatg acccaggcagcaccttctatcccggtaaccccaggcgagtctgtatct atcagttgtcggtccagcaagtctcttctcaacagtaatggcaataca tatctttactggttcctccaaaggcctgggcaaagtcctcaacttctt atatatcggatgtccaatcttgcgagtggcgtacccgacaggttttca gggtctgggagcggaacagcttttacgttgagaatatccagggtagaa gctgaggacgtcggtgtatattattgcatgcaacatctcgaataacccc tttaccttcggcgctggtacaaagctcgaattgaaacgcagcgatcca accacgacgccagcgccacgaccacctacgcccgctccaactattgcc tcccagcccctgagtcttcggccagaagcgtgtagacctgctgccggc ggggccgttcatacgcgggccttgactttgcatgtgatatctatata tgggctcctttggcgggaacttgcggagtgcttcttttgtcactcgtg ataacgttgtattgtaaaaggggtcgaaagaaactcctctatatattt aagcagccctttatgaggcccgtgcaaacaacacaagaagaggacgga tgctcttgtcgattccggaagaggaggaggggggggtgtgagctcagg gtcaagtttctcgctctgccgacgcgccagcctatcaacagggccaa aaccagctgtataacgaactcaacctcgggcgccgggaagagtatgac gtccttgacaaacggcgcggtcgcgaccctgaaatgggtggaaaaccg aggcgaaagaaccccaggagggactttacaacgaattgcaaaaagac aagatggccgaagcctattccgaaattggaatgaaaggcgagcggaga cgaggtaaggggcacgacggcctgtatcaagggctctctacggccacg aaggatacttacgacgcccttcatatgcaagctcttccaccacgggt tcgagcggcagtggagagggcagaggaagtctgctaacatgcggtgac gtcgaggagaatcctggcccaatgagtggggaaagtatgaacttcagc gatgtatttgactcctccgaagattactttgtatctgtgaatacgagc tattactccgtcgatagtgaaatgctgctctgtagtctccaagaagtc cgccaattcagtcgcctcttcgttcccatcgcgtactcccttatttgt gttttttggccttctgggtaacatcctggttgtaatcacattcgctttc tataaaaaagctcggagtatgactgatgtttaccttcttaacatggct atagcggacattctttttgtgcttactctcccattctgggctgtgagc catgcaacaggggcgtgggttttttcaaatgccacatgtaagctgctt aaagggatctatgcaataaacttcaattgcgggatgctcctgctgaca tgcatcagtatggatcgatacatagctatagtacaggcgactaagtcc ttccgcctgcgatcccgcacactgcctaggagcaaaattatttgcctc gtcgtatggggctctcagtgatcatctcctccagtacgtttgtcttt aaccagaaatataacacacagggttctgatgtatgtgaaccaaagcat cagacagtgagtgaaccaatacggtggaagttgcttatgttgggcttg gagctgcttttgggttttcatcccactgatgttcatgattttctgt tatacatttattgttaagaccttggttcaggcgcaaaatagcaagaga cataaggcaattcgagtcatcattgccgtggtgttggtcttcttggcc tgtcagatcccccataatatggttctgctcgtcaccgccgctaacttg ggtaagatgaatcgatcttgtcagtccgagaagttgatcggatacacc aaaactgtgacagaagtgctggccttccttcactgttgtctgaaccca gttttgtatgcttttataggacagaagtttcgaaattacttcttgaaa atcctcaaggacctctggtgtgttcgaaggaagtacaagagctctggc tttagttgcgctgggcgctacagtgagaatatatcccggcagacctcc gagactgctgataatgacaacgcaagttccttcactatgggatccggc gcaacaaacttctctctgctgaaacaagccggagatgtcgaagagaat cctggaccggtgagcaagggcgaggagctgttcaccggggtggtgccc atcctggtcgagctggacggcgacgtaaacggccacaagttcagcgtg tctggcgagggcgagggcgatgccacctacggcaagctgaccctgaag ttcatctgcaccaccggcaagctgcccgtgccctggcccaccctcgtg accaccctgacctacggcgtgcagtgcttcagccgctaccccgaccac atgaagcagcacgacttcttcaagtccgccatgcccgaaggctacgtc caggagcgcaccatcttcttcaaggacgacggcaactacaagacccgc gccgaggtgaagttcgagggcgacaccctggtgaaccgcatcgagctg aagggcatcgacttcaaggaggacggcaacatcctggggcacaagctg gagtacaactacaacagccacaacgtctatatcatggccgacaagcag aagaacggcatcaaggcgaacttcaagatccgccacaacatcgaggac ggcagcgtgcagctcgccgaccactaccagcagaacacccccatcggc gacggccccgtgctgctgcccgacaaccactacctgagcacccagtcc gccctgagcaaagaccccaacgagaagcgcgatcacatggtcctgctg gagttcgtgaccgccgcgggatcactctcggcatggacgagctgtac aagtaa Construct 2 MHC CAR region (MHC-CAR1 part B, MHC-CAR1 part A region) is provided below:

(SEQ ID NO: 431)
MVCLKLPGGSCMTALTVTLMVLSSPLALASDENPVVHFFKNIVTPRTP
PGGGGSGGGGSGGSGDTRPRFLWQPKRECHFFNGTERVRFLDRYFYNQ
SSSVRFDSDVGEFRAVTELGRPDAEYWNSQKDILSQARAAVDTYCRHN
YGVVESFTVQRRVQPKVTVYPSKTQPLQHHNLLVCSVSGFYPGSIEVR
WFLNGQEEKAGMVSTGLIQNGDWTFQTLVMLETVPRSGEVYTCQVEHP
SVTSPLTVEWRARSESAQSKMLSGVGGFVLGLLFLGAGLFIYFRNQTS
RVKFSRSADAPAYQQGQNQLYNELNLGRREEYDVLDKRRGRDPEMGGK
PRRKNPQEGLYNELQKDKMAEAYSEIGMKGERRRGKGHDGLYQGLSTA
TKDTYDALHMQALPPRGSSGSGEGRGSLLTCGDVEENPGPMAISGVPV
LGFFIIAVLMSAQESWAIKEEHVIIQAEFYLNPDQSGEFMFDFDGDEI
FHVDMAKKSTVWRLESFGRFASFEAQGALANIAVDKANLEIMTKRSNY
TPITNVPPEVTVLTNSPVELREPNVLICFIDKFTPPVVNVTWLRNGKP
VTTGVSETVFLPREDHLFRKFHYLPFLPSTEDVYDCRVEHWGLDEPLL
KHWEFDAPSPLPETTENVVCALGLTVGLVGIIIGTIFIIKGLTSRVKF
SRSADAPAYQQGQNQLYNELNLGRRSEYDVLDKRRGRDPEMGGKPRRK
NPQEGLYNELQKDKMAEAYSEIGMKGERRRGKGHDGLYQGLSTATKDT
YDALHMQALPPR

An example nucleic acid sequence encoding the Construct 2 MHC CAR region (MHC-CAR1 part B, MHC-CAR1 part A) is provided below:

(SEQ ID NO: 71)
atggtatgcttgaagctcccgggcgggtcctgcatgaccgctctcact
gttactctcatggtccttagttcaccgccttgccctggcatctgatga
gaatcccgtggtccatttttttaagaacatcgtcacaccgcgcacccc
acctgggcggaggcggatctggcggaggcgggagtggaggctcaggag
acacaagaccccgattcttgtggcagcccaaaaggcgagtgccatttt
ttcaatgggacggaacgagttcgcttccttgatcggtacttttacaac
caagaagagagtgtaccggttcgactcagatgccggcgagttccgagc
ggttacggaattggggcgacctgacgcggagtactggaactccccaaa
aggatattttggagcaggcacgagcagctgtggcacctattgtcgac
ataaccatggtgtggtggaatcccttacagttcagcggcgggtgcaa
cctaaagtgaccgtgtatccatctaaaacgcaaccoctccaacaccat
aaccctcctggtgtgttccgtaagcggcttctatcccgggtcaattga
ggtcaggtggttcctcaacggtcaggaggagcaaggccggaatggtaa
gtactggtcttatccagaacggagactggaccttccaaactttggtaa
tgttggaaacgcgtgccgcgatccggggaggtgtatacatgccaagtt
gaacacccgagtgttacgagcccctgacggttgagtggcagggcgcg
gtcagagagcgcacaatctaaatgctgtcaggagtaggcggatttgt
actcggactcctcttttttgcggcgctgggttgtttatctactttagaa
accaaacaagtagagtaaagttttcccgaagtgcggacgctcccgcgc
tatcagcaaggtcaaaaccagctttacaacgaactgaacttgggacga cgcgaagagtacgatgttcttgataagccggagagggcgcgatcccga
aatgggggaaagcctcggaggaagaacccacaagaaggcctttataa
tgaaccgccagaaggacaagatggcqgaggcgtattccgaaataggca
tgaaggtgaacggaggagaggaaagqgacatgaccggactttatcaa
ggattgtctaccgcaactaaagacacctatgacgcgttgcacatgcag
gctctccctccgagacggttcgagcggcagtggagagggcagaggaag
tctgctaacatgcggtgacgtcgaggagaatcctggcccaatgcgcaa
tatctggtgttcctgtcctcgggttttttatcatagccgtactgatgt
cagcacaggaatcatgggcgatacaaagaagagcacgtgataatacag
gcggagttttatttgaacccggaccagagcggtgagttcatgttcgat
tttcgatggcgacgagatatctcacgttgacatggcaaaaaaggaaac
ggtgcggagacttgaggagtttggacgattccgcatcatttgaggcac
aaggagcactcgccaatatcgcggtggacaaggccaacctggagatca
tgacaaaacgcctccaattatacgcctatcactaatgtgcccctgag
gttactgtgctcacaaattctcccgtagaacttagggaaccctaacgt
cctcatatgtttcatcgacaagttcactcctccggtggtcaatgtaac
gtggcttcggaatggtaagcccggtcaccacgggtgtctcagagaccg
tatttctgcccagagaagaccacctcttccgcaaatttcattaccttc
cccttctccttcaacggaagacgtttacgactgcagggtcgaacat
tgggggcttgacgaaccacttctcaagccattgggagttcgacgcccc
atcaccgcttccagaaacgactgaaaacgttgtctgcgctcttggcct
gacagtgcggcctggtaggcattattatcgggaccatctttatcatca
aaggtttgacttcccgggtcaaatttagcagatcccgctgacgcaccg
gcccaccagcagggccagaaccaactctacaacgagctgaatctcggc
cgacgggaagagtatcgacgtactcgacaagcggagaggtcgagaccc
tgagatgggcggtaaaccgagacggaaaaatccccaagagggtcctttt
ataatgaactccagaaggacaagatggctgaagcctattctgagatag
ggatgaaaggcgagcggcggaggcggtaagggccatgatggcctttac
cagggactctccacggcaaccaaagatacttacgacgcccttcacatg
caacgcctcccgccacgc Construct 2 kill switch and MHC CAR region (RQR8, MHC-CART part B, MHC-CAR1 part A region) is provided below:

(SEQ ID NO: 211)
MGTSLLCWMALCLLGADHADACPYSNPSLCSGGGGSELPTQGTFSNVS
TNVSPAKPTTTACPYSNPSLCSGGGGSPAPRPPTPAPTIASQPLSLRP
EACRPAAGGAVHTRGLDFACDIYIWAPLAGTCGVLLLSLVITLYCNHR
NRRRVCKCPRPVVRSGSGQCTNYALLKLAGDVESNPGPPTGMVCLKLP
GGSCMTALTVTLMVLSSPLALASDENPVVHFFKNIVTPRTPPGGGGSG
GGGSGGSGDTRPRFLWQPKRECHFFNGTERVRFLDRYFYNQEESVRFD
SDVGEFRAVTELGRPDASYWNSQKDILEQARAAVDTYCRHNYGVVESF

TVQRRVQPKVTVYPSKTQPLQHHNLLVCSVSGFYPGSIEVRWFLNGQE
EKAGMVSTGLIQNGDWTFQTLVMLETVPRSGEVYTCQVEHPSVTSPLT
VEWRARSESAQSKMLSGVGGFVLGLLFLGAGLFIYFRNQTSRVKFSRS
ADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDA
LHMQALPPRGSSGSGEGRGSLLTCGDVEENPGPMAISGVPVLGFFIIA
VLMSAQESWAIKEEHVIIQAEFYLNPDQSGEFMFDFDGDEIFHVDMAK
KETVWRLEEFGRFASFSAQGALANIAVDKANLEIMTKRSNYTPITNVP
PEVTVLTNSPVELREPNVLICFIDKFTPPVVNVTWLRNGKPVTTGVSE
TVFLPREDHLFRKFHYLPFLPSTEDVYDCRVEHWGLDEPLLKHWEFDA
PSPLPETTENVVCALGLTVGLVGIIIGTIFIIKGLTSRVKFSRSADAP
AYQQGQNQLYNELNLGRREEYDVLDKRRGRDPEMGGKPRRKNPQEGLY
NELQKDKMAEAYSEIGMKGERRRGKGHDGLYQGLSTATKDTYDALHWQ
ALPPR

An example nucleic acid sequence encoding Construct 2 kill switch and MHC CAR region (RQR8, MHC-CAR1 part B, MHC-CAR1 part A region) is provided below:

(SEQ ID NO: 403)
atgggtacttcactgttgtgctggatggcactttgtcttttgggtgcc gatcatgctgatgcatgtccgtactccaatcctagcctgtgctccggg gggggagggagtgaactccctacacagggaaccttctctaatgtctcc accaacgtctccctgcaaaaccgaccacaacagcttgcccctatagt aacccttccctctgtagtggaggggggggttcacctgctccacgccct cctaccccgcgccaacgatcgcgccacaaccgctcagtcttaggccg gaagcctgtaggccagcggctggcggtgcggttcatacgcgggattg gattttgcctgcgacatttacatttgggctccgctggccggtacttgt ggggtattgctgttgtctcttgttattacgctttattgcaatcacagg aacaggcgacgagtatgcaaatgcccgcggcccgtcgtgagatctggg tccggccaatgtactaactacgctttgttgaaactcgctggcgatgtt gaaagtaaccccggtcctccaacaggtatggtatgcttgaagctccg ggcgggtcctgcatgaccgctctcactgttactcttatggtccttagt tcaccgcttgccctggcatctgatgagaatcccgtggttcatttttt aagaacatcgtcacaccgcgcacccacctggggagcggatctggc ggaggcgggagtggaggctcaggagacacaagacccgattcttgtgg cagcccaaaagggagtgccatttttcaatgggacggaacgagttcgc ttccttgatcggtacctctacaaccaagaagagtgtacggttcgac tcagatgtcggcgagttccgagcggttacggaatcggggcgacctgac gcggagtactggaactcccaaaaggatattttggagcaggcacgagca gctgtggacaccttattgtcgacataattatggtgtggtggaatcctt acagttcagcggcgggtgcaacctaaagtgaccgtgtatccatctaaa acgcaacccctccaacaccataacctcctggtgtgttccgtaagcggc ttctatcccgggtcaattgaggtcaggtggttcctcaacggtcaggag gagaaggccggaatggtaagtactggtcttatccagaacggagactgg accttccaaactttggtaatgttggaaacggtgccgcgatccggggag gtgtatacatgccaagttgaacacccgagtgttacgagcccctgacg gttgagtggagggcgcggtcagagagcgcacaatctaaatgctgtca ggagtaggcggatttgtactcggactcctcttttttgggcgctgggttg tttatctactttagaaaccaaacaagtagagtaaagttttcccgaagt gcggacgccccgcgtatcagcaaggccaaaaccagcttacaacgaa ctgaacttgggacgacgcgaagagtacgatgttcttgataagcggaga gggcgcgatcccgaaatgggggaaagcctcggaggaagaacccacaa gaaggcctttataatgaactgcagaaggacaagatggcggaggcgtat tccgaaataggcatgaagggtgaacggaggagaggaaagggacatgac ggactttatcaaggattgtctaccgcaactaaagacacctatgacgcg ttgcacatgcaggctctccctccgagaggttcgagcggcagtggagag ggcagaggaagtccgctaacatgcggtgacgtcgaggagaatcctggc ccaatggcaatatctggtgttcctgtcctcgggttttttatcatagcc gtactgatgtcagcacaggaatcatgggcgataaaagaagagcacgtg ataatacaggcggagttttatttgaacccggaccagagcggtgagttc atgttcgattttgatggcgacgagatatttcacgttgacatggcaaaa aaggaaacggtgtggagacttgaggagtttggacgattcgcaccatt gaggcacaaggagcactcgccaatatcgcggtggacaaggccaacctg gagatcatgacaaaacgctccaattatacgcctatcactaatgtgccc cctgaggttactgtgctcacaaattctcccgtagaacttagggaacct aacgtcctcatatgtttcatcgacaagttcactcctccggtggtcaat gtaacgtggcttcggaatggtaagccggtcaccacgggtgtctcagag accgtatttctgcccagagaagaccacctcttccgcaaatttcattac cttccctttcttccttcaacggaagacgtttacgactgcagggtcgaa cattgggggcttgacgagccacttctcaagcattgggagttcgacgcc ccatcaccgcttccagaaacgactgaaaacgttgtctgcgctcttggc ctgacagtgggcctggtaggcattattatcgggaccatctttatcatc aaaggtttgacttcccgggtcaaatttagcagatccgctgacgcaccg gcctaccagcagggccagaaccaactctacaacgagctgaatctcggc cgacgggaagagtatgacgtactcgacaagcggagaggtcgagaccct gagatgggcggtaaaccgagacggaaaaatccccaagagggtctttat aatgaactccagaaggataagatggctgaagcctattctgagataggg atgaaaggcgagcggcggaggggtaagggccatgatggcctCCaccag ggactctccacggcaaccaaagatacttacgacgcccttcacatgcaa gccctcccgccacgc Construct 2 (RQR8, MHC-CAR1 part B, MHC-CAR1 part A, GFP region) is provided below.

(SEQ ID NO: 405)
MGTSLLCWMALCLLGADHADACPYSNPSLCSGGGGSELPTQGTFSNVS
TNVSPAKPTTTACPYSNPSLCSGGGGSPAPRPPTPAPTIASQPLSLRP
EACRPAAGGAVHTRGLDFACDIYIWAPLAGTCGVLLLSLVITLYCNHR
NRRRVCKCPRPVVRSGSGQCTNYALLKLAGDVESNPGPPTGMVCKLP
GGSCMTALTVTLMVLSSPLALASDENPVVHFFKNIVTPRTPPGGGGSG
GGGSGGSGDTRPRFLWQPKRECHFFNGTERVRFLDRYFYNQEESVRFD
SDVGEFRAVTELGRPDAEYWNSQKDILEQARAAVDTYCRHNYGVVESF
TVQRRVQPKVTVYPSKTQPLQHHNLLVCSVSGFYPGSIEVRWFLNGQE
EKAGMVSTGLIQNGDWTFQTLVMLETVPRSGEVYTCQVEHPSVTSPLT
VEWRARSESAQSKMLSGVGGFVLGLLFLGAGLFIYFRNQTSRVKFSRS
ADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDA
LHMQALPPRGSSGSGEGRGSLLTCGDVEENPGPMAISGVPVLGFFTIA
VLMSAQSSWAIKEEHVIIQAEFYLNPDQSGEFMFDFDGDEIFHVDMAK
KETVWRLEEFGRFASFEAQGALANIAVDKANLSIMTKRSNYTPITNVP
PEVTVLTNSPVELREPNVLICFIDKFTPPVVNVTWLRNGKPVTTGVSE
TVFLPREDHLFRKFHYLPFLPSTEDVYDCRVEHWGLDEPLLKHWEFDA
PSPLPETTENVVCALGLTVGLVGIIIGTIFIIKGLTSRVKFSRSADAP
AYQQGQNQLYNELNLGRREEYDVLDKRRGRDPEMGGKPRRKNPQEGLY
NELQKDKMAEAYSEIGMKGERRRGKGHDGLYQGLSTATKDTYDALHMQ
ALPPRGSGATNFSLLKQAGDVEENPGPVSKGEELFTGVVPILVELDGD
VNGHKFSVSGEGSGDATYGKLTLKFICTTGKLPVPWPTLVTTLTYGVQ
CFSRYPDHMKQHDFFKSAMPEGYVQERTIFFKDDGNYKTRAEVKFEGD
TLVNRIELKGIDFKEDGNILGHKLEYNYNSHNVYIMADKQKNGIKANF
KIRHNIEDGSVQLADHYQQNTPIGDGPVLLPDNHYLSTQSALSKDPNE
KRDHMVLLEFVTAAGITLGMDSLYK*

An example nucleic acid sequence encoding Construct 2 (RQR8, MHC-CAR1 part B, MHC-CAR1 part A, GFP region) is provided below:

(SEQ ID NO: 409)
atgggtacttcactgttgtgctggatggcactttgtcttttgggtg
ccgatcatgctgatgcatgtccgtactccaatcctagcctgtgctc
cggggggggagggagtgaactccctacacagggaaccttctctaat
gtctccaccaacgtctccctgcaaaaccgaccacaacagcttgcc
cctatagtaacccttccctctgcagtggagggggggggttcacctgc
tccacgccctcctaccccgcgcaacgatcgcgtcacaaccgctc
agtcttaggccggaagcctgtaggccagcggctggcggtgcggttc
atacgcggggattggattttgcctgcacatttacatttgggctcc
gctggccggtacttgtggggtattgctgttgtctcttgttattacg
ctttattgcaatcacaggaacaggcgacgagtatgcaaatgcccgc
ggccccgtcgtgagatctgggtccggccaatgtactaactacgcttt
gttgaaacccgctggcgatgttgaaagcaaccccggtcctccaaca
ggtatggtatgctcgaagctcccgggcgggccctgcatgaccgctc
tcactgttactcttatggtccttagttcaccgcttgccctggcatc
tgatgagaatcccgtggttcatttttttaagaacatCgtcacaccg
cgcaccccacctggggggaggcggatctggcggaggcgggagtggag
gctcaggagacacaagaccccgattcttgtggcagcccaaaaggga
gtgccatttttttcaatgggacggaacgagttcgcttccttgatcgg
tacttttacaaccaagaagagagtgtacggctcgactcagatgtcg
gcgagttccgagcggtcacggaattggggcgacctgacgcggagta
ctggaactcccaaaaggatattttggagcaggcacgagcagctgtg
gacacctattgtcgacataattatggtgtggtggaatcctttacag
ttcagcggcgggtgcaacctaaagtgaccgtgtatccacctaaaac
gcaaccccccaacaccataacctcctggtgtgttccgtaagcggc
ttctatcccgggtcaattgaggtcaggtggttcctcaacggtcagg
aggagaaggccggaatggtaagtactggtcttatccagaacggaga
ctggaccttccaaactttggtaatgttggaaacggtgccgcgatcc
ggggaggtgtatacatgccaagttgaacacccgagtgttacgagcc
ccctgacggttgagtggagggcgcggtcagagagcgcacaatctaa
aatgctgtcaggagtaggcggatttgtactcggactcctctttttg
ggcgctggttgtttatctacttagaaaccaaacaagtagagtaa
agttttcccgaagtgcggacgctcccgcgtatcagcaaggtcaaaa
ccagctttacaacgaactgaacttgggacgacgcgaagagtacgat
gttctcgataagcggagagggcgcgatcccgaaatgggggaaagc
ctcggaggaagaacccacaagaaggcctttataatgaactgcagaa
ggacaagatggcggaggcgtattccgaaataggcatgaagggtgaa
cggaggagaggaaagggacatgacggactttatcaaggattgccta
ccgcaactaaagacacctatgacgcgttgcacatgcaggctctccc
tccgagaggttcgagcggcagtggagagggcagaggaagtctgcta
acatgcggtgacgtcgaggagaatcctggcccaatggcaatatctg
gtgttcctgtcctcgggttttttatcatagccgtactgatgtcagc
acaggaatcatgggcgataaagaagagcacgtgataatacaggcg
gagttttatttgaacccggaccagagcggtgagttcatgttcgatt
ttgatggcgacgagatatttcacgttgacatgcaaaaaaggaaac
ggtgtggagacttgaggagtttggacgattcgcatcatttgaggca
caaggagcactcgccaataccgcggtggacaaggcaacctggaga
tcatgacaaaacgctccaattatacgcctatcactaatgtgccccc
tgaggttactgtgctcacaaattctcccgtagaacttagggaacct
aacgtcctcatatgtttcatcgacaagttcactcctccggtggtca
atgtaacgtggcttcggaatggtaagccggtcaccacgggtgtctc
agagaccgtatttctgcccagagaagaccacccccttccgcaaattt -continued

```
cattaccttcccttcttccttcaacggaagacgtctacaactgca
gggtcgaacattgggggcttgacgagccacttctcaagcatcggga
gttcgacgcccatcaccgcttccagaaacgactgaaaacgttgtc
tgcgctcttggcctgacagtgggcctggtaggcattattatcggga
ccatctttatcatcaaaggtttgacttcccgggtcaaatttagcag
atccgctgacgcaccggcctaccagcagggccagaaccaactctac
aacgagctgaatctcggccgacgggaagagtatgacgtactcgaca
agcggagaggtcgagaccctgagatgggcggtaaaccgagacggaa
aaatccccaagagggtctttataatgaactccagaaggataagatg
gctgaagcctattctgagatagggatgaaaggcgagcggcggaggg
gtaagggccatgatggcctttaccagggactctccacggcaaccaa
agatacttacgacgccttcacatgcaagccctcccgccacgcgga
tccggcgcaacaaacttctctctgctgaaacaagccggagatgtcg
aagagaatcctggaccggtgagcaagggcgaggagctgttcaccgg
ggtggtgcccatcctggtcgagctggacggcgacgtaaacggccac
aagttcagcgtgtctggcgagggcgagggcgatgccacctacggca
```

-continued

```
agctgaccctgaagttcatctgcaccaccggcaagctgcccgtgcc
ctagcccaccctcgtgaccaccctgacctacggcgtgcagtgcttc
agccgctaccccgaccacatgaagcagcacgacttcttcaagtccg
ccatgcccgaaggctacgtccaggagcgcaccatcttcttcaagga
cgacggcaactacaagacccgcgccgaggtgaagttcgagggcgac
accctggtgaaccgcatcgagctgaagggcatcgacttcaaggagg
acggcaacatcctggggcacaagctggagtacaactacaacagcca
caacgtctatatcatggccgacaagcagaagaacggcatcaaggcg
aacttcaagatccgccacaacatcgaggacggcagcgtgcagctcg
ccgaccactaccagcagaacacccccatcggcgacggccccgtgct
gctgcccgacaaccactacctgagcacccagtccgccctgagcaaa
gaccccaacgagaagcgcgatcacatggtcctgctggagttcgtga
ccgccgccgggatcactctcggcatggacgagctgtacaagtaa
```

The amino acid sequences of exemplary CS-1 targeting CAR constructs are provided below (note that these designs contain a 4-1BB domain which may be replaced with a CD28 domain):

Anti-CS1-CAR-v1 (Luc63-V1 CAR):

(SEQ ID NO: 129)
MALPVTALLLPLALLLHAARPEVKLLESGGGLVQPGGSLKLSCAASGFDFSRYWMSWVRQAPGKGLEWIGEINPD
SSTINYTPSLKDKFIISRDNAKNTLYLQMSKVRSEDTALYYCARPDGNYWYFDVWGAGTTVTVSSGGGGSGGGGS
GGGGSDIVMTQSHKFMSTSVGDRVSITCKASQDVGIAVAWYQQKPGQSPKLLIYWASTRHTGVPDRFTGSGSGTD
FTLTISNVQSEDLADYFCQQYSSYPYTFGGGTKLEIKGLAVSTISSFFPPGYQKRGRKKLLYIFKQPFMRPVQTT
QEEDGCSCRFPEEEEGGCELRVKFSRSADAPAYQQGQNQLYNELNLGRREEYDVLDKRRGRDPEMGGKPRRKNPQ
EGLYNELQKDKMAEAYSEIGMKGERRRGKGHDGLYQGLSTATKDTYDALHMQALPPR

Anti-CS1-CAR-v2 (Luc63-V2 CAR):

(SEQ ID NO: 130)
MALPVTALLLPLALLLHAARPEVKLLESGGGLVQPGGSLKLSCAASGFDFSRYWMSWVRQAPGKGLEWIGEINPD
SSTINYTPSLKDKFIISRDNAKNTLYLQMSKVRSEDTALYYCARPDGNYWYFDVWGAGTTVTVSSGGGGSGGGGS
GGGGSDIVMTQSHKFMSTSVGDRVSITCKASQDVGIAVAWYQQKPGQSPKLLIYWASTRHTGVPDRFTGSGSGTD
FTLTISNVQSEDLADYFCQQYSSYPYTFGGGTKLEIKTTTPAPRPPTPAPTIASQPLSLRPEACRPAAGGAVHTR
GLDFACDIYIWAPLAGTCGVLLLSLVITLYCKRGRKKLLYIFKQPFMRPVQTTQEEDGCSCRFPEEEEGGCELRV
KFSRSADAPAYQQGQNQLYNELNLGRREEYDVLDKRRGRDPEMGGKPRRKNPQEGLYNELQKDKMAEAYSEIGMK
GERRRGKGHDGLYQGLSTATKDTYDALHMQALPPR

Anti-CS1-CAR-v3 (Luc63-V3 CAR):

(SEQ ID NO: 131)
MALPVTALLLPLALLLHAARPEVKLLESGGGLVQPGGSLKLSCAASGFDFSRYWMSWVRQAPGKGLEWIGEINPD
SSTINYTPSLKDKFIISRDNAKNTLYLQMSKVRSEDTALYYCARPDGNYWYFDVWGAGTTVTVSSGGGGSGGGGS
GGGGSDIVMTQSHKFMSTSVGDRVSITCKASQDVGIAVAWYQQKPGQSPKLLIYWASTRHTGVPDRFTGSGSGTD
FTLTISNVQSEDLADYFCQQYSSYPYTFGGGTKLEIKEPKSPDKTHTCPPCPAPPVAGPSVFLFPPKPKDTLMIA
RTPEVTCVWDVSHEDPEVKFNVfYVDGVEVHNAKTKPREEQYNSTYRVVSVLTVLHQDWLNGKSYKCKVSNKALP
APIEKTISKAKGQPREPQVYTLPPSRDELTKNQVSLTCLVKGFYPSDIAVEWESNGQPENNYKTTPPVLDSDGSF
FLYSKLTVDKSRWQQGNVFSCSVMHEALHNHYTQKSLSLSPGKKRGRKKLLYIFKQPFMRPVQTTQEEDGCSCRF
```

-continued

PEEEEGGCELRVKFSRSADAPAYQQGQNQLYNELNLGRREEYDVLDKRRGRDPEMGGKPRRKNPQEGLYNSLQKD

KMAEAYSEIGMKGERRRGKGHDGLYQGLSTATKDTYDALHMQALPPR

Anti-CS1-CAR-v4 (Luc90-V1 CAR):

(SEQ ID NO: 132)
MALPVTALLLPLALLLHAARPQVQLQQPGASLVRPGASVKLSCKASGYSFTTYWMNWVKQRPGQGLEWIGMIHPS

DSETRLNQKFKDKATLTVDKSSSTAYMQLSSPTSEDSAVYYCARSTMIATRAMDYWGQGTSVTVSSGGGGSGGGG

SGGGGSDIVMTQSQKSMSTSVGDRVSITCKASQDVITGVAWYQQKPGQSPKLLIYSASYRYTGVPDRFTGSGSGT

DFTFTISNVQAEDLAVYYCQQHYSTPLTFGAGTKLELKGLAVSTISSFFPPGYQKRGRKKLLYIFKQPFMRPVQT

TQEEDGCSCREPESEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR

Anti-CS1-CAR-v5 (Luc90-V2 CAR):

(SEQ ID NO: 133)
MALPVTALLLPLALLLHAARPQVQLQQPGAELVRPGASVKLSCKASGYSFTTYWMNWVKQRPGQGLEWIGMIHPS

DSETRLNQKFKDKATLTVDKSSSTAYMQLSSPTSEDSAVYYCARSTMIATRAMDYWGQGTSVTVSSGGGGSGGGG

SGGGGSDIVMTQSQKSMSTSVGDRVSITCKASQDVITGVAWYQQKPGQSPKLLIYSASYRYTGVPDRFTGSGSGT

DFTFTISNVQAEDLAVYYCQQHYSTPLTFGAGTKLELKTTTPAPRPPTPAPTIASQPLSLRPSACRPAAGGAVHT

RGLDFACDIYIWAPLAGTCGVLLLSLVITLYCKRGRKKLLYIFKQPFMRPVQTTQSEDGCSCRFPEEEEGGCELR

VKFSRSADAPAYQQGQNQLYNSLNLGRREEYDVLDKRRGRDPEMGGKPRRKNPQEGLYNELQKDKMAEAYSEIGM

KGERRRGKGHDGLYQGLSTATKDTYDALHMQALPPR

Anti-CS1-CAR-v6 (Luc90-V3 CAR):

(SEQ ID NO: 134)
MALPVTALLLPLALLLHAARPQVQLQQPGAELVRPGASVKLSCKASGYSFTTYWMNWVKQRPGQGLEWIGMIHPS

DSETRLNQKFKDKATLTVDKSSSTAYMQLSSPTSEDSAVYYCARSTMIATRAMDYWGQGTSVTVSSGGGGSGGGG

SGGGGSDIVMTQSQKSMSTSVGDRVSITCKASQDVITGVAWYQQKPGQSPKLLIYSASYRYTGVPDRFTGSGSGT

DFTFTISNVQAEDLAVYYCQQHYSTPLTFGAGTKLELKSPKSPDKTHTCPPGPAPPVAGPSVFLFPPKPKDTLMI

ARTPEVTCVVVDVSHEDPEVKFNWYVDGVSVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGKKRGRKKLLYIFKQPFMRPVQTTQEEDGCSCR

FPEEEEGGCELRVKFSRSADAPAYQQGQNQLYNELNLGRREEYDVLDKRRGRDPEMGGKPRRKNPQEGLYNSLQK

DKMAEAYSEIGMKGSRRRGKGHDGLYQGLSTATKDTYDALHMQALPPR

Anti-CA1-CAR-v7 (Luc34-V1 CAR):

(SEQ ID NO: 135)
MALPVTALLLPLALLLHAARPQVQLQQSGAELARPGASVKLSCKASGYTFTSYWMQWVKQRPGQGLEWIGAIYPG

DGDTRYTQKFKGKATLTADKSSSTAYMQLSSLASEDSAVYYCARGKVYYGSNPFAYWGQGTLVTVSAGGGGSGGG

GSGGGGSDIQMTQSSSYLSVSLGGRVTITCKASDHINNWLAWYQQKPGNAPRLLISGATSLETGVPSRFSGSGSG

KDYTLSITSLQTEDVATYYCQQYWSTPWTFGGGTKLEIKGLAVSTISSFFPPGYQKRGRKKLLYIFKQPFMRPVQ

TTQEEDGCSCRFPEEEEGGCELRVKFSRSADAPAYQQGQNQLYNELNLGRREEYDVLDKRRGRDPEMGGKPRRKN

PQEGLYNELQKDKMAEAYSEIGMKGERRRGKGHDGLYQGLSTATKDTYDALHMQALPPR

Anti-CS1-CAR-v8 (Luc34-V2 CAR):

(SEQ ID NO: 136)
MALPVTALLLPLALLLHAARPQVQLQQSGAELARPGASVKLSCKASGYTFTSYWMQWVKQRPGQGLEWIGAIYPG

DGDTRYTQKFKGKATLTADKSSSTAYMQLSSLASEDSAVYYCARGKVYYGSNPFAYWGQGTLVTVSAGGGGSGGG

GSGGGGSDIQMTQSSSYLSVSLGGRVTITCKASDHINNWLAWYQQKPGNAPRLLISGATSLETGVPSRFSGSGSG

KDYTLSITSLQTEDVATYYCQQYWSTPWTFGGGTKLEIKTTTPAPRPPTPAPTIASQPLSLRPEACRPAAGGAVH

TRGLDFACDIYIWAPLAGTCGVLLLSLVITLYCKRGRKKLLYIFKQPFMRPVQTTQEEDGCSCRFPEEEEGGCEL

-continued

RVKFSRSADAPAYQQGQNQLYNELNLGRREEYDVLDKRRGRDPEMGGKPRRKNPQEGLYNELQKDKMAEAYSEIG

MKGERRRGKGHDGLYQGLSTATKDTYDALHMQALPPR

Anti-CS1-CAR-v9 (Luc34-V3 CAR):

(SEQ ID NO: 137)

MALPVTALLLPLALLLHAARPQVQLQQSGAELARPGASVKLSCKASGYTFTSYWMQWVKQRPGQGLEWIGAIYPG

DGDTRYTQKFKGKATLTADKSSSTAYMQLSSLASEDSAVYYCARGKVYYGSNPFAYWGQGTLVTVSAGGGGSGGG

GSGGGGSDIQMTQSSSYLSVSLGGRVTITCKASDHINNWLAWYQQKPGNAPRLLISGATSLETGVPSRFSGSGSG

KDYTLSITSLQTEDVATYYCQQYWSTPWTFGGGTKLEIKEPKSPDKTHTCPPCPAPPVAGPSVFLFPPKPKDTLM

IARTPEVTCVVVDVSHEDPSVKFNWYVDGVEVHNAKTKPREEQYNSTYRVVSVLTVLHQDWLNGKEYKCKVSNKA

LPAPIEKTISKAKGQPREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGKKRGRKKLLYIFKQPFMRPVQTTQEEDGCSC

RFPEEEEGGCELRVKFSRSADAPAYQQGQNQLYNELNLGRREEYDVLDKRRGRDPEMGGKPRRKNPQEGLYNELQ

KDKMAEAYSEIGMKGERRRGKGHDGLYQGLSTATKDTYDALHMQALPPR

Anti-CS1-CAR-v10 (LucX1-V1 CAR)

(SEQ ID NO: 138)

MALPVTALLLPLALLLHAARPQVQLQQSGPELVKPGASVKISCKASGYAFSSSWMNWVKQRPGQGLEWIGRIYPG

DGDTKYNGKFKGKATLTADKSSSTAYMQLSSLTSVDSAVYFCARSTMIATGAMDYWGQGTSVTVSSGGGGSGGGG

SGGGGSETTVTQSPASLSMAIGEKVTIRCITSTDIDDDMNWYQQKPGEPPKLLISEGNTLRPGVPSRFSSSGYGT

DFVFTIENMLSEDVADYYCLQSDNLPLTFGGGTKLEIKGLAVSTISSFFPPGYQKRGRKKLLYIFKQPFMRPVQT

TQEEDGCSCRFPEEEEGGCELRVKFSRSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDALHMQALPPR

Anti-CS1-CAR-v11 (LucX1-V2 CAR)

(SEQ ID NO: 139)

MALPVTALLLPLALLLHAARPQVQLQQSGAELARPGASVKLSCKASGYTFTSYWMQWVKQRPGQGLEWIGAIYPG

DGDTRYTQKFKGKATLTADKSSSTAYMQLSSLASEDSAVYYCARGKVYYGSNPFAYWGQGTLVTVSAGGGGSGGG

GSGGGGSDIQMTQSSSYLSVSLGGRVTITCKASDHINNWLAWYQQKPGNAPRLLISCATSLETGVPSRFSGSGSG

KDYTLSITSLQTEDVATYYCQQYWSTPWTFGGGTKLEIKTTTPAPRPPTPAPTIASQPLSLRPFACRPAAGGAVH

TRGLDFACDIYIWAPLAGTCGVLLLSLVITLYCKRGRKKLLYIFKQPFMRPVQTTQEEDGCSCRFPEEEEGGCEL

RVKFSRSADPAYQQGQNQLYNELNLGRREEYDVLDKRRGRDPEMGGKPRRKNPQEGLYNELQKDKMAEAYSEIGM

KGERRRGKGHDGLYQGLSTATKDTYDALHMQALPPR

Anti-CS1-CAR-v12 (LucX1-V3 CAR):

{SEQ ID NO: 140)

MALPVTALLLPLALLLHAARPQVQLQQSGPELVKPGASVKISCKASGYAFSSSWMNWVKQRPGQGLEWIGRIYPG

DGDTKYNGKFKGKATLTADKSSSTAYMQLSSLTSVDSAVYFCARSTMIATGAMDYWGQGTSVTVSSGGGGSGGGG

SGGGGSETTVTQSPASLSMAIGEKVTIRCITSTDIDDDMNWYQQKPGEPPKLLISEGNTLRPGVPSRFSSSGYGT

DFVFTIENMLSEDVADYYCLQSDNLPLTFGGGTKLEIKEPKSPDKTHTCPPCPAPPVAGPSVFLFPPKPKDTLMI

ARTPEVTCVVVDVSHEDPEVKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGKKRGRKKLLYIFKQPFMRPVQTTQEEDGCSCR

FPEEEEGGCELRVKFSRSADAPAYQQGQNQLYNELNLGRREEYDVLDKRRGRDPEMGGKPRRKNPQEGLYNELQK

DKMAEAYSEIGMKGSRRGKGHDGLYQGLSTATKDTYDALHMQALPPR

Anti-CS1-CAR-v13 (LucX2-V1 CAR):

(SEQ ID NO: 141)

MALPVTALLLPLALLLHAARPQVQLQQSGPELVKPGASVKISCKASGYAFSSSWMNWVKQRPGQGLEWIGRIYPG

DGDTKYNGKFKGKATLTADKSSSTAYMQLSSLTSVDSAVYFCARSTMIATGAMDYWGQGTSVTVSSGGGGSGGGG

```
SGGGGSDIVMTQSHKFMSTSVGDRVSITCKASQDVSTAVAWYQQKPGQSPKLLIYSASYRYTGVPDRFTGSGSGTD

FTFTISSVQAEDLAVYYCQQHYSTPPYTFGGGTKLEIKGLAVSTISSFFPPGYQKRGRKKLLYIFKQPFMRPVQT

TQEEDGCCRFPEEEEGGCELRVKFSRSADAPAYQQGQNQLYNELNLGRREEYDVLDKRRGRDPEMGGKPRRKNPQ

EGLYNELQKDKMAEAYSEIGMKGERRRGKGHDGLYQGLSTATKDTYDALHMQALPPR

Anti-CS1-CAR-v14(LucX2-V2 CAR):
                                                        (SEQ ID NO: 142)
MALPVTALLLPLALLLHAARPQVQLQQSGPSLVKPGASVKISCKASGYAFSSSWMNWVKQRPGQGLEWIGRIYPG

DGDTKYNGKFKGKATLTADKSSSTAYMQLSSLTSVDSAVYFCARSTMIATGAMDYWGQGTSVTVSSGGGGSGGGG

SGGGGSDIVMTQSHKFMSTSVGDRVSITCKASQDVSTAVAWYQQKPGQSPKLLIYSASYRYTGVPDRFTGSGSGT

DFTFTISSVQAEDLAVYYCQQHYSTPPYTFGGGTKLEIKTTTPAPRPPTPAPTIASQPLSLRPEACRPAAGGAVH

TRGLDFADIYIWAPLAGTCGVLLLSLVITLYCKRGRKKLLYIFKQPFMRPVQTTQEEDGCSCRFPEEEEGGCELR

VKFSRSADAPAYQQGQNQLYNELNLGRREEYDVLDKRRGRDPEMGGKPRRKNPQEGLYNELQKDKMAEAYSSIGM

KGERRRGKGHDGLYQGLSTATKDTYDALHMQALPPR

Anti-CS1-CAR-v15 (LucX2-V3 CAR):
                                                        (SEQ ID NO: 143)
MALPVTALLLPLALLLHAARPQVQLQQSGPSLVKPGASVKISCKASGYAFSSSWMNWVKQRPGQGLEWIGRIYPG

DGDTKYNGKFKGKATLTADKSSSTAYMQLSSLTSVDSAVYFCARSTMIATGAMDYWGQGTSVTVSSGGGGSGGGG

SGGGGSDIVMTQSHKFMSTSVGDRVSITCKASQDVSTAVAWYQQKPGQSPKLLIYSASYRYTGVPDRFTGSGSGT

DFTFTISSVQAEDLAVYYCQQHYSTPPYTFGGGTKLEIKEPKSPDKTHTCPPCPAPPVAGPSVFLFPPKPKDTLM

IARTPEVCVVVDVSHEDPEVKFNWYVDGVEVHNAKTKPREEQYNSTYRVVSVLTVLHQDWLNGKEYKCKVSNKAL

PAPIEKTISKAKGQPREPQVYTLPPSRDELTKNQVSLTCLVKGFYPSDIAVEWESNGQPENNYKTTPPVLDSDGS

FFLYSKLTVDKSRWQQGNVFSCSVMHEALHNHYTQKSLSLSPGKKRGRKKLLYIFKQPFMRPVQTTQEEDGCSCR

FPEEEEGGCELRVKFSRSADAPAYQQGQNQLYNELNLGRREEYDVLDKRRGRDPEMGGKPRRKNPQEGLYNSLQK

DKMAEAYSEIGMKGERRRGKGHDGLYQGLSTATKDTYDALHMQALPPR
```

(iii) Preparation of MHC-CARs

Any of the MHC-CAR constructs described herein can be prepared by a routine method, such as recombinant technology. Methods for preparing the chimeric receptors herein involve generation of a nucleic acid or a nucleic acid set that encodes or collectively encodes a MHC-CAR construct (including a single polypeptide or two subunits). In some embodiments, the nucleic acid also encodes a self-cleaving peptide (e.g., P2A, T2A, or E2A peptide) between the coding sequences for the two subunits of a MHC-CAR, or between the coding sequence for a MHC-CAR and the coding sequence for other genes to be co-expressed with the MHC-CAR in a host cell (see discussions below).

Sequences of each of the components of the MHC-CARS may be obtained via routine technology, e.g., PCR amplification from any one of a variety of sources known in the art. In some embodiments, sequences of one or more of the components of the MHC-CARs are obtained from a human cell. Alternatively, the sequences of one or more components of the MHC-CARS can be synthesized. Sequences of each of the components (e.g., domains) can be joined directly or indirectly (e.g., using a nucleic acid sequence encoding a peptide linker) to form a nucleic acid sequence encoding the MHC-CAR, using methods such as PCR amplification or ligation. Alternatively, the nucleic acid encoding the MHC-CAR may be synthesized. In some embodiments, the nucleic acid is DNA. In other embodiments, the nucleic acid is RNA.

Any of the MHC-CAR proteins, nucleic acid encoding such, and expression vectors carrying such nucleic acid, all of which are within the scope of the present disclosure, can be mixed with a pharmaceutically acceptable carrier to form a pharmaceutical composition, which is also within the scope of the present disclosure. "Acceptable" means that the carrier is compatible with the active ingredient of the composition (e.g., the nucleic acids, vectors, cells, or therapeutic antibodies) and does not negatively affect the subject to which the composition(s) are administered. Any of the pharmaceutical compositions to be used in the present methods can comprise pharmaceutically acceptable carriers, excipients, or stabilizers in the form of lyophilized formations or aqueous solutions.

Pharmaceutically acceptable carriers, including buffers, are well known in the art, and may comprise phosphate, citrate; and other organic acids; antioxidants including ascorbic acid and methionine; preservatives; low molecular weight polypeptides; proteins, such as serum albumin, gelatin, or immunoglobulins; amino acids; hydrophobic polymers; monosaccharides; disaccharides; and other carbohydrates; metal complexes; and/or non-ionic surfactants. See, e.g. Remington: The Science and Practice of Pharmacy 20th Ed. (2000) Lippincott Williams and Wilkins, Ed. K. E. Hoover.

II. Genetically Engineered Immune Cells Expressing MHC-CARs (i) MHC-CAR-Expressing Immune Cells Immune cells expressing the MHC-CAR described herein provide a specific population of cells that can recognize pathogenic cells (e.g., autoreactive T cells) involved in autoimmune diseases via MHC/peptide-TCR engagement.

The interaction between the MHC-peptide portion of the MHC-CAR and the cognate TCR on the pathogenic cells would activate the MHC-CAR expressing immune cells via the signaling domains(s) of the MHC-CAR (optionally by recruiting cell membrane signaling molecules of the immune cells), leading to proliferation and/or effector functions of the MHC-CAR-expressing immune cells, which in turn eliminate the pathogenic cells. The immune cells can be T cells, NK cells, macrophages; neutrophils, eosinophils, or any combination thereof. In some embodiments, the immune cells are T cells. In some embodiments, the immune cells are NK cells. Specific examples are provided in Examples below.

The population of immune cells can be obtained from any source, such as peripheral blood mononuclear cells (PBMCs), bone marrow, tissues such as spleen, lymph node, thymus, tumor tissue, or established cell lines. A source suitable for obtaining the type of immune cells desired would be evident to one of skill in the art. In some embodiments, the population of immune cells is derived from PBMCs. The type of immune cells desired (e.g., T cells, NK cells, macrophages, neutrophils, eosinophils, or any combination thereof) may be expanded within the population of cells obtained by co-incubating the cells with stimulatory molecules, for example, anti-CD3 and anti-CD28 antibodies may be used for expansion of T cells.

To construct the immune cells that express any of the MHC-CAR constructs described herein, expression vectors for stable or transient expression of the chimeric receptor construct may be constructed via conventional methods as described herein and introduced into immune host cells. For example, nucleic acids encoding the MHC-CAR may be cloned into a suitable expression vector, such as a viral vector (e.g., a lentiviral vector) in operable linkage to a suitable promoter. The nucleic acids and the vector may be contacted, under suitable conditions, with a restriction enzyme to create complementary ends on each molecule that can pair with each other and be joined with a ligase. Alternatively, synthetic nucleic acid linkers can be ligated to the termini of the nucleic acid encoding the chimeric receptors. The synthetic linkers may contain nucleic acid sequences that correspond to a particular restriction site in the vector. The selection of expression vectors/plasmids/viral vectors would depend on the type of host cells for expression of the chimeric receptors, but should be suitable for integration and replication in eukaryotic cells.

A variety of promoters can be used for expression of the MHC-CAR constructs described herein, including, without limitation, cytomegalovirus (CMV) intermediate early promoter, a viral LTR such as the Rous sarcoma virus LTR, HIV-LTR, HTLV-1 LTR, the simian virus 40 (SV40) early promoter, herpes simplex tk virus promoter. Additional promoters for expression of the chimeric receptors include any constitutively active promoter in an immune cell. Alternatively, any regulatable promoter may be used, such that its expression can be modulated within an immune cell.

Additionally, the vector may contain, for example, some or all of the following: a selectable marker gene, such as the neomycin gene for selection of stable or transient transfectants in host cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; internal ribosome binding sites (IRESes), versatile multiple cloning sites; T7 and SP6 RNA promoters for in vitro transcription of sense and antisense RNA; a "suicide switch" or "suicide gene" which when triggered causes cells carrying the vector to die (e.g., HSV thymidine kinase, an inducible caspase such as iCasp9), and reporter gene for assessing expression of the MHC-CAR.

In some embodiments, the marker/sorting/suicide molecules for use in the present disclosure can be used for killing with rituximab and/or for sorting with QBEND. Philip et al., Blood 124(8):1277-87; 2014). One example is RQR8, which contains rituximab mimotope and QBEND-10 epitope. Exemplary sequences are provided below:

```
                                    (SEQ ID NO: 144)
MGTSLLCWMALCLLGADHADACPYSNPSLCSGGGGSELPTQGTFSNVSTN

VSPAKPTTTACPYSNPSLCSGGGGSPAPPPTPAPTIASQPLSLRPEACRP

AAGGAVHTRGLDFACDIYIWAPLAGTCGVLLLSLVITLYCNHRNRRRVCK

CPRPVV
```

```
                                    (SEQ ID NO: 394)
MGTSLLCWMALCLLGADHADACPYSNPSLCSGGGGSELPTQGTFSNVSTN

VSPAKPTTTACPYSNPSLCSGGGGSPAPRPPTPATIASQPLSLRPEACRP

AAGGAVHTRGLDFACDIYIWAPLAGTCGVLLLSLVITLYCNHRNRRRVCK

CPRPVV
```

An exemplary nucleic acid sequence encoding a RQR8 is provided below.

```
                                    (SEQ ID NO: 395)
ATGGGTACTTCACTGTTGTGCTGGATGGCACTTTGTCTTTTGGGTGCCGA

TCATGCTGATGCATGTCCGTACTCCAATCCTAGCCTGTGCTCCGGGGGGG

GAGGGAGTGAACTCCCTACACAGGGAACCTTCTCTAATGTCTCCACCAAC

GTCTCCCCTGCAAAACCGACCACAACAGCTTGCCCCTATAGTAACCCTTC

CCTCTGTAGTGGAGGGGGGGGTTCACCTGCTCCACGCCCTCCTACCCCCG

CGCCAACGATCGCGTCACAACCGCTCAGTCTTAGGCCGGAAGCCTGTAGG

CCAGCGGCTGGCGGTGCGGTTCATACGCGGGGATTGGATTTTGCCTGCGA

CATTTACATTTGGGCTCCGCTGGCCGGTACTTGTGGGGTATTGCTGTTGT

CTCTTGTTATTACGCTTTATTGCAATCACAGaAACAGGCGACGAGTATGC

AAATGCCCGCGGCCCGTCTG
```

In another example, the following exemplary RQR sequence tag can be affixed to a MHC-CAR construct as disclosed herein:

```
                                    (SEQ ID NO: 145)
ACPYSNPSLCSGGGGS ELPTQGTFSNVSTNVSPAKPTTTA CPYSNPSLCS

GGGGS
```

The boldfaced fragment is the rituximab minotope and the underlined/italicized fragment is the QBEND-10 epitope.

Suitable vectors and methods for producing vectors containing transgenes are well known and available in the art. Any of the vectors comprising a nucleic acid sequence that encodes a MHC-CAR construct described herein is also within the scope of the present disclosure. Such a vector may be delivered into host immune cells by a suitable method. Methods of delivering vectors to immune cells are well known in the art and may include DNA electroporation, RNA electroporation, transfection reagents such as liposomes, or viral transduction. In some embodiments, the vectors for expression of the MHC-CAR are delivered to host cells by viral transduction. Exemplary viral methods for delivery include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors, and adeno-associated virus (AAV) vectors (see, e.g., PCT Publication Nos. WO 94/12649, WO 93/03769; WO 93/19191; WO 94/28938; WO 95/11984 and WO 95/00655). In some embodiments, the vectors for expression of the chimeric receptors are retroviruses. In some embodiments, the vectors for expression of the chimeric receptors are lentiviruses.

In examples in which the vectors encoding chimeric receptors are introduced to the host cells using a viral vector, viral particles that are capable of infecting the immune cells and carry the vector may be produced by any method known in the art and can be found, for example in PCT Application No. WO 1991/002805A2, WO 1998/009271 A1, and U.S. Pat. No. 6,194,191. The viral particles are harvested from the cell culture supernatant and may be isolated and/or purified prior to contacting the viral particles with the immune cells.

Following introduction into the host cells a vector encoding any of the MHC-CAR provided herein, the cells are cultured under conditions that allow for expression of the chimeric receptor. In examples in which the nucleic acid encoding the MHC-CAR is regulated by a regulatable promoter, the host cells are cultured in conditions wherein the regulatable promoter is activated. In some embodiments, the promoter is an inducible promoter and the immune cells are cultured in the presence of the inducing molecule or in conditions in which the inducing molecule is produced. Determining whether the MHC-CAR is expressed will be evident to one of skill in the art and may be assessed by any known method, for example, detection of the chimeric receptor-encoding mRNA by quantitative reverse transcriptase PCR (qRT-PCR) or detection of the chimeric receptor protein by methods including Western blotting, fluorescence microscopy, and flow cytometry. See also Examples below. Alternatively, expression of the MHC-CAR may take place in vivo after the immune cells are administered to a subject.

Alternatively, expression of a MHC-CAR construct in any of the immune cells disclosed herein can be achieved by introducing RNA molecules encoding the MHC-CAR constructs. Such RNA molecules can be prepared by in vitro transcription or by chemical synthesis. The RNA molecules can then introduced into suitable host cells such as immune cells (e.g., T cells, NK cells, macrophages, neutrophils, eosinophils, or any combination thereof) by, e.g., electroporation. For example, RNA molecules can be synthesized and introduced into host immune cells following the methods described in Rabinovich et al., Human Gene Therapy, 17:1027-1035 and WO WO2013/040557.

The methods of preparing host immune cells expressing any of the MHC-CARs described herein may comprise expanding the host immune cells ex vivo. Expanding host immune cells may involve any method that results in an increase in the number of cells expressing MHC-CAR, for example, allowing the host cells to proliferate or stimulating the host cells to proliferate. Methods for stimulating expansion of host cells will depend on the type of host cell used for expression of the chimeric receptors and will be evident to one of skill in the art. In some embodiments, the host immune cells expressing any of the MHC-CAR described herein can be expanded ex vivo prior to administration to a subject.

(ii) Additional Genetic Modifications

One or more additional genetic modifications can be introduced into host immune cells before, concurrently with, or after the transfection of the MHC-CAR construction. For example, one or more marker and/or suicide genes may be introduced into the host immune cells. Examples include green fluorescent protein (GFP), enhanced blue fluorescent protein (eBFP), and RQR genes, such as RQR8 (a compact marker/suicide gene for T cells which combines target epitopes from CD34 and CD20. Philip et al., Blood 124(8): 1277-87; 2014). Such marker/suicide genes may be constructed in one expression cassette with the MHC-CAR components.

An example of an amino acid sequence of GFP is provided below:

(SEQ ID NO: 427)
VSKGEELFTGVVPILVELDGDVNGHKFSVSGEGEGDATYGKLTLKFICTT

GKLPVPWPTLVTTLTYGVQCFSRYPDHMKQHDFFKSAMPEGYVQERTIFF

KDDGNYKTRAEVKFEGDTLVNRIELKGIDFKEDGNILGHKLEYNYNSHNV

YIMADKQKNGIKANFKIRHNIEDGSVQLADHYQQNTPIGDGPVLLPDNHY

LSTQSALSKDPNEKRDHMVLLEFVTAAGITLGMDELYK

An example of a nucleic acid sequence encoding GFP is provided below:

(SEQ ID NO: 428)
gtgagcaagggcgaggagctgttcaccggggtggtgcccatcctggtgga gctggacggcgacgtaaacggccacaagttcagcgtgtctggcgagggcg agggcgatgccacctacggcaagctgaccctgaagttcatctgcaccacc ggcaagctgcccgtgccctggcccaccctcgtgaccaccctgacctacgg cgtgcagtgcttcagccgctaccccgaccacatgaagcagcacgacttct tcaagtccgccatgcccgaaggctacgtccaggagcgcaccatcttcttc aaggacgacggcaactacaagacccgcgccgaggtgaagttcgagggcga caccctggtgaaccgcatcgagctgaagggcatcgacttcaaggaggacg gcaacatcctggggcacaagctggagtacaactacaacagccacaacgtc tatatcatggccgacaagcagaagaacggcatcaaggcgaacttcaagat ccgccacaacatcgaggacggcagcgtgcagctcgccgaccactaccagc agaacacccccatcggcgacggccccgtgctgctgcccgacaaccactac ctgagcacccagtccgccctgagcaaagaccccaacgagaagcgcgatca catggtcctgctggagttcgtgaccgccgccgggatcactctcggcatgg acgagctgtacaagtaa In some instances, the endogenous TCR (alpha chain, beta chain, or both) can be disrupted such that the host immune cells do not express the endogenous TCR. Deficiency in endogenous TCR could avoid undesired T cell activation. Alternative or in addition, certain cell surface receptors can be knocked out. Such surface receptors may be target receptors for disease treatment, for example, CD52, which is a target for MS treatment. Knock-out such target receptors from the MHC-CAR immune cells allows for the co-use of the MHC-CAR immune cells with therapeutic agents specific to the target receptor (e.g., and anti-CD52 antibodies such as alemtuzumab).

In some embodiments, the host immune cells may be modified with synthetic surface proteins to enhance their retention in a specific organ or tissue, for example, in the lymph nodes, in tertiary lymphoid organs, or at sites of inflammation. Doing so would allow the modified immune cells to access target pathogenic cells, while minimizing fatal off-target effects due to penetration of the blood brain barrier or free travel of the immune cells through peripheral blood. Cells early in the T cell differentiation pathway (e.g., naïve, stem cell memory, and central memory T cells) travel freely to the lymph nodes. As differentiation progresses, most effector T cells leave the lymph node. Pathologic immune cells can also travel to and accumulate at sites of inflammation. Treatment by activated CAR-T cells has a number of undesirable effects when they react with undesired targets. Interaction with heart tissue can be fatal to cardiac protein, and permeation of the brain can lead to fatal cerebral edema. Recent progress has been made in treatment of the brain cancer gliobastoma using lower doses of CAR T therapy than in systemic treatments for cancer using CD19 CAR T therapy. Brown et al., New England Journal of Medicine, 375(26):2561-2569, 2016. Resolution of inflammation has the potential to transform pathologic to protective environments. Gagliani et al., Nature, 523(7559):221-225, 2015.

Introducing one or more of lymph node retention proteins into the immune cells can enhance retention of the immune cells in the lymph node, wherein the immune cells still have access to target pathogenic cells, while undesired effects as noted above can be significantly reduced. Naïve lymphocytes enter the lymph node via high endothelial venules (HEVs). Thus, expressing or overexpressing proteins involved in HEV anchoring and/or entry can facilitate the immune cells entering into lymph node. Exemplary lymph node retention proteins include, but are not limited to, CCR7 (a chemokine receptor). MECA79 (a peripheral lymph node addressin), vascular adhesion protein-1 (VAP-1) and CD62 (selectin, a family of the cell adhesion molecules). Azzi et al., Blood 124(4):476-477, 2016; Streeter et al., J. Cell. Biol. 107:1853-186; 1988; Michie et al., Amer, J. Path. 143:1688-1698; 1993; Berg et al., J. Cell. Biol. 114:343-349; 1991; Berg et al., Nature 366:695-698; 1993; and Hemmerich et al., J. Exp. Med. 180:2219-2226; 1994. Alternatively, genes encoding proteins (e.g., sphingosine-1-phosphate receptor-1 or S1P) involved in lymphocyte egress from the thymus and lymph organs can be knocked out from the immune cells.

Chemokine receptors and adhesion receptors that promote trafficking to sites of inflammation can also bring MHC-CAR immune cells in contact with pathogenic cells that propagate immune disease [Barreiro et al., Cardiovascular research, 86(2):174-182, 2010] see Table 3 and 4. Receptors involved in recruiting immune cells that propagate inflammation include receptors (i.e., CXCR5, CCR7, CCR6) that recruit to tertiary lymphoid organs (where CXCL13, CCL19, CCL20, CCL21 are expressed).

One or more genes encoding proteins involved in targeting other organs/tissues, for example, brain/CNS, bone marrow, pancreas, intestine, liver, lungs, spleen, and/or thymus, may also be introduced into or knocked-out from the immune cells.

The genes (in Table 3 and 4), by means of virally induced or temporary RNA mediated expression (possibly combined with knockout of the endogenous gene) in the therapeutic cell, may be used to route either Treg or CM cells to the desired location or to treat/remove the desired cells. Barreiro, et al. Cardiovascular research, 86(2):174-182, 2010. If mRNA transfection is utilized then it can allow expression of the chemokine or adhesion receptor for a week. Wang and Rivière. Molecular Therapy-Oncolytics, 3:16015 2016.

TABLE 3

Chemokine receptors and natural context

| Receptor | Typically expressed on | GenBank Accession number | Ligands |
| --- | --- | --- | --- |
| CXCR1 | Neutrophils | AAY21515.1 | CXCL8, CXCL6 |
| CXCR2 | Neutrophils | NP_001548.1 | CXCL1, 2, 3, 4, 5, 7 |
| CXCR3 | T cells and some B cells | NP_001495.1 | CXCL9, 10, 11 |
| CXCR4 | Most mature and immature hematopoietic cells | CAA12166.1 | CXCL12 |
| CXCR5 | B cells and Tfh cells | NP_001707.1 | CXCL13 |
| CXCR6 | Inflammation response T cells but weak chemotaxis | NP_006555.1 | CXCL16 |
| CXCR7 | Memory B cells, T cells | NP_064707.1 | CXCL12 |
| CCR1 | Peripheral lymphocytes, memory T cells | NP_001286.1 | CCL4, CCL5, CCL6, CCL14, CCL15, CCL16, CCL23 |
| CCR2 | Monocytes, activated memory T cells, B cells, basophils | AAA19119.1 | CCL11, CCL26, CCL7, CCL13, CCL15, CCL24 & CCL5, CCL28 |
| CCR3 | Plays a role in allergic reactions, B and T cells to mucous, eosinophils, basophils | NP_001828.1 | CCL11, CCL26, CCL7, CCL13, CCL15, CCL24, CCL5 |

TABLE 3-continued

Chemokine receptors and natural context

| Receptor | Typically expressed on | GenBank Accession number | Ligands |
|---|---|---|---|
| CCR4 | Th2 lymphocytes, dendritic cells | NP_005499.1 | CCL3, CCL5, CCL17, CCL22 |
| CCR5 | Peripheral blood dendritic cells, CD34+ hematopoietic progenitors, activated/memory Th1 | NP_000570.1 | CCL2, CCL3, CCL4, CCL5, CCL11, CCL13, CCL14, CCL16 |
| CCR6 | Inactivated memory T cells, dendritic cells, Th17, downregulated on activated T cells | AAC51124.1 | CCL20 |
| CCR7 | Trafficking of B, T, and dendritic cells across HEV and into T cell zone of lymph nodes | AAH35343.1 | CCL19, CCL21 |
| CCR8 | Th2 cells, thymus, lymph nodes, spleen, brain, monocytes | NP_005192.1 | CCL1, CCL16 |
| CCR9 | Thymus, gut | NP_112477.1 | CCL25 |
| CCR10 | Skin, mucous layers, regulatory T cells | NP_057686.2 | CCL27, CCL28 |
| XCR1 | | NP_005274.1 | XCL1, XCL2 |
| CX3CR1 | | NP_001164642.1 | CX3CL1 |

The amino acid sequence of CCR6, provided by AAC51124.1 is shown below:

(SEQ ID NO: 391)
MSGESMNFSDVFDSSEDYEVSVNTSYYSVDSEMLLCSLQEVRQFSRLFVP

IAYSLICVFGLLGNILVVITFAFYKKARSMTDVYLLNMAIADILFVLTLP

FWAVSHATGAWVFSNATCKLLKGIYAINFNCGMLLLTCISMDRYIAIVQA

TKSFRLRSRTLPRSKIICLVVWGLSVIISSSTFVFNQKYNTQGSDVCEPK

YQTVSEPIRWKLLMLGLELLFGFFIPLMFMIFCYTFIVKTLVQAQNSKRH

KAIRVIIAVVLVFLACQIPHNMVLLVTAANLGKMNRSCQSEKLIGYTKTV

TEVLAFLHCCLNPVLYAFIGQKFRNYFLKILKDLWCVRRKYKSSGFSCAG

RYSENISRQTSETADNDNASSFTM

Example nucleic acid sequences of CCR6 are shown below:

(SEQ ID NO: 392)
atgagtggggaaagtatgaacttcagcgatgtatttgactcctccgaaga ttactttgtatctgtgaatacgagctattactccgtcgatagtgaaatgc tgctctgtagtctccaagaagtccgccaattcagtcgcctcttcgttccc atcgcgtactcccttatttgtgttttggccttctgggtaacatcctggt tgtaatcacattcgcttcctataaaaaagctcggagtatgactgatgttt accttcttaacatggctatagcggacattcttttttgtgcttactctcca ttctgggctgtgagccatgcaacaggggcgtgggttttttcaaatgccac atgtaagctgcttaaagggatctatgcaataaacttcaattgcgggatgc tcctgctgacatgcatcagtatggatcgatacatagctatagtacaggcg actaagtccttccgcctgcgatcccgcacactgcctaggagcaaaattat ttgcctcgtcgtatgggggctctcagtgatcatctcctccagtacgtttg tctttaaccagaaatataacacacagggttctgatgtatgtgaaccaaag tatcagacagtgagtgaaccaatacggtggaagttgcttatgttgggctt ggagctgctttttgggttttcatcccactgatgttcatgattttctgtt atacatttattgttaagaccttggttcaggcgcaaaatagcaagagacat aaggcaattcgagtcatcattgccgtggtgttggtcttcttggcctgtca gatcccccataatatggttctgctcgtcaccgccgctaacttgggtaaga tgaatcgatcttgtcagtcgagaagttgatggatacaccaaaactgtg acagaagtgctggccttccttcactgttgtctgaacccagttttgtatgc ttttataggacagaagtttcgaaattacttcttgaaaatcctcaaggacc tctggtgtgttcgaaggaagtacaagagctctggctttagttgcgctggg cgctacagtgagaatatcccggcagacctccgagactgctgataatga caacgcaagttccttcactatg (SEQ ID NO: 393)
ATGAGCGGGGAATCAATGAATTTCAGCGATGTTTTCGACTCCAGTGAAGA

TTATTTTGTGTCAGTCAATACTTCATATTACTCAGTTGATTCTGAGATGT

TACTGTGCTCCTTGCAGGAGGTCAGGCAGTTCTCCAGGCTATTTGTACCG

ATTGCCTACTCCTTGATCTGTGTCTTTGGCCTCCTGGGGAATATTCTGGT

GGTGATCACCTTTGCTTTTTATAAGAAGGCCAGGTCTATGACAGACGTCT

-continued
```
ATCTCTTGAACATGGCCATTGCAGACATCCTCTTTGTTCTTACTCTCCCA

TTCTGGGCAGTGAGTCATGCCACTGGTGCGTGGGTTTTCAGCAATGCCAC

GTGCAAGTTGCTAAAAGGCATCTATGCCATCAACTTTAACTGCGGGATGC

TGCTCCTGACTTGCATTAGCATGGACCGGTACATCGCCATTGTACAGGCG

ACTAAGTCATTCCGGCTCCGATCCAGAACACTACCGCGCACGAAAATCAT

CTGCCTTGTTGTGTGGGGGCTGTCAGTCATCATCTCCAGCTCAACTTTTG

TCTTCAACCAAAAATACAACACCCAAGGCAGCGATGTCTGTGAACCCAAG

TACCAGACTGTCTCGGAGCCCATCAGGTGGAAGCTGCTGATGTTGGGGCT

TGAGCTACTCTTTGGTTTCTTTATCCCTTTGATGTTCATGATATTTTGTT

ACACGTTCATTGTCAAAACCTTGGTGCAAGCTCAGAATTCTAAAAGGCAC

AAAGCCATCCGTGTAATCATAGCTGTGGTGCTTGTGTTTCTGGCTTGTCA

GATTCCTCATAACATGGTCCTGCTTGTGACGGCTGCAAATTTGGGTAAAA

TGAACCGATCCTGCCAGAGCGAAAAGCTAATTGGCTATACGAAAACTGTC

ACAGAAGTCCTGGCTTTCCTGCACTGCTGCCTGAACCCTGTGCTCTACGC

TTTTATTGGGCAGAAGTTCAGAAACTACTTTCTGAAGATCTTGAAGGACC

TGTGGTGTGTGAGAAGGAAGTACAAGTCCTCAGGCTTCTCCTGTGCCGGG

AGGTACTCAGAAAACATTTCTCGGCAGACCAGTGAGACCGCAGATAACGA

CAATGCGTCGTCCTTCACTATG
```

TABLE 4

Adhesion receptors and natural context

| Receptor | Typically expressed on | Accession number | Ligands |
|---|---|---|---|
| VLA-1 or $\alpha_1\beta_1$ | Many cell types | NP_852478.1, AAH20057.1 | Collagens, laminins |
| VLA-2 or $\alpha_2\beta_1$ | Many cell types | NP_002194.2, AAH20057.1 | Collagens, laminins |
| VLA-3 or $\alpha_3\beta_1$ | Many cell types | AAI50191.1, AAH20057.1 | Laminin-5 |
| VLA-4 or $\alpha_4\beta_1$ | Hematopoietic cells | NP_000876.3, AAH20057.1 | Fibronectin and proteinases |
| VLA-5 or $\alpha_5\beta_1$ | Many cell types | NP_002196.4, AAH20057.1 | Fibronectin, VCAM-1 |
| VLA-6 or $\alpha_6\beta_1$ | Many cell types | AAI36456.1, AAH20057.1 | Laminins |
| $\alpha_4\beta_7$ | Gut | NP_000876.3, NP_00880.1 | MADCAM1 |
| $\alpha_7\beta_1$ | Muscle | AAQ89241.1, AAH20057.1 | Laminins |
| $\alpha_L\beta_2$ | T lymphocytes | NP_002200.2, NP_000202.3 | I-CAM1, I-CAM2 |
| MAC-1 or $\alpha_M\beta_2$ | Neutrophils and monocytes | AAB24821.1, NP_000202.3 | I-CAM1 |
| $\alpha_{IIb}\beta_3$ | Platelets | AAI26443.1, AAI27668.1 | Fibrinogen, fibronectin |
| $\alpha_v\beta_1$ | Melanocytes | AAA61631.1, AAH20057.1 | Vitronectin, fibrinogen |
| $\alpha_v\beta_3$ | Activated endothelial cells | AAA61631.1, AAI27668.1 | Vitronectin, fibronectin, fibrinogen, osteopontin, Cyr61, tyroxine, Tetrac |
| $\alpha_v\beta_5$ | Epithelial cells and fibroblasts | AAA61631.1, NP_002204.2 | Vitronectin |
| $\alpha_v\beta_6$ | Lung, mammary gland | AAA61631.1, NP_000879.2 | Fibrinonectin and TGF-β 1, 3 |
| $\alpha_v\beta_8$ | Neural tissues | AAA61631.1, NP_002205.1 | Fibrinonectin and TGF-β 1, 3 |
| $\alpha_6\beta_4$ | Epithelial cells | AAA61631.1, CAB61345.1 | Laminin |

Alternatively or in addition, genes that may enhance immune cell functions, e.g., proliferation, cytotoxicity, etc., can also be introduced into or knocked-out from the immune cells. Examples include TNF/TNFR2 overexpression (for short-lived but more effective CD8 T cells), gld (FasL mutant; for lymphoproliferation; CTLs do not kill via Fas-FasL pathway); lpr (Fas mutant; for upregulation of FasL-target cells resistant to FasL-mediated apoptosis); Granzyme B* deficient (delayed nuclear apoptotic changes in target cells); Granzyme A & B* deficient (delayed nuclear apoptotic changes in target cells); Perforin deficient (complete absence of granule-mediated apoptosis); Perforin and Fast, deficient (defective granule-mediated and Fas-mediated apoptosis); Cathepsin C (dipeptidyl-peptidase 1) deficient (fails to produce active granzymes and some haematopoietic serine proteases); FAS (CD95) underexpression; and/or FASL overexpression.

Table 5 below lists additional genetic modifications of the MHC-CAR T cells or co-treatment described herein and the accompanying advantages arising therefrom.

TABLE 5

Genetic Modifications or Co-Treatment and Benefits Thereof

| Genetic Modifications | Advantages |
|---|---|
| TCR knockout CIITA deletion (to remove endogenous MHC class II expression) CS-1 (CD319) deletion (which is present on T cells) | Reduce fraternal killing of MHC-CAR T cells by natural CD8+ T cells with an affinity to the peptide-MHC in the MHC-CAR, thereby extending the life-span of the MHC-CAR T cells. (Without the genetic modifications, the MHC-CAR T cells would still be cytotoxic and effective, but would have a short life-span.) |
| Fas deletion, which optionally can be in combination of FasL overexpression PD-1 deletion, which optionally can be in combination with PD-L1 and/or PD-L2 overexpression Co-express of CS-1 CAR (conventional CAR construct having an extracellular domain specific to CS-1) Co-express of CD19 CAR (conventional CAR construct having an extracellular domain specific to CD19) | Enhance activity to eliminate CD8 cytotoxic T cells, antigen-presenting cells (APCs), and/or B cells |
| PD-L1 overexpression, which may optionally be in combination with PD-1 deletion PD-L1 + CTLA4-Ig, which may optionally may be in combination with PD-1 deletion | Reduce the level of MHC-CAR T cell elimination by other immune cells; Inclusion of hinge may decrease/prevent killing with cell TCR by, e.g., decreasing ability for |

TABLE 5-continued

Genetic Modifications or Co-Treatment and Benefits Thereof

| Genetic Modifications | Advantages |
|---|---|
| FasL overexpression, which may optionally be in combination with Fas deletion | it to engage CD4 or CD8 |
| Galectin 9 expression, which may optionally be in combination with Tim-3 deletion | |
| CS-1 deletion (when CS-1 CAR is used to reduce fraternal killing) | |
| Include a hinge in a MHC-CAR | |
| TCR knockout when allogenic cells are used (cells can be sorted to remove non-edited cells) | Reduce the risk of graft-v-host disease |
| Treg cells expressing MHC-CAR PD-1 and/or PD-L1 knockout CXCR5 expression | Reduce humoral responses to the peptide-MHC of interest (e.g., antibody responses), especially a B cell response |
| IL-35 expression | Reduce inflammation and/or enhance tolerogenic environment |
| Inhibitors (e.g., antibodies) targeting cytokine producing B cells (e.g., targeting CD10) and/or other activated immune cells (e.g., targeting CS-1) | |
| Relevent chemokine receptor expression to either direct to relevant organ (Schall et al., Nature Reviews Immunology, 11(5): 355-363, 2011) or to interact with relevant cell type (example, CXCR5 for B cell, CCR6 for Th17) | Routing to inflamed or antigen presenting or antigen targeting environment |
| Antigen targeting antibody scFv that contains a CD8 hinge, a transmembrane domain, and optional stimulatory and co-stimulatory domain (for Treg only). (for example an anti-MOG antibody). The relevant antibody sequence (for a subset of antigen targets in Table 1) can be generated from sequencing of commercially available human-targeted monoclonal variants using mass spectrometry. Tran et al. Scientific reports, 6: 31730, 2016. | |
| Genetically encoded kill-switches | Reduce cytokine crisis |

In some embodiments, genetic modification that lead to PD blockade can be introduced into the immune cells that express a MHC-CAR as described herein. Such modifications include one or more of PD-1 knockout, PD-L1 or L2 overexpression, or PD-L1 knockout, PD blockade may be combined with an immune-inhibitor (e.g., knockouts of CTLA-4, TIM-3, LAG3, TIGIT, IDO, or Arginase, or CTLA-4Ig secretion), an immunostimulator (e.g., anti-OX40, anti-CD137, IL-2, TLR ligands, or STING), and/or a kinase inhibitor Braf inhibitor or MEK inhibitor)

Table 6 below provides exemplary genetic modifications for PD blockade, immune inhibitor, death receptor, immunostimulator, toll like receptor, kinase inhibition, master regulator, cytokine signaling, cell interaction reduction, and drug interaction related edits. The tables also provides target sequences for guide RNA using Cas9 in T cells as well as Genbank accession numbers for sequences that can be used for expression/overexpression. Genome editing using gRNAs is performed through transduction of lentivirus (lentiCRISPRv2) containing the desired gRNA and the *Streptococcus pyogenes* Cas9 nuclease. This can be perform as an alternative to delivery of TALEN RNA in the protocols. Sanjana, et al. *Nature Methods* (2014) 11(8):783-784.

TABLE 6

Exemplary Genes for Genetic Modification and Corresponding Cas9-Mediated Edits

| PD blockade related edits | Genbank accession no. | Genomic sequences (gRNA) for Cas9 targeting |
|---|---|---|
| Programmed cell death protein 1 (PDCD1) | NP_005009.2 | TGACGTTACCTCGTGCGGCC (SEQ ID NO: 146), CACGAAGCTCTCCGATGTGT (SEQ ID NO: 147), GCGTGACTTCCACATGAGCG (SEQ ID NO: 148), TTGGAACTGGCCGGCTGGCC (SEQ ID NO: 149), GTGGCATACTCCGTCTGCTC (SEQ ID NO: 150), GATGAGGTGCCCATTCCGCT (SEQ ID NO: 151), |
| Programmed cell death 1 ligand 1 (CD274) | NP_005009.2 | TACCGCTGCATGATCAGCTA (SEQ ID NO: 152), AGCTACTATGCTGAACCTTC (SEQ ID NO: 153), GGATGACCAATTCAGCTGTA (SEQ ID NO: 154), ACCCCAAGGCCGAAGTCATC (SEQ ID NO: 155), TCTTTATATTCATGACCTAC (SEQ ID NO: 156), ACCGTTCAGCAAATGCCAGT (SEQ ID NO: 157) |

TABLE 6-continued

Exemplary Genes for Genetic Modification and Corresponding Cas9-Mediated Edits

| Immune-inhibitor related edits | Genbank accession no. | Genomic sequences for Cas9 targeting |
|---|---|---|
| Cytotoxic T-lymphocyte protein 4 (CTLA4) | NP_005205.2 | GTACCCACCGCCATACTACC (SEQ ID NO: 158), TTGCCTATGCCCAGGTAGTA (SEQ ID NO: 159), CCTTGTGCCGCTGAAATCCA (SEQ ID NO: 160), ACCCCGAACTAACTGCTGCA (SEQ ID NO: 161), ACATAGACCCCTGTTGTAAG (SEQ ID NO: 162), ATCCTTGCAGCAGTTAGTTC (SEQ ID NO: 163) |
| CTLA4-Ig (Orencia) | APZ76727.1 | |
| Serine/threonine-protein phosphatase 2A catalytic subunit alpha isoform (PPP2CA) | NP_002706.1 | ACATCGAACCTCTTGCACGT (SEQ ID NO: 164), TACAGCTCACCTTCTCGCAG (SEQ ID NO 165):, GGTATATCTCCTCGAGGAGC (SEQ ID NO: 166), TACACTGCTTGTAGCTCTTA (SEQ ID NO: 167), GAGCTCTAGACACCAACGTG (SEQ ID NO: 168), CAAGCAGCTGTCCGAGTCCC (SEQ ID NO: 169) |
| Serine/threonine-protein phosphatase 2A catalytic subunit beta isoform (PPP2CB) | CAA31183.1 | AATGTGTAGCCAGCACCACG (SEQ ID NO: 170), GAACTTCCTGTAAACGATCC (SEQ ID NO: 171), TACATACCTCCATTACAAGC (SEQ ID NO: 172), CCATCTACTAAAGCTGTAAG (SEQ ID NO: 173), CTCAATATTGTAATGCGTTC (SEQ ID NO: 174), CTCTCCATCCATAGACACAC (SEQ ID NO: 175) |
| Protein tyrosine phosphatase, non-receptor type 6 (PTPN6) | AAA35963.1 | TAAGACCTACATCGCCAGCC (SEQ ID NO: 176), GAAGAACTTGCACCAGCGTC (SEQ ID NO: 177), GTCAGCCGCATTCACCCTCG (SEQ ID NO: 178), CTGCCAGAAGTCATTGACCG (SEQ ID NO: 179), CCCAGCCGTACTATGCCACG (SEQ ID NO: 180), GCCGCTGCCCTTCCAGACGC (SEQ ID NO: 181) |
| Tyrosine-protein phosphatase non-receptor type 22 (PTPN22) | AAD00904.1 | GTAGCGGAATCCTCATCAG (SEQ ID NO: 182), CAAAACCTATCCTACAACTG (SEQ ID NO: 183), TTAGGGAGTTTATGGACCCA (SEQ ID NO: 184), CTCAGCCACAGTTGTAGGAT (SEQ ID NO: 185), TCACTGTACCTTAATGAAGT (SEQ ID NO: 186), TCCTTTATCTACAACCCTCC (SEQ ID NO: 187) |
| Lymphocyte activation gene 3 protein (LAG3) | CAA36243.3 | TCCATAGGTCCCCAACGCTC (SEQ ID NO: 188), GTTCCGGAACCAATGCACAG (SEQ ID NO: 189), GCGAGAAGTCCCCGCGCTGC (SEQ ID NO: 190), TGACCCCTGCTCTTCGCAGA |

TABLE 6-continued

Exemplary Genes for Genetic Modification and Corresponding Cas9-Mediated Edits

| Gene | Accession | Sequences |
|---|---|---|
| | | (SEQ ID NO: 191), CGCCGGCGAGTACCGCGCCG (SEQ ID NO: 192), TGGGCGGTCAGGGCGGCTGA (SEQ ID NO: 193) |
| Hepatitis A virus cellular receptor 2 (Tim3, HAVCR2) | AAM19100.1 | CTAAATGGGGATTTCCGCAA (SEQ ID NO: 194), ATCCCCATTTAGCCAGTATC (SEQ ID NO: 195), GTGAAGTCTCTCTGCCGAGT (SEQ ID NO: 196), AGGTCACCCCTGCACCGACT (SEQ ID NO: 197), CTTACTGTTAGATTTATATC (SEQ ID NO: 198), TATAGCAGAGACACAGACAC (SEQ ID NO: 199) |
| B- and T-lymphocyte attenuator (BTLA) | AAP44003.1 | GTGACTTGGTGCAAGCTCAA (SEQ ID NO: 200), TCTGCTTGCCATTTCGTCCT (SEQ ID NO: 201), CTGTTAGCACAGTATTTCAC (SEQ ID NO: 202), CCAAAGGAAGTAAACGATAC (SEQ ID NO: 203), ATGTTCCAGATGTCCAGATA (SEQ ID NO: 204), CTTCTTCTTAATCCCATATC (SEQ ID NO: 205) |
| CD160 antigen (CD160) | AAC72302.1 | AGTTTAGTCGCGTTCCTTCC (SEQ ID NO: 206), CACTGTGCAACGGTGTGACT (SEQ ID NO: 207), GGATGTCCACAATTGCCAGC (SEQ ID NO: 208), AACTGAGAGTGCCTTCATTA (SEQ ID NO: 209), GACAGGGAACTACACAGTGA (SEQ ID NO: 210), GACAGGGAACTACACAGTGA (SEQ ID NO: 210), ATTGTGGACATCCAGTCTGG (SEQ ID NO: 212) |
| T-cell immunoreceptor with Ig and ITIM domains (TIGIT) | BAC04973.1 | TCGCTGACCGTGAACGATAC (SEQ ID NO: 213), TGGGGCCACTCGATCCTTGA (SEQ ID NO: 214), GCAGATGACCACCAGCGTCG (SEQ ID NO: 215), TCAGGCCTTACCTGAGGCGA (SEQ ID NO: 216), CATCTGCACAGCAGTCATCG (SEQ ID NO: 217), ATTGAAGTAGTCATGCAGCT (SEQ ID NO: 218) |
| T-cell surface protein tactile (CD96) | AAA36662.1 | AGGCACAGTAGAAGCCGTAT (SEQ ID NO: 219), GCTGTCTATCATCCCCAATA (SEQ ID NO: 220), ACTTACCACCGACCATGCAT (SEQ ID NO: 221) |
| Cytotoxic and regulatory T-cell molecule (CRTAM) | AAC80267.1 | CACACTTTAGAGTGAGCGTC (SEQ ID NO: 222), CTCCAGTGGCTGACCCCCTC (SEQ ID NO: 223), CCACAGCAGCCCACCAGTAC (SEQ ID NO: 224) |
| Leukocyte-associated immunoglobulin-like receptor 1 (LAIR1) | AF013249.1 | TTATAATAGATGCAGCGATA (SEQ ID NO: 225), TCATTGIGACTGTTGTCCGA |

TABLE 6-continued

Exemplary Genes for Genetic Modification and Corresponding Cas9-Mediated Edits

| | | |
|---|---|---|
| | | (SEQ ID NO: 226), GCCAGGCACCGTGATCCCCC (SEQ ID NO: 227) |
| Sialic acid-binding Ig-like lectin 7 (SIGLEC7) | AF170485.1 | CATCCTTATCCCCGGTACCC (SEQ ID NO: 228), CAGAGAGCTTCTGAGCTCGAC (SEQ ID NO: 229), AGTGTTGCTGGGGGCGGTCG (SEQ ID NO: 230 |
| Sialic acid-binding Ig-like lectin 9 (SIGLEC9) | AF135027.1 | GACGATGCAGAGTTCCGTGA (SEQ ID NO: 231), ACTCACAGGACACGTTGAGA (SEQ ID NO: 232), TACCCTGGCCCAGTAGTTCA (SEQ ID NO: 233) |
| Natural killer cell receptor 2B4 (CD244) | AF105261.1 | ACCTTCGTCTGTATGCTGTT (SEQ ID NO: 234), ACCAAACAGCATACAGACGA (SEQ ID NO: 235), CTACTCTATGATCCAGTCCC (SEQ ID NO: 236) |

Death receptors and pathway edits

| | | |
|---|---|---|
| Tumor necrosis factor ligand superfamily member 10 (TRAIL) | AAC50332.1 | ACTCCGTCAGCTCGTTAGAA (SEQ ID NO: 237), GTTCATACTCTCTTCGTCAT (SEQ ID NO: 238), AGAGTAGCAGCTCACATAAC (SEQ ID NO: 239) |
| Tumor necrosis factor receptor superfamily member 10B (TNFRSF10B) | AF018657.1 | TTCCAGAGCTCACAACGACC (SEQ ID NO: 240), ATAGTCCTGTCCATATTTGC (SEQ ID NO: 241), AGATACTCACGATCTCATTG (SEQ ID NO: 242) |
| Tumor necrosis factor receptor superfamily member 10A (TNFRSF10A) | AAC51226.1 | AGGTCAAGGATTGTACGCCC (SEQ ID NO: 243), GAAGTCCCTGCACCACGACC (SEQ ID NO: 244), TTTGGTTGTTCCGTTGCTGT (SEQ ID NO: 245) |
| Caspase-8 (CASP8) | CAA66853.1 | TGATCGACCCTCCGCCAGAA (SEQ ID NO: 246), GGGTCGATCATCTATTAATA (SEQ ID NO: 247), TCCTTTGCGGAATGTAGTCC (SEQ ID NO: 248) |
| Caspase-10 (CASP10) | AAC50644.1 | CTATGTATCCTTTCGGCATG (SEQ ID NO: 249), TCTTCTGCCGTATGATATAG (SEQ ID NO: 250), GTGAGACATGATCTCCCGAA (SEQ ID NO: 251) |
| Caspase-3 (CASP3) | AAA65015.1 | ATGTCGATGCAGCAAACCTC (SEQ ID NO: 252), ATTATACATAAACCCATCTC (SEQ ID NO: 253), AATGGACTCTGGAATATCCC (SEQ ID NO: 254) |
| Caspase-6 (CASP6) | AAC50168.1 | ATAGAGACAATCTTACCCGC (SEQ ID NO: 255), AAGATTGTCTCTATCTGCGC (SEQ ID NO: 256), AAATGTGATTGCCTTCGCCA (SEQ ID NO: 257) |

TABLE 6-continued

Exemplary Genes for Genetic Modification and Corresponding Cas9-Mediated Edits

| | | |
|---|---|---|
| Caspase-7 (CASP7) | AAC50303.1 | CGTTTGTACCGTCCCTCTTC (SEQ ID NO: 258), TGCGATCCATCAAGACCACC (SEQ ID NO: 259), TTGATATTTAGGCTTGCCGA (SEQ ID NO: 260) |
| FAS-associated death domain protein (FADD) | AAA86517.1 | AGTCGTCGACGCGCCGCAGC (SEQ ID NO: 261), AGCGGCCCATCAGGACGCTT (SEQ ID NO: 262), GCGGCGCGTCGACGACTTCG (SEQ ID NO: 263) |
| Tumor necrosis factor receptor superfamily member 6 (FAS) | AAA63174.1 | GTGTAACATACCTGGAGGAC (SEQ ID NO: 264), TACATCTGCACTTGGTATTC (SEQ ID NO: 265), CTAAAACTTACTTGGTGCAA (SEQ ID NO: 266) |
| IDO | AAA36081.1 | TCTCAACTCTTTCTCGAAGC (SEQ ID NO: 267), CTGCCTGATCTCATAGAGTC (SEQ ID NO: 268), CAGATACTTACTCATAAGTC (SEQ ID NO: 269) |
| Arginase EIF2AK4 | AAH09350.2 | CGCTGAGAAATGACTGCACG (SEQ ID NO: 270), CATATACTTCTTCACCAGTT (SEQ ID NO: 271), ATGTACTCACACATCTGGAT (SEQ ID NO: 272) |
| Immunostimulator edits | | |
| OX40 (TRAF2) | BAA14259.1 | ACCGAATGTCCCGCGTGCAA (SEQ ID NO: 273), GCCTTTGCACGCGGGACATT (SEQ ID NO: 274), GGGGACCCTGAAAGAATACG (SEQ ID NO: 275) |
| CD137 (TNFRSF9) | TNFRSF9 | CCTGCGCTGGAGAAACTATT (SEQ ID NO: 276), CCTTGTAGTAACTGCCCAGC (SEQ ID NO: 277), CATAGTAGCCACTCTGTTGC (SEQ ID NO: 278) |
| IL2 | CAA25292.1 | CAATATCAACGTAATAGTTC (SEQ ID NO: 279), GACTTAGTGCAATGCAAGAC (SEQ ID NO: 280), GATATTGCTGATTAAGTCCC (SEQ ID NO: 281) |
| Stimulator of interferon genes protein (STING or TMEM173) | AC146648.1 | GCGGGCCGACCGCATTTGGG (SEQ ID NO: 282), CATATTACATCGGATATCTG (SEQ ID NO: 283), ACTCTTCTGCCGGACACTTG (SEQ ID NO: 284) |
| Toll like receptor edits | | |
| TLR1 | AAC34137.1 | TTATAGAGGAACCCTACTAA (SEQ ID NO: 285), TTGTGGGCACCTTACTGAGT (SEQ ID NO: 286), CGAACACATCGCTGACAACT (SEQ ID NO: 287) |
| TLR2 | AAC34377.1 | GTTAACGTTTCCACTTTACC (SEQ ID NO: 288), TTCCCGCTGAGCCTCGTCCA |

TABLE 6-continued

Exemplary Genes for Genetic Modification and Corresponding Cas9-Mediated Edits

| | | |
|---|---|---|
| | | (SEQ ID NO: 289), TATCTAATTTATCGTCTTCC (SEQ ID NO: 290) |
| TLR3 | AAC34134.1 | TTCGGAGCATCAGTCGTTGA (SEQ ID NO: 291), TTCAACGACTGATGCTCCGA (SEQ ID NO: 292), CATGCACTCTGTTTGCGAAG (SEQ ID NO: 293) |
| TLR4 | AAC80227.1 | TTCTCCCAGAACCAAACGA (SEQ ID NO: 294), GATGATGTCTGCCTCGCGCC (SEQ ID NO: 295), ATGCCCCATCTTCAATTGTC (SEQ ID NO: 296) |
| TLR5 | AAC34376.1 | TATTCGGCCATCAAAGGAGC (SEQ ID NO: 297), GACTAAGCCTCAACTCCAAC (SEQ ID NO: 298), TATACAACICTATTAGCTGCG (SEQ ID NO: 299) |
| TLR6 | BAA78631.1 | GAACTACATCGCTGAGCTIC (SEQ ID NO: 300), GCCATCCTATTGTGAGTTTC (SEQ ID NO: 301), TGTCTCCAATTTAACTAACG (SEQ ID NO: 302) |
| TLR7 | AAF60188.1 | AAGGAATAGTCACCTCCGTA (SEQ ID NO: 303), AATGGGGCATTATAACAACG (SEQ ID NO: 304), GGTGAGGTTCGTGGTGTTCG (SEQ ID NO: 305) |
| TLR8 | AAF64061.1 | GTGCAGCAATCGTCGACTAC (SEQ ID NO: 306), AATCCCGGTATACAATCAAA (SEQ ID NO: 307), CTCGAGTTGCTTGACTTACG (SEQ ID NO: 308) |
| TLR9 | AAF72189.1 | GGCTCACGGCTATTCGGCCG (SEQ ID NO: 309), GCGTCTCCGTGACAATTACC (SEQ ID NO: 310), CCGACAGGTCCACGTAGCGC (SEQ ID NO: 311) |
| TLR10 | AAK26744.1 | CCCACATTTACGCCTATCCT (SEQ ID NO: 312), TAACATTAATAGCAGCTCGA (SEQ ID NO: 313), GACCCCAGCCACAACGACAC (SEQ ID NO: 314) |
| Kinase inhibition edits | | |
| Serine/threonine-protein kinase B-raf (BRAF) | AAA35609.2 | CCCCACCAAATTTGTCCAAT (SEQ ID NO: 315), GAGGCCCTATTGGACAAATT (SEQ ID NO: 316), GTTGCTCCGTGCCACATCTG (SEQ ID NO: 317) |
| Dual specificity mitogen-activated protein kinase kinase 1 (MAP2K or MEK) | AAA36318.1 | CCATACTTACTCCGCAGAGC (SEQ ID NO: 318), TATGGTGCGTTCTACAGCGA (SEQ ID NO: 319), CCCGACGGCTCTGCAGTTAA (SEQ ID NO: 320) |

TABLE 6-continued

Exemplary Genes for Genetic Modification and Corresponding Cas9-Mediated Edits

| | | |
|---|---|---|
| Master regulator edits | | |
| FoxP3 | AA053607.I | |
| Cytokine signaling edits (The goal of one or both of these edits is to prevent or minimize conversion of therapeutic Tregs into Th17 cells due to endogeonous IL-6, Gagliani et al. *Nature*, 523(7559): 221-225 2015, Korn et al, *Proceedings of the National Academy of Sciences*, 105(47): 18460-18465, 2008. | | |
| Interleukin-6 receptor subunit alpha (IL6R) | CAA31312.1 | TCGGTGCAGCTCCACGACTC (SEQ ID NO: 321), AACTATTCATGCTACCGGGC (SEQ ID NO: 322), CGTGGTGCAGCTTCGTGCCC (SEQ ID NO: 323) |
| Interleukin-6 receptor subunit beta (IL6ST or GP130) | AAA59155.1 | AGATGCCTCAACTTGGAGCC (SEQ ID NO: 324), TTTGAGTTGCATTGTGAACG (SEQ ID NO: 325), ATTCGCTGTATGAAGGAAGA (SEQ ID NO: 326) |
| Cell interaction reducing edits TCR alpha see preferred talen edit) TCR beta (see preferred talen edit) | | |
| CIITA | CAA52354.1 | TTCCTACACAATGCGTTGCC (SEQ ID NO: 327), GATATTGGCATAAGCCTCCC (SEQ ID NO: 328), TCAACTGCGACCAGTTCAGC (SEQ ID NO: 329) |
| B7-1(CD80) | AAA36045.1 | TCGTATGTGCCCTCGTCAGA (SEQ ID NO: 330), GAGTGAATCAGACCTTCAAC (SEQ ID NO: 331), TATGGCCCGAGTACAAGAAC (SEQ ID NO: 332) |
| B7-2(CD86) | AAB03814.1 | GTAACCGTGTATAGATGAGC (SEQ ID NO: 333), ATACTCGATAGTTGAATTCT (SEQ ID NO: 334), CATCAGATCTTTCAGGTATA (SEQ ID NO: 335) |
| b2m | AAA51811.1 | ACTCACGCTGGATAGCCTCC (SEQ ID NO: 336), GAGTAGCGCGAGCACAGCTA (SEQ ID NO: 337), CAGTAAGTCAACTTCAATGT (SEQ ID NO: 338) |
| UL18 | CAA68399.1 | |
| PDL2 | AAK31105.1 | |
| FasL | AAC50071.1 | GGTTGTTGCAAGATTGACCC (SEQ ID NO: 339), GAGGAACTCTAAGTATCCCC (SEQ ID NO: 340), TCTGGTTGCCTTGGTAGGAT (SEQ ID NO: 341) |
| Perforin (PRF1) | CAA31612.1 | CGCAGCCACAAGTTCGTGCC (SEQ ID NO: 342), GGAGCTGGGTGGCCGCATAT (SEQ ID NO: 343), CCCGAACAGCAGGTCGTTAA |

TABLE 6-continued

Exemplary Genes for Genetic Modification and Corresponding Cas9-Mediated Edits (SEQ ID NO: 344)

| | | |
|---|---|---|
| Galectin 9 (LGALS9) | AA88922.1 | |
| PVT/CD155 | AAA36461.1 | |
| Drug interaction related edits | | |
| CD52 | CAA44323.1 | CTCTTACCTGTACCATAACC (SEQ ID NO: 345), AATGCCTCCGCTTATGTTGC (SEQ ID NO: 346), TGGCATTGGCCACGAAGAAA (SEQ ID NO: 347) |
| tocilizumab-like heavy chain (for scfv) | BAJ21229.1 | |
| tocilizumab-like light chain (for scfv) | BAJ21230.1 | |
| Integrin alpha-4 (ITGA4) | CAA34852.1 | CGACTACTTCGGTAGTATGC (SEQ ID NO: 348), CAGCATACTACCGAAGTAGT (SEQ ID NO: 349), GTGTTTGTGTACATCAACTC (SEQ ID NO: 350) |

The table below provides target sequences for TALEN edits as well as protein sequences.

TABLE 7

Primarily TALEN mediated edits

| CS1 edit related | Sequence or Genbank Accession no. |
|---|---|
| CS1 | NP_067004.3 |
| CS1v1 TALEN target | tgacttccagagag caatatggct ggttccccaa catgcctca (SEQ ID NO: 351) |
| CS1v1 left TALEN target | tgacttccagagagcaa (SEQ ID NO: 352) |
| CS1v1 left TALEN protein | MDYKDHDGDYKDHDIDYKDDDDKMAPKKKRKVGIHGVPAAVDTATLGYSQQQQEKIKPK VRSTVAQHHEALVGHGFTHAHIVALSQHPAALGTVAVKYQDMIAALPEATHEAIVGVGKQ WSGARALEALLTVAGE-LRGPPLQLDTGQLLKIAKRGGVTAVEAVHAWRNALTGAPLNLTP EQVNAIASNNGGKQALETVQRLLPVLCQAHGLTPEQVVAIASNIGGKQALETVQLLPVLC QAHGLTPEQVVAIASHDGGKQALETVQRLLPVLCQAHGLTPEQVVAIASNGGGKQALETVQ RLLPVLCQAHGLTPEQVVAIASNGGGKQALETVQRLLPVLCQAHGLTPEQVVAIASHDGGK QALETQRLLPVLCQAHGLTPEQVVAIASHDGGKQALETVQRLLPVLCQAHGLTPEQVVAI ASNIGGKQALETVQRLLPVLCQAHGLTEQVVAIASNNGGKQALETVQRLLPVLCQAHGLT PEQVVAIASNIGGKQALETVQRLLPVLCQAHGLTPEQVVAIASNNGGKQALETVQRLLPVLC QAHGLTPEQVVAIASNIGGKQALETVQRLLPVLCQAHGLTPEQVVAIASNNGGKQALETVQ RLLPVLCQAHGLTPEQVVAIASHDGGKQALETVQRELLPVLCQAHGLTPEQVVAIASNIGGKQ ALETVQRLLPVLCQAHGLTPEQVVAIASNIGGRPALESIVQLSRPDPALAALTNDHLVALA CLGGRPALDAVKKGLPHAPALIKRTNRRIPERTSHRVAGSQLVKSELEEKKSELRHKLKYVP HEYIELIEIARNSQDRILEMKVMEFFMKVYGYRGKHLGGSRKPDGAIYTVGSPIDYGVIVDT KAYSGGYNLPIGQADEMQRYVEENQTRNKHINPNEWWKVYPSSVTEFKFLFVSGHFKGNY KAQLTRLNHITNCNGAVLSVEELLIGGEMIKAGTLTLEEVRRKFNNGEINFRS (SEQ ID NO: 353) |
| CS1v1 right TALEN target | aacatgcctc accctca (SEQ ID NO: 354) |
| CS1v1 right TALEN protein | MDYKDHDGDYKDHDIDYKDDDDKMAPKKKRKVGIHGVPAAVDLRTLGYSQQQQEKIKPK VRSTVAQHHEALVGHGFTHAHIVALSQHPAALGTVAVKYQDMIAALPEATHEAIVGVGKQ WSGARALEALLTVAGELRGPPLQLDTGQLLKIAKRGGVTAVEAVHAWRNALTGAPLNLTP EQVNAIASNNGGKQALETVQRLLPVLCQAHGLTPEQVVAIASNIGGKQALETVQRLLPVLC QNHGLTPEQVVAIASNNGGKQALETVQRLLPVLCQAHGLTPEQVVAIASNNGGKQALETVQ RLLPVLCQAHGLTPEQVVAIASNNGGKQALETVQRLLPVLCQAHGLTPEQVVAIASNGGGK QALETVQALLPVLCQAHGLTPEQVVAIASNNGGKQALETVQRLLPVLCQAHGLTPEQVVAI ASNIGGKQALETNQRLLPVLCQAHGLTPEQVVAIASNNGGKQALETVQRLLPVLCQAHGLT PEQVVAIASNNGGIKQALETVQRLLPVLCQAHGLTPEQVVAIASHDGGKQALETVQRLLPVL CQAHGLTPEQVVIVASNIGGKQALETVQRLLPVLCQAHGLTPEQVVAIASNGGGKQALETV QRLLPVLCQAHGLTPEQVVAIASNNGGKQALETVQRLLPVLCQAHGLTPEQVVAIASNGGG KQALETVQRLLPVLCQAHGLTPEQVVAIASNGGGRPALESIVAQLSRPDRALAALTNDHLVA LACLGGRPALDAVKKGLPHAPALIKRTNRRIPERTSHRVAGSQLVKSELEEKKSELRHKLKY |

TABLE 7-continued

Primarily TALEN mediated edits

| | |
|---|---|
| | VPHEYIELIEIARNSTQDRILEIMVMEFFMKVYGYRGKHLGGSRKPDGAIYTVGSPIDYGVIV DTKAYSGGYNLPIGQADEMQRYVEENQTRNKHINPNEWWKVYPSSVTEFKFLFVSGHFKG NYKAQLTRLNHITNCNGAVLSVEELLIGGEMIKAGTLTLEEVRRKFTNNGEINFRS (SEQ ID NO: 355) |
| CS1v2 TALEN target | ttccagagag caatatggct ggttccccaa catgcctcac cctcatcta (SEQ ID NO: 356) |
| CS1v2 left TALEN target | ttccagagag caatatg (SEQ ID NO: 357) |
| CS1v2 left TALEN protein | MDYKLMIDGDYKTYRDIDYKDDDDKMARKKKRKVGIEGVPAAVDERTLGYSQQQQEKIKPK VRSTVAQHHEALVGHGFTHAHIVALSQHPAALGTVAVKYQDMIAALPEATHEAIVGVGKQ WSGARALEALLTVAGELRGPPLQLDTGQLLKIAKRGGVTAVEAVHAWRNALTGAPLNLTP EQVVAIASNGGGKQALETNQRLLPVLCQAHGLTPEQVVAIASHDGGKQALETVQRLLPVLC QAHGLTPEQVVAIASHDGGKQALETVQRLLPVLCQAHGLTPEQVVAIASNIGGKQALETVQ RLLPVCQAHGLTPEQVVAIASNNGGKQALETVQRLLPVLCQAHGLTPEQVVAIATASNIGGKQ ALETVQRLLPVLCQAHGLTPEQVVAIASNNGGKQALETVQRLLPVLCQAHGLTPEQVVAIA SNIGGKQALETVQRLLPVLCQAHGLTPEQVVAIASNNGGKQALETVQRLLPVLCQAHGLTP EQVVAIASHDGGKQALETVQRLLPVLCQAHGLTPEQVVAIASNIGGKQALETVQRLLPVLC QAHGLTPEQVVAIASNIGGKQALETVQRLLPVLCQAHGLTPEQVVAIASNGGGKQALETVQ RLLPVLCQAHGLTPEQVVAIASNIGGKQALETVQRLLPVLCQAHGLTPEQVVAIASNGGGKQ ALETVQRLLPVLCQAHGLTPEQVVAIASNNGGKQALETVQRLLPVLCQAHGLTPEQVVALA CLGGRPALDAVKKGLPHAPALIKRTNRRIPERTSHRVAGSQLVKSELEEKKSELRHKLKYVP HEYIELIEIARNSTQDRTIEMKVMEFFMKVYGYRGKHLGGSRKPDGAIYTVGSPIDYGVIVDT KAYSGGYNLPIGQADEMQRYVEENQTRNKHINPNEWWKVYPSSVTEFKFLFVSGHFKGY KAQLTRLNHTITNCNGAVLSVEELLIGGEMIKAGTLTLEEVRRKFNNGEINFRS (SEQ ID NO: 358) |
| CS1v2 right TALEN target | tgcctcaccc tcatcta (SEQ ID NO: 359) |
| CS1v2 right TALEN protein | MDYKDHDGDYKDHDIDYKDDDDKMAPKKKRKVGIHGVPAAVDLRTLGYSQQQQEKIKPK VRSTVAQHHEALVGHGFTHAHIVALSQHPAALGTVAYKYQDMIAALPEATHEAIVGVGKQ WSGARALEALLTVAGELRGPPLQLDTGQLLKIAKGGVTAVTAVEAVHAWRNALTGAPLNLTP EQVVAIASNIGGKQALETVQRLLPVLCQAHGLTPEQVVAIASNNGGKQALETVQRLLPVLC QAHGLTPEQVVAIASNIGGKQALETVQRLLPVLCQAHGLTPEQVVAIASNGGGKQALETVQ RLLPVLCQAHGLTPEQVVAIASNNGGKQALETVQRLLPVLCQAHGLTPEQVVAIASNIGGKQ ALETVQRLLPVLCQAHGLTPEQVVAIASNNGGKQALETVQALLPVLCQAHGLTPEQVVAIA SNNGGKQALETVQRLLPVLCQAHGLTPEQVVAIASNNGGKQALETVQRLLPVLCQAHGLTP EQVVAIASNGGGKQALETVQRLLPVLCQAHGLTPEQVVAIASNNGGKQALETVQRLLPVLC QAHGLTPEQVVAIASNIGGKQALETVQRLLPVLCQAHGLTPEQVVAIASNNG GKQALETVQRLLPVLCQAHGLTPEQVVAIASNNGGKQALETVQRLLPVLCQAHGLTPEQVV AIASHDGGKQALETVQRLLPVLCQAHGLFPEQVVAIASNIGGRPALESIVAQLSRPDPALAAL TNDHLVALACLGGRPALDAVKKGLPHAPALIKRTNRRIPERTSHRVAGSQLVKSELEEKKSE LRHKLKYVPHEYIELIEIARNSTQDRILEMKVMEFFMKVYGYRGKHLGGSRKPDGAIYTVGS PIDYGVIVDTKAYSGCNLPIGQADEMQRYVEENQTRNKNHINPNEWWKYPSSVTEFKFLF VSGHFKGNYKAQLTRLNHITNCNGAVLSVEELLIGGEMIKAGTLTLEEVRRKFNNGEINFRS (SEQ ID NO: 360) |
| CS1v3 target | ttgactctat tgtctgacc ttcaacacaa cccctcttgt caccataca (SEQ ID NO: 361) |
| CS1v3 left TALEN target | ttgactctat tgtagg (SEQ ID NO: 362) |
| CS1v3 left TALEN protein | MDYKDHDGDYKDHDIDYKDDDDKMAPKKKRKVGIHGVPAAVDLRTLGYSQQQQEKIKPK VRSTVAQHHEALVGHGFTHAHIVALSQHPAALGTVAVKYQDMIAALPEATHEAIVGVGKQ WSGARALEALLTVAGELRGPPLQLDTGQLLKIAKRGGVTAVEAVHAWRNALTGAPLNLTP EQVVAIASNGGGKQALETVQRLLPVLCQAHGLTPEQVVAIASNNGGKQALETVQRLLPVLC QAHGLTPEQVVAIASNIGGKQALETVQRLLPVLCQAHGLTPEQVVAIASHDGGKQALETVQ RLLPVLCQAHGLTPEQVVAIASNGGGKQALETVQRLLPVLCQAHGLTPEQVVAIASHDGGK QALETVQRLLPVLCQAHGLTPEQVVAIASNGGGKQALETVQRLLPVLCQAHGLTPEQVVAI ASNIGGKQALETVQRLLPVLCQAHGLTPEQVVAIASNGGGKQALETVQRLLPVLCQAHGLT PEQVVAIASNGGGKQALETVQRLLPVLCQAHGLTPEQVVAIASNNGGKQALETVQRLLPVL CQAHGLTPEQVVIVASNGGGKQALETVQRLLPVLCQAHGLTPEQVVAIASHDGGKQALETV QRLLPVLCQAHGLTPEQVVAIASNGGGKQALETVQRLLPVLCQAHGLTPEQVVAIASNNGG KQALETVQRLLPVLCQAHGLTPEQVVAIASNNGGRPALESIVAQLSRPDPALAALTNDHLVA LACLGGRPALDAVKKGLPHAPALIKRTNRRIPERTSHRVAGSQLVKSELEEKKSELRHKLKY VPHEYIELIEIARNSTQDRILEMKVMEFFMKVYGYRGKHLGGSRKPDGAIYTVGSPIDYGVIV DTKAYSGGYNLPIGQADEMQRYVEENQTRNKHINPNEWWKVYPSSVTEFKFLFVSGHFKG NYKAQLTRLNHITNCNGAVLSVEELLIGGEMIKAGTLTLEEVRRKFNNGEINFRS (SEQ ID NO: 363) |
| CS1v3 right TALEN target | cacttgtca ccataca (SEQ ID NO: 364) |
| Cs1v3 right TALEN protein | MDYKDHDGDYKDHDIDYKDDDDKMAPKKKRKVGIHGVPAAVDLRTLGYSQQQQEKIKPK VRSTVAQHHEALVGHGFTHAHIVALSQHPAALGTVAVKYQDMIAALPEATHEAIVGVGKQ WSGARALEALLTVAGELRGPPLQLDTGQLLKIAKRGGVTAVEAVHAWRNALTGAPLNLTP EQVVAIASNGGGKQALETVQRLLPVLCQAHGLTPEQVVAIASNGGGKQALETVQRLLPVLC QAHGLTPEQVVAIASNIGGKQALETVQRLLPVLCQAHGLTPEQVVAIASNGGGKQALETVQ |

TABLE 7-continued

| Primarily TALEN mediated edits | |
|---|---|
| | RLLPVLCQAHGLTPEQYVAIASNNGGKQALETVQRLLPVLCQAHGLTPEQVVAIASNNGGK<br>QALETVQRLLPVLCQAHGLTPEQVVAIASNGGGKQALETVQRLLPVLCQAHGLTPEQVVAI<br>ASNNGGKQALETVQRLLPVLCQAHGLTPEQVVAIASNIGGKQALETVQRLLPVLCQAHGLT<br>PEQVVAIASHDGGKQALETVQRLLPVLCQAHGLTPEQVVAIASNIGGKQALETVQRLLPVLC<br>QAHGLTPEQVVAIASNIGGKQALETVQRLLPVLCQAHGLTPEQVVAIASNNGGKQALETVQ<br>RLLPVLCQAHGLTPEQVVAIASNIGGKQALETVQRLLPVLCQAHGLTPEQVVAIASNNGGKQ<br>ALETVQRLLPVLCQAHGLTPEQVVAIASNNGGRPALESIVAQLSRPDPALAALTNDHLVALA<br>CLGGRPALDAVKKGLPHAPALIKRTNRRIPERTSHRVAGSQLVKSELEEKKSELRLHKLKYVP<br>HEYIELIEIARNSTQDRILEMKVMEFFMKVYGYRGKHLGGSRKPDGAIYTVGSPIDYGVIVDT<br>KAYSGGYNLPIGQADEMQRYVEENQTRNKHINPNEWWKVYRSSVTEFKFLFVSGHFKGNY<br>KAQLTRLNHITNCNGAVLSVEELLIGGEMIKAGTLTLEEVRRKFNNGEINFRS (SEQ ID NO: 365) |
| CIITA edit related | Sequence or Genbank Accession no. |
| CIITA | NP_001273331.1 |
| CIITA TALEN target | TTCCCTCCCAGGCAGCTCacagtgtgccaccaTGGAGTTGGGGCCCCT<br>A (SEQ ID NO: 366) |
| CIITA left TALEN target | TTCCCTCCCAGGCAGCTC (SEQ ID NO: 367) |
| CITTA left TALEN protein | MDYKDHDGDYKDHDIDYKDDDDKMAPKKKRKVGIHGVPAAVDERTLGYSQQQQEKIKPK<br>VRSTVAQHHEALVGHGFTHAHIVALSQHPAALGTVAVKYQDMIAALPEATHEAWGVGKQ<br>WSGSRALEALLTVGELRGPPLQLDTGQLLKIAKRGGVTAVEAVHAWRNALTGAPLNLTP<br>EQVVAIASNGGGKQALETVQRLLPVLCQAHGLTPEQVVAIASHDGGKQALTEVQRLLPVLC<br>QAHGLTPEQVVAIASHDGGKQALETVQRLLPVLCQAHGLTPEQVVAIASHDGGKQALETVQ<br>RLLPVLCQAHGLTPEQVVAIANGGGKQALETVQRLLPVLCQAHGLTPEQVVAIASHDGGK<br>QALETVQRLLPVLCQAHGLTPEQVVAIASHDGGKQALETVQRLLPVLCQAHGLTPEQVVAI<br>ASHDGGKQALETVQRLLPVLCQAHGLTPEQVVAIASNIGGKQALETVQRLLPVLCQAHGLT<br>PEQVVAIASNNGGKQALETVQRLLPVLCQAHGLTPEQVVAIASNNGGKQALETVQRLLPVL<br>CQAHGLTPEQVVAIASHDGGKQALETVQRLLPVLCQAHGLTPEQVVAIASNIGGKQALETV<br>QRLLPVLCQAHGLTPEQVVAIASSNNGGKQALETVQRLLPVLCQAHGLTPEQVVAIASHDGG<br>KQALETVQRLLPVLCQAHGLTPEQVVAIASNGGGKQALETVQRLLPVLCQAHGLTPEQVVA<br>IASHDGGRPALESIVAQLSRPDPALAALTNDHLVALACLGGRPALDAYKKGLPHAPLIKRT<br>NRRIPERTSHRVAGSQLVKSELEEKKSELRHKLKYVPHEYIELIEIARNSTQDRILEMKVMEFF<br>MKVYGYRGKHLGGSRKPDGAIYTVGSPIDYGVIVDTKAYSGGYNLPIGQADEMQRYNEEN<br>QTRNKHINPNEWWKVYPSSVTEFKFLFVSGHFKGNYKAQLTRLNHITNCNGAVLSVEELLIG<br>GEMIKAGTLTLEEVRRKFNGEINFRS (SEQ ID NO: 368) |
| CIITA right target | TGGAGTTGGGGCCCCTA (SEQ ID NO: 369) |
| CIITA right protein | MDYKDHDGDYKDHDIDYKDDDDKMAPKKKRKVGIHGVPAAVDLRTLGYSQQQQEKIKPK<br>VRSTVAQHEEALVGHGFTHIAHIVALSQHPAALGTVAVKYQDMIAALPEATHEAIVGVGKQ<br>WSGARALEALLTVAGELRGPRLQLDTGQLLKIAKRGGVTAVEAVHAWRNALTGAPLNLTP<br>EQVVAIASNIGGKQALETVQRLLPVLCQAHGLTPEQVVAIASNNGGKQALETVQRLLPVLC<br>QAHGLTPEQVVAIASNNGGKQALETVQRLLPVLCQAHGLTPEQVVAIASNNGGKQALETVQ<br>RLLPVLCQAHGLTPEQVVAIASNNGGKQALETVQRLLPVLCQAHGLTPEQVVAIASHDGGK<br>QALETVQRLLPVLCQAHGLTPEQVVAIASHDGGKQALETVQRLLPVLCQAHGLTPEQVVAI<br>ASHDGGKQALETVQRLLPVLCQAHGLTPEQVVAILASHDGGKQALETVQRLLPVLCQAHGLT<br>PEQVVAIASNIGGKQALETVQRLLPVLCQAHGLTPEQVVAIASNIGGKQALETVQRLLPVLC<br>QAHGLTPEQVVAIASHDGGKQALETVQRLLPVLCQAHGLTPEQVVAIASNGGGKQALETVQ<br>RLLPVLCQAHGLTPEQVVAIASHDGGKQALETVQRLLPVLCQAHGLTPEQVVAIASHDGGK<br>QALETVQRLLPVLCQAHGLTPEQVVAIASNIGGRPALESIVAQLSRPDPALAALTNDHLVAL<br>ACLGGRPALDAVKKGLPHAPALIKRINRKPERTSHRVAGSQLVKSELEEKKSELRHKLKYV<br>PHEYIELIEIARNSTQDRILEMIKVMEFFMKVYGYRGKHLGGSRKPDGAIYTVGSPIDYGVIVD<br>TKAYSGGYNLPIGQADEMQRYVEENQTRNKHKNPNEWWKVYPSSVTEFKFLSGHFKGN<br>YKAQLTRLNHITNCNGAVLSVEELLIGGEMIKAGTLTLEEVRRKFNNGEINFRS (SEQ ID NO: 370) |
| CD52 edit related | Sequence or Genbank Accession no. |
| CD52 | NP_001794.2 |
| CD52 target | TTCCTCCTACTCACCATcagcctcctggtttatGGTACAGGTAAGAGCAA<br>(SEQ ID NO: 371) |
| CD52 left target | TTCCTCCTACTCACCAT (SEQ ID NO: 372) |
| CD52 left protein | MDYKDHDGDYKDHDIDYKDDDDKMAPKKKRKVGIHGVPAAVDLRTLGYSQQQQEKIKPK<br>VRSTVAQHHEALVGHGFTHAHIVALSQHPAALGTVAVKYQDMIAALPEATHAIVGVGKQ<br>WSGARALEALLTVGELRGPPLQLDTGQLLKIAKRGGVTAVEAVHAWRNALTGAPLNLTP<br>EQVVAIASNGGGKQALETVQRLLPVLCQAHGLTPEQVVAIAHDGGKQALETVQRLLPVLC<br>QAHGLTPEQVVAIAHDGGKQALETVQRLLPVLCQAHGLTPEQVVAIASNGGGKQALETVQ<br>RLLPVLCQAHGLTPEQVVAIASHDGGKQALETVQRLLPVLCQAHGLTPEQVVAIASHDGGK<br>QALETVQRLLPVLCQAHGLTPEQVVAIASNGGGKQALETVQRLLPVLCQAHGLTPEQVVAI<br>ASNIGGKQALETVQRLLPVLCQAHGLTPEQVVAIASHDGGKQALETVQRLLPVLCQAHGLT<br>PEQVVAIASNGGGKQALETVQRLLPVLCQAHGLTPEQVVAIASHDGGKQALETVQRLLPVL |

TABLE 7-continued

| Primarily TALEN mediated edits | |
|---|---|
| | CQAHGLTPEQVVAIASNIGGKQALETVQRLLPVLCQAHGLTPEQVVAIASHDGGKQALETV<br>QRLLPVLCQAHGLTPEQVVAIASHDGGKQALETVQRLLPVLCQAHGLTPEQVVAIASNIGGK<br>QALETVQRLLPVLCQAHGLTPEQVVAIASNGGGRPALESIVAQLSRPDPALAALTNDHLVAL<br>ACLGGRPALDAVKKGLPHAPALIKRTNRRIPERTSHRVAGSQLVKSELEEKKSELRHKLKYV<br>PHEYIELEIARNSTQDRILEMKVMEFEMKVYGYRGKHLGGSRKPDGAIYINGSPIDYGVIND<br>TKAYSGGYNLPIGQADEMQRYVLENQTRNKHINPNEWWKVYPSSVTEFKFLEVSGHFKGN<br>YKAQLTRLNHITNCNGAVLSVEELLIGGEMIKAGTLTLEEVRRKFNNGEINFRS (SEQ ID<br>NO: 373) |
| CD52 right target | GGTACAGGTAAGAGCAA (SEQ ID NO: 374) |
| CD52 right protein | MDYKDHDGDYKDHDIDYKDDDDKMAPKKKRKVGIHGVPAAVDLRTLGYSQQQQEKIKPK<br>VRSTVAQHHEALVGHGFTHAHIVALSQHPAALGTVAVKYQDMIAALPEATHEAIVGVGKQ<br>WSGARALEALLTVAGELRGPPLQLDTGQLLKIAKRGGVTAVEAVHAWRNALTGAPLNLTP<br>EQVVAIASNGGGKQALETVQRLLPVLCQAHGLTPEQVVAIASNNGGKQALETVQRLLPVLC<br>QAHGLTPEQVVAIASHDGGKQALETVQRLLPVLCQAHGLTPEQVVAIASNGGGKQALETVQ<br>RLLPVLCQAHGLTPEQVVAIASHDGGKQALETVQRLLPVLCQAHGLFPEQVVAIASNGGGK<br>QALETVQRLLPVLCQAHGLTPEQVVAIASNGGGKQALETVQRLLPVLCQAHGLTPEQVVAI<br>ASNIGGKQALETVQRLLPVLCQAHGLTPEQVVAIASHDGGKQALETVQRLLPVLCQAHGLT<br>PEQVVAIASHDGGKQALETVQRLLPVLCQAHGLTPEQVVAIASNGGGKQALETVQRLLPVL<br>CQAHGLTPEQVVAIASNNGGKQALETVQRLLPVLCQAHGLTPEQVVAIASNGGGKQALETV<br>QRLLPVLCQAHGLTPEQVVAIASNIGGKQALETVQRILLPVLCQAHGLTPEQVVAIASHDGGK<br>QALETVQRLLPVLCQAHGLTPEQVVAIASHDGGRPALESIVAQLSRPDPALAALTNDHLVAL<br>ACLGGRPALDAVKKGLPHAPALIKRTNRRIPERTSHRVAGSQLVKSLLEEKKSELRHKLKYV<br>PHEYIELEIARNSTQDRILEMKVMEFFMKVYGYRGKHLGGSRKPDGAIYTVGSPIDYGVIVD<br>TKAYSGGYNLPIGQADEMQRYVEENQTRNKHINPNEWWKVYPSSVTEFKFLFVSGHFKGN<br>YKAQLTRLNHITNCNGAVLSVEELLIGGEMIKAGTLTLEEVRRKFNNGEINFRS (SEQ ID<br>NO: 375) |
| TRAC edit related | Sequence or Genbank Accession no. |
| TRAC | CAA26435.1 |
| TRAC TALEN target | TTGTCCCACAGATATCCagaaccctgaccctgCCGTGTACCAGCTGAGA<br>(SEQ ID NO: 376) |
| TRAC left TALEN target | TTCTTCCCACAGATATCC (SEQ ID NO: 377) |
| TRAC left protein | MDYKDHDGDYKDHDIDYKDDDDKMAPKKKRKVGIHGVPAAVDLRTLGYSQQQQEKIKPK<br>VRSTVAQHHEALVGHGFTHAHIVALSQHPAALGTVAVKYQDMIAALPEATHEAIVGVGKQ<br>WSGARALEALLTVAGELRGPPLQLDTGQLLKIAKRGGVTAVEAVHAWRNALTGAPLNLTP<br>EQVVAIASNGGGKQALETVQRLLPVLCQAHGLTPEQVVAIASNNGGKQALETVQRLLPVLC<br>QAHGLTPEQVVAIASNGGGKQALETVQRLLPVLCQAHGLTPEQVVAIASHDGGKQALETVQ<br>RLLPVLCQAHGLTPEQVVAIASHDGGKQALETVQRLLPVLCQAHGLTPEQVVAIASHDGGK<br>QALETVQRLLPVLCQAHGLTPEQVVAIASNIGGKQALETVQRLLPVLCQAHGLTPEQVVAIA<br>SHDGGKQALETVQRLLPVLCQAHGLTPEQVVAIASNIGGKQALETVQRLLPVLCQAHGLTP<br>EQVVAIASNNGGKQALETVQRLLPVLCQAHGLTPEQVVAIASNIGGKQALETVQRLLPVLC<br>QAHGLTPEQVVAIASNGGGKQALETVQRLLPVLCQAHGLTPEQVVAIASNIGGKQALETVQ<br>RLLPVLCQAHGLTPEQVVAIASNGGGKQALETVQRELPVLCQAHGLTPEQVVAIASHDGGK<br>QALETVQRLLPVLCQAHGLTPEQVVAIASHDGGRPALESIVAQLSRPDPALAALTNDHLVAL<br>ACLGGRPALDAVKKGLHNPALIKRTNRRIPERTSHRVAGSQLVKSELEEKKSELRHKLKYV<br>PHEYIELIEIARNSTQDRILEMKVMEFFMKVYGYRGKHLGGSRKPDGAIYTVGSPIDYGVIVD<br>TKAYSGGYNLPIGQADEMQRYVEENQTRNKHINPNEWWKVYPSSVTEFKFLFVSGHFKGN<br>YKAQLTRLNTNUGAVLSVEELLIGGEMIKAGTLTLEEVRRKFNNGEINFRS (SEQ ID<br>NO: 378) |
| TRAC right TALEN target | CCGTGTACCAGCTGAGA (SEQ ID NO: 379) |
| TRAC TALEN right | MDYKDHDGDYKDRDIDYKDDDDKMAPKKKRKVGIHGVPAAVDLRELGYSQQQQEKIKPK<br>VRSTVAQHEEALVGHGFTHAHIVALSQHPAALGTVAVKYQDMIAALPEATHEAIVGVGKQ<br>WSGARALEALLTVAGELRGPPLQLDTGQLLKIAKRGGVTAVEAVHAWRNALTGAPLNTP<br>EQVVAIASHDGGKQALETVQRLLVVLCQAHGLITEQVVATASNGGGKQALETVQRLLPVLC<br>QAHGLTPEQVVAIASHDGGKQALETVQRLLPVLCQAHGLTPEQVVAIASNIGGKQALETVQ<br>RLLPVLCQAHGLTPEQVVAIASNNGGKQALETVQRLLPVLCQAHGLTPEQVVAIASHDGGK<br>QALETVQRLLPVLCQAHGLTPEQVVAIASNGGGKQALETVQRLLPVLCQAHGLTPEQVVAI<br>ASNNGGKQALETVQRLLPVLCQAHGLTPEQVVAIASNNGGKQALETVQRLLPVLCQAHGLT<br>PEQVVAIASNGGGKQALETVQRLLPVLCQAHGLTPEQVVAIASNIGGKQALETVQRLLPVLC<br>QAHGLTPEQVVAIASHDGGKQALETVQRLLPVLCQAHGLTPEQVVAIASNIGGKQALETVQ<br>RLLPVLCQAHGLTPEQVVAIASHDGGKQALETVQRELLPVLCQAHGLTPEQVVAIASNNGGK<br>QALETVQRLLPVLQAHGLTPEQVVAIASNNGGRPALESIVAQLSRPDPALAALTNDHLVAL<br>ACLGGRPALDAVKKGLPHAPALIKRTNRRIPERTSHRVAGSQLVKSELEEKKSELRHKLKYV<br>PHEYIELIEIARNSTQDRILEMKVMEFFMKVYGYRGKHLGGSRKPDGAINTVGSPIDYGVIVD<br>TKAYSGGYNLPIGQADEMQRYVEENQTRNKHINPNEWWKVYPSSVTEFKFLFVSGHFKGN<br>YKAQLTRLNHITNCNGAVLSVEELLIGGEMIKAGTLTLEEVRRKFNNGEINFRS (SEQ ID<br>NO: 380) |

TABLE 7-continued

Primarily TALEN mediated edits

| PDCD1 edit related | Sequence or Genbank Accession no. |
|---|---|
| PDCD1 | NG_012110:1 |
| PDCD1 talen target | ttctccccag ccctgctcgt ggtgaccgaa ggggacaacg ccaccttca (SEQ ID NO: 381) |
| PDCD1 talen left | MGDPKKKRKVIDYPYDVPDYAIDIADLRTLGYSQQQQEKIKPKVRSTVAQHHEALVGHGFT HAHIVALSQHPAALGTVAVKYQDMIAALPEATHEAIVGVGKQWSGARALEALLTVAGELR GPPLQLDTGQLLKIAKRGGVTAVEAVHAWRNALTGARLNLTPQQVVAIASNGGGKQALET VQRLLPVLCQAHGLTPEQVVAIASHDGGKQALETVQRLLPVLCQAGLTPQQVVAIASNGG GKQALETVQRLLPVLCQAHGLTEQVVAIASHDGGKQALETVQRLLPVLCQAHGLTPEQVV AIASHDGGKQALETVQRLLPVLCQAHGLTPEQVVAIASHDGGKQALETVQRLLPVLCQAHG LTPEQVVAIASHDGGKQALETVQRLLPVLCQAHGLTPEQVVAIASNIGGKQALETVQALLTV LCQAHGLTPQQVVAIASNNGGKQALETVQRLLPVLCQAHGLTPEQVVAIASHDGGKQALET VQRLLPVLCQAHGLTPEQVVAIASHDGGKQALETVQRLLPVLCQAHGLTPEQVVAIASHDG GKQALETVQRLLPVLCQAHGLTPQQVVAIASNGGGKQALETVQRLLPVLCQAHGLTPQQV VAIASNNGGKQALETVQRLLPVLCQAHGLTPEQVVAIASHDGGKQALETVQRLLPVLCQAH GLTPQQVVAIASNGGGRPALESIVAQLRPDPALAALTNDHLVALACLGGRPALDAVKKGL GDPISRSQLVKSELEEKKSELRHKLKYVPHEYIELIEIARNSTQDRILEMKVMEFFMKVYGYR GKHLGGSRKPDGAIYTVGSPIDYGVIVDTKAYSGGYNLPIGQADEMQRYVEENQTRNKHIN PNEWWKVYPSSVTEFKFLFVSGHFKGNYKAQLTRLNHITNCNGAVLSVEELLIGGEMIKAG TLTLEEVRRKFNNGEINFAAD (SEQ ID NO: 382) |
| PDCD1 talen right | MGDPKKKRKVIDKETAAAKFERQHMDSIDIADLRTLGYSQQQQEKIKPKVRSTVAQHHEAL VGHGFTHAHIVALSQHPAALGTVAVKYQDMIAALPEATHEAIVGVGKQWSGARALEALLT VAGELRGPPLQLDTGQLLKIAKRGGVTAVEAVHAWRNALTGAPLNLTPEQVVAIASHDGG KQALETVQRLLPVLCQAHGLTPQQVVAIASNGGGKQALETVQRLLPVLCQAHGLTPEQVVA IASHDGGKQALETVQRLLPVLCQAHGLTPQQVVALASNGGGKQALETVQRLLPVLCQAHGL TPQQVVAIASNGGGKQALETVQRLLPVLCQAHGLTPQQAVVAIASNGGGKQALETVQRLLPV LCQAHGLTPQQVVAIASNNGGKQALETVQRLLPVLCQAHGLTPEQVVAIASNIGGKQALET VQALLPVLCQAHGLTPQQVVVAIASNGGGKQALETVQRLLPVLCQAHGLTPEQVVAIASHDG GKQALETVQRLLPVLCQAHGLTPQQVVAIASNGGGKQALETVQRLLPVLCQAHGLTPQQV VAIASNNGGKQALETVQRLLPVLCQAHGLTPEQVVAIASNGGKQALETVQRLLPVLCQAHG LTPQQVVAIASNNGGKQALETVQRLLPVLCQAHGLTPEQVVAIASHDGGKQALETVQRLLP VLCQAHGLTPQQVVAIASNGGGRPALESIVAQLSRPDPALAALTNDHLVALACLGGRPALD AVKKGLGDPISRSQLVKSELEEKKSELRHKLKYVPHEYIELIEIARNSTQDRILEMKVMEFFM KVYTYRGKHLGGSRKPDGAIYTVGSPIDYGVIVDTKAYSGGYNLPIGQADEMQRYVEENQT RNKHINPNEWWKVYPSSVTEFKFLFVSGHFKGNYKAQLTRLNHITNCNGAVLVEELLIGGE MIKAGTLTLEEVRRKFNNGEINFAAD (SEQ ID NO: 383) |

(iii) Exemplary Genetic Modification Approaches

Any conventional genetic modification approaches can be used to genetically modify the immune cells in a manner as described herein. In some embodiments, the genetic modification is performed using genome editing. "Genome editing" refers to a method of modifying the genome, including any protein-coding or non-coding nucleotide sequence, of an organism to knock out the expression of a target gene. In general, genome editing methods involve use of an endonuclease that is capable of cleaving the nucleic acid of the genome, for example at a targeted nucleotide sequence. Repair of the double-stranded breaks in the genome may be repaired introducing mutations and/or exogenous nucleic acid may be inserted into the targeted site.

Genome editing methods are generally classified based on the type of endonuclease that is involved in generating double stranded breaks in the target nucleic acid. These methods include use of zinc finger nucleases (ZFN), transcription activator-like effector-based nuclease (TALEN), meganucleases, and CRISPR/Cas systems.

In some instances, genetic modification of the immune cells as described herein is performed using the TALEN technology known in the art. TALENs are engineered restriction enzymes that can specifically bind and cleave a desired target DNA molecule. A TALEN typically contains a Transcriptional Activator-Like Effector (TALE) DNA-binding domain fused to a DNA cleavage domain. The DNA binding domain may contain a highly, conserved 33-34 amino acid sequence with a divergent 2 amino acid RVD (repeat variable dipeptide motif) at positions 12 and 13. The RVD motif determines binding specificity to a nucleic acid sequence and can be engineered according to methods known to those of skill in the art to specifically bind a desired DNA sequence (see, e.g., Juillerat, et al. (January 2015). Scientific reports, 5; Miller et al. (February 2011). Nature Biotechnology 29 (2): 143-8; Zhang et. al. (February 2011). Nature Biotechnology 29 (2): 149-53; Geiβler, et al., Boch, (2011), PLoS ONE 6 (5): e19509; Boch (February 2011). Nature Biotechnology 29 (2): 135-6; Boch, et. al. (December 2009). Science 326 (5959): 1509-12; and Moscou et al, (December 2009). Science 326 (5959): 1501. The DNA cleavage domain may be derived from the FokI endonuclease, which is active in many different cell types. The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) Nature Biotech. 29: 143-8.

TALENs specific to sequences in a target gene of interest (e.g., TCR, CD52, MHC, and others described herein) can be constructed using any method known in the art, including various schemes using modular components. Zhang et al. (2011) Nature Biotech. 29: 149-53; Geibler et al. (2011) PLoS ONE 6: e19509.

A TALEN specific to a target gene of interest can be used inside a cell to produce a double-stranded break (DSB). A mutation can be introduced at the break site if the repair mechanisms improperly repair the break via non-homologous end joining. For example, improper repair may introduce a frame shift mutation. Alternatively, a foreign DNA molecule having a desired sequence can be introduced into the cell along with the TALEN Depending on the sequence of the foreign DNA and chromosomal sequence, this process can be used to correct a defect or introduce a DNA fragment into a target gene of interest, or introduce such a detect into the endogenous gene, thus decreasing expression of the target gene.

In some instances, genetic modification of the immune cells as described herin is performed using CRISPR technology as known in the art (CRISPR/Cas systems). Such modification may include the deletion or mutation of a sequence in a target gene of interest can be constructed using a CRISPR-Cas system, where the Clustered Regularly Interspaced Short Palindromic Repeats (CRISPR)-Cas system is an engineered, non-naturally occurring CRISPR-Cas system. The present disclosure utilizes the CRISPR/Cas system that hybridizes with a target sequence in a target gene of interest, where the CRISPR/Cas system comprises a Cas endonuclease and an engineered crRNA/tracrRNA (or single guide RNA ("sgRNA"). In some embodiments, the CRISPR/Cas system includes a crRNA and does not include a tracrRNA sequence. CRISPR/Cas complex can bind to the lineage specific protein polynucleotide and allow the cleavage of the protein polynucleotide, thereby modifying the polynucleotide.

The CRISPR/Cas system of the present disclosure may bind to and/or cleave the region of interest within a target gene of interest, within or adjacent to the gene, such as, for example, a leader sequence, trailer sequence or intron, or within a non-transcribed region, either upstream or downstream of the coding region. The guide RNAs (gRNAs) used in the present disclosure may be designed such that the gRNA directs binding of the Cas enzyme-gRNA complexes to a pre-determined cleavage sites (target site) in a genome. The cleavage sites may be chosen so as to release a fragment that contains a region of unknown sequence, or a region containing a SNP, nucleotide insertion, nucleotide deletion, rearrangement, etc. Cleavage of a gene region may comprise cleaving one or two strands at the location of the target sequence by the Cas enzyme. In one embodiment, such cleavage can result in decreased transcription of a target gene. In another embodiment, the cleavage can further comprise repairing the cleaved target polynucleotide by homologous recombination with an exogenous template polynucleotide, wherein the repair results in an insertion, deletion, or substitution of one or more nucleotides of the target polynucleotide.

The terms "gRNA," "guide RNA" and "CRISPR guide sequence" may be used interchangeably throughout and refer to a nucleic acid comprising a sequence that determines the specificity of a Cas DNA binding protein of a CRISPR/Cas system. A gRNA hybridizes to (complementary to, partially or completely) a target nucleic acid sequence in the genome of a host cell. The gRNA or portion thereof that hybridizes to the target nucleic acid may be between 15-25 nucleotides, 18-22 nucleotides, or 19-21 nucleotides in length. In some embodiments, the gRNA sequence that hybridizes to the target nucleic acid is 15, 16, 17, 18, 19, 20, 21, 22, 23, 24, or 25 nucleotides in length. In some embodiments, the gRNA sequence that hybridizes to the target nucleic acid is between 10-30, or between 15-25, nucleotides in length.

In addition to a sequence that binds to a target nucleic acid, in some embodiments, the gRNA also comprises a scaffold sequence. Expression of a gRNA encoding both a sequence complementary to a target nucleic acid and scaffold sequence has the dual function of both binding (hybridizing) to the target nucleic acid and recruiting the endonuclease to the target nucleic acid, which may result in site-specific CRISPR activity. In some embodiments, such a chimeric gRNA may be referred to as a single guide RNA (sgRNA).

As used herein, a "scaffold sequence," also referred to as a tracrRNA, refers to a nucleic acid sequence that recruits a Cas endonuclease to a target nucleic acid bound (hybridized) to a complementary gRNA sequence. Any scaffold sequence that comprises at least one stem loop structure and recruits an endonuclease may be used in the genetic elements and vectors described herein. Exemplary scaffold sequences will be evident to one of skill in the art and can be found, for example, in Jinek, et al. Science (2012) 337(6096):816-821, Ran, et al. Nature Protocols (2013) 8:2281-2308, PCT Application No. WO2014/093694, and PCT Application No. WO2013/176772. In some embodiments, the CRISPR-Cas system does not include a tracrRNA sequence.

In some embodiments, the gRNA sequence does not comprise a scaffold sequence and a scaffold sequence is expressed as a separate transcript. In such embodiments, the gRNA sequence further comprises an additional sequence that is complementary to a portion of the scaffold sequence and functions to bind (hybridize) the scaffold sequence and recruit the endonuclease to the target nucleic acid.

In some embodiments, the gRNA sequence is at least 50%, 55%, 60%, 65%, 70%, 75%, 80%, 85%, 90%, 95%, 96%, 97%, 98%, 99%, or at least 100% complementary to a target nucleic acid (see also U.S. Pat. No. 8,697,359, which is incorporated by reference for its teaching of complementarity of a gRNA sequence with a target polynucleotide sequence). It has been demonstrated that mismatches between a CRISPR guide sequence and the target nucleic acid near the 3' end of the target nucleic acid may abolish nuclease cleavage activity (Upadhyay, et al. Genes Genome Genetics (2013) 3(12):2233-2238). In some embodiments, the gRNA sequence is at least 50%, 55%, 60%, 65%, 70%, 75%, 80%, 85%, 90%, 95%, 96%, 97%, 98%, 99%, or at least 100% complementary to the 3' end of the target nucleic acid (e.g., the last 5, 6, 7, 8, 9, or 10 nucleotides of the 3' end of the target nucleic acid).

Example sgRNA sequences, including both modified and unmodified sgRNAs, targeting the T cell receptor alpha constant (TRAC) gene are provided herein. As will be evident to one of ordinary skill in the art, selection of sgRNA sequences may depend on factors such as the number of predicted on-target and/or off-target binding sites. In some embodiments, the sgRNA sequence is selected to maximize potential on-target and minimize potential off-target sites.

In some embodiments, the Cas endonuclease is a Cas9 nuclease (or variant thereof) or a Cpf1 nuclease (or variant thereof). Cas9 endonucleases cleave double stranded DNA of a target nucleic acid resulting in blunt ends, whereas cleavage with Cpf1 nucleases results in staggered ends of the nucleic acid.

In general, the target nucleic acid is flanked on the 3' side or 5' side by a protospacer adjacent motif (PAM) that may interact with the endonuclease and be further involved in targeting the endonuclease activity to the target nucleic acid.

It is generally thought that the PAM sequence flanking the target nucleic acid depends on the endonuclease and the source from which the endonuclease is derived. For example, for Cas9 endonucleases that are derived from *Streptococcus pyogenes*, the PAM sequence is NGG, although the PAM sequences NAG and NGA may be recognized with lower efficiency. For Cas9 endonucleases derived from *Staphylococcus aureus*, the PAM sequence is NNGRRT. For Cas9 endonucleases that are derived from *Neisseria meningitidis*, the PAM sequence is NNNNGATT. Cas9 endonucleases derived from *Streptococcus thermophilus*, St1Cas9 an dSt3Cas9, the PAM sequences are NNAGAAW and NGGNG, respectively. For Cas9 endonuclease derived from *Treponema denticola*, the PAM sequence is NAAAAC. In some embodiments, the Cas endonuclease is a Cpf1 nuclease. In contrast to Cas9 endonucleases, Cpf1 endonuclease generally do not require a tracrRNA sequence and recognize a PAM sequence located at the 5' end of the target nucleic acid. For a Cpf1 nuclease, the PAM sequence is TTTN, in some embodiments, the Cas endonuclease is MAD7 (also referred to as Cpf1 nuclease from Eubacterium rectale) and the PAM sequence is YTTTN.

In some embodiments, genetically engineering a cell also comprises introducing a Cas endonuclease, or nucleic acid sequence encoding such (e.g., mRNA encoding a Cas endonuclease), into the cell. In some embodiments, the Cas endonuclease and the nucleic acid encoding the gRNA are provided on the same nucleic acid (e.g., a vector). In some embodiments, the Cas endonuclease and the nucleic acid encoding the gRNA are provided on different nucleic acids (e.g., different vectors). In some embodiments, the Cas endonuclease is provided as an mRNA encoding the Cas endonuclease and the gRNA is provided as a modified gRNA molecule. Alternatively or in addition, the Cas endonuclease may be provided or introduced into the cell in protein form.

In some embodiments, the Cas endonuclease is a Cas9 enzyme or variant thereof. In some embodiments, the Cas9 endonuclease is derived from *Streptococcus pyogenes, Staphylococcus aureus, Neisseria meningitidis, Streptococcus thermophilus*, or *Treponema denticola*. In some embodiments, the nucleotide sequence encoding the Cas endonuclease may be codon optimized for expression in a host cell. In some embodiments, the endonuclease is a Cas9 homolog or ortholog.

In some embodiments, the nucleotide sequence encoding the Cas9 endonuclease is further modified to alter the activity of the protein. In some embodiments, the Cas9 endonuclease has been modified to inactivate one or more catalytic resides of the endonuclease. In some embodiments, the Cas9 endonuclease has been modified to inactivate one of the catalytic residues of the endonuclease, referred to as a "nickase" or "Cas9n", Cas9 nickase endonucleases cleave one DNA strand of the target nucleic acid. In some embodiments, the methods described herein involve two distinct cleavage reactions, in which one Cas9 nickase is directed to cleave one DNA strand of the target nucleic acid and a Cas9 nickase is directed to cleave the second DNA strand of the target nucleic acid.

(iv) MHC-CAR Regulatory T Cells (Treg)

Any of the MHC-CAR-expressing T cells disclosed herein can be regulatory T cells (Treg), which may mimic the immune modulation activity of follicular regulatory cells. As used herein, regulatory T cells or Treg cells, which are also known as suppressor T cells, refer to a subpopulation of T cells that modulate the immune system, maintain tolerance to self-antigens, and/or prevent autoimmune disease. Treg cells function as immunesuppressors to suppress or downregulate induction and/or proliferation of effector T cells, such as pathologic CD4+ and/or CD8+ cells involved in autoimmune diseases.

The genetically modified Treg cells disclosed herein express one or more of the biomarkers associated with Treg cells in nature, for example, CD4, FOXP3, CD25, CD45R e.g., CD45RA or CD45RO), or a combination thereof. The Treg cells may be prepared using (derived from) peripheral blood mononuclear cells (PBMCs) isolated from a suitable donor (e.g., the human patient subject to the treatment). Methods for isolating the subpopulation of Treg cells from PBMCs are well known in the art, for example, cell sorting. Expression vectors for a suitable MHC-CAR construct, as well as other genetic modification (e.g., those described herein) can be introduced into the Treg subpopulation via methods as described herein, or other methods known in the art. Alternatively, the genetically modified. Treg cells may be prepared by introducing a transgene coding for CD25 and/or other Treg cell markers into suitable T cells, which can be further modified to introduce the expression cassette for the MHC-CAR and optionally other genetic modification as described herein.

In some embodiments, the genetically modified Treg cells may be further modified to display (e.g., surface express or surface attach) molecules targeting a specific type of pathologic cells (e.g., CD4+ cells or CD8+ cells) and/or display molecules targeting a specific tissue site lymph node or an inflammation site).

In some examples, the genetically modified Treg cells further express a chimeric receptor (CAR) comprising an extracellular domain such as a single-chain antibody (scFv) specific to a B cell surface marker, for example, CD19. Alternatively or in addition, the Treg cells may further express a chimeric receptor comprising an extracellular domain (e.g., scFv) specific to a T cell surface marker, for example, CS-1. Such a chimeric receptor can be a cell-surface receptor comprising an extracellular domain, a transmembrane domain, and a cytoplasmic domain (e.g., comprising a co-stimulatory domain, a cytoplasmic signaling domain such as CD3ζ, or a combination thereof) in a combination that is not naturally found together on a single protein.

The Treg cell may further display a molecule targeting lymph nodes and/or germinal center, for example, CXCR5, and/or display a molecule targeting an inflammation site, for example, CCR6. Targeting germinal center B cells (GC B cells) may be mediated, at least in part, by a specialized helper T cell subset, the CXCR5highPD-1high T follicular helper (TFH) cells. Foxp3+ Treg can be diverted to become TFH repressors pia expression of Bcl6 and SAP-mediated interaction with B cells. The resulting follicular regulatory T cells (TFR) are expected to share features of both TFH and Treg cells, localize to germinal centers, and regulate the size of the TFH cell population and germinal centers in vivo.

Further, the Treg cells disclosed herein may include one or more of the additional genetic modification as described herein, for example, checkpoint molecule knock out.

The Treg cells expressing B-cell or T-cell specific CAR may target pathologic B cells and/or T cells involved in an autoimmune disease. For example, the genetically modified Treg cells as described herein would be expected to exhibit functions similar to follicular regulatory cells, e.g., targeting B cells, T cells, and/or dendritic cells, thereby, e.g., down-regulating B cell stimulation, secreting suppressive cytokines that can inhibit activation of germinal center (GCB cells (such as Il-10 and TGF-Beta), inducing cytolysis of Tfh (through MHC CAR) and GC) B (e.g., through the CD19 CAR), and/or mechanical disrupting signaling transduction to GC B cells or to T follicular helper (Tfh) cells (e.g., through binding to GC B and MHC-peptide Tfh). Alternatively or in addition, the Treg cells may potentially engage both helper T cells, B cells, and/or antigen presenting cells, or in some instances, physically blocking the engagement.

III. Application of Immune Cells Expressing MHC-CAR in Immunotherapy

Host immune cells expressing MHC-CAR (the encoding nucleic acids or vectors comprising such) described herein are useful for targeting and eliminating pathogenic cells involved in autoimmune diseases, such as MS, type 1 diabetes, lupus, rheumatoid arthritis, etc. In some embodiments, the subject is a mammal, such as a human, monkey, mouse, rabbit, or domestic mammal. In some embodiments, the subject is a human, for example, a human patient having, suspected of having, or at risk for an autoimmune disease (e.g., MS).

The MHC-CAR-expressing immune cells can be mixed with a pharmaceutically acceptable carrier to form a pharmaceutical composition, which is also within the scope of the present disclosure. To perform the methods described herein, an effective amount of the immune cells expressing any of the MHC-CAR constructs described herein can be administered into a subject in need of the treatment. The immune cells may be autologous to the subject, i.e., the immune cells are obtained from the subject in need of the treatment, genetically engineered for expression of the MHC-CAR constructs and optionally contains one or more of the additional genetic modifications as described herein, and then administered to the same subject. Administration of autologous cells to a subject may result in reduced rejection of the immune cells as compared to administration of non-autologous cells. Alternatively, the immune cells are allogeneic cells, i.e., the cells are obtained from a first subject, genetically engineered for expression of the MHC-CAR construct, and administered to a second subject that is different from the first subject but of the same species. For example, allogeneic immune cells may be derived from a human donor and administered to a human recipient who is different from the donor.

In some embodiments, the immune cells are co-used with a therapeutic agent for the target immune disease, for example, Alemtuzumah for treating MS. Such immunotherapy is used to treat, alleviate, or reduce the symptoms of the target immune disease for which the immunotherapy is considered useful in a subject.

The efficacy of the MHC-CAR immunotherapy may be assessed by any method known in the art and would be evident to a skilled medical professional. For example, the efficacy of the immunotherapy may be assessed by survival of the subject and/or reduction of disease symptoms in the subject.

In some embodiments, the immune cells expressing any of the MHC-CAR disclosed herein are administered to a subject who has been treated or is being treated with a therapeutic agent for an autoimmune disease. The immune cells expressing any one of the MHC-CAR disclosed herein may be co-administered with the therapeutic agent. For example, the immune cells may be administered to a human subject simultaneously with the therapeutic agent. Alternatively, the immune cells may be administered to a human subject during the course of a treatment involving the therapeutic agent. In some examples, the immune cells and the therapeutic agent can be administered to a human subject at least 4 hours apart, e.g., at least 12 hours apart, at least 1 day apart, at least 3 days apart, at least one week apart, at least two weeks apart, or at least one month apart.

To practice the method disclosed herein, an effective amount of the immune cells expressing MHC-CAR or compositions thereof can be administered to a subject (e.g., a human MS patient) in need of the treatment via a suitable route, such as intravenous administration. Any of the immune cells expressing MHC-CAR or compositions thereof may be administered to a subject in an effective amount. As used herein, an effective amount refers to the amount of the respective agent the immune cells expressing MHC-CAR or compositions thereof) that upon administration confers a therapeutic effect on the subject. Determination of whether an amount of the cells or compositions described herein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. In some embodiments, the effective amount alleviates, relieves, ameliorates, improves, reduces the symptoms, or delays the progression of any disease or disorder in the subject. In some embodiments, the subject is a human. In some embodiments, the subject is a human cancer patient.

In some embodiments, the subject is a human patient suffering from an autoimmune disease, which is characterized by abnormal immune responses attacking a normal body part. Examples of autoimmune diseases include multiple sclerosis, systemic lupus erythematosus, rheumatoid arthritis, juvenile idiopathic arthritis (also known as juvenile idiopathic arthritis), Sjögren's syndrome, systemic sclerosis, ankylosing spondylitis, Type 1 diabetes, autoimmune thyroid diseases (Grave's and Hashimoto's), multiple sclerosis myasthenia gravis, inflammatory bowel disease (Crohn's or ulcerative colitis), Psoriasis, or a diseases mentioned in Table 1.

There are numerous stages in the immune cascade where, in general, an autoimmune disease can be impacted. There is a continuum of interventions made possible by the combination of edits that the methods disclosed herein comprises. For example, Treg cells displaying a distinct set of surface molecules, in addition to the MHC-CAR, can be used for treating the autoimmune disease at different stages.

In the early stage of many immune disorders, including MS, there exist unexplained deficits in regulatory mechanisms and/or tolerance induction exists in MS and there begin repeated attacks on the nervous system by T cells. Treg cells expressing a suitable MHC-CAR and anti-CD19 CAR (optionally with other genetic modifications as described herein) may be used for intervention.

An advantage of autoreactive Treg cells is their ability to act as "bystander" suppressors, to dampen inflammation at a site-specific manner in response to cognate antigen expressed locally by affected tissues. The induction of regulatory T cells (by autoantigens) can suppress disease progression even when there are a variety of autoantigens (or when the initiating/primary) autoantigen is unknown. Tregs can travel relatively freely, and inhibit T cells and B cells and prevent return to an inflammatory environment. These autoreactive Tregs are advantageous in their ability to act as bystander suppressors and dampen inflammation in a site-specific manner in response to cognate antigen expressed locally by affected tissues.

Thus, the genetically modified Treg cells may be designed to mimic the suppressor function of the autoreactive Treg cells. Such Treg cells may be modified, for example, to have PD-L1/PD-1 knocked out, to display CCR6 and/or scFv targeting MOG to route to the site of inflammation, to express a suitable MHC-CAR and/or anti-CD19-CAR. Alternatively, the Treg cells may be modified, for example, to have PD-L1/PD-1 knocked out, to display CXCR5 to route to germinal centers and/or ectopic lymph nodes, to express a suitable MHC-CAR and/or anti-CD19-CAR. These types of Treg cells may interact with pathogenic cells at the site of inflammation, block pathogenic interactions, and/or calm inflammatory environment. They can be used at an early disease stage (to inhibit pathogenicity) or after cytotoxic therapy (to prevent return to an inflammatory environment).

Relapsing-remitting MS (mid-stage) naturally regulates itself, and treatments which augment these natural regulatory mechanisms will help control the disease process. In successful disease treatment, there is a shift from Th1 cells to Th2 and Th3 cells, and the appearance of other regulatory cells. At this stage, therapeutic targets will include both pathogenic B and pathogenic T cells. Treg cells for treating such mid-stage disease may express a suitable MHC-CAR as described herein, and an additional CAR targeting B cells (e.g., an anti-CD19 CAR) or targeting T cells such as CD8+ cells. The Treg cells may further display CXCR5 or free of CXCR5 targeting. Treg cells expressing anti-CD19 CAR may be used to eliminate B cells in the germinal center.

When MS changes from relapsing remitting to the chronic progressive form (late-stage), T cells enter a state of chronic activation and degenerative processes occur. Aggressive treatment against cytotoxic CD8+ cells requires a CAR augmentation that is sufficiently cytotoxic. At this point, a treatment may shift from one primarily driven by Treg cells to one driven by MHC-CAR CD8+ T cells and even MHC-CAR CS-1 cells. The ultimate goal remains the same: to suppress pathology through cytotoxicity enhanced by bystander effect. Genetically engineered T cells for use at this disease stage may express a suitable MHC-CAR, and an additional CAR targeting pathologic T cells involved in the late stage of the disease, for example, CD5+ cells. In some examples, the additional CAR may target CS-1 (also known as SLAMF7), which is a glycoprotein expressed on CD8+ T cells. CS1 is a promising antigen that can be used to target and kill CD8+ T cells and plasma cells. CS1-CAR T cells secrete more IFN-gamma as well as IL-2, expressing higher levels of activation marker CD69, higher capacity for degranulation, and display enhanced cytotoxicity. Anti-CS1 CAR will target CD8+ T-cells. The genetically modified T cells may further display a molecule for bone-marrow targeting of plasma cells, such as CXCR4, and their targeting to inflamed tissues, with CXCR3.

Hiepe et al., Nature Reviews Rheumatology, 7(3):170-178, 2011. Examples include targeting of plasma cells in lupus.

IV. Kits for Therapeutic Uses

The present disclosure also provides kits for use of the MHC-CAR-expressing immune cells for use in suppressing pathogenic immune cells such as autoreactive T cells in autoimmunity. Such kits may include one or more containers comprising compositions comprising immune cells expressing MAR-CAR such as those described herein), and a pharmaceutically acceptable carrier.

In some embodiments, the kit can comprise instructions for use in any of the methods described herein. The included instructions can comprise a description of administration of the MHC-CAR-expressing immune cells to a subject who needs the treatment, e.g., an MS patient. The kit may further comprise a description of selecting a subject suitable for treatment based on identifying whether the subject is in need of the treatment. In some embodiments, the instructions comprise a description of administering the immune cells to a subject who is in need of the treatment.

The instructions relating to the use of the immune cells expressing the MHC-CAR described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device. A kit may have a sterile access port (for example, the container may be an intravenous solution bag or a vial having a stopper pierceable by a hypodermic injection needle). The container may also have a sterile access port. At least one active agent in the pharmaceutical composition is immune cells expressing MHC-CAR as described herein.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The instant examples focuses on the development of a cellular immunotherapy utilizing chimeric receptors to selectively redirect therapeutic T cells against myelin basic protein (MBP)-specific T lymphocytes implicated in MS [16]. The results of this program can support the further development of redirected therapeutic T cells able to counteract pathologic, self-specific T lymphocytes, and specifically validate humanized MBP-DR2-chimeric receptors as a therapeutic target in MS [29].

Example 1: Construction of Modified T-Cells Specific to Myelin Basic Protein

A construct for an antigen-specific T-cell receptor (TCR) that targets a MBP-loaded major histocompatibility complex-chimeric antigen receptor (MHC-CAR) is designed for reintroduction into cells with TCR knockouts for assays. Design of the TCR constructs is based on an antigen-specific TCR with a published structure and TCR expression constructs validated in human cell lines [17, 46, 51, 52], Green fluorescent protein (eGFP) or luciferase is genetically encoded for labeling [28]. Exemplary lentiviral expression vectors comprising the TCR construct and reporting gene are provided in FIG. 1.

Several cell lines are selected for testing TCR expression and activity, including Jurkat E6-1 (a control strain that expresses TCR), Jurkat J.RT3-T3.5 (a strain that lacks TCRb), SupT1 (a strain with damaged TCRa), and primary human T cells (which contain a diverse population of TCR clonotypes).

Jurkat E6-1 cells are an established human T lymphocyte cell line from peripheral blood. It is used as a control cell line expressing TCR [15, 18].

Jurkat RT3-T3.5 lacks TCRβ due to a mutation that precludes expression of the TCR β-chain. It also fails to express surface CD3 or produce the T-cell receptor α,β heterodimer. It is therefore used for validating T-cell receptor gene transfer [1, 6, 21, 49].

SupT1 is a human lymphoblast line expressing multiple lineage markers and is used because it encodes a non-functional receptor and fails to express TCRα [49].

PMBC-derived primary human T cells contain a diverse repertoire of TCR clonotypes.

Lentiviral vectors containing the antigen-specific TCR as illustrated in FIG. 1 are used to transduce cancer cell lines lacking at least one TCR chain, and are subsequently assessed for expression using fluorescence-activated cell sorting (FACs). In cancer cell lines containing the antigen-specific TCR, luciferase is added to the cell line following successful stable expression to enable its use in mouse studies.

TCR constructs for mRNA, multicistronic mRNA, and lentiviral transduction proceed straightforwardly, via a screen based on the genetically encoded eGFP and labeling with anti-TCR or anti-CD3 antibody [3, 19].

Figure 2:
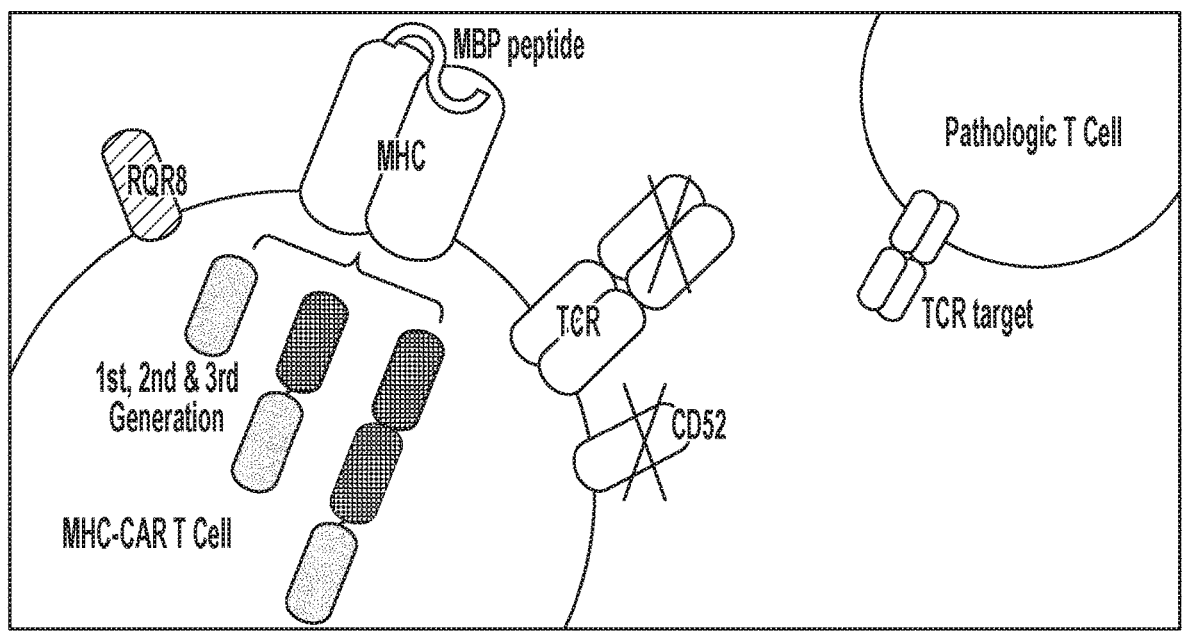
FIG. 2 is a schematic illustration of an MHC-CAR T cell, which expresses various designs of MHC-CAR as indicated in conjugation with a myelin basic protein (MBP) peptide for targeting pathologic T cells involved in multiple sclerosis (MS). Optionally, the MHC-CAR T cell may have the endogenous TCR and/or CD52 knocked out. The MHC-CAR T cell may further express RQR8 on the cell surface.

Example 2: Construction of MHC-Based Chimeric Receptors (MHC-CAR) and T-Cells Expressing Such (i) Design MHC-CAR Constructs Receptors for adoptive cell therapy that genetically link the MBP 84-102 epitope to human leukocyte antigen HLADR2 are generated and, either incorporate or lack chimeric intracellular signaling domains [29]. The antigen-major histocompatibility complex (Ag-MHC) domain serves as receptor, binding the TCR of MBP-specific target cells. The Ag-MHC-CAR has been validated in preclinical mouse models with CD3-ζ (i.e. a first-generation signaling domain), which may optionally be in combination with additional co-stimulatory signaling domains (i.e. second- or third-generation signaling domains) for efficacy in humans, following the methodology provided in [9, 25]. A schematic illustration of the various designs of MHC-CAR is provided in FIG. 2.

Figure 3:
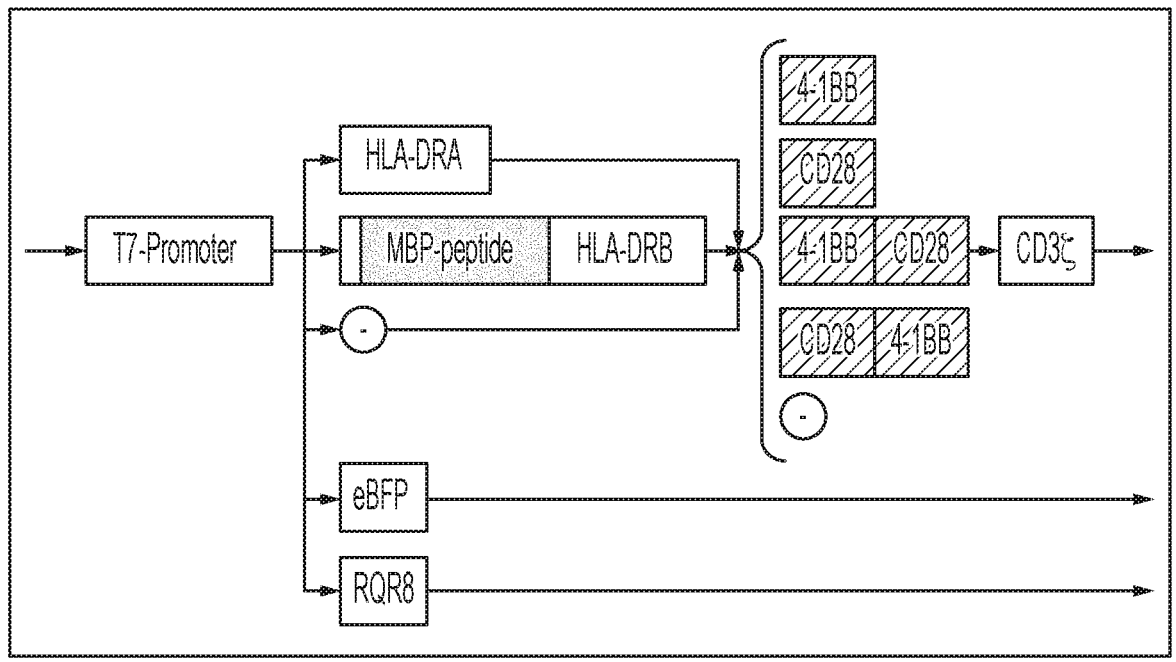
FIG. 3 is a schematic illustration of exemplary designs for various MHC-CAR constructs. The exemplary MHC-CAR constructs may have two subunits: an α-chain containing a leader sequence, a DRA*1010 domain, and a cytoplasmic domain, and a β-chain that includes a leader sequence from HLA-DRB1*1501, a peptide from MBP, and a domain from HLA-DRB1*1501. The DNA used to create mRNA contains either single chains or are multicistronic and separated by orthogonal 2A sequences. RQR8 and eBFP (or GFP) are used for both cell control and labeling.
Figure 4:
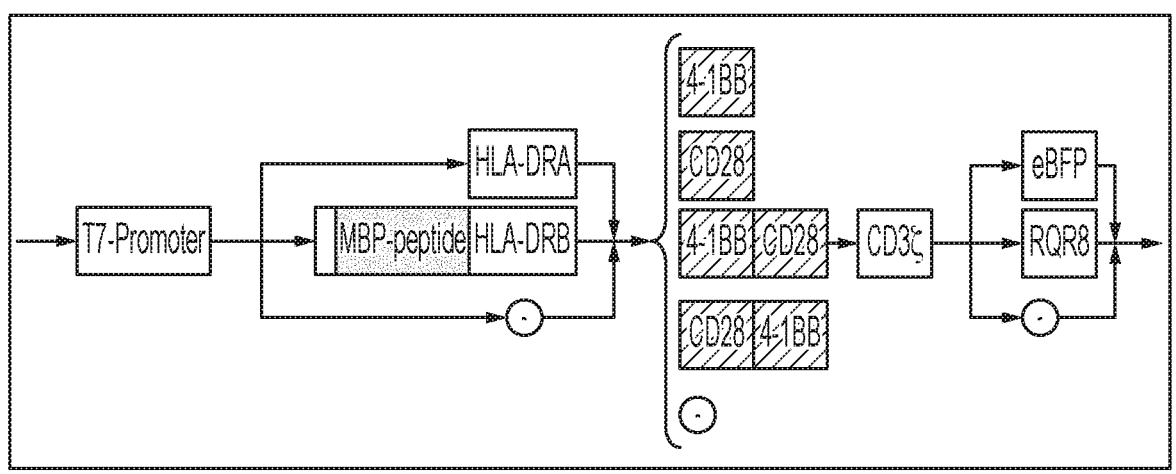
FIG. 4 is a schematic illustration of exemplary designs of expression cassettes for various MHC-CAR constructs containing a MBP peptides, which may further include eBFP (or GFP) or RQR8.
Figure 5:
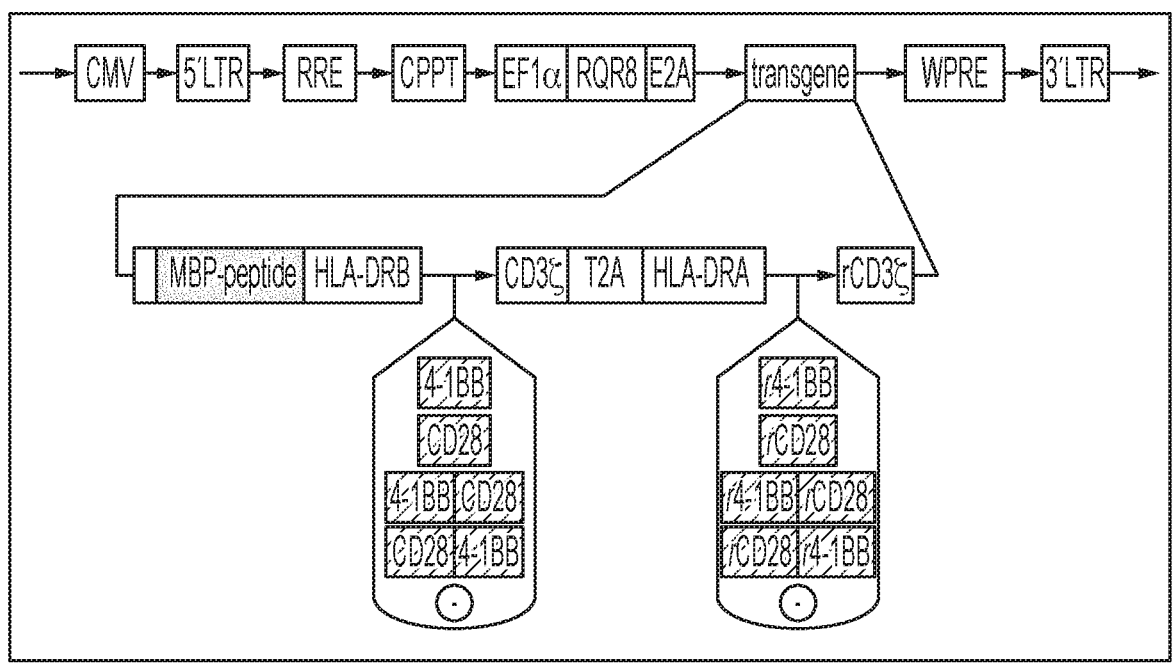
FIG. 5 is a schematic illustration of an exemplary design of a lentiviral expression construct for MHC-CARs and optionally label proteins such as eBFP and/or RQR8. Such an expression cassette would be sufficiently small to be included in one lentiviral package.

MHC-CARs are designed based on the structure of HLA-DR, and combined with a variety of internal cytoplasmic costimulatory domains. The MHC-CAR has two subunits: (i) an α-chain that contains the leader sequence, DRA*1010 domain, and a cytoplasmic domain; and (ii) a β-chain that contains a leader sequence (from HLA-DRB1*1501), a peptide (DENPVVHFFKNIVTRPP (SEQ ID NO: 15) from myelin basic protein), a domain (from HLA-DRB1*1501), and a cytoplasmic signal domain, for example, CD3z [29]. FIG. 3. The DNA used to create mRNA contains either single chains (shown as one embodiment in FIG. 4) or are multicistronic and separated by orthogonal 2A sequences as illustrated in FIG. 5. Genetically encoded eBFP or RQR8 are introduced into the cells for cell-labeling or to provide a mechanism for depletion [4, 5, 37, 40]. FIGS. 3 and 5.

Figure 6:
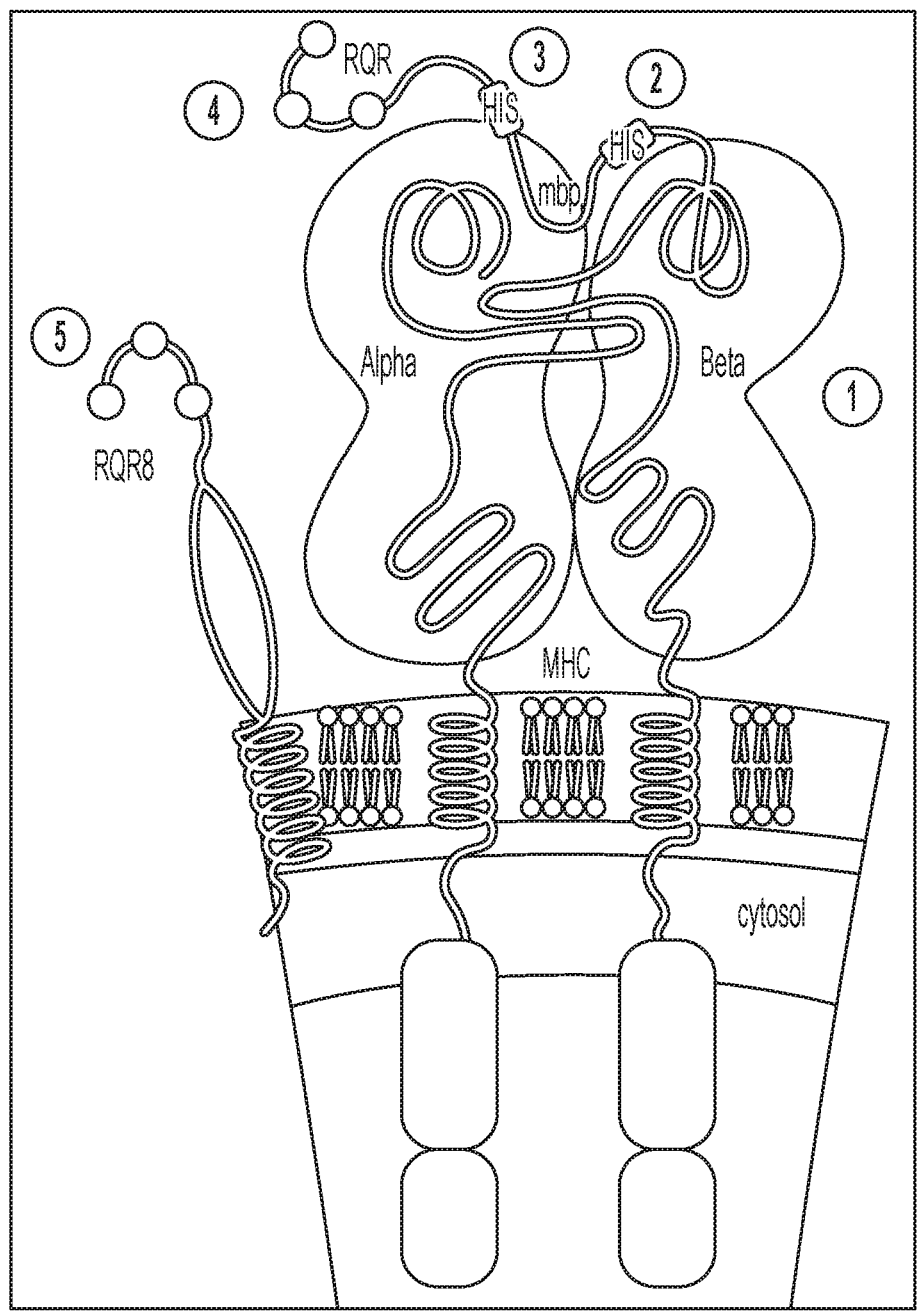
FIG. 6 is a schematic illustration of an exemplary design of MHC-CAR, which may include a number of sites for tagging. Site 1 is an HLA-DR antibody binding site for cases where naïve HLA-DR is either not expressed or due to CIITA editing. Sites 2 and 3 are potential insertion sites for polyhistidine-tag motifs. Sites 4 and 5 represent RQR and RQR8, respectively.

As illustrated in FIG. 6, the designed MHC-CAR has a number of sites for tagging. Site 1 is an HLA-DR antibody binding site for cases where native HLA-DR is either not expressed due to CIITA editing [26, 38]. Sites 2 and 3 are potential insertion sites for polyhistidine-tag motifs [24]. Sites 4 and 5 represent RQR and RQR8, respectively [37]. Multiple sclerosis is shown to affect blood brain barrier permeability, so in order to enhance the safety of therapeutic MHC-CAR, genetically encoded RQR would allow for rapid depletion of MHC-CAR T cells upon administration of rituximab, a chimeric monoclonal antibody treatment used offlabel in the treatment of severe MS [42].

(ii) Construction of T Cell Lines Expressing MHC-CAR

A number of cell lines discussed below are selected for testing the MHC-CAR construct. Assays are then continued in human T cells in order to establish clinically translatable protocols.

K56 cells lack Class I and Class II MHC, allowing for tagless verification of HLA-DR expression using antibodies (HLA-DR is a component of the MHC-CAR) [45]. Expression assays will allow assessment of the MHC-CAR expression relative to RQR8 expression using flow cytometry, and the same lentiviral construct is then used in PMBC-derived T cells [23].

KM-H2 is a human Hodgkin's lymphoma line that can be used as an HLA-DR positive control line [34, 44]. Jurkat E6-1, as noted above, conditionally express HLA-DR upon delivery of CIITA and can be used to evaluate CIITA TALEN if CIITA knockout is used [33].

In addition, primary human T cells can be used. PMBC-derived primary human T cells are purified and enriched from Whole blood, and then activated. Transduction follows enrichment. The cells are incubated with recombinant human interleukin-2 (and/or IL-7 and/or IL-15) [7, 12, 43]. Based on preclinical studies and the anticipated therapeutic course, the desired cell type is CD5+ T cells with the molecular and functional features of stem cell memory TSCM, central memory TCM, and naive cells TN [11, 22, 32, 35]. Antibody staining allows for cell immunotyping [27].

Initial constructs, including a permutation of signaling domains (CD3z, 41BB, CD28) are expressed using mRNA, multicistronic mRNA, and lentiviral strategies in K562 cells. The cell line's lack of MHC Class I and II allow the tagless verification of MHC-CAR expression using the HLA-DR antibodies, following a successfully employed strategy [29]. Quantification of the expression efficiency in more clinically relevant cell lines, including therapeutic T cells, depends on construct, and will be measured using genetically encoded fluorescent reporters (BFP) or antibody staining of the RQR site, a polyhistidine-(HIS)-tag, or the MHCCAR (with an HLA-DR antibody if CIITA is inactivated using TALEN). Labeling sites are indicated in FIG. 6. To test rates of MHC-CAR delivery as a potential therapeutic vector, BFP is removed from constructs while RQR is retained to provide for depletion control. Expression rates of the clinically relevant construct are measured using antibody staining post-editing.

The transcription activator-like effector technology (TALEN) can also be used for preparing T cells expressing MHC-CAR. Human T cell lines are activated, transfected with TALEN, and either transfected or transduced with MHC-CAR. They are then stained and analyzed by flow cytometry to assess TALEN gene inactivation and MHC-CAR expression. Upon verification of construct expression in desired cell lines, TALEN transduction (TCRa and CD52 or CIITA as discussed below) into human T cell lines is performed. TALEN is introduced into activated human T cell lines, and the MHC-CAR is subsequently introduced into the same T cell lines for evaluation. The modification of the human T cells can be performed in this order to prevent incidental fratricidal killing of MEW modified cells due to the native TCR [10]. The activity of TALEN-edited MHC-CAR T-cells is to be confirmed.

(iii) Modification of MHC-CAR-Expressing T Cells Via Transcription Activator-Like Effectors (TALENs)

Human T cells are selected to confirm inactivation of TCRa, and CD52 or CIITA genes by TALEN, followed by evaluation in combination with MHC-CAR, using TALENs. Transcription activator-like effectors (TALENs) bind DNA in a sequence-specific manner. The DNA binding domain contains a highly conserved 33-34 amino acid sequence with a divergent 2 amino acid RVD (repeat variable dipeptide motif) conferring specific nucleotide recognition [23, 31].

Mutation of either α or β chain of the TCR is sufficient for disruption of surface TCR expression [15, 36]. TALEN is used to inhibit expression of two genes in the therapeutic cell without introducing a proliferative advantage through undesired translocations [39][47]. TCR expression is inhibited through a TRAC-targeted TALEN to prevent graft versus host disease (GvHD) and allow for the creation of an allogeneic therapy [15, 39, 47].

CD52 deletion can be made for alemtuzumab compatibility. Alemtuzumab is a humanized anti-CD52 IgG-1 monoclonal antibody that targets and depletes circulating T and B lymphocytes [41]. Alemtuzumab can be used as rescue therapy or as first line drug in severe-onset MS [50], and will be co-administered in the human patient population. TALEN knockout will make MHC-CAR compatible with concurrent treatment in patients [14, 39], Further. CIITA deletion can be made for characterization of HLA-DR in MHC-CAR CIITA is a protein coding gene essential for the transcriptional activity of HLA Class II promoter [26]. Knockout would allow for the direct measurement of HLA-DR using antibodies for characterization of MHC-CAR expression [38, 53]. The inhibition of CD52 expression allows for concurrent treatment with Lemtrada R (alemtuzumab), an FDA-approved treatment for multiple sclerosis [42]. Alemtuzumab is also used as a lympho-depleting/lympho-suppressive agent that aids in the engraftment of CAR T therapies [39]. A CAR T-cell therapy modified with TRAC- and CD52-targeted TALENs is currently being tested in clinical trials [38, 40, 43].

TALEN to inactivate MHC Class II transactivator (CIITA) in place of CD52, as inactivation of CIITA is expected to inhibit HLA-DR expression [26][38], thus allowing for the direct identification of MHC-CAR-containing cells by HLA-DR antibody staining. Validated TALENs (TRAC: TTGTCCCACAGA-TATCCagaaccctgaccctgCCGTGTACCAGCTGAGA (SEQ ID NO: 376), CD52:TTCCTCCTACTCACCATcagcctcctgt-tatGGTACAGGTAAGAGCAA (SEQ ID NO: 371), CIITA: TTCCCTCCCAGGCAGCTCacagtgtgccaccaTG-GAGTTGGGGCCCCTA (SEQ ID NO: 366)) are obtained from Cellectis or designed to target previously validated sites [38, 43].

Human T cells are activated and electroporated with mRNA encoding variants of 3 different TALEN: TCR-alpha constant chain, CD52, and CIITA. Cells are surface stained with anti-CD3 or anti-TCR (TCR-alpha constant chain), anti-CD52 (CD52), or anti-HLA-DR (CIITA), and then analyzed by flow cytometry.

In the TALEN expression assays, the ability of previously validated TALENs to inactive target genes are re-validated [39]. Translocation studies and off-target studies are reperformed, and several whole-genome sequences confirm results. GUIDE-seq can be used as an alternative to whole genome sequencing to confirm on- and off-target editing [8].

One of more of the following endogenous genes are to be edited to reduce interaction with other cells: TCR (through TCR alpha or beta chain; to reduce targeting to undesired cells), CIITA (regulates expression of MHC Class II genes; target cells for taster deletion), B7-1 (CD80) and/or B7-2 (CD86) knockout, and b2m (regulates expression of MHC Class I genes) with NKG2D ligands or UL18.

Further, one or more of the following genes can be edited to modify the function of an interacting PD-L1+/−CTLA4-Ig overexpression; PD-L1/2 overexpression+/−PD-1 knockout; FasL overexpression+/−Fas knockout; Galectin 9 overexpression+/−TIM3 knockout; and/or PVT/CD155 overexpression+/−TIGIT knockout. Defects in PD-1, Fas, TIm3, TIGIT predispose patients to autoimmunity. Some drugs can restore function (for example: Tim3, glatiramer acetate and IFN-beta). If autologous cells from a patient suffering autoimmune disease are utilized they may require patient specific correction of defective genes that influence CM and Treg function. Their personal mutation set may also determine whether CTL or Treg cells will be the most therapeutically relevant, and whether some cellular modification will be effective, if either autologous or allogeneic cells are used.

Further, the following edits may modify the location and/or function of the cells (for example, to make it more like a follicular regulatory cell):

MHC-CAR-(FOX3P)-(CS1 or CD19 CAR)/(CS-1 knockout required for CS-1 CAR)

MHC-CAR-(FOX3P)-(CCR7 or CXCR5)

Moreover, the following edits can enable combination therapies for autoimmune diseases (e.g., MS specific therapeutics)

RQR tag: engineered T cells can be removed with rituximab (kill switch). A tag for the newly approved anti-CD20 antibody Ocrevus could be generated.

Rapamycin switch: CARs only in/active when patient is treated with rapamycin (tacrolimus)

CD52 knockout: allows pretreatment with Lemtrada (alemtuzumab) to decrease number of immune cells present VLA-4 knockout: can treat with tysabri to move pathogenic immune cells to periphery but engineered cells are forced to stay there (may not be ideal for patients with established MS as cells that are stuck in the brain spinal cord; however, simultaneous mRNA expression of VLA-4 can provide temporary access to those locations)

IL-6 antibody (Toclizumab) secretion from engineered T cell: helpful when the engineered T cell must access the brain and spinal cord, but this drug cannot access the locations due to the BBB Example 3: Investigation of MHC-CAR Activities (i) Preparation of Primary T Cells Expressing MHC-CAR Primary T cells can be prepared as follows. T cells are isolated from peripheral blood mononuclear cells (EasySep Human T Cell Enrichment Kit, Stemcell Technologies) and activated (Dynabeads Human T-Activator CD3/CD28, Life Technologies) with (X-Vivo 15 medium, Lonza; 20 mg/ml. Il-2, Miltenyi; 5% human AB serum, Seralab). A suitable MHC-CAR construct containing a MBP antigenic peptide is introduced into the primary T cells using a conventional method. Surface expression of the MHC-CAR construct is verified by FACS and antibody staining.

(ii) MHC-CAR Activity Tests In Vitro

Upon verification of construct trafficking and expression (with mRNA, multicistronic mRNA, Lentivirus), activity tests are conducted in vitro. All tests are conducted at different effector:target (E:F) cell concentrations. The in vitro tests provide an initial evaluation of MHC-CAR signaling domains and T cell subsets.

(iii) Signaling Domain Assessment by IL-2 Production 24 hours post electroporation, human T cells transiently engineered with MHC-CAR are stimulated with plate-bound HLA-DR antibody, to determine whether MHC-CAR (containing various signaling domains) is functional. Il-2 production is measured 24 hours later using a StemCell IL-2 ELISA kit. This test provides a quick assay as to whether variants should be reengineered or abandoned [29].

(iv) Interaction MHC-CAR Cells and Pathogenic TCR Cells Through Proliferation Assay Target cell lines transiently expressing TCR are magnetically sorted for TCR expression 24 hours after electroporation and irradiated, in order to test whether engagement of the MHC-CAR with antigen-specific TCR stimulates proliferation of MHC-CAR containing T cells. Alternatively, target cell lines that stably express TCR are irradiated. The irradiated cells displaying (+/−antigen-specific) TCR are incubated with CFSE-labeled MHCCAR cells and proliferation is measured after culture at different T:E ratios [30].

(v) Degranulation Assay

CAR T-cells are labeled through epitopes on RQR (which are not being expressed on the target cells used) or eBFP instead of T cell markers. The assay is performed for cell lines with transient or stable expression (the example of transient expression is described). 24 hours post-electroporation, MHC-CAR human T-cells with either RQR8 or BFP are co-cultured with target (antigen-specific TCR SupT1 or Jurkat) or control (+/−TCR Jurkat or TCR-SupT1) cells for 6 hours. Transiently expressed (and later stably expressing) target cells are electroporated with antigen-specific TCR and sorted with CD3 magnetic beads post-electroporation. The RQR+ or BFP+ MHC-CAR T-cells (as identified with anti-rituximab antibody, QBEnd10 antibody) are analyzed by flow cytometry to detect the expression of the degranulation marker CD107a on their surface [2].

(vi) Cytokine Secretion Assay

The assay is performed for cell lines with transient or stable expression (transient expression is described). The human T cells transiently expressing the MHC-CARs are assessed for cytokine secretion following co-culture with target cells 24 hours post electroporation. Human T cells transiently expressing the MHC-CARs are co-cultured with target (antigen-specific TCR containing Jurkat or SupT1 cells) or control (+/−non-antigen-specific Jurkat or SupT1) cells for 24 hours. The antigen-specific TCR is then killed by irradiation before the assay. The supernatants are harvested and analyzed using the TH1/TH2 cytokine cytometric bead array kit to quantify the cytokines produced by T cells [13]. In MHC-CAR T-cells produce IFN and other cytokines in co-culture with antigen-specific TCR expressing target cells but not in co-culture with control cells.

(vii) IFNγ Release Assay

Various levels of MHC-CAR expressing cells are incubated with irradiated TCR T-cells 24 hours after transfection. Co-cultures are maintained for 24 hours. After incubation and centrifugation, supernatants are tested with IFNγ detection by ELISA.

(viii) Cytotoxicity Assay

TCR T-cells are incubated with therapeutic MHC-CAR as well as control cells. Target and control cells are labeled with fluorescent intracellular dyes (CFSE or Cell Trace Violet) before co-culturing with MHC-CAR T-cells. The co-cultures are incubated for 4 hours. After this incubation period, cells are labeled with a fixable viability dye and analyzed by flow cytometry. Viability of each cell population (target or negative control) is determined and the percentage of specific cell lysis is calculated. Cytotoxicity assays are carried out 48 hours after transduction.

(ix) Inhibition Assay

PBMCs are co-cultured with irradiated or mitomycin-treated engineered cells expressing the MHC-CAR construct. As control, PBMCs are co-cultured with irradiated or mitomycin-treated engineered T cells that do not express the MHC-CAR construct. 7 days later, cell proliferation from a human patient donor A is measured by XTT colorimetric assay or by CFSE dilution (FACS analysis). Although cell proliferation would be observed in control, no or limited cell proliferation is expected when engineered T cells express secreted FP. The results from this experiment aim to show that alloreactive T cells proliferation is inhibited when the MHC-CAR expressing T cells express FP.

(x) Proliferation

To test whether engagement of the MHC-CAR with antigen-specific TCR stimulates proliferation of MHC-CAR containing T cells, target cell lines transiently expressing TCR are magnetically sorted for TCR expression 24 hours after electroporation and irradiated. Alternatively, target cell lines that stably express TCR are irradiated. The irradiated cells displaying (+/−antigen-specific) TCR are incubated with CFSE-labeled MHC-CAR cells and proliferation is measured after culture at different T:E ratios.

(xi) In Vivo Tests

MHC-CAR (with mouse and human MHC) in mouse T cells has previously shown therapeutic efficacy in experimental allergic encephalomyelitis, the mouse model for multiple sclerosis [25, 29], Here we test whether MHC-CAR in human cells can target human TCR in human T cell lines, using an in vivo mouse model analogous to that in prior CAR preclinical studies [39]. The in vivo tests allow further evaluation of MHC-CAR signaling domains and T cell subsets.

The in vivo activity of MHC-CAR T-cells can be verified in a mouse xenograft model as illustrated in FIG. 7.

Immunodefficient NOG mice are intravenously injected with antigen-specific TCR-luciferase expressing T-cells as an MS xenograft mouse model. Mice then receive intravenous doses of MHC-CAR T-cells tested at different doses, either 2 or 7 days post-injection with tumor cell line. Intravenous injection with T-cells that are not transduced with the CAR lentiviral vector serve as control. Bioluminescent signals are determined at the day of T-cell injection (DO), at D7, 14, 21, 28 and 40 after 'T'-cell injection in order to follow the expansion of TCR-luciferase expressing cells in different animals [39].

CAR T-cells with similar background modifications (TALEN to inactivate native TCR and minimize graft vs host, TALEN to inactivate CD52 and allow simultaneous treatment with alemtuzumab, and RQR8 to allow depletion) to the ones shown here have been previously validated in mouse models and are now used in a UCART19 clinical trial [39].

(xii) Kill-Switch Verification

Transduced T cells are exposed to 25% baby-rabbit complement (AbD Serotec) for 4 hours with or without inclusion of pharmaceutical complements (rituximab, tysabri, or alemtuzumab) to examine complement-dependent cytotoxicity (CDC)-mediated sensitivity. Miltenyi CD34 magnetic bead-selected-transduced RQR8 T-cells are compared against a similarly treated population of Q8-transduced T cells to demonstrate specificity of CDC-mediated deletion. Further examination of CDC assay parameters was achieved through time-course/dose-titration assays using RQR8-transduced T cells incubated with pharmaceutical complement at 12.5, 25, 50, and 100 mg/mL and time-point assessments ranging between 1 to 120 minutes.

Example 4: Regulatory T Cells (Treg) Expressing MHC-CAR

Therapies that antigen specifically target pathologic T lymphocytes responsible for multiple sclerosis and other autoimmune diseases are expected to have improved therapeutic indices compared with antigen-nonspecific therapies. This example provides an exemplary cellular immunotherapy that uses chimeric antigen receptors to selectively redirect therapeutic T cells against myelin basic protein-specific T lymphocytes implicated in MS Treg Cell Sorting, Transduction, and Expansion CD4+ T cells are isolated from PMBC via RosetteSep (STEMCELL Technologies) and enriched for CD25+ cells (Miltenyi Biotec) prior to sorting into live CD4+CD45RO−CD45RA+CD25+ Tregs and CD4+CD45RO−CD45RA+CD25− control T cells by FACS. Sorted T cells are stimulated with artificial APCs (aAPCs) loaded with aCD3 niAbs in 1,000 U/ml or 100 U/ml of IL-2, for Tregs or non-reg control T, respectively. One day later, cells are transduced with lentivirus. At day 7, ΔNGFR+ cells were purified with magnetic selection (Miltenyi Biotec), then re-stimulated with aAPCs as above and expanded for 6 to 7 days.

Flow Cytometry:

For phenotypic analysis, cells were stained with fixable viability dye (FVD) (65-0865-14 and 65-0866-14, eBioscience) and for surface markers before fix/perm with FOXP3/Transcription Factor Staining Buffer Set (eBioscience), followed by staining for intracellular proteins. For analysis of cytokine production, cells were stimulated with 10 ng ml PMA and 500 ng/ml ionomycin, in the presence of brefeldin A (10 μg/ml) (all Sigma-Aldrich) for 4 hours. Samples were analyzed by flow cytometry.

Microscopy:

PBMCs are labeled with PKH26 or PKH67 (Sigma-Aldrich, PKH26GL-1KT and PKH67GL-1KT), and Tregs are labeled with cell proliferation dye (CPD) eFluor450 (eBiosciences, 65-0842-85) and then suspended in a 3D gel of 1.5% rat tail collagen type I (Ibidi) composed of 1×DMEM and 10% FCS per the manufacturer's general 3D gel protocol. The cell suspension is pipetted into μ-Slide Chemotaxis3D and allowed to polymerize for 30 minutes in a humidified incubator at 35° C. and 5% CO2 (Tokai Hit) on a Leica TCS SP8 confocal microscope. The outer chambers are filled with 1×DMEM and images recorded using a ×10/0.30 objective every 2 minutes for 3 hours. eFluor450, and PKH26 were excited at 405 nm, 488 nm, and 561 nm, and the fluorescence emission is collected at 415-470 nm, 495-525 nm, and 570-650 nm, respectively. The number of interactions between CAR-Tregs and either target or control cells is quantified every 20 minutes. Cells that do not move were excluded from the analysis. The total numbers of each labeled cell type per field of view can be counted using the analyze particles function in ImageJ (imagej.nih.gov/ij/).

Treg-Specific Demethylated Region (TSDR) Analysis

Treg stable expression of stable Foxp3 is associated with selective demethylation of TSDR within the Foxp3 locus. In order to test for stable expression, DNA from frozen T cell pellets is was isolated with the DNeasy Blood and Tissue Kit (QIAGEN) and bisulfite converted with the EZ Direct Kit (Zymo Research). PCR of BisDNA was performed with the Human FOXP3 Kit (Epigen DX) and prepared for pyrosequencing using PyroMark buffers (QIAGEN), then assayed on a Biotage PyroMark Q96 MD pyrosequencer (QIAGEN). Results were calculated with Pyro Q-CpG software (Biotage).

Cytokine Production

To measure cytokine production, T cell lines are stimulated with K562 cells (1 K562:2 T cells) for 48 hours. Supernatants are collected and cytokine concentration was determined by the Human Th1/Th2/Th17 Cytokine Kit (BD Biosciences) and analyzed.

Suppression of MHC CAR-Specific Proliferation

To test whether Treg specific for target were also capable of suppressing CD4+ T cell proliferation, MHC CAR-specific CD4+ T clones are isolated. An Epstein Barr Virus-tranformed B lymphablastoid cell line was transduced with MHC-CAR using lentivirus. EBV cell lines were were grown overnight, irradiated at 150 Gy, and cocultured with CPD-labeled MHC CAR-specific CD4+ T clones in the absence or presence of CAR-expressing Tregs or conventional T cells. Proliferation is determined after 4 days, and percentage of suppression of MHC CAR-specific clones calculated using percentage of proliferation as follows: (100−[(% proliferated MHC CAR+test)/(% proliferated MHC CAR alone)]×100).

Upon verification of construct trafficking and expression (with mRNA, multicisttronic mRNA, and/or lentivirus), activity tests will begin in vitro. All tests are conducted at different effector:target (E:F) cell concentrations. The in vitro tests are expected to provide an initial evaluation of MHC-CAR signaling domains and T cell subsets.

Transient or Lentiviral Expression of Chemokine and Adhesion Receptors in T Cells Receptors are expressed in human T cells after electroporation of mono/polycistronic mRNA or lentiviral transduction. Expression of the receptor is analyzed using flow cytometry. In summary: $5\times10^6$ T cells preactivated several days (3-5) with anti CD3/CD28 coated beads and IL2 were re-suspended in cytoporation buffer T, and electroporated with 45 μg of mRNA. Twenty-four hours after electroporation, human T cells engineered using polycistronic mRNAs encoding the multi-chain CARs were labeled with a fixable viability dye eFluor-780 and a PE-conjugated goat anti mouse IgG F(ab')2 fragment specific, and analyzed by flow cytometry. Alternately the receptors were vectorized in lentivirus, expressed, and analyzed similarly.

In Vitro Chemotaxis Assay

Transduced T cells were used in chemotaxis assays as previously described [Bürkle et al., *Blood*, 110(9):3316-3325, 2007; Wu and Hwang, *Journal of immunology*, 168 (10):5096, 2002.; Singh et al., Journal of immunology, 180(1): 214-221, 2008.; Ryu et al., Molecules and *Cells*, 39.12:898-908, 2016.]. Cells (~20,000 cells in medium, one million cells, $5\times10^6$/mL) were placed on top of the 5-μm pore size filters in duplicate, whereas medium with and without chemokines were placed into the lower chamber. After 30 min, 1 h, 3 h, 5 hr, 24 hr at 37° C., migrated cells that had fallen to the bottom of the plate were:

A. photographed using a 4× objective. Three random views from each of two wells were counted using Image Pro Plus (Media Cybernetics, Silver Spring, MD). Three independent experiments were performed with similar results.

B. 400 μL of the cell suspension was added to 100 μL of a solution containing 4×10−7 M FITC-labeled phalloidin, 0.5 mg/mL 1-alpha-lysophosphatidylcholine (both from Sigma, St Louis, MO), and 7% formaldehyde in phosphate-buffered saline (PBS). The fixed cells were analyzed by flow cytometry on a FACSCalibur, and all time points are plotted relative to the mean relative fluorescence of the sample before addition of the chemokine.

C. the cells in the lower chamber were counted using Countess II FL (Thermo Fisher Scientific. USA) or the O.D. value at 450 nm was measured using a Versamax microplate reader (Molecular Devices).

Example 5: Expression of MHC-Based Chimeric Receptors (MHC-CAR) Ins HEK293 Cells Constructs encoding MHC-CARs were constructed as discussed in Example 2 and assessed for expression in HEK293 cells. Briefly, Construct 1 includes an EF1alpha short promoter, CD19 CAR (4G7-CAR), CCR6, and GFP (provided by SEQ ID NO: 426); and Construct 2 includes a EF1alpha short promoter, RQR8, MHC-CAR1 part B MHC-CAR1 part A, and GFP (provided by SEQ ID NO: 409).

Constructs 1, 2, or media control (non-transfected) was transfected into HEK293 cells and cultured. The cells were assessed for expression by microscopy based on GFP expression. Populations of GF-positive cells were observed in the groups that were transfected with Construct 1 or Construct 2. The cells were also assessed for expression of the components encoded by the constructs by flow cytometry. Tables 8 and 9.

Construct 1 Expression

For detection of CCR6, cells were incubated with an anti-CCR6 monoclonal antibody conjugated to APC (17-1969-42, eBioscience); and for detection of CD19, cells were incubated with a biotinylated CD19 (Acro CD9-H8259, Acro Biosystems) followed by a streptavidin-PE (405203, BioLegend®).

TABLE 8

Expression of Construct 1

|  | FITC (GFP) | APC (CCR6) | PE (CD19) |
|---|---|---|---|
| CCR6 Expression |  |  |  |
| Unstained | 71.9 | 0.1 | 17.4 |
| CCR6 | 71.3 | 81.9 | 16.9 |
| CD19 Expression |  |  |  |
| Unstained | 71.9 | 0.1 | 17.4 |
| CD19 | 71.3 | 0.1 | 33.3 |
| streptavidin-PE only | 71.5 | 0.1 | 18.5 |

Construct 2 Expression

For detection of CD34 expression from the epitope included in RQR8, cells were incubated with an anti-CD34 APC-conjugated monoclonal antibody; and for detection of MHC-CAR expression; the cells were incubated an anti-HLA-DR antibody.

TABLE 9

Construct 2 Expression

| GFP Expression | FITC (GFP) | APC (CD34) | PE |
|---|---|---|---|
| Unstained | 62.3 | 0.1 | 2.4 |
| RQR Expression | FITC (GFP) | APC (CD34) | PE |
| Unstained | 62.3 | 0.0 | 2.4 |
| CD34 | 61.8 | 58.0 | 2.5 |
| MHC CAR Expression | FITC (GFP) | APC (HLA-DR) | PE |
| Unstained | 62.3 | 0.0 | 2.4 |
| HLA-DR | 63.9 | 98.1 | 2.1 |

```
Nucleic acid sequence of Construct 1 (SEQ ID NO: 426)
                                                        (SEQ ID NO: 426)
atggagacagacactcttctcctttgggtcttgctgctgtgggttcccggaagcacaggagaagcacagttgcaa cagtctgggccagaactcatcaaacccggagcttctgtaaaaatgtcatgcaaagctagtggatatacatttact tcttacgtgatgcactgggtaaaacagaaacctggtcaggggcttgagtggatcgggtacattaacccatataat gacggcaccaaatataacgagaaattcaagggaaaggctacgcttacatcagataagtccagtagcaccgcttat atggaacttagcagccttacttccgaagattccgcggtgtattactgcgcgagagggacttactactacgggagt cgagtattcgattattgggtcaaggcacgacgctcacggtgagctcaggtggtggagggtctggggtggcggc agtggtggggggctcagacatcgtgatgacccaggcagcaccttctatcccggtaacccaggcgagtctgta tctatcagttgtcggtccagcaagtctcttctcaacagtaatggcaatacatatctttactggttcctccaaagg cctgggcaaagtcctcaacttcttatatatcggatgtccaatcttgcgagtggcgtaccagacaggttttcaggg tctgggagcggaacagcttttacgttgagaatatccagggtagaagctgaggacgtcggtgtatattattgcatg caacatctcgaatacccctttaccttcggcgctggtacaaagctcgaattgaaacgcagcgatccaaccacgacg ccagcgccacgaccacctacgcccgctccaactattgcctcccagccctgagtcttcggccagaagcgtgtaga cctgctgccggcggggccgttcatacgcggggccttgactttgcatgtgatatctatatgggctccttttggcg ggaacttgcggagtgcttcttttgtcactcgtgataacgttgtattgtaaaagggtcgaaagaaactcctctat
```

-continued atatttaagcagcccctttatgaggcccgtgcaaacaacacaagaagaggacggatgctcttgtcgattcccggaa gaggaggaaggggggtgtgagcttagggtcaagttttctcgctctgccgacgcgccagccctcaacagggccaa aaccagctgtataacgaactcaacctcgggcgccgggaagagtatgacgtccttgacaaacggcgcggtcgcgac cctgaaatgggtggaaaaccgaggcgaaagaaccccccaggagggactttacaacgaattgcaaaaagacaagatg gccgaagcctattccgaaattggaatgaaaggcgagcggagacgaggtaaggggcatgacggcctgtatcaaggg ctctctacggccacgaaggatacttacgacgcccttcatatgcaagctcttccaccacggggttcgagcggcagt ggagagggcagaggaagtctgctaacatgcggtgacgtcgaggagaatcctggcccaatgagtggggaaagtatg aacttcagcgatgtatttgactcctccgaagattactttgtatctgtgaatacgagccattactccgtcgatagt gaaatgctgctctgtagtctccaagaagtccgccaattcagtcgcctcctcgttcccatcgcgtactcccttatt tgtgttttttggccttctgggtaacatcctggttgtaatcacattcgctttctataaaaaagctcggagtatgact gatgtttaccttcttaacatggctatagoggacattcttttgtgcttactctcccattctgggctgtgagccat gcaacagggcgtgggttttttcaaatgccacatgtaagctgcttaaagggatctatgcaataaacttcaattgc gggatgctcctgctgacatgcatcagtatggatcgatacatagctatagtacacaggactaagtccttccgcctg cgatcccgcacactgcctaggagcaaaattatttgcctcgtcgtatgggggctctcagtgatcatctcctccagt acgtttgtctttaaccagaaatataacacacagggttctgatgtatgtgaaccaaagtatcagacagtgagtgaa ccaatacggtggaagttgcttatgttgggcttggagctgcttttggttttttcatcccactgatgttcatgatt ttctgttatacatttattgttaagaccttggttcaggcgcaaaatagcaagagacataaggcaattcgagtcacc attgccgtggtgttggtcttcttggcctgtcagatcccccataatatggttctgctcgtcaccgccgctaacttg ggtaagatgaatcgatcttgtcagtccgagaagttgatcggatacaccaaaactgtgatagaagtgctggccttc cttcactgttgtctgaacccagttttgtatgcttttataggacagaagtttcgaaattacttcttgaaaatcctc aaggacctctggtgtgttcgaaggaagtacaagagctctggctttagttgcgctgggcgctacagtgagaatata tcccggcagacctccgagactgctgataatgacaacgcaagttccttcactatg Nucleic acid sequence of Construct 2 (SEQ ID NO: 409)

(SEQ ID NO: 409)

atgggtacttcactgttgtgctggatggcactttgtcttttgggtgccgatcatgctgatgcatgtccgtactcc aatcctagcctgtgctccggggggggagggagtgaactccctacacagggaaccttctctaatgtctccaccaac gtctcccctgcaaaaccgatcacaatagcttgcccctatagtaaccctttccctctgtagtggaggggggggttca cctgctccacgccctcctaccccgcgccaacgatcgcgtcacaaccgctcagtcttaggccggaagcctgtagg ccagcggctggcggtgcggttcatacgcggggattggattttgcctgcgacatttacatttgggctccgctggcc ggtacttgtggggtattgctgttgtctottgttattacgctttattgcaatcacaggaacaggcgacgagtatgc aaatgcccgcggcccgtcgtgagatctgggtccggccaatgtactaactacgctttgttgaaactcgctggcgat gttgaaagtaacccccggtcctccaacaggtatggtatgcttgaagctcccggggcgggtcctgcatgaccgctctc actgttactcttatggtccttagttcaccgcttgccctggcatctgatgagaatcccgtggttcattttttaag aacatcgtcacaccgcgcaccccacctgggggaggcggatctggcggaggcgggagtggaggctcaggagacaca agaccccgattcttgtggcagcccaaaagggagtgccattttttcaatgggacggaacgagttcgcttccttgat gggcgacctgacgcggagtactggaactcccaaaaggatattttggagcaggcacgagcagctgtggacacctat tgtcgacataattatggtgtggtggaatcctttacagttcagcggcgggtgcaacctaaagtgaccgtgtatcca tctaaaacgcaaccccctccaacaccataacctcctggtgtgttccgtaagcggcttctatcccgggtcaattgag gtcaggtggttcctcaacggtcaggaggagaaggccggaatggtaagtactggtcttatccagaacggagactgg accttccaaactttggtaatgttggaaacggtgccgcgatccggggaggtgtatacatgccaagttgaacacccg agtgttacgagcccctgacggttgagtggagggcgcggtcagagagcgcacaatctaaaatgctgtcaggagta ggcggatttgtactcggactcctctttttgggcgctgggttgtttatctactttagaaaccaaacaagtagagta -continued

```
aagtttccccgaagtgcggacgcccccgcgtatcagcaaggtcaaaaccagctttataacgaactgaacttggga cgacgcgaagagtacgatgttcttgataagcggagagggcgcgatcccgaaatgggggaaagcctcggaggaag aacccacaagaaggcctttataatgaactgcagaaggacaagatggcggaggcgtattccgaaataggcatgaag ggtgaacggaggagaggaaagggacatgacggactttatcaaggattgtctaccgcaactaaagacacctatgac gcgttgcacatgcaggctctccctccgagaggttcgagcggcagtggagagggcagaggaagtctgctaacatgc ggtgacgtcgaggagaatcctggcccaatggcaatatctggtgttcctgtcctcgggttttttatcatagccgta ctgatgtcagcacaggaatcatgggcgataaaagaagagcacgtgataatacaggcggagttttatttgaacccg gaccagagcggtgagttcatgttcgattttgatggegacgagatatttcacgttgacatggcaaaaaaggaaacg gtgtggagacttgaggagtttggacgattcgcatcatttgaggcacaaggagcactcgccaatatcgcggtggac aaggccaacctggagatcatgacataacgctccaattatacgcctatcactaatgtgcccctgaggttactgtg ctcacaaattctcccgtagaacttagggaacctaacgtcctcatatgtttcatcgacaagttcactcctccggtg gtcaatgtaacgtggcttcggaatggtaagccggtcaccacgggtgtctcagagaccgtatttctgcccagagaa gaccacctcttccgcaaatttcattaccttccctttcttccttcaacggaagacgtttacgactgcagggtcgaa cattgggggcttgacgagccacttctcaagcattgggagttcgacgcccatcaccgcttccagaaacgactgaa aacgttgtctgcgctcttggcctgacagtgggcctggtaggcattattatcgggaccatctttatcatcaaggt ttgacttcccgggtcaaatttagcagatccgctgacgcaccggcctaccagcagggccagaaccaactctacaac gagctgaatctcggccgacgggaagagtatgacgtactcgacaagcggagaggtcgagaccctgagatgggcggt aaaccgagacggaaaaatccccaagagggtctttataatgaactccagaaggataagatggctgaagcctattct gagatagggatgaaaggcgagcggcggaggggtaagggccatgatggcctttaccagggactctccacggcaacc aaagatacttacgacgcccttcacatgcaagccctcccgccacgcggatccggcgcaacaaacttctctctgctg aaacaagccggagatgtcgaagagaatcctggaccggtgagcaagggcgaggagctgttcaccggggtggtgccc atcctggtcgagctggacggcgacgtaaacggccacaagttcagcgtgtctggcgagggcgagggcgatgccacc tacggcaagctgaccctgaagttcatctgcaccaccggcaagctgcccgtgccctggcccaccctcgtgaccacc ctgacctacggcgtgcagtgcttcagccgctaccccgaccacatgaagcagcacgacttcttcaagtccgccatg cccgaaggctacgtccaggagcgcaccatcttcttcaaggacgacggcaactacaagacccgcgccgaggtgaag ttcgagggcgacaccctggtgaaccgcatcgagctgaagggcatcgacttcaaggaggacggcaacatcctgggg cacaagctggagtacaactacaacagccacaacgtctatatcatggccgacaagcagaagaacggcatcaaggcg aacttcaagatccgccacaacatcgaggacggcagcgtgcagctcgccgaccactaccagcagaacacccccatc ggcgacggccccgtgctgctgcccgacaaccactacctgagcacccagtccgccctgagcaaagaccccaacgag aagcgcgatcacatggtcctgctggagttcgtgaccgccgcgggatcactctcggcatggacgagctgtacaag taa'
```

Example 6: Expression of CD3

Expression of CD3 was assessed to determine the efficacy of CRISPR methods targeting the T cell receptor alpha constant (TRAC) gene. Briefly, sgRNAs targeting the TRAC gene were generated by amplifying the target site using forward primer 5'-AGCGCTCTCGTACAGAGTTGG-3' (SEQ ID NO: 385)) and reverse primer (5'-AAAAAAAGCACCGACTCGGTGCC-3' (SEQ ID NO: 386).

The unmodified sgRNA is provided by the nucleic acid sequence:

(SEQ ID NO: 384)
5'-GAG AAU CAA AAU CGG UGA AUG UUU UAG AGC UAG AAA UAG CAA GUU AAA AUA AGG CUA GUC CGU UAU CAA CUU GAA AAA GUG GCA CCG AGU CGG UGC UUU U-3.

The modified sgRNA is provided by the nucleic acid sequence:

(SEQ ID NO: 337)
5'-2'OMe(G(ps)A(ps)G(ps)) AAU CAA AAU CGG UGA AUG UUU UAG AGC UAG AAA UAG CAA GUU AAA AUA

-continued

```
AGG CUA GUC CGU UAU CAA CUU GAA AAA GUG GCA CCG

AGU CGG UGC 2'OMe(U(ps)U(ps)U(ps) U-3'.
2'OMe = 2'O)-methyl RNA and ps = phosphorothioate.
```

Figure 11:
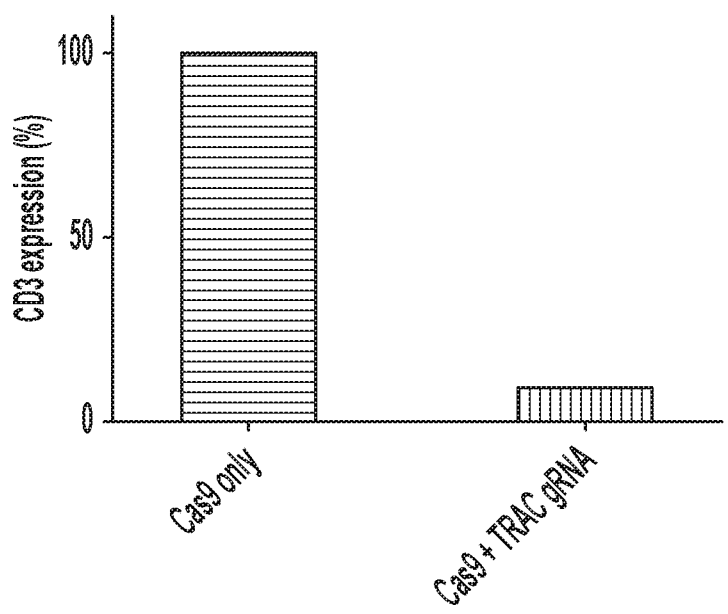
FIG. 11 is a plot showing CD3 expression on primary human stimulated CD3+ T cells (TCELL-0028) transfected with an mRNA encoding Cas9 ("Cas9 only") or an mRNA encoding Cas9 ("Cas9 only") and sgRNAs targeting the gene encoding T cell receptor alpha domain (TRAC) ("Cas9+ TRAC gRNA").

Primary human stimulated CD3+ T-cells were transfected with an mRNA encoding Cas9 (Cas9 only) or both an snRNA encoding Cas9 and sgRNAs targeting the TRAC gene. After 7 days post-transfection, expression of CD3 was assessed by flow cytometry. The cells were incubated with a 1:100 dilution of an anti-CD3-APC antibody (clone OKT3; BioLegend® cat. no. 317318). As shown in FIG. 11, transfection of an mRNA encoding Cas9 and sgRNAs targeting the TRAC gene resulted in a substantial reduction in CD3 expression.

Example 7: Kill Switch Verification

Efficacy of the RQR8 kill switch encoded in example Construct 2 was assessed using a cell viability assay. Briefly, HEK cells were transfected with media only, Construct 1 (SEQ ID NO: X), Construct 2 (which encodes the rituximab-mediated RQR8 kill switch, SEQ ID NO: X), or both Construct 1 and Construct 2. The transfected HEK293 cells were harvested, counted, and resuspended at 1×10^6 cells/mL. 300 uL of the cellular suspension was transferred into each of 4 wells of a 48-well tissue culture plate. 100 uL of complete medium and 4 uL of Rituximab were added to the second well, and 100 uL of freshly prepared baby rabbit complement and 4 uL of Rituximab were added to the fourth well. The plates were incubated for 2, 4, or 24 hours. The assay was terminated by the adding 1 uL of chilled Annexin buffer (150 mMNaCl, 10 mM/HEPES, 10 mM CaCl), and then the sample was transferred into a pre-prepared flow cytometry tube containing 3 ml, of Annexin V buffer.

Samples were harvested by centrifugation and any residual buffer was blotted with paper towels. The samples were then stained with 1 uL of Annexin V APC, vortexed, and placed in subdued lighting for 15 minutes. The samples were then washed with Annexin V buffer and supplemented with 5 uL of propridium iodide/mL buffer and placed on ice pending flow cytometry performed immediately following final suspension.

Figure 12:
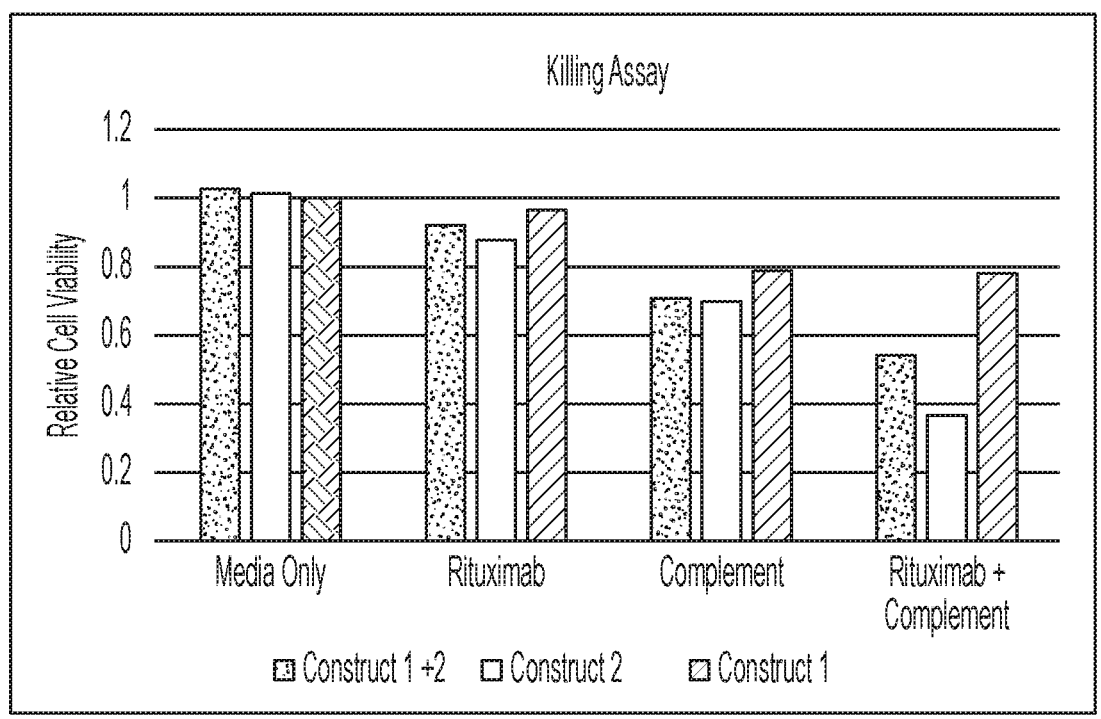
FIG. 12 is a plot showing relative cell viability in a killing assay. HEK-293 cells transfected with Construct 1, Construct 2, or both Constructs 1 and 2 were incubated with media only, rituximab, complement, or both rituximab and complement.

The percentage of GFP-positive cells was quantified to quantify the killing induced by the RQR8 kill switch. As shown in FIG. 12, incubation with complement alone resulted in some cell death, however this reduction in viability was observed in all of the groups of cells. Cell death was observed in cells that expressed Construct 2 or both Constructs 1 and 2 the presence of the combination of rituximab and complement, indicating specific RQR8-mediated cell death.

REFERENCES

[1] Corlien et al., International journal of cancer, 99(1):7-13, 2002.
[2] Betts et la., Methods in cell biology, 75:497-512, 2004.
[3] Birnbaum et al. Proceedings of the National Academy of Sciences of the United States of America, 111(49):17576, 2014.
[4] Boissel et al., Nucleic acids research, 42(4):2591-2601, 2014.
[5] Cai et al., Blood, 128(22):4039, 2016.
[6] Chung et al., Proceedings of the National Academy of Sciences, 92(9):3712-3716, 1995.
[7] Cieri et al., Blood, 121(4):573-584, 2013.
[8] Corrigan-Curay et al., Molecular Therapy, 23(5):796-806, 2015.
[9] Doth et al., Immunological reviews, 257(1):107-126, 2014.
[10] WO2015121454
[11] Farber et al., Nature Reviews Immunology, 14(1):24-35, 2014.
[12] US20170183413
[13] Galetto. Publication No. EP3137498 A1, 2017.
[14] US20140120905
[15] Galetto et al., Molecular Therapy-Methods & Clinical Development, 1:14021, 2014.
[16] Goehels et a., Brain, 123(3):508-518, 2000.
[17] Hahn et al., Nature immunology, 6(5):490-496, 2005.
[18] Hall et al., International Immunology, 3(4):359-368, 1991.
[19] Hart et al., Gene Therapy, 15:625-631, 2008.
[20] Hohlfeld et al., Proceedings of the National Academy of Sciences, 101 (suppl 2):14599-14606, 2004.
[21] Hoist et al., Nature Protocols Electronic Edition, 1(1): 406, 2006.
[22] Jensen et al., Immunological reviews, 257(1):127-144, 2014.
[23] Juillerat et al., Scientific reports, 5:8150, 2015.
[24] Justesen et al., Immunome research, 5(1):2, 2009.
[25] Jyothi et al., Nature biotechnology, 20(12):1215-1220, 2002.
[26] Mach et al., Immunological reviews, 138(1):207-221, 1994.
[27] Maecker et al., Nature Reviews Immunology, 12(3): 191-200, 2012.
[28] Mamonkin et al., Blood, 126(8):983-992, 2015.
[29] Moisini et al., The Journal of Immunology, 180(5): 3601-3611, 2008.
[30] Morris et al., Science translational medicine, 7(272): 272ra10-272ra10, 2015.
[31] Moscou et al., Science, 326(5959):1501-1501, 2009.
[32] Mueller et al., Nature reviews immunology, 16(2):79-89, 2016.
[33] Nagarajan et al., The Journal of Immunology, 168(4): 1780-1786, 2002.
[34] Nagy et al., Nature medicine, 8(8):801-807, 2002.
[35] Ophir et al., Blood, 121(7):1220-1228, 2013,
[36] Osborn et al., Molecular therapy, 24(3):570-581, 2016.
[37] Philip et al., Blood, 124(8):1277-1287, 2014.
[38] US20170016025
[39] Poirot et al., Cancer research, 75(18):3853-3864, 2015.
[40] Qasim et al., Science translational medicine, 9(374): eaaj2013, 2017.
[41] Ruck et al., International journal of molecular sciences, 16(7):16414-16439, 2015.
[42] Salzer et al., Neurology, 87(20):2074-2081, 2016.
[43] Smith et al., U.S. patent application Ser. No. 14/018, 021, 2013.
[44] Steidl et al., Nature, 471(7338):377-381, 2011.
[45] Suhoski et al., Molecular Therapy, 15(5):981-988, 2007.
[46] Taylor et al., Cell, 169(1):108-119, 2017.
[47] Valton et al., Molecular Therapy, 23(9):1507-1518, 2015.
[48] Vanderlugt et al., Nature Reviews Immunology, 2(2): 85-95, 2002.
[49] Wifichli et al., PloS one, 6(11):e27930, 2011.
[50] Wingerchuk et al., Mayo Clinic Proceedings, 89:225-240, 2014.
[51] Yang et al., Gene Therapy, 15(21):1411-1423, 2008.

[52] Yang, Journal of Immunotherapy, 31(9):830, 2008.
[53] Zhou et al., Immunology, 122(4):476-485, 2007.
Jiang et al., international immunology, 25(4):235-246, 2013.
Busch et al., The EMBO journal, 15(2):418, 1996.
Akalin et al., Molecular Therapy, 17:S25, 2009.
Jin et al., Proceedings of the National Academy of Sciences, 111(10):3787-3792, 2014.
Tanimura et al., Blood, 125(18):2835-2844, 2015,
Hamano et al., Alveolar Macrophage Biology B32:A3147-A3147, 2016.
Arase et al., Journal of Dermatological Science, 84(1):e87, 2016.
Tanimura et al., Placenta, 46:108, 2016.
Hiwa et al., Arthritis & Rheumatology, 69(10):2069-2080, 2017.
Hansen et al. Trends in immunology, 31(10):363, 2010.
Hacohen et al., Cancer immunology research, 1(1):11-15, 2013.
Owens et al., Annals of neurology, 65(60):639-649, 2009.
Chastre et al., New England Journal of Medicine, 374(15): 1495-1496, 2016.
Housley et al., Clinical Immunology, 161(1):51-58, 2015.
Larman et al., 2013. Journal of autoimmunity, 43:1-9, 2013,
Wu et al., *Science,* 350(6258):aab4077, 2015
Tran et al. Scientific reports, 6:31730, 2016
Schall et al., Nature Reviews Immunology, 11(5):355-363, 2011.
Tabarkiewicz et al., Archivum immunologiae et therapiae experimentalis, 63(6):435-449, 2015.
Brown et al., New England Journal of Medicine, 375(26): 2561-2569, 2016.
Gagliani et al., Nature. 523(7559):221-225, 2015.
Barreiro, et al. Cardiovascular research, 86(2):174-182, 2010
Wang and Rivière. Molecular Therapy-Oncolytics, 3:16015 2016.
Bürkle et al., Blood, 110(9):3316-3325, 2007.
Wu and Hwang, Journal of immunology, 168(10):5096, 2002.
Singh et al., Journal of immunology, 180(1):214-221, 2008.
Ryu et al., Molecules and Cells, 39.12:898-908, 2016.
Hiepe et al., Nature Reviews Rheumatology, 7(3):170-178, 2011
Garboczi, et al. *The Journal of Immunology,* 157(12):5403-5410, 1996.
Quaresma, et al., 2015. Viruses, 8(1):5 2015.
Sanjana, et al. Nature methods, 11(8):783-784, 2014.
Korn et al. *Proceedings of the National Academy of Sciences,* 105(47):18460-18465, 2008.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

SEQUENCE LISTING

```
<160> NUMBER OF SEQ ID NOS: 431

<210> SEQ ID NO 1
<211> LENGTH: 203
<212> TYPE: PRT
<213> ORGANISM: Homo Sapiens

<400> SEQUENCE: 1

Met Ala Ser Gln Lys Arg Pro Ser Gln Arg His Gly Ser Lys Tyr Leu
1               5                   10                  15

Ala Thr Ala Ser Thr Met Asp His Ala Arg His Gly Phe Leu Pro Arg
            20                  25                  30

His Arg Asp Thr Gly Ile Leu Asp Ser Ile Gly Arg Phe Phe Gly Gly
        35                  40                  45

Asp Arg Gly Ala Pro Lys Arg Gly Ser Gly Lys Val Pro Trp Leu Lys
    50                  55                  60

Pro Gly Arg Ser Pro Leu Pro Ser His Ala Arg Ser Gln Pro Gly Leu
65                  70                  75                  80

Cys Asn Met Tyr Lys Asp Ser His His Pro Ala Arg Thr Ala His Tyr
                85                  90                  95

Gly Ser Leu Pro Gln Lys Ser His Gly Arg Thr Gln Asp Glu Asn Pro
            100                 105                 110

Val Val His Phe Phe Lys Asn Ile Val Thr Pro Arg Thr Pro Pro Pro
        115                 120                 125

Ser Gln Gly Lys Gly Arg Gly Leu Ser Leu Ser Arg Phe Ser Trp Gly
    130                 135                 140
```

```
Ala Glu Gly Gln Arg Pro Gly Phe Gly Tyr Gly Arg Ala Ser Asp
145                 150                 155                 160

Tyr Lys Ser Ala His Lys Gly Phe Lys Gly Val Asp Ala Gln Gly Thr
                165                 170                 175

Leu Ser Lys Ile Phe Lys Leu Gly Gly Arg Asp Ser Arg Ser Gly Ser
            180                 185                 190

Pro Met Ala Arg Arg His His His His His His
            195                 200
```

<210> SEQ ID NO 2
<211> LENGTH: 40
<212> TYPE: PRT
<213> ORGANISM: Homo Sapiens

<400> SEQUENCE: 2

```
Gly Ser Lys Tyr Leu Ala Thr Ala Ser Thr Met Asp His Ala Arg His
1               5                   10                  15

Gly Phe Leu Pro Arg His Arg Asp Thr Gly Ile Leu Asp Ser Ile Gly
            20                  25                  30

Arg Phe Phe Gly Gly Asp Arg Gly
            35                  40
```

<210> SEQ ID NO 3
<211> LENGTH: 20
<212> TYPE: PRT
<213> ORGANISM: Homo Sapiens

<400> SEQUENCE: 3

```
Lys Tyr Leu Ala Thr Ala Ser Thr Met Asp His Ala Arg His Gly Phe
1               5                   10                  15

Leu Pro Arg His
            20
```

<210> SEQ ID NO 4
<211> LENGTH: 23
<212> TYPE: PRT
<213> ORGANISM: Homo Sapiens

<400> SEQUENCE: 4

```
Ala Thr Ala Ser Thr Met Asp His Ala Arg His Gly Phe Leu Pro Arg
1               5                   10                  15

His Arg Asp Thr Gly Ile Leu
            20
```

<210> SEQ ID NO 5
<211> LENGTH: 20
<212> TYPE: PRT
<213> ORGANISM: Homo Sapiens

<400> SEQUENCE: 5

```
Arg Asp Thr Gly Ile Leu Asp Ser Ile Gly Arg Phe Phe Gly Gly Asp
1               5                   10                  15

Arg Gly Ala Pro
            20
```

<210> SEQ ID NO 6
<211> LENGTH: 29
<212> TYPE: PRT
<213> ORGANISM: Homo Sapiens

<400> SEQUENCE: 6

Ile Gly Arg Phe Phe Gly Gly Asp Arg Gly Ala Pro Lys Arg Gly Ser
1               5                   10                  15

Gly Lys Asp Ser His His Pro Ala Arg Thr Ala His Tyr
            20                  25

<210> SEQ ID NO 7
<211> LENGTH: 19
<212> TYPE: PRT
<213> ORGANISM: Homo Sapiens

<400> SEQUENCE: 7

Ala Pro Lys Arg Gly Ser Gly Lys Asp Ser His His Ala Ala Arg Thr
1               5                   10                  15

Ala His Tyr

<210> SEQ ID NO 8
<211> LENGTH: 20
<212> TYPE: PRT
<213> ORGANISM: Homo Sapiens

<400> SEQUENCE: 8

Gly Ser Gly Lys Asp Ser His His Pro Ala Arg Thr Ala His Tyr Gly
1               5                   10                  15

Ser Leu Pro Gln
            20

<210> SEQ ID NO 9
<211> LENGTH: 19
<212> TYPE: PRT
<213> ORGANISM: Homo Sapiens

<400> SEQUENCE: 9

His His Pro Ala Arg Thr Ala His Tyr Gly Ser Leu Pro Gln Lys Ser
1               5                   10                  15

His Gly Arg

<210> SEQ ID NO 10
<211> LENGTH: 19
<212> TYPE: PRT
<213> ORGANISM: Homo Sapiens

<400> SEQUENCE: 10

His Ala Ala Arg Thr Ala His Tyr Gly Ser Leu Pro Gln Lys Ser Gln
1               5                   10                  15

Gly His Arg

<210> SEQ ID NO 11
<211> LENGTH: 19
<212> TYPE: PRT
<213> ORGANISM: Homo Sapiens

<400> SEQUENCE: 11

Ser Leu Pro Gln Lys Ser His Gly Arg Thr Gln Asp Glu Asn Pro Val
1               5                   10                  15

Val His Phe

<210> SEQ ID NO 12
<211> LENGTH: 20
<212> TYPE: PRT
<213> ORGANISM: Homo Sapiens

<400> SEQUENCE: 12

```
Pro Gln Asp Glu Asn Pro Val Val His Phe Phe Lys Asn Ile Val Thr
1               5                   10                  15

Pro Arg Thr Pro
            20
```

<210> SEQ ID NO 13
<211> LENGTH: 20
<212> TYPE: PRT
<213> ORGANISM: Homo Sapiens

<400> SEQUENCE: 13

```
Thr Gln Asp Glu Asn Pro Val Val His Phe Phe Lys Asn Ile Val Thr
1               5                   10                  15

Pro Arg Thr Pro
            20
```

<210> SEQ ID NO 14
<211> LENGTH: 19
<212> TYPE: PRT
<213> ORGANISM: Homo Sapiens

<400> SEQUENCE: 14

```
Gln Asp Glu Asn Pro Val Val His Phe Phe Lys Asn Ile Val Thr Pro
1               5                   10                  15

Arg Thr Pro
```

<210> SEQ ID NO 15
<211> LENGTH: 19
<212> TYPE: PRT
<213> ORGANISM: Homo Sapiens

<400> SEQUENCE: 15

```
Asp Glu Asn Pro Val Val His Phe Phe Lys Asn Ile Val Thr Pro Arg
1               5                   10                  15

Thr Pro Pro
```

<210> SEQ ID NO 16
<211> LENGTH: 15
<212> TYPE: PRT
<213> ORGANISM: Homo Sapiens

<400> SEQUENCE: 16

```
Glu Asn Pro Val Val His Phe Phe Lys Asn Ile Val Thr Pro Arg
1               5                   10                  15
```

<210> SEQ ID NO 17
<211> LENGTH: 17
<212> TYPE: PRT
<213> ORGANISM: Homo Sapiens

<400> SEQUENCE: 17

```
Glu Asn Pro Val Val His Phe Phe Lys Asn Ile Val Thr Pro Arg Thr
1               5                   10                  15

Pro
```

<210> SEQ ID NO 18
<211> LENGTH: 14
<212> TYPE: PRT
<213> ORGANISM: Homo Sapiens

<400> SEQUENCE: 18

-continued

Glu Asn Pro Val Val His Phe Phe Lys Asn Ile Val Thr Pro
1               5                   10

<210> SEQ ID NO 19
<211> LENGTH: 20
<212> TYPE: PRT
<213> ORGANISM: Homo Sapiens

<400> SEQUENCE: 19

Asn Pro Val Val His Phe Phe Lys Asn Ile Val Thr Pro Arg Thr Pro
1               5                   10                  15

Pro Pro Ser Gln
            20

<210> SEQ ID NO 20
<211> LENGTH: 13
<212> TYPE: PRT
<213> ORGANISM: Homo Sapiens

<400> SEQUENCE: 20

Val Val His Phe Phe Lys Asn Ile Val Thr Pro Arg Thr
1               5                   10

<210> SEQ ID NO 21
<211> LENGTH: 20
<212> TYPE: PRT
<213> ORGANISM: Homo Sapiens

<400> SEQUENCE: 21

Val Val His Phe Phe Lys Asn Ile Val Thr Pro Arg Thr Pro Pro Pro
1               5                   10                  15

Ser Gln Gly Lys
            20

<210> SEQ ID NO 22
<211> LENGTH: 19
<212> TYPE: PRT
<213> ORGANISM: Homo Sapiens

<400> SEQUENCE: 22

Lys Asn Ile Val Thr Pro Arg Thr Pro Pro Pro Ser Gln Gly Lys Gly
1               5                   10                  15

Arg Gly Leu

<210> SEQ ID NO 23
<211> LENGTH: 19
<212> TYPE: PRT
<213> ORGANISM: Homo Sapiens

<400> SEQUENCE: 23

Pro Ser Gln Gly Lys Gly Arg Gly Leu Ser Leu Ser Arg Phe Ser Trp
1               5                   10                  15

Gly Ala Glu

<210> SEQ ID NO 24
<211> LENGTH: 20
<212> TYPE: PRT
<213> ORGANISM: Homo Sapiens

<400> SEQUENCE: 24

Gly Lys Gly Arg Gly Leu Ser Leu Ser Arg Phe Ser Trp Gly Ala Glu
1               5                   10                  15

```
Gly Gln Arg Pro
         20

<210> SEQ ID NO 25
<211> LENGTH: 19
<212> TYPE: PRT
<213> ORGANISM: Homo Sapiens

<400> SEQUENCE: 25

Leu Ser Arg Phe Ser Trp Gly Ala Glu Gly Gln Arg Pro Gly Phe Gly
1               5                   10                  15

Tyr Gly Gly

<210> SEQ ID NO 26
<211> LENGTH: 19
<212> TYPE: PRT
<213> ORGANISM: Homo Sapiens

<400> SEQUENCE: 26

Gln Arg Pro Gly Phe Gly Tyr Gly Gly Arg Ala Ser Asp Tyr Lys Ser
1               5                   10                  15

Ala His Lys

<210> SEQ ID NO 27
<211> LENGTH: 19
<212> TYPE: PRT
<213> ORGANISM: Homo Sapiens

<400> SEQUENCE: 27

Ala Ser Asp Tyr Lys Ser Ala His Lys Gly Phe Lys Gly Val Asp Ala
1               5                   10                  15

Gln Gly Thr

<210> SEQ ID NO 28
<211> LENGTH: 19
<212> TYPE: PRT
<213> ORGANISM: Homo Sapiens

<400> SEQUENCE: 28

Phe Lys Gly Val Asp Ala Gln Gly Thr Leu Ser Lys Ile Phe Lys Leu
1               5                   10                  15

Gly Gly Arg

<210> SEQ ID NO 29
<211> LENGTH: 20
<212> TYPE: PRT
<213> ORGANISM: Homo Sapiens

<400> SEQUENCE: 29

Val Asp Ala Gln Gly Thr Leu Ser Lys Ile Phe Lys Leu Gly Gly Arg
1               5                   10                  15

Asp Ser Arg Ser
         20

<210> SEQ ID NO 30
<211> LENGTH: 20
<212> TYPE: PRT
<213> ORGANISM: Homo Sapiens

<400> SEQUENCE: 30

Ser Lys Ile Phe Lys Leu Gly Gly Arg Asp Ser Arg Ser Gly Ser Pro
1               5                   10                  15
```

```
Met Ala Arg Arg
            20

<210> SEQ ID NO 31
<211> LENGTH: 247
<212> TYPE: PRT
<213> ORGANISM: Homo Sapiens

<400> SEQUENCE: 31

Met Ala Ser Leu Ser Arg Pro Ser Leu Pro Ser Cys Leu Cys Ser Phe
1               5                   10                  15

Leu Leu Leu Leu Leu Leu Gln Val Ser Ser Ser Tyr Ala Gly Gln Phe
            20                  25                  30

Arg Val Ile Gly Pro Arg His Pro Ile Arg Ala Leu Val Gly Asp Glu
        35                  40                  45

Val Glu Leu Pro Cys Arg Ile Ser Pro Gly Lys Asn Ala Thr Gly Met
    50                  55                  60

Glu Val Gly Trp Tyr Arg Pro Pro Phe Ser Arg Val Val His Leu Tyr
65                  70                  75                  80

Arg Asn Gly Lys Asp Gln Asp Gly Asp Gln Ala Pro Glu Tyr Arg Gly
                85                  90                  95

Arg Thr Glu Leu Leu Lys Asp Ala Ile Gly Glu Gly Lys Val Thr Leu
            100                 105                 110

Arg Ile Arg Asn Val Arg Phe Ser Asp Glu Gly Gly Phe Thr Cys Phe
        115                 120                 125

Phe Arg Asp His Ser Tyr Gln Glu Ala Ala Met Glu Leu Lys Val
    130                 135                 140

Glu Asp Pro Phe Tyr Trp Val Ser Pro Gly Val Leu Val Leu Leu Ala
145                 150                 155                 160

Val Leu Pro Val Leu Leu Gln Ile Thr Val Gly Leu Val Phe Leu
                165                 170                 175

Cys Leu Gln Tyr Arg Leu Arg Gly Lys Leu Arg Ala Glu Ile Glu Asn
            180                 185                 190

Leu His Arg Thr Phe Asp Pro His Phe Leu Arg Val Pro Cys Trp Lys
        195                 200                 205

Ile Thr Leu Phe Val Ile Val Pro Val Leu Gly Pro Leu Val Ala Leu
    210                 215                 220

Ile Ile Cys Tyr Asn Trp Leu His Arg Arg Leu Ala Gly Gln Phe Leu
225                 230                 235                 240

Glu Glu Leu Arg Asn Pro Phe
            245

<210> SEQ ID NO 32
<211> LENGTH: 277
<212> TYPE: PRT
<213> ORGANISM: Homo Sapiens

<400> SEQUENCE: 32

Met Gly Leu Leu Glu Cys Cys Ala Arg Cys Leu Val Gly Ala Pro Phe
1               5                   10                  15

Ala Ser Leu Val Ala Thr Gly Leu Cys Phe Phe Gly Val Ala Leu Phe
            20                  25                  30

Cys Gly Cys Gly His Glu Ala Leu Thr Gly Thr Glu Lys Leu Ile Glu
        35                  40                  45

Thr Tyr Phe Ser Lys Asn Tyr Gln Asp Tyr Glu Tyr Leu Ile Asn Val
    50                  55                  60
```

```
Ile His Ala Phe Gln Tyr Val Ile Tyr Gly Thr Ala Ser Phe Phe Phe
 65                  70                  75                  80

Leu Tyr Gly Ala Leu Leu Ala Glu Gly Phe Tyr Thr Thr Gly Ala
                 85                  90                  95

Val Arg Gln Ile Phe Gly Asp Tyr Lys Thr Thr Ile Cys Gly Lys Gly
                100                 105                 110

Leu Ser Ala Thr Val Thr Gly Gly Gln Lys Gly Arg Gly Ser Arg Gly
                115                 120                 125

Gln His Gln Ala His Ser Leu Glu Arg Val Cys Thr Cys Leu Gly Lys
130                 135                 140

Trp Leu Gly His Pro Asp Lys Phe Val Gly Ile Thr Tyr Ala Leu Thr
145                 150                 155                 160

Val Val Trp Leu Leu Val Phe Ala Cys Ser Ala Val Pro Val Tyr Ile
                165                 170                 175

Tyr Phe Asn Thr Trp Thr Thr Cys Gln Ser Ile Ala Phe Pro Ser Lys
                180                 185                 190

Thr Ser Ala Ser Ile Gly Ser Leu Cys Ala Asp Ala Arg Met Tyr Gly
                195                 200                 205

Val Leu Pro Trp Asn Ala Phe Pro Gly Lys Val Cys Gly Ser Asn Leu
210                 215                 220

Leu Ser Ile Cys Lys Thr Ala Glu Phe Gln Met Thr Phe His Leu Phe
225                 230                 235                 240

Ile Ala Ala Phe Val Gly Ala Ala Thr Leu Val Ser Leu Leu Thr
                245                 250                 255

Phe Met Ile Ala Ala Thr Tyr Asn Phe Ala Val Leu Lys Leu Met Gly
                260                 265                 270

Arg Gly Thr Lys Phe
            275

<210> SEQ ID NO 33
<211> LENGTH: 582
<212> TYPE: PRT
<213> ORGANISM: Homo Sapiens

<400> SEQUENCE: 33

Met Ile Phe Leu Thr Ala Leu Pro Leu Phe Trp Ile Met Ile Ser Ala
  1               5                  10                  15

Ser Arg Gly Gly His Trp Gly Ala Trp Met Pro Ser Ser Ile Ser Ala
                 20                  25                  30

Phe Glu Gly Thr Cys Val Ser Ile Pro Cys Arg Phe Asp Phe Pro Asp
                 35                  40                  45

Glu Leu Arg Pro Ala Val Val His Gly Val Trp Tyr Phe Asn Ser Pro
 50                  55                  60

Tyr Pro Lys Asn Tyr Pro Pro Val Val Phe Lys Ser Arg Thr Gln Val
 65                  70                  75                  80

Val His Glu Ser Phe Gln Gly Arg Ser Arg Leu Leu Gly Asp Leu Gly
                 85                  90                  95

Leu Arg Asn Cys Thr Leu Leu Leu Ser Asn Val Ser Pro Glu Leu Gly
                100                 105                 110

Gly Lys Tyr Tyr Phe Arg Gly Asp Leu Gly Gly Tyr Asn Gln Tyr Thr
                115                 120                 125

Phe Ser Glu His Ser Val Leu Asp Ile Val Asn Thr Pro Asn Ile Val
                130                 135                 140

Val Pro Pro Glu Val Val Ala Gly Thr Glu Val Glu Val Ser Cys Met
```

-continued

```
           145                 150                 155                 160
       Val Pro Asp Asn Cys Pro Glu Leu Arg Pro Glu Leu Ser Trp Leu Gly
                       165                 170                 175
       His Glu Gly Leu Gly Glu Pro Ala Val Leu Gly Arg Leu Arg Glu Asp
                       180                 185                 190
       Glu Gly Thr Trp Val Gln Val Ser Leu Leu His Phe Val Pro Thr Arg
                       195                 200                 205
       Glu Ala Asn Gly His Arg Leu Gly Cys Gln Ala Ser Phe Pro Asn Thr
           210                 215                 220
       Thr Leu Gln Phe Glu Gly Tyr Ala Ser Met Asp Val Lys Tyr Pro Pro
       225                 230                 235                 240
       Val Ile Val Glu Met Asn Ser Ser Val Glu Ala Ile Glu Gly Ser His
                       245                 250                 255
       Val Ser Leu Leu Cys Gly Ala Asp Ser Asn Pro Pro Pro Leu Leu Thr
                       260                 265                 270
       Trp Met Arg Asp Gly Thr Val Leu Arg Glu Ala Val Ala Glu Ser Leu
                       275                 280                 285
       Leu Leu Glu Leu Glu Glu Val Thr Pro Ala Glu Asp Gly Val Tyr Ala
           290                 295                 300
       Cys Leu Ala Glu Asn Ala Tyr Gly Gln Asp Asn Arg Thr Val Gly Leu
       305                 310                 315                 320
       Ser Val Met Tyr Ala Pro Trp Lys Pro Thr Val Asn Gly Thr Met Val
                       325                 330                 335
       Ala Val Glu Gly Glu Thr Val Ser Ile Leu Cys Ser Thr Gln Ser Asn
                       340                 345                 350
       Pro Asp Pro Ile Leu Thr Ile Phe Lys Glu Lys Gln Ile Leu Ser Thr
                       355                 360                 365
       Val Ile Tyr Glu Ser Glu Leu Gln Leu Glu Leu Pro Ala Val Ser Pro
                       370                 375                 380
       Glu Asp Asp Gly Glu Tyr Trp Cys Val Ala Glu Asn Gln Tyr Gly Gln
       385                 390                 395                 400
       Arg Ala Thr Ala Phe Asn Leu Ser Val Glu Phe Ala Pro Val Leu Leu
                       405                 410                 415
       Leu Glu Ser His Cys Ala Ala Ala Arg Asp Thr Val Gln Cys Leu Cys
                       420                 425                 430
       Val Val Lys Ser Asn Pro Glu Pro Ser Val Ala Phe Glu Leu Pro Ser
                       435                 440                 445
       Arg Asn Val Thr Val Asn Glu Ser Glu Arg Glu Phe Val Tyr Ser Glu
           450                 455                 460
       Arg Ser Gly Leu Val Leu Thr Ser Ile Leu Thr Leu Arg Gly Gln Ala
       465                 470                 475                 480
       Gln Ala Pro Pro Arg Val Ile Cys Thr Ala Arg Asn Leu Tyr Gly Ala
                       485                 490                 495
       Lys Ser Leu Glu Leu Pro Phe Gln Gly Ala His Arg Leu Met Trp Ala
                       500                 505                 510
       Lys Ile Gly Pro Val Gly Ala Val Ala Phe Ala Ile Leu Ile Ala
                       515                 520                 525
       Ile Val Cys Tyr Ile Thr Gln Thr Arg Arg Lys Lys Asn Val Thr Glu
           530                 535                 540
       Ser Pro Ser Phe Ser Ala Gly Asp Asn Pro Pro Val Leu Phe Ser Ser
       545                 550                 555                 560
       Asp Phe Arg Ile Ser Gly Ala Pro Glu Lys Tyr Glu Ser Lys Glu Val
                       565                 570                 575
```

```
Ser Thr Leu Glu Ser His
            580

<210> SEQ ID NO 34
<211> LENGTH: 20
<212> TYPE: PRT
<213> ORGANISM: Artificial Sequence
<220> FEATURE:
<223> OTHER INFORMATION: Synthetic

<400> SEQUENCE: 34

Thr Tyr Glu Ile Ala Pro Val Phe Val Leu Leu Phe Tyr Val Thr Leu
1               5                   10                  15

Lys Lys Met Arg
            20

<210> SEQ ID NO 35
<211> LENGTH: 31
<212> TYPE: PRT
<213> ORGANISM: Artificial Sequence
<220> FEATURE:
<223> OTHER INFORMATION: Synthetic

<400> SEQUENCE: 35

Leu Leu Glu Cys Cys Ala Arg Cys Leu Val Gly Ala Pro Phe Ala Ser
1               5                   10                  15

Leu Val Ala Thr Gly Leu Cys Phe Phe Gly Val Ala Leu Phe Cys
            20                  25                  30

<210> SEQ ID NO 36
<211> LENGTH: 20
<212> TYPE: PRT
<213> ORGANISM: Artificial Sequence
<220> FEATURE:
<223> OTHER INFORMATION: Synthetic

<400> SEQUENCE: 36

Leu Val Gly Ala Pro Phe Ala Ser Leu Val Ala Thr Gly Leu Cys Phe
1               5                   10                  15

Phe Gly Val Ala
            20

<210> SEQ ID NO 37
<211> LENGTH: 31
<212> TYPE: PRT
<213> ORGANISM: Artificial Sequence
<220> FEATURE:
<223> OTHER INFORMATION: Synthetic

<400> SEQUENCE: 37

Phe Gly Val Ala Leu Phe Cys Gly Cys Glu Val Glu Ala Leu Thr Gly
1               5                   10                  15

Thr Glu Lys Leu Ile Glu Thr Tyr Phe Ser Lys Asn Tyr Gln Asp
            20                  25                  30

<210> SEQ ID NO 38
<211> LENGTH: 20
<212> TYPE: PRT
<213> ORGANISM: Artificial Sequence
<220> FEATURE:
<223> OTHER INFORMATION: Synthetic

<400> SEQUENCE: 38

Leu Phe Cys Gly Cys Gly His Glu Ala Leu Thr Gly Thr Glu Lys Leu
```

Ile Glu Thr Tyr
            20

<210> SEQ ID NO 39
<211> LENGTH: 20
<212> TYPE: PRT
<213> ORGANISM: Artificial Sequence
<220> FEATURE:
<223> OTHER INFORMATION: Synthetic

<400> SEQUENCE: 39

Thr Gly Thr Glu Lys Leu Ile Glu Thr Tyr Phe Ser Lys Asn Tyr Gln
1               5                   10                  15

Asp Tyr Glu Tyr
            20

<210> SEQ ID NO 40
<211> LENGTH: 21
<212> TYPE: PRT
<213> ORGANISM: Artificial Sequence
<220> FEATURE:
<223> OTHER INFORMATION: Synthetic

<400> SEQUENCE: 40

Thr Gly Thr Glu Lys Leu Ile Glu Thr Tyr Phe Ser Lys Asn Tyr Gln
1               5                   10                  15

Asp Tyr Glu Tyr Leu
            20

<210> SEQ ID NO 41
<211> LENGTH: 32
<212> TYPE: PRT
<213> ORGANISM: Artificial Sequence
<220> FEATURE:
<223> OTHER INFORMATION: Synthetic

<400> SEQUENCE: 41

Tyr Phe Ser Lys Asn Tyr Gln Asp Tyr Glu Tyr Leu Ile Asn Val Ile
1               5                   10                  15

His Ala Phe Gln Tyr Val Ile Tyr Gly Thr Ala Ser Phe Phe Phe Leu
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic

<400> SEQUENCE: 42

Gly Thr Ala Ser Phe Phe Phe Leu Tyr Gly Ala Leu Leu Leu Ala Tyr
1               5                   10                  15

Gly Phe Tyr Thr Thr Gly Ala Val Arg Gln Ile Phe Gly Asp Tyr Lys
            20                  25                  30

<210> SEQ ID NO 43
<211> LENGTH: 20
<212> TYPE: PRT
<213> ORGANISM: Artificial Sequence
<220> FEATURE:
<223> OTHER INFORMATION: Synthetic

<400> SEQUENCE: 43

```
Leu Tyr Gly Ala Leu Leu Leu Ala Glu Gly Phe Tyr Thr Thr Gly Ala
1               5                   10                  15

Val Arg Gln Ile
            20

<210> SEQ ID NO 44
<211> LENGTH: 21
<212> TYPE: PRT
<213> ORGANISM: Artificial Sequence
<220> FEATURE:
<223> OTHER INFORMATION: Synthetic

<400> SEQUENCE: 44

Phe Tyr Tyr Thr Thr Gly Ala Val Arg Gln Ile Phe Gly Asp Tyr Lys
1               5                   10                  15

Thr Thr Ile Cys Gly
            20

<210> SEQ ID NO 45
<211> LENGTH: 22
<212> TYPE: PRT
<213> ORGANISM: Artificial Sequence
<220> FEATURE:
<223> OTHER INFORMATION: Synthetic

<400> SEQUENCE: 45

Ala Val Arg Gln Ile Phe Gly Asp Tyr Lys Thr Thr Ile Cys Gly Lys
1               5                   10                  15

Gly Leu Ser Ala Thr Val
            20

<210> SEQ ID NO 46
<211> LENGTH: 31
<212> TYPE: PRT
<213> ORGANISM: Artificial Sequence
<220> FEATURE:
<223> OTHER INFORMATION: Synthetic

<400> SEQUENCE: 46

Arg Gln Ile Phe Gly Asp Tyr Lys Thr Thr Cys Gly Lys Gly Leu Ser
1               5                   10                  15

Ala Thr Val Thr Gly Gly Gln Lys Gly Arg Gly Ser Arg Gly Gln
            20                  25                  30

<210> SEQ ID NO 47
<211> LENGTH: 20
<212> TYPE: PRT
<213> ORGANISM: Artificial Sequence
<220> FEATURE:
<223> OTHER INFORMATION: Synthetic

<400> SEQUENCE: 47

Lys Gly Leu Ser Ala Thr Val Thr Gly Gly Gln Lys Gly Arg Gly Tyr
1               5                   10                  15

Arg Gly Gln His
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic

<400> SEQUENCE: 48
```

Gln Lys Gly Arg Gly Ser Arg Gly Gln His Gln Ala His Ser Leu Glu
1               5                   10                  15

Arg Val Cys His
            20

<210> SEQ ID NO 49
<211> LENGTH: 32
<212> TYPE: PRT
<213> ORGANISM: Artificial Sequence
<220> FEATURE:
<223> OTHER INFORMATION: Synthetic

<400> SEQUENCE: 49

Lys Gly Arg Gly Ser Arg Gly Gln His Gln Ala His Ser Leu Glu Arg
1               5                   10                  15

Val Cys His Cys Leu Gly Cys Trp Leu Gly His Pro Asp Lys Phe Val
            20                  25                  30

<210> SEQ ID NO 50
<211> LENGTH: 32
<212> TYPE: PRT
<213> ORGANISM: Artificial Sequence
<220> FEATURE:
<223> OTHER INFORMATION: Synthetic

<400> SEQUENCE: 50

Leu Gly His Pro Asp Lys Phe Val Gly Ile Thr Tyr Ala Leu Thr Val
1               5                   10                  15

Val Trp Leu Leu Val Phe Ala Cys Ser Ala Val Pro Val Tyr Ile Tyr
            20                  25                  30

<210> SEQ ID NO 51
<211> LENGTH: 32
<212> TYPE: PRT
<213> ORGANISM: Artificial Sequence
<220> FEATURE:
<223> OTHER INFORMATION: Synthetic

<400> SEQUENCE: 51

Ser Ala Val Pro Val Tyr Ile Tyr Phe Asn Thr Trp Thr Thr Cys Gln
1               5                   10                  15

Ser Ile Ala Ala Pro Cys Lys Thr Ser Ala Ser Ile Gly Thr Leu Cys
            20                  25                  30

<210> SEQ ID NO 52
<211> LENGTH: 20
<212> TYPE: PRT
<213> ORGANISM: Artificial Sequence
<220> FEATURE:
<223> OTHER INFORMATION: Synthetic

<400> SEQUENCE: 52

Ala Val Pro Val Tyr Ile Tyr Phe Asn Thr Trp Thr Thr Cys Gln Ser
1               5                   10                  15

Ile Ala Phe Pro
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic

<400> SEQUENCE: 53

Trp Thr Thr Cys Gln Ser Ile Ala Phe Pro Ser Lys Thr Ser Ala Ser
1               5                   10                  15

Ile Gly Ser Leu
            20

<210> SEQ ID NO 54
<211> LENGTH: 32
<212> TYPE: PRT
<213> ORGANISM: Artificial Sequence
<220> FEATURE:
<223> OTHER INFORMATION: Synthetic

<400> SEQUENCE: 54

Ser Ala Ser Ile Gly Thr Leu Cys Ala Asp Ala Arg Met Tyr Gly Val
1               5                   10                  15

Leu Pro Trp Asn Ala Phe Phe Gly Lys Val Cys Gly Ser Asn Leu Leu
            20                  25                  30

<210> SEQ ID NO 55
<211> LENGTH: 32
<212> TYPE: PRT
<213> ORGANISM: Artificial Sequence
<220> FEATURE:
<223> OTHER INFORMATION: Synthetic

<400> SEQUENCE: 55

Lys Val Cys Gly Ser Asn Leu Leu Ser Ile Cys Lys Thr Ala Glu Phe
1               5                   10                  15

Gln Met Thr Phe His Leu Phe Ile Ala Ala Phe Val Gly Ala Ala Ala
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Synthetic

<400> SEQUENCE: 56

Ala Ala Phe Val Gly Ala Ala Ala Thr Leu Val Ser Leu Leu Thr Phe
1               5                   10                  15

Met Ile Ala Ala Thr Tyr Asn Phe Ala Val Leu Lys Leu Met Gly Arg
            20                  25                  30

<210> SEQ ID NO 57
<211> LENGTH: 20
<212> TYPE: PRT
<213> ORGANISM: Artificial Sequence
<220> FEATURE:
<223> OTHER INFORMATION: Synthetic

<400> SEQUENCE: 57

Met Ile Ala Ala Thr Tyr Asn Phe Ala Val Leu Lys Leu Met Gly Arg
1               5                   10                  15

Gly Thr Lys Phe
            20

<210> SEQ ID NO 58
<211> LENGTH: 19
<212> TYPE: PRT
<213> ORGANISM: Artificial Sequence
<220> FEATURE:
<223> OTHER INFORMATION: Synthetic

```
<400> SEQUENCE: 58

Met Ala Ala Thr Tyr Asn Phe Ala Val Leu Lys Leu Met Gly Arg Phe
1               5                   10                  15

Thr Lys Phe

<210> SEQ ID NO 59
<211> LENGTH: 42
<212> TYPE: PRT
<213> ORGANISM: Artificial Sequence
<220> FEATURE:
<223> OTHER INFORMATION: Synthetic

<400> SEQUENCE: 59

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 60
<211> LENGTH: 47
<212> TYPE: PRT
<213> ORGANISM: Artificial Sequence
<220> FEATURE:
<223> OTHER INFORMATION: Synthetic

<400> SEQUENCE: 60

Pro Gly Lys Arg Gly Arg Lys Lys Leu Leu Tyr Ile Phe Lys Gln Pro
1               5                   10                  15

Phe Met Arg Pro Val Gln Thr Thr Gln Glu Glu Asp Gly Cys Ser Cys
            20                  25                  30

Arg Phe Pro Glu Glu Glu Glu Gly Gly Cys Glu Leu Ala His Ala
        35                  40                  45

<210> SEQ ID NO 61
<211> LENGTH: 41
<212> TYPE: PRT
<213> ORGANISM: Artificial Sequence
<220> FEATURE:
<223> OTHER INFORMATION: Synthetic

<400> SEQUENCE: 61

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 62
<211> LENGTH: 46
<212> TYPE: PRT
<213> ORGANISM: Artificial Sequence
<220> FEATURE:
<223> OTHER INFORMATION: Synthetic

<400> SEQUENCE: 62

Pro Gly Arg Ser Lys Arg Ser Arg Gly Gly His Ser Asp Tyr Met Asn
1               5                   10                  15

Met Thr Pro Arg Arg Pro Gly Pro Thr Arg Lys His Tyr Gln Pro Tyr
```

```
                    20                  25                  30

Ala Pro Pro Arg Asp Phe Ala Ala Tyr Arg Ser Ala His Ala
        35                  40                  45

<210> SEQ ID NO 63
<211> LENGTH: 87
<212> TYPE: PRT
<213> ORGANISM: Artificial Sequence
<220> FEATURE:
<223> OTHER INFORMATION: Synthetic

<400> SEQUENCE: 63

Glu Met Trp His Glu Gly Leu Glu Glu Ala Ser Arg Leu Tyr Phe Gly
1               5                   10                  15

Glu Arg Asn Val Lys Gly Met Phe Glu Val Leu Glu Pro Leu His Ala
                20                  25                  30

Met Met Glu Arg Gly Pro Gln Thr Leu Lys Glu Thr Ser Phe Asn Gln
            35                  40                  45

Ala Tyr Gly Arg Asp Leu Met Glu Ala Gln Glu Trp Cys Arg Lys Tyr
        50                  55                  60

Met Lys Ser Gly Asn Val Lys Asp Leu Leu Gln Ala Trp Asp Leu Tyr
65                  70                  75                  80

Tyr His Val Phe Arg Arg Ile
                85

<210> SEQ ID NO 64
<211> LENGTH: 115
<212> TYPE: PRT
<213> ORGANISM: Artificial Sequence
<220> FEATURE:
<223> OTHER INFORMATION: Synthetic

<400> SEQUENCE: 64

Gly Ser Ser Ser Gly Ser Ser Gly Ser Ser Ser Gly Ser Ser Ser
1               5                   10                  15

Glu Met Trp His Glu Gly Leu Glu Glu Ala Ser Arg Leu Tyr Phe Gly
                20                  25                  30

Glu Arg Asn Val Lys Gly Met Phe Glu Val Leu Glu Pro Leu His Ala
            35                  40                  45

Met Met Glu Arg Gly Pro Gln Thr Leu Lys Glu Thr Ser Phe Asn Gln
        50                  55                  60

Ala Tyr Gly Arg Asp Leu Met Glu Ala Gln Glu Trp Cys Arg Lys Tyr
65                  70                  75                  80

Met Lys Ser Gly Asn Val Lys Asp Leu Leu Gln Ala Trp Asp Leu Tyr
                85                  90                  95

Tyr His Val Phe Arg Arg Ile Gly Ser Ser Ser Gly Ser Ser Ser Gly
                100                 105                 110

Ser Ser Ser
        115

<210> SEQ ID NO 65
<211> LENGTH: 107
<212> TYPE: PRT
<213> ORGANISM: Artificial Sequence
<220> FEATURE:
<223> OTHER INFORMATION: Synthetic

<400> SEQUENCE: 65

Gly Val Gln Val Glu Thr Ile Ser Pro Gly Asp Gly Arg Thr Phe Pro
1               5                   10                  15
```

```
Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
 50                  55                  60

Gln Met Ser Val Gly Gln Arg Ala Lys Leu Thr Ile Ser Pro Asp Tyr
 65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 66
<211> LENGTH: 135
<212> TYPE: PRT
<213> ORGANISM: Artificial Sequence
<220> FEATURE:
<223> OTHER INFORMATION: Synthetic

<400> SEQUENCE: 66

```
Gly Ser Ser Ser Gly Ser Ser Gly Ser Ser Gly Ser Ser Ser
 1               5                  10                  15

Gly Val Gln Val Glu Thr Ile Ser Pro Gly Asp Gly Arg Thr Phe Pro
            20                  25                  30

Lys Arg Gly Gln Thr Cys Val Val His Tyr Thr Gly Met Leu Glu Asp
        35                  40                  45

Gly Lys Lys Phe Asp Ser Ser Arg Asp Arg Asn Lys Pro Phe Lys Phe
 50                  55                  60

Met Leu Gly Lys Gln Glu Val Ile Arg Gly Trp Glu Glu Gly Val Ala
 65                  70                  75                  80

Gln Met Ser Val Gly Gln Arg Ala Lys Leu Thr Ile Ser Pro Asp Tyr
                85                  90                  95

Ala Tyr Gly Ala Thr Gly His Pro Gly Ile Ile Pro Pro His Ala Thr
            100                 105                 110

Leu Val Phe Asp Val Glu Leu Leu Lys Leu Glu Gly Ser Ser Ser Gly
            115                 120                 125

Ser Ser Ser Gly Ser Ser Ser
            130                 135
```

<210> SEQ ID NO 67
<211> LENGTH: 112
<212> TYPE: PRT
<213> ORGANISM: Artificial Sequence
<220> FEATURE:
<223> OTHER INFORMATION: Synthetic

<400> SEQUENCE: 67

```
Arg Val Lys Phe Ser Arg Ser Ala Asp Ala Pro Ala Tyr Gln Gln Gly
 1               5                  10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
```

```
                        65                  70                  75                  80
Arg Arg Gly Lys Gly His Asp Gly Leu Tyr Gln Gly Leu Ser Thr Ala
                    85                  90                  95

Thr Lys Asp Thr Tyr Asp Ala Leu His Met Gln Ala Leu Pro Pro Arg
                100                 105                 110
```

<210> SEQ ID NO 68
<211> LENGTH: 15
<212> TYPE: PRT
<213> ORGANISM: Artificial Sequence
<220> FEATURE:
<223> OTHER INFORMATION: Synthetic

<400> SEQUENCE: 68

```
Gly Gly Gly Gly Ser Gly Gly Gly Ser Gly Gly Gly Gly Ser
1               5                   10                  15
```

<210> SEQ ID NO 69
<211> LENGTH: 15
<212> TYPE: PRT
<213> ORGANISM: Artificial Sequence
<220> FEATURE:
<223> OTHER INFORMATION: Synthetic

<400> SEQUENCE: 69

```
Gly Gly Gly Gly Gly Gly Ser Gly Gly Ser Gly Gly Ser Gly Gly
1               5                   10                  15
```

<210> SEQ ID NO 70
<211> LENGTH: 20
<212> TYPE: PRT
<213> ORGANISM: Artificial Sequence
<220> FEATURE:
<223> OTHER INFORMATION: Synthetic

<400> SEQUENCE: 70

```
Gly Gly Gly Gly Ser Gly Gly Gly Gly Ser Gly Gly Gly Gly Ser Gly
1               5                   10                  15

Gly Gly Gly Ser
            20
```

<210> SEQ ID NO 71
<211> LENGTH: 2340
<212> TYPE: DNA
<213> ORGANISM: Artificial Sequence
<220> FEATURE:
<223> OTHER INFORMATION: Synthetic

<400> SEQUENCE: 71

```
atggtatgct tgaagctccc gggcgggtcc tgcatgaccg ctctcactgt tactcttatg    60
gtccttagtt caccgcttgc cctggcatct gatgagaatc ccgtggttca ttttttttaag   120 aacatcgtca caccgcgcac cccacctggg ggaggcggat ctggcggagg cgggagtgga   180
ggctcaggag acacaagacc ccgattcttg tggcagccca aaagggagtg ccatttttttc   240 aatgggacgg aacgagttcg cttccttgat cggtactttt acaaccaaga agagagtgta   300
cggttcgact cagatgtcgg cgagttccga gcggttacgg aattggggcg acctgacgcg   360
gagtactgga actcccaaaa ggatattttg gagcaggcac gagcagctgt ggacacctat   420
tgtcgacata attatggtgt ggtggaatcc tttacagttc agcggcgggt gcaacctaaa   480
gtgaccgtgt atccatctaa aacgcaaccc ctccaacacc ataacctcct ggtgtgttcc   540
gtaagcggct ctatcccgg tcaattgag gtcaggtggt cctcaacgg tcaggaggag   600
```

-continued

```
aaggccggaa tggtaagtac tggtcttatc cagaacggag actggacctt ccaaactttg      660
gtaatgttgg aaacggtgcc gcgatccggg gaggtgtata catgccaagt tgaacacccg      720
agtgttacga gcccctgac ggttgagtgg agggcgcggt cagagagcgc acaatctaaa       780
atgctgtcag gagtaggcgg atttgtactc ggactcctct tttgggcgc tgggttgttt       840 atctacttta gaaccaaac aagtagagta aagttttccc gaagtgcgga cgctcccgcg       900
tatcagcaag gtcaaaacca gctttacaac gaactgaact tgggacgacg cgaagagtac      960
gatgttcttg ataagcggag agggcgcgat cccgaaatgg ggggaaagcc tcggaggaag     1020
aacccacaag aaggccttta taatgaactg cagaaggaca gatggcgga ggcgtattcc      1080 gaaataggca tgaagggtga acggaggaga ggaaagggac atgacggact ttatcaagga     1140
ttgtctaccg caactaaaga cacctatgac gcgttgcaca tgcaggctct ccctccgaga     1200
ggttcgagcg gcagtggaga gggcagagga agtctgctaa catgcggtga cgtcgaggag     1260
aatcctggcc caatggcaat atctggtgtt cctgtcctcg gtttttttat catagccgta     1320
ctgatgtcag cacaggaatc atgggcgata aagaagagc acgtgataat acaggcggag      1380
ttttatttga acccggacca gagcggtgag ttcatgttcg attttgatgg cgacgagata     1440
tttcacgttg acatggcaaa aaaggaaacg gtgtggagac ttgaggagtt tggacgattc     1500
gcatcatttg aggcacaagg agcactcgcc aatatcgcgg tggacaaggc caacctggag     1560
atcatgacaa aacgctccaa ttatacgcct atcactaatg tgcccctga ggttactgtg      1620 ctcacaaatt ctcccgtaga acttagggaa cctaacgtcc tcatatgttt catcgacaag     1680
ttcactcctc cggtggtcaa tgtaacgtgg cttcggaatg gtaagccggt caccacgggt     1740
gtctcagaga ccgtatttct gcccagagaa gaccacctct tccgcaaaatt tcattacctt    1800 cccttcttc cttcaacgga agacgtttac gactgcaggg tcgaacattg ggggcttgac     1860
gagccacttc tcaagcattg ggagttcgac gccccatcac cgcttccaga acgactgaa     1920 aacgttgtct gcgctcttgg cctgacagtg ggcctggtag gcattattat cgggaccatc     1980
tttatcatca aaggtttgac ttcccggggtc aaatttagca gatccgctga cgcaccggcc    2040
taccagcagg gccagaacca actctacaac gagctgaatc tcggccgacg ggaagagtat     2100
gacgtactcg acaagcggag aggtcgagac cctgagatgg gcggtaaacc gagacggaaa     2160
aatccccaag agggtcttta taatgaactc cagaaggata gatggctga agcctattct     2220 gagatagggga tgaaaggcga gcggcggagg ggtaagggcc atgatggcct ttaccaggga    2280
ctctccacgg caaccaaaga tacttacgac gcccttcaca tgcaagccct cccgccacgc    2340
```

<210> SEQ ID NO 72
<211> LENGTH: 8
<212> TYPE: PRT
<213> ORGANISM: Artificial Sequence
<220> FEATURE:
<223> OTHER INFORMATION: Synthetic

<400> SEQUENCE: 72

Gly Ser Gly Ser Gly Ser Gly Ser
1               5

<210> SEQ ID NO 73
<211> LENGTH: 21
<212> TYPE: PRT
<213> ORGANISM: Artificial Sequence
<220> FEATURE:
<223> OTHER INFORMATION: Synthetic

<400> SEQUENCE: 73

Ile Tyr Ile Trp Ala Pro Leu Ala Gly Thr Cys Gly Val Leu Leu
1               5                   10                  15

Ser Leu Val Ile Thr
            20

<210> SEQ ID NO 74
<211> LENGTH: 21
<212> TYPE: PRT
<213> ORGANISM: Artificial Sequence
<220> FEATURE:
<223> OTHER INFORMATION: Synthetic

<400> SEQUENCE: 74

Ile Trp Ala Pro Leu Ala Gly Ile Cys Val Ala Leu Leu Ser Leu
1               5                   10                  15

Ile Ile Thr Leu Ile
            20

<210> SEQ ID NO 75
<211> LENGTH: 267
<212> TYPE: PRT
<213> ORGANISM: Artificial Sequence
<220> FEATURE:
<223> OTHER INFORMATION: Synthetic

<400> SEQUENCE: 75

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
                20                  25                  30

Gly Lys Lys Phe Asp Ser Ser Arg Asp Arg Asn Lys Pro Phe Lys Phe
            35                  40                  45

Met Leu Gly Lys Gln Glu Val Ile Arg Gly Trp Glu Glu Gly Val Ala
        50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu Glu Ala Ala Ala Arg
            100                 105                 110

Glu Ala Ala Ala Arg Glu Ala Ala Ala Arg Glu Ala Ala Ala Arg Gly
        115                 120                 125

Arg Val Ala Ile Leu Trp His Glu Met Trp His Glu Gly Leu Glu Glu
    130                 135                 140

Ala Ser Arg Leu Tyr Phe Gly Glu Arg Asn Val Lys Gly Met Phe Glu
145                 150                 155                 160

Val Leu Glu Pro Leu His Ala Met Met Glu Arg Gly Pro Gln Thr Leu
                165                 170                 175

Lys Glu Thr Ser Phe Asn Gln Ala Tyr Gly Arg Asp Leu Met Glu Ala
            180                 185                 190

Gln Glu Trp Cys Arg Lys Tyr Met Lys Ser Gly Asn Val Lys Asp Leu
        195                 200                 205

Leu Gln Ala Trp Asp Leu Tyr Tyr His Val Phe Arg Arg Ile Thr Thr
    210                 215                 220

Thr Pro Ala Pro Arg Pro Pro Thr Pro Ala Pro Thr Ile Ala Ser Gln
225                 230                 235                 240

Pro Leu Ser Leu Arg Pro Glu Ala Cys Arg Pro Ala Ala Gly Gly Ala
            245                 250                 255

Val His Thr Arg Gly Leu Asp Phe Ala Cys Asp
            260                 265

<210> SEQ ID NO 76
<211> LENGTH: 45
<212> TYPE: PRT
<213> ORGANISM: Artificial Sequence
<220> FEATURE:
<223> OTHER INFORMATION: Synthetic

<400> SEQUENCE: 76

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Ser Gly Gly Gly Ser
        35                  40                  45

<210> SEQ ID NO 77
<211> LENGTH: 13
<212> TYPE: PRT
<213> ORGANISM: Artificial Sequence
<220> FEATURE:
<223> OTHER INFORMATION: Synthetic

<400> SEQUENCE: 77

Leu Arg Trp Glu Pro Pro Pro Ser Thr Val Ser Asn Met
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic

<400> SEQUENCE: 78

Leu Arg Trp Glu Pro Ser Ser Gln Pro Thr Ile Pro Ile
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Synthetic

<400> SEQUENCE: 79

Leu Arg Trp Glu Leu Ser Ser Gln Pro Thr Ile Pro Ile
1               5                   10

<210> SEQ ID NO 80
<211> LENGTH: 30
<212> TYPE: PRT
<213> ORGANISM: Artificial Sequence
<220> FEATURE:
<223> OTHER INFORMATION: Synthetic

<400> SEQUENCE: 80

Gln Thr Thr Pro Gly Glu Arg Ser Ser Leu Pro Ala Phe Tyr Pro Gly
1               5                   10                  15

Thr Ser Gly Ser Cys Ser Gly Cys Gly Ser Leu Ser Leu Pro

```
            20                  25                  30
```

<210> SEQ ID NO 81
<211> LENGTH: 46
<212> TYPE: PRT
<213> ORGANISM: Artificial Sequence
<220> FEATURE:
<223> OTHER INFORMATION: Synthetic

<400> SEQUENCE: 81

```
Gly Ser Ser Ser Gly Ser Ser Ser Gly Ser Ser Ser Gly Ser Ser Ser
1               5                   10                  15

Gln Thr Thr Pro Gly Glu Arg Ser Ser Leu Pro Ala Phe Tyr Pro Gly
            20                  25                  30

Thr Ser Gly Ser Cys Ser Gly Cys Gly Ser Leu Ser Leu Pro
        35                  40                  45
```

<210> SEQ ID NO 82
<211> LENGTH: 19
<212> TYPE: PRT
<213> ORGANISM: Artificial Sequence
<220> FEATURE:
<223> OTHER INFORMATION: Synthetic

<400> SEQUENCE: 82

```
Leu Arg Pro Val Gln Ala Gln Ala Gln Ser Asp Cys Ser Cys Ser Thr
1               5                   10                  15

Val Ser Pro
```

<210> SEQ ID NO 83
<211> LENGTH: 35
<212> TYPE: PRT
<213> ORGANISM: Artificial Sequence
<220> FEATURE:
<223> OTHER INFORMATION: Synthetic

<400> SEQUENCE: 83

```
Gly Ser Ser Ser Gly Ser Ser Ser Gly Ser Ser Ser Gly Ser Ser Ser
1               5                   10                  15

Leu Arg Pro Val Gln Ala Gln Ala Gln Ser Asp Cys Ser Cys Ser Thr
            20                  25                  30

Val Ser Pro
        35
```

<210> SEQ ID NO 84
<211> LENGTH: 16
<212> TYPE: PRT
<213> ORGANISM: Artificial Sequence
<220> FEATURE:
<223> OTHER INFORMATION: Synthetic

<400> SEQUENCE: 84

```
Gly Leu Ala Val Ser Thr Ile Ser Ser Phe Phe Pro Pro Gly Tyr Gln
1               5                   10                  15
```

<210> SEQ ID NO 85
<211> LENGTH: 45
<212> TYPE: PRT
<213> ORGANISM: Artificial Sequence
<220> FEATURE:
<223> OTHER INFORMATION: Synthetic

<400> SEQUENCE: 85

```
Thr Thr Thr Pro Ala Pro Arg Pro Pro Thr Pro Ala Pro Thr Ile Ala
```

```
                1               5                   10                  15
            Ser Gln Pro Leu Ser Leu Arg Pro Glu Ala Cys Arg Pro Ala Ala Gly
                                20                  25                  30

Gly Ala Val His Thr Arg Gly Leu Asp Phe Ala Cys Asp
                                35                  40                  45

<210> SEQ ID NO 86
<211> LENGTH: 231
<212> TYPE: PRT
<213> ORGANISM: Artificial Sequence
<220> FEATURE:
<223> OTHER INFORMATION: Synthetic

<400> SEQUENCE: 86

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ala Arg Thr Pro Glu Val Thr Cys Val Val Val
                35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65              70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
        130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
        210                 215                 220

Leu Ser Leu Ser Pro Gly Lys
225                 230

<210> SEQ ID NO 87
<211> LENGTH: 13
<212> TYPE: PRT
<213> ORGANISM: Artificial Sequence
<220> FEATURE:
<223> OTHER INFORMATION: Synthetic

<400> SEQUENCE: 87

Glu Phe Asp Ala Pro Ser Pro Leu Pro Glu Thr Thr Glu
1               5                   10

<210> SEQ ID NO 88
<211> LENGTH: 13
```

```
<212> TYPE: PRT
<213> ORGANISM: Artificial Sequence
<220> FEATURE:
<223> OTHER INFORMATION: Synthetic

<400> SEQUENCE: 88

Val Glu Trp Arg Ala Arg Ser Glu Ser Ala Gln Ser Lys
1               5                   10

<210> SEQ ID NO 89
<211> LENGTH: 24
<212> TYPE: PRT
<213> ORGANISM: Artificial Sequence
<220> FEATURE:
<223> OTHER INFORMATION: Synthetic

<400> SEQUENCE: 89

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 90
<211> LENGTH: 24
<212> TYPE: PRT
<213> ORGANISM: Artificial Sequence
<220> FEATURE:
<223> OTHER INFORMATION: Synthetic

<400> SEQUENCE: 90

Val Gly Ile Ile Ala Gly Leu Val Leu Phe Gly Ala Val Ile Thr Gly
1               5                   10                  15

Ala Val Val Ala Ala Val Met Trp
            20

<210> SEQ ID NO 91
<211> LENGTH: 24
<212> TYPE: PRT
<213> ORGANISM: Artificial Sequence
<220> FEATURE:
<223> OTHER INFORMATION: Synthetic

<400> SEQUENCE: 91

Val Gly Ile Ile Ala Gly Leu Val Leu Leu Gly Ala Val Ile Thr Gly
1               5                   10                  15

Ala Val Val Ala Ala Val Met Trp
            20

<210> SEQ ID NO 92
<211> LENGTH: 21
<212> TYPE: PRT
<213> ORGANISM: Artificial Sequence
<220> FEATURE:
<223> OTHER INFORMATION: Synthetic

<400> SEQUENCE: 92

Leu Cys Tyr Leu Leu Asp Gly Ile Leu Phe Ile Tyr Gly Val Ile Leu
1               5                   10                  15

Thr Ala Leu Phe Leu
            20

<210> SEQ ID NO 93
<211> LENGTH: 21
<212> TYPE: PRT
<213> ORGANISM: Artificial Sequence
```

```
<220> FEATURE:
<223> OTHER INFORMATION: Synthetic

<400> SEQUENCE: 93

Met Leu Ser Gly Val Gly Gly Phe Val Leu Gly Leu Phe Leu Gly
1               5                   10                  15

Ala Gly Leu Phe Ile
            20

<210> SEQ ID NO 94
<211> LENGTH: 26
<212> TYPE: PRT
<213> ORGANISM: Artificial Sequence
<220> FEATURE:
<223> OTHER INFORMATION: Synthetic

<400> SEQUENCE: 94

Met Leu Ser Gly Val Gly Gly Phe Val Leu Gly Leu Phe Leu Gly
1               5                   10                  15

Ala Gly Leu Phe Ile Tyr Phe Arg Asn Gln
            20                  25

<210> SEQ ID NO 95
<211> LENGTH: 326
<212> TYPE: PRT
<213> ORGANISM: Artificial Sequence
<220> FEATURE:
<223> OTHER INFORMATION: Synthetic

<400> SEQUENCE: 95

Ile Leu Asp Tyr Ser Phe Thr Gly Gly Ala Gly Arg Asp Ile Pro Pro
1               5                   10                  15

Pro Gln Ile Glu Glu Ala Cys Glu Leu Pro Glu Cys Gln Val Asp Ala
            20                  25                  30

Gly Asn Lys Val Cys Asn Leu Gln Cys Asn Asn His Ala Cys Gly Trp
        35                  40                  45

Asp Gly Gly Asp Cys Ser Leu Asn Phe Asn Asp Pro Trp Lys Asn Cys
    50                  55                  60

Thr Gln Ser Leu Gln Cys Trp Lys Tyr Phe Ser Asp Gly His Cys Asp
65                  70                  75                  80

Ser Gln Cys Asn Ser Ala Gly Cys Leu Phe Asp Gly Phe Asp Cys Gln
                85                  90                  95

Leu Thr Glu Gly Gln Cys Asn Pro Leu Tyr Asp Gln Tyr Cys Lys Asp
            100                 105                 110

His Phe Ser Asp Gly His Cys Asp Gln Gly Cys Asn Ser Ala Glu Cys
        115                 120                 125

Glu Trp Asp Gly Leu Asp Cys Ala Glu His Val Pro Glu Arg Leu Ala
    130                 135                 140

Ala Gly Thr Leu Val Leu Val Val Leu Pro Pro Asp Gln Leu Arg
145                 150                 155                 160

Asn Asn Ser Phe His Phe Leu Arg Glu Leu Ser His Val Leu His Thr
                165                 170                 175

Asn Val Val Phe Lys Arg Asp Ala Gln Gly Gln Gln Met Ile Phe Pro
            180                 185                 190

Tyr Tyr Gly His Glu Glu Glu Leu Arg Lys His Pro Ile Lys Arg Ser
        195                 200                 205

Thr Val Gly Trp Ala Thr Ser Ser Leu Leu Pro Gly Thr Ser Gly Gly
    210                 215                 220
```

```
Arg Gln Arg Arg Glu Leu Asp Pro Met Asp Ile Arg Gly Ser Ile Val
225                 230                 235                 240

Tyr Leu Glu Ile Asp Asn Arg Gln Cys Val Gln Ser Ser Ser Gln Cys
            245                 250                 255

Phe Gln Ser Ala Thr Asp Val Ala Ala Phe Leu Gly Ala Leu Ala Ser
        260                 265                 270

Leu Gly Ser Leu Asn Ile Pro Tyr Lys Ile Glu Ala Val Lys Ser Glu
    275                 280                 285

Pro Val Glu Pro Pro Leu Pro Ser Gln Leu His Leu Met Tyr Val Ala
        290                 295                 300

Ala Ala Ala Phe Val Leu Leu Phe Phe Val Gly Cys Gly Val Leu Leu
305                 310                 315                 320

Ser Arg Lys Arg Arg Arg
                325

<210> SEQ ID NO 96
<211> LENGTH: 363
<212> TYPE: PRT
<213> ORGANISM: Artificial Sequence
<220> FEATURE:
<223> OTHER INFORMATION: Synthetic

<400> SEQUENCE: 96

Pro Cys Val Gly Ser Asn Pro Cys Tyr Asn Gln Gly Thr Cys Glu Pro
1               5                   10                  15

Thr Ser Glu Asn Pro Phe Tyr Arg Cys Leu Cys Pro Ala Lys Phe Asn
            20                  25                  30

Gly Leu Leu Cys His Ile Leu Asp Tyr Ser Phe Thr Gly Gly Ala Gly
        35                  40                  45

Arg Asp Ile Pro Pro Gln Ile Glu Glu Ala Cys Glu Leu Pro Glu
    50                  55                  60

Cys Gln Val Asp Ala Gly Asn Lys Val Cys Asn Leu Gln Cys Asn Asn
65                  70                  75                  80

His Ala Cys Gly Trp Asp Gly Gly Asp Cys Ser Leu Asn Phe Asn Asp
                85                  90                  95

Pro Trp Lys Asn Cys Thr Gln Ser Leu Gln Cys Trp Lys Tyr Phe Ser
            100                 105                 110

Asp Gly His Cys Asp Ser Gln Cys Asn Ser Ala Gly Cys Leu Phe Asp
        115                 120                 125

Gly Phe Asp Cys Gln Leu Thr Glu Gly Gln Cys Asn Pro Leu Tyr Asp
    130                 135                 140

Gln Tyr Cys Lys Asp His Phe Ser Asp Gly His Cys Asp Gln Gly Cys
145                 150                 155                 160

Asn Ser Ala Glu Cys Glu Trp Asp Gly Leu Asp Cys Ala Glu His Val
                165                 170                 175

Pro Glu Arg Leu Ala Ala Gly Thr Leu Val Leu Val Val Leu Leu Pro
            180                 185                 190

Pro Asp Gln Leu Arg Asn Asn Ser Phe His Phe Leu Arg Glu Leu Ser
        195                 200                 205

His Val Leu His Thr Asn Val Val Phe Lys Arg Asp Ala Gln Gly Gln
    210                 215                 220

Gln Met Ile Phe Pro Tyr Tyr Gly His Glu Glu Leu Arg Lys His
225                 230                 235                 240

Pro Ile Lys Arg Ser Thr Val Gly Trp Ala Thr Ser Ser Leu Leu Pro
            245                 250                 255
```

```
Gly Thr Ser Gly Gly Arg Gln Arg Arg Glu Leu Asp Pro Met Asp Ile
            260                 265                 270

Arg Gly Ser Ile Val Tyr Leu Glu Ile Asp Asn Arg Gln Cys Val Gln
        275                 280                 285

Ser Ser Ser Gln Cys Phe Gln Ser Ala Thr Asp Val Ala Ala Phe Leu
    290                 295                 300

Gly Ala Leu Ala Ser Leu Gly Ser Leu Asn Ile Pro Tyr Lys Ile Glu
305                 310                 315                 320

Ala Val Lys Ser Glu Pro Val Glu Pro Leu Pro Ser Gln Leu His
                325                 330                 335

Leu Met Tyr Val Ala Ala Ala Phe Val Leu Leu Phe Phe Val Gly
            340                 345                 350

Cys Gly Val Leu Leu Ser Arg Lys Arg Arg
        355                 360

<210> SEQ ID NO 97
<211> LENGTH: 18
<212> TYPE: PRT
<213> ORGANISM: Artificial Sequence
<220> FEATURE:
<223> OTHER INFORMATION: Synthetic

<400> SEQUENCE: 97

Met Leu Arg Leu Leu Leu Ala Leu Asn Leu Phe Pro Ser Ile Gln Val
1               5                   10                  15

Thr Gly

<210> SEQ ID NO 98
<211> LENGTH: 20
<212> TYPE: PRT
<213> ORGANISM: Artificial Sequence
<220> FEATURE:
<223> OTHER INFORMATION: Synthetic

<400> SEQUENCE: 98

Met Ser Arg Ser Val Ala Leu Ala Val Leu Ala Leu Leu Ser Leu Ser
1               5                   10                  15

Gly Leu Glu Ala
            20

<210> SEQ ID NO 99
<211> LENGTH: 24
<212> TYPE: PRT
<213> ORGANISM: Artificial Sequence
<220> FEATURE:
<223> OTHER INFORMATION: Synthetic

<400> SEQUENCE: 99

Met Ala Val Met Ala Pro Arg Thr Leu Leu Leu Leu Leu Ser Gly Ala
1               5                   10                  15

Leu Ala Leu Thr Gln Thr Trp Ala
            20

<210> SEQ ID NO 100
<211> LENGTH: 25
<212> TYPE: PRT
<213> ORGANISM: Artificial Sequence
<220> FEATURE:
<223> OTHER INFORMATION: Synthetic

<400> SEQUENCE: 100

Met Ala Ile Ser Gly Val Pro Val Leu Gly Phe Phe Ile Ile Ala Val
```

```
                1               5                  10                  15
Leu Met Ser Ala Gln Glu Ser Trp Ala
                20                  25

<210> SEQ ID NO 101
<211> LENGTH: 28
<212> TYPE: PRT
<213> ORGANISM: Artificial Sequence
<220> FEATURE:
<223> OTHER INFORMATION: Synthetic

<400> SEQUENCE: 101

Met Val Cys Leu Lys Leu Pro Gly Gly Ser Cys Met Thr Ala Leu Thr
1               5                  10                  15

Val Thr Leu Met Val Leu Ser Ser Pro Leu Ala Leu
                20                  25

<210> SEQ ID NO 102
<211> LENGTH: 29
<212> TYPE: PRT
<213> ORGANISM: Artificial Sequence
<220> FEATURE:
<223> OTHER INFORMATION: Synthetic

<400> SEQUENCE: 102

Met Val Cys Leu Lys Leu Pro Gly Gly Ser Tyr Met Ala Lys Leu Thr
1               5                  10                  15

Val Thr Leu Met Val Leu Ser Ser Pro Leu Ala Leu Ala
                20                  25

<210> SEQ ID NO 103
<211> LENGTH: 100
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (16)..(100)
<223> OTHER INFORMATION: may be absent

<400> SEQUENCE: 103

Gly Gly Gly Gly Ser Gly Gly Gly Ser Gly Gly Gly Gly Ser Gly
1               5                  10                  15

Gly Gly Gly Ser Gly Gly Gly Gly Ser Gly Gly Gly Gly Ser Gly Gly
                20                  25                  30

Gly Gly Ser Gly Gly Gly Gly Ser Gly Gly Gly Gly Ser Gly Gly Gly
            35                  40                  45

Gly Ser Gly Gly Gly Gly Ser Gly Gly Gly Gly Ser Gly Gly Gly Gly
        50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser Gly Gly Gly Gly Ser Gly
                85                  90                  95

Gly Gly Gly Ser
            100

<210> SEQ ID NO 104
<211> LENGTH: 30
<212> TYPE: PRT
<213> ORGANISM: Artificial Sequence
<220> FEATURE:
<223> OTHER INFORMATION: Synthetic
```

<400> SEQUENCE: 104

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser
            20                  25              30

<210> SEQ ID NO 105
<211> LENGTH: 60
<212> TYPE: PRT
<213> ORGANISM: Artificial Sequence
<220> FEATURE:
<223> OTHER INFORMATION: Synthetic

<400> SEQUENCE: 105

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Ser Gly Gly
        35                  40              45

Gly Ser Gly Gly Gly Gly Ser Gly Gly Gly Ser
    50                  55              60

<210> SEQ ID NO 106
<211> LENGTH: 75
<212> TYPE: PRT
<213> ORGANISM: Artificial Sequence
<220> FEATURE:
<223> OTHER INFORMATION: Synthetic

<400> SEQUENCE: 106

Gly Gly Gly Gly Ser Gly Gly Gly Ser Gly Gly Gly Ser Gly
1               5                   10                  15

Gly Gly Gly Ser Gly Gly Gly Ser Gly Gly Gly Ser Gly Gly
            20                  25                  30

Gly Gly Ser Gly Gly Gly Gly Ser Gly Gly Gly Ser Gly Gly
        35                  40              45

Gly Ser Gly Gly Gly Gly Ser Gly Gly Gly Ser Gly Gly Gly
    50                  55                  60

Ser Gly Gly Gly Gly Ser Gly Gly Gly Ser
65                  70              75

<210> SEQ ID NO 107
<211> LENGTH: 9
<212> TYPE: PRT
<213> ORGANISM: Artificial Sequence
<220> FEATURE:
<223> OTHER INFORMATION: Synthetic

<400> SEQUENCE: 107

Lys Leu Ile Glu Thr Tyr Phe Ser Lys
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic

<400> SEQUENCE: 108

Leu Leu Phe Gly Tyr Pro Val Tyr Val
1               5

<210> SEQ ID NO 109
<211> LENGTH: 271
<212> TYPE: PRT
<213> ORGANISM: Artificial Sequence
<220> FEATURE:
<223> OTHER INFORMATION: Synthetic

<400> SEQUENCE: 109

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
        35                  40                  45

Ala Pro Trp Ile Glu Gln Glu Gly Pro Glu Tyr Trp Asp Gly Glu Thr
    50                  55                  60

Arg Lys Val Lys Ala His Ser Gln Thr His Arg Val Asp Leu Gly Thr
65                  70                  75                  80

Leu Arg Gly Tyr Tyr Asn Gln Ser Glu Ala Gly Ser His Thr Val Gln
                85                  90                  95

Arg Met Tyr Gly Cys Asp Val Gly Ser Asp Trp Arg Phe Leu Arg Gly
            100                 105                 110

Tyr His Gln Tyr Ala Tyr Asp Gly Lys Asp Tyr Ile Ala Leu Lys Glu
        115                 120                 125

Asp Leu Arg Ser Trp Thr Ala Ala Asp Met Ala Ala Gln Thr Thr Lys
    130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ala Pro Lys Thr His Met Thr His His
            180                 185                 190

Ala Val Ser Asp His Glu Ala Thr Leu Arg Cys Trp Ala Leu Ser Phe
        195                 200                 205

Tyr Pro Ala Glu Ile Thr Leu Thr Trp Gln Arg Asp Gly Glu Asp Gln
    210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Gln Glu Gln Arg
                245                 250                 255

Tyr Thr Cys His Val Gln His Glu Gly Leu Pro Lys Pro Leu Thr
            260                 265                 270

<210> SEQ ID NO 110
<211> LENGTH: 271
<212> TYPE: PRT
<213> ORGANISM: Artificial Sequence
<220> FEATURE:
<223> OTHER INFORMATION: Synthetic

<400> SEQUENCE: 110

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

```
Phe Val Arg Phe Asp Ser Asp Ala Ala Ser Gln Arg Met Glu Pro Arg
         35                  40                  45

Ala Pro Trp Ile Glu Gln Glu Gly Pro Glu Tyr Trp Asp Gln Glu Thr
 50                  55                  60

Arg Asn Val Lys Ala Gln Ser Gln Thr Asp Arg Val Asp Leu Gly Thr
 65                  70                  75                  80

Leu Arg Gly Tyr Tyr Asn Gln Ser Glu Ala Gly Ser His Thr Ile Gln
                 85                  90                  95

Ile Met Tyr Gly Cys Asp Val Gly Ser Asp Gly Arg Phe Leu Arg Gly
            100                 105                 110

Tyr Arg Gln Asp Ala Tyr Asp Gly Lys Asp Tyr Ile Ala Leu Asn Glu
            115                 120                 125

Asp Leu Arg Ser Trp Thr Ala Ala Asp Met Ala Ala Gln Ile Thr Lys
130                 135                 140

Arg Lys Trp Glu Ala Ala His Glu Ala Glu Gln Leu Arg Ala Tyr Leu
145                 150                 155                 160

Asp Gly Thr Cys Val Glu Trp Leu Arg Arg Tyr Leu Glu Asn Gly Lys
                165                 170                 175

Glu Thr Leu Gln Arg Thr Asp Pro Pro Lys Thr His Met Thr His His
            180                 185                 190

Pro Ile Ser Asp His Glu Ala Thr Leu Arg Cys Trp Ala Leu Gly Phe
            195                 200                 205

Tyr Pro Ala Glu Ile Thr Leu Thr Trp Gln Arg Asp Gly Glu Asp Gln
210                 215                 220

Thr Gln Asp Thr Glu Leu Val Glu Thr Arg Pro Ala Gly Asp Gly Thr
225                 230                 235                 240

Phe Gln Lys Trp Ala Ala Val Val Val Pro Ser Gly Glu Glu Gln Arg
                245                 250                 255

Tyr Thr Cys His Val Gln His Glu Gly Leu Pro Lys Pro Leu Thr
            260                 265                 270

<210> SEQ ID NO 111
<211> LENGTH: 4
<212> TYPE: PRT
<213> ORGANISM: Artificial Sequence
<220> FEATURE:
<223> OTHER INFORMATION: Synthetic

<400> SEQUENCE: 111

Leu Arg Trp Glu
1

<210> SEQ ID NO 112
<211> LENGTH: 271
<212> TYPE: PRT
<213> ORGANISM: Artificial Sequence
<220> FEATURE:
<223> OTHER INFORMATION: Synthetic

<400> SEQUENCE: 112

Gly Ser His Ser Met Arg Tyr Phe Phe Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Gln Arg Met Glu Pro Arg
         35                  40                  45

Ala Pro Trp Ile Glu Gln Glu Gly Pro Glu Tyr Trp Asp Gly Glu Thr
```

```
            50                  55                  60
Arg Lys Val Lys Ala His Ser Gln Thr His Arg Val Asp Leu Gly Thr
 65                  70                  75                  80

Leu Arg Gly Tyr Tyr Asn Gln Ser Glu Ala Gly Ser His Thr Val Gln
                     85                  90                  95

Arg Met Tyr Gly Cys Asp Val Gly Ser Asp Trp Arg Phe Leu Arg Gly
                100                 105                 110

Tyr His Gln Tyr Ala Tyr Asp Gly Lys Asp Tyr Ile Ala Leu Lys Glu
            115                 120                 125

Asp Leu Arg Ser Trp Thr Ala Ala Asp Met Ala Ala Gln Thr Thr Lys
        130                 135                 140

His Lys Trp Glu Ala Ala His Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Thr Asp Ser Pro Lys Ala His Val Thr His His
            180                 185                 190

Ser Arg Pro Glu Asp Lys Val Thr Leu Arg Cys Trp Ala Leu Gly Phe
        195                 200                 205

Tyr Pro Ala Asp Ile Thr Leu Thr Trp Gln Leu Asn Gly Glu Glu Leu
    210                 215                 220

Ile Gln Asp Met Glu Leu Val Glu Thr Arg Pro Ala Gly Asp Gly Thr
225                 230                 235                 240

Phe Gln Lys Trp Ala Ser Val Val Pro Leu Gly Lys Glu Gln Tyr
                245                 250                 255

Tyr Thr Cys His Val Tyr His Gln Gly Leu Pro Glu Pro Leu Thr
                260                 265                 270

<210> SEQ ID NO 113
<211> LENGTH: 271
<212> TYPE: PRT
<213> ORGANISM: Artificial Sequence
<220> FEATURE:
<223> OTHER INFORMATION: Synthetic

<400> SEQUENCE: 113

Gly Ser His Ser Met Arg Tyr Phe Phe Thr Ser Val Ser Arg Pro Gly
 1               5                  10                  15

Arg Gly Glu Pro Arg Phe Ile Ala Val Gly Tyr Val Asp Asp Thr Gln
                20                  25                  30

Phe Val Arg Phe Asp Ser Asp Ala Ala Ser Gln Arg Met Glu Pro Arg
            35                  40                  45

Ala Pro Trp Ile Glu Gln Glu Gly Pro Glu Tyr Trp Asp Gln Glu Thr
        50                  55                  60

Arg Asn Val Lys Ala Gln Ser Gln Thr Asp Arg Val Asp Leu Gly Thr
 65                  70                  75                  80

Leu Arg Gly Tyr Tyr Asn Gln Ser Glu Ala Gly Ser His Thr Ile Gln
                     85                  90                  95

Ile Met Tyr Gly Cys Asp Val Gly Ser Asp Gly Arg Phe Leu Arg Gly
                100                 105                 110

Tyr Arg Gln Asp Ala Tyr Asp Gly Lys Asp Tyr Ile Ala Leu Asn Glu
            115                 120                 125

Asp Leu Arg Ser Trp Thr Ala Ala Asp Met Ala Ala Gln Ile Thr Lys
        130                 135                 140

Arg Lys Trp Glu Ala Ala His Glu Ala Glu Gln Leu Arg Ala Tyr Leu
```

```
145                 150                 155                 160
Asp Gly Thr Cys Val Glu Trp Leu Arg Arg Tyr Leu Glu Asn Gly Lys
                165                 170                 175

Glu Thr Leu Gln Arg Thr Asp Ser Pro Lys Ala His Val Thr His His
                180                 185                 190

Ser Arg Pro Glu Asp Lys Val Thr Leu Arg Cys Trp Ala Leu Gly Phe
                195                 200                 205

Tyr Pro Ala Asp Ile Thr Leu Thr Trp Gln Leu Asn Gly Glu Glu Leu
            210                 215                 220

Ile Gln Asp Met Glu Leu Val Glu Thr Arg Pro Ala Gly Asp Gly Thr
225                 230                 235                 240

Phe Gln Lys Trp Ala Ser Val Val Pro Leu Gly Lys Glu Gln Tyr
                245                 250                 255

Tyr Thr Cys His Val Tyr His Gln Gly Leu Pro Glu Pro Leu Thr
                260                 265                 270

<210> SEQ ID NO 114
<211> LENGTH: 99
<212> TYPE: PRT
<213> ORGANISM: Homo Sapiens

<400> SEQUENCE: 114

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
                20                  25                  30

Ser Asp Ile Glu Val Asp Leu Leu Lys Asn Gly Glu Arg Ile Glu Lys
            35                  40                  45

Val Glu His Ser Asp Leu Ser Phe Ser Lys Asp Trp Ser Phe Tyr Leu
50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met

<210> SEQ ID NO 115
<211> LENGTH: 99
<212> TYPE: PRT
<213> ORGANISM: Musmusculus

<400> SEQUENCE: 115

Ile Gln Lys Thr Pro Gln Ile Gln Val Tyr Ser Arg His Pro Pro Glu
1               5                   10                  15

Asn Gly Lys Pro Asn Ile Leu Asn Cys Tyr Val Thr Gln Phe His Pro
                20                  25                  30

Pro His Ile Glu Ile Gln Met Leu Lys Asn Gly Lys Lys Ile Pro Lys
            35                  40                  45

Val Glu Met Ser Asp Met Ser Phe Ser Lys Asp Trp Ser Phe Tyr Ile
50                  55                  60

Leu Ala His Thr Glu Phe Thr Pro Thr Glu Thr Asp Thr Tyr Ala Cys
65                  70                  75                  80

Arg Val Lys His Ala Ser Met Ala Glu Pro Lys Thr Val Tyr Trp Asp
                85                  90                  95

Arg Asp Met
```

<210> SEQ ID NO 116
<211> LENGTH: 149
<212> TYPE: DNA
<213> ORGANISM: Artificial Sequence
<220> FEATURE:
<223> OTHER INFORMATION: Synthetic

<400> SEQUENCE: 116
agcgctctcg tacagagttg gcattataat acgactcact ataggggaga atcaaaatcg     60
gtgaatgttt tagagctaga aatagcaagt taaaataagg ctagtccgtt atcaacttga    120
aaaagtggca ccgagtcggt gcttttttt                                      149

<210> SEQ ID NO 117
<211> LENGTH: 185
<212> TYPE: PRT
<213> ORGANISM: Artificial Sequence
<220> FEATURE:
<223> OTHER INFORMATION: Synthetic

<400> SEQUENCE: 117

Gly Asp Thr Arg Pro Arg Phe Leu Trp Gln Pro Lys Arg Glu Cys His
1               5                   10                  15

Phe Phe Asn Gly Thr Glu Arg Val Arg Phe Leu Asp Arg Tyr Phe Tyr
                20                  25                  30

Asn Gln Glu Glu Ser Val Arg Phe Asp Ser Asp Val Gly Glu Phe Arg
            35                  40                  45

Ala Val Thr Glu Leu Gly Arg Pro Asp Ala Glu Tyr Trp Asn Ser Gln
        50                  55                  60

Lys Asp Ile Leu Glu Gln Ala Arg Ala Ala Val Asp Thr Tyr Cys Arg
65                  70                  75                  80

His Asn Tyr Gly Val Val Glu Ser Phe Thr Val Gln Arg Arg Val Gln
                85                  90                  95

Pro Lys Val Thr Val Tyr Pro Ser Lys Thr Gln Pro Leu Gln His His
            100                 105                 110

Asn Leu Leu Val Cys Ser Val Ser Gly Phe Tyr Pro Gly Ser Ile Glu
        115                 120                 125

Val Arg Trp Phe Leu Asn Gly Gln Glu Glu Lys Ala Gly Met Val Ser
    130                 135                 140

Thr Gly Leu Ile Gln Asn Gly Asp Trp Thr Phe Gln Thr Leu Val Met
145                 150                 155                 160

Leu Glu Thr Val Pro Arg Ser Gly Glu Val Tyr Thr Cys Gln Val Glu
                165                 170                 175

His Pro Ser Val Thr Ser Pro Leu Thr
            180                 185

<210> SEQ ID NO 118
<211> LENGTH: 178
<212> TYPE: PRT
<213> ORGANISM: Artificial Sequence
<220> FEATURE:
<223> OTHER INFORMATION: Synthetic

<400> SEQUENCE: 118

Ile Lys Glu Glu His Val Ile Ile Gln Ala Glu Phe Tyr Leu Asn Pro
1               5                   10                  15

Asp Gln Ser Gly Glu Phe Met Phe Asp Phe Asp Gly Asp Glu Ile Phe
                20                  25                  30

His Val Asp Met Ala Lys Lys Glu Thr Val Trp Arg Leu Glu Glu Phe

```
                35                  40                  45
Gly Arg Phe Ala Ser Phe Glu Ala Gln Gly Ala Leu Ala Asn Ile Ala
 50                  55                  60

Val Asp Lys Ala Asn Leu Glu Ile Met Thr Lys Arg Ser Asn Tyr Thr
 65                  70                  75                  80

Pro Ile Thr Asn Val Pro Pro Glu Val Thr Val Leu Thr Asn Ser Pro
                 85                  90                  95

Val Glu Leu Arg Glu Pro Asn Val Leu Ile Cys Phe Ile Asp Lys Phe
            100                 105                 110

Thr Pro Pro Val Val Asn Val Thr Trp Leu Arg Asn Gly Lys Pro Val
        115                 120                 125

Thr Thr Gly Val Ser Glu Thr Val Phe Leu Pro Arg Glu Asp His Leu
    130                 135                 140

Phe Arg Lys Phe His Tyr Leu Pro Phe Leu Pro Ser Thr Glu Asp Val
145                 150                 155                 160

Tyr Asp Cys Arg Val Glu His Trp Gly Leu Asp Glu Pro Leu Leu Lys
                165                 170                 175

His Trp

<210> SEQ ID NO 119
<211> LENGTH: 185
<212> TYPE: PRT
<213> ORGANISM: Artificial Sequence
<220> FEATURE:
<223> OTHER INFORMATION: Synthetic

<400> SEQUENCE: 119

Ile Lys Glu Glu His Val Ile Ile Gln Ala Glu Ser Tyr Leu Asn Pro
 1               5                  10                  15

Asp Gln Ser Gly Glu Phe Lys Phe Asp Phe Asp Gly Asp Glu Ile Phe
                 20                  25                  30

His Val Asp Met Ala Lys Lys Glu Thr Val Trp Arg Leu Glu Glu Phe
             35                  40                  45

Gly Arg Phe Ala Ser Phe Glu Ala Gln Gly Ala Leu Ala Asn Ile Ala
 50                  55                  60

Val Asp Lys Ala Asn Leu Glu Ile Met Thr Lys Arg Ser Asn Tyr Thr
 65                  70                  75                  80

Pro Ile Glu Glu Thr Glu Val Pro Thr Ser Leu Arg Arg Leu Glu Gln
                 85                  90                  95

Pro Asn Val Ala Ile Ser Leu Ser Arg Thr Glu Ala Leu Asn His His
            100                 105                 110

Asn Thr Leu Val Cys Ser Val Thr Asp Phe Tyr Pro Ala Lys Ile Lys
        115                 120                 125

Val Arg Trp Phe Arg Asn Gly Gln Glu Glu Thr Val Gly Val Ser Ser
    130                 135                 140

Thr Gln Leu Ile Arg Asn Gly Asp Trp Thr Phe Gln Val Leu Val Met
145                 150                 155                 160

Leu Glu Met Thr Pro His Gln Gly Glu Val Tyr Thr Cys His Val Glu
                165                 170                 175

His Pro Ser Leu Lys Ser Pro Ile Thr
            180                 185

<210> SEQ ID NO 120
<211> LENGTH: 183
<212> TYPE: PRT
<213> ORGANISM: Artificial Sequence
```

<220> FEATURE:
<223> OTHER INFORMATION: Synthetic

<400> SEQUENCE: 120

Ile Lys Glu Glu His Val Ile Ile Gln Ala Glu Ser Tyr Leu Asn Pro
1               5                   10                  15

Asp Gln Ser Gly Glu Phe Lys Phe Asp Phe Gly Asp Glu Ile Phe
            20                  25                  30

His Val Asp Met Ala Lys Lys Glu Thr Val Trp Arg Leu Glu Glu Phe
        35                  40                  45

Gly Arg Phe Ala Ser Phe Glu Ala Gln Gly Ala Leu Ala Asn Ile Ala
    50                  55                  60

Val Asp Lys Ala Asn Leu Glu Ile Met Thr Lys Arg Ser Asn Tyr Thr
65                  70                  75                  80

Pro Ile Ala Thr Asn Glu Ala Pro Gln Ala Thr Val Phe Pro Lys Ser
                85                  90                  95

Pro Val Leu Leu Gly Gln Pro His Thr Leu Ile Cys Phe Val Asp Asn
            100                 105                 110

Ile Phe Pro Pro Val Ile Asn Ile Thr Trp Leu Arg Asn Ser Lys Ser
        115                 120                 125

Val Thr Asp Gly Val Tyr Glu Thr Ser Phe Leu Val Asn Arg Asp His
    130                 135                 140

Ser Phe His Lys Leu Ser Tyr Leu Thr Phe Ile Pro Ser Asp Asp Asp
145                 150                 155                 160

Ile Tyr Asp Cys Lys Val Glu His Trp Gly Leu Glu Glu Pro Val Leu
                165                 170                 175

Lys His Trp Glu Pro Glu Ile
            180

<210> SEQ ID NO 121
<211> LENGTH: 90
<212> TYPE: PRT
<213> ORGANISM: Artificial Sequence
<220> FEATURE:
<223> OTHER INFORMATION: Synthetic

<400> SEQUENCE: 121

Arg Pro Arg Phe Leu Trp Gln Ser Lys Arg Glu Cys His Phe Phe Asn
1               5                   10                  15

Gly Thr Glu Arg Val Arg Phe Leu Asp Arg Tyr Phe Tyr Asn Gln Glu
            20                  25                  30

Glu Ser Val Arg Phe Asp Ser Asp Val Gly Glu Phe Arg Ala Val Thr
        35                  40                  45

Glu Leu Gly Arg Pro Asp Ala Glu Tyr Trp Asn Ser Gln Lys Asp Ile
    50                  55                  60

Leu Glu Gln Ala Arg Ala Ala Val Asp Thr Tyr Cys Arg His Asn Tyr
65                  70                  75                  80

Gly Val Val Glu Ser Phe Thr Val Gln Arg
                85                  90

<210> SEQ ID NO 122
<211> LENGTH: 82
<212> TYPE: PRT
<213> ORGANISM: Artificial Sequence
<220> FEATURE:
<223> OTHER INFORMATION: Synthetic

<400> SEQUENCE: 122

Ile Lys Glu Glu His Val Ile Ile Gln Ala Glu Ser Tyr Leu Asn Pro
1               5                   10                  15

Asp Gln Ser Gly Glu Phe Lys Phe Asp Phe Asp Gly Asp Glu Ile Phe
            20                  25                  30

His Val Asp Met Ala Lys Lys Glu Thr Val Trp Arg Leu Glu Glu Phe
            35                  40                  45

Gly Arg Phe Ala Ser Phe Glu Ala Gln Gly Ala Leu Ala Asn Ile Ala
            50                  55                  60

Val Asp Lys Ala Asn Leu Glu Ile Met Thr Lys Arg Ser Asn Tyr Thr
65                  70                  75                  80

Pro Ile

<210> SEQ ID NO 123
<211> LENGTH: 272
<212> TYPE: PRT
<213> ORGANISM: Artificial Sequence
<220> FEATURE:
<223> OTHER INFORMATION: Synthetic

<400> SEQUENCE: 123

Met Glu Thr Leu Leu Gly Val Ser Leu Val Ile Leu Trp Leu Gln Leu
1               5                   10                  15

Ala Arg Val Asn Ser Gln Gln Gly Glu Glu Asp Pro Gln Ala Leu Ser
            20                  25                  30

Ile Gln Glu Gly Glu Asn Ala Thr Met Asn Cys Ser Tyr Lys Thr Ser
            35                  40                  45

Ile Asn Asn Leu Gln Trp Tyr Arg Gln Asn Ser Gly Arg Gly Leu Val
            50                  55                  60

His Leu Ile Leu Ile Arg Ser Asn Glu Arg Glu Lys His Ser Gly Arg
65                  70                  75                  80

Leu Arg Val Thr Leu Asp Thr Ser Lys Lys Ser Ser Leu Leu Ile
                85                  90                  95

Thr Ala Ser Arg Ala Ala Asp Thr Ala Ser Tyr Phe Cys Ala Thr Ala
                100                 105                 110

Ala Val Gly Gly Phe Lys Thr Ile Phe Gly Ala Gly Thr Arg Leu Phe
            115                 120                 125

Val Lys Ala Asn Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
            195                 200                 205

Asn Asn Ser Ile Ile Pro Glu Asp Thr Phe Phe Pro Ser Pro Glu Ser
210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

```
<210> SEQ ID NO 124
<211> LENGTH: 312
<212> TYPE: PRT
<213> ORGANISM: Artificial Sequence
<220> FEATURE:
<223> OTHER INFORMATION: Synthetic

<400> SEQUENCE: 124
```

Met Leu Leu Leu Leu Leu Leu Gly Leu Ala Gly Ser Gly Leu Gly
1               5                   10                  15

Ala Val Val Ser Gln His Pro Ser Trp Val Ile Ser Lys Ser Gly Thr
            20                  25                  30

Ser Val Lys Ile Glu Cys Arg Ser Leu Asp Phe Gln Ala Thr Thr Met
        35                  40                  45

Phe Trp Tyr Arg Gln Phe Pro Lys Gln Ser Leu Met Leu Met Ala Thr
    50                  55                  60

Ser Asn Glu Gly Ser Lys Ala Thr Tyr Glu Gln Gly Val Glu Lys Asp
65                  70                  75                  80

Lys Phe Leu Ile Asn His Ala Ser Leu Thr Leu Ser Thr Leu Thr Val
                85                  90                  95

Thr Ser Ala His Pro Glu Asp Ser Ser Phe Tyr Ile Cys Ser Ala Arg
            100                 105                 110

Asp Leu Thr Ser Gly Ala Asn Asn Glu Gln Phe Phe Gly Pro Gly Thr
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Ser
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

```
<210> SEQ ID NO 125
<211> LENGTH: 278
<212> TYPE: PRT
<213> ORGANISM: Artificial Sequence
<220> FEATURE:
<223> OTHER INFORMATION: Synthetic

<400> SEQUENCE: 125
```

```
Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
            35                  40                  45

Cys Asp Tyr Thr Asn Ser Met Phe Asp Tyr Phe Leu Trp Tyr Lys Lys
50                  55                  60

Tyr Pro Ala Glu Gly Pro Thr Phe Leu Ile Ser Ile Ser Ser Ile Lys
65                  70                  75                  80

Asp Lys Asn Ala Asp Gly Arg Phe Thr Val Phe Leu Asn Lys Ser Ala
            85                  90                  95

Lys His Leu Ser Leu His Ile Val Pro Ser Gln Pro Gly Asp Ser Ala
            100                 105                 110

Val Tyr Phe Cys Ala Ala Met Glu Gly Ala Gln Lys Leu Val Phe Gly
            115                 120                 125

Gln Gly Thr Arg Leu Thr Ile Asn Pro Asn Ile Gln Asn Pro Asp Pro
130                 135                 140

Ala Val Tyr Gln Leu Arg Asp Ser Lys Ser Ser Asp Lys Ser Val Cys
145                 150                 155                 160

Leu Phe Thr Asp Phe Asp Ser Gln Thr Asn Val Ser Gln Ser Lys Asp
            165                 170                 175

Ser Asp Val Tyr Ile Thr Asp Lys Thr Val Leu Asp Met Arg Ser Met
            180                 185                 190

Asp Phe Lys Ser Asn Ser Ala Val Ala Trp Ser Asn Lys Ser Asp Phe
            195                 200                 205

Ala Cys Ala Asn Ala Phe Asn Asn Ser Ile Ile Pro Glu Asp Thr Phe
210                 215                 220

Phe Pro Ser Pro Glu Ser Ser Cys Asp Val Lys Leu Val Glu Lys Ser
225                 230                 235                 240

Phe Glu Thr Asp Thr Asn Leu Asn Phe Gln Asn Leu Ser Val Ile Gly
            245                 250                 255

Phe Arg Ile Leu Leu Leu Lys Val Ala Gly Phe Asn Leu Leu Met Thr
            260                 265                 270

Leu Arg Leu Trp Ser Ser
            275

<210> SEQ ID NO 126
<211> LENGTH: 312
<212> TYPE: PRT
<213> ORGANISM: Artificial Sequence
<220> FEATURE:
<223> OTHER INFORMATION: Synthetic

<400> SEQUENCE: 126

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
            50                  55                  60

Ile His Tyr Ser Val Gly Ala Gly Ile Thr Asp Gln Gly Glu Val Pro
65                  70                  75                  80
```

```
Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

Ser Tyr Pro Gly Gly Gly Phe Tyr Glu Gln Tyr Phe Gly Pro Gly Thr
        115                 120                 125

Arg Leu Thr Val Thr Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Ala
        195                 200                 205

Leu Ser Ser Arg Leu Arg Val Ser Ala Thr Phe Trp Gln Asp Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 127
<211> LENGTH: 461
<212> TYPE: PRT
<213> ORGANISM: Artificial Sequence
<220> FEATURE:
<223> OTHER INFORMATION: Synthetic

<400> SEQUENCE: 127

Met Ala Leu Pro Val Thr Ala Leu Leu Leu Pro Leu Ala Leu Leu Leu
1               5                   10                  15

His Ala Ala Arg Pro Glu Val Gln Leu Gln Gln Ser Gly Pro Glu Leu
            20                  25                  30

Ile Lys Pro Gly Ala Ser Val Lys Met Ser Cys Lys Ala Ser Gly Tyr
        35                  40                  45

Thr Phe Thr Ser Tyr Val Met His Trp Val Lys Gln Lys Pro Gly Gln
    50                  55                  60

Gly Leu Glu Trp Ile Gly Tyr Ile Asn Pro Tyr Asn Asp Gly Thr Lys
65                  70                  75                  80

Tyr Asn Glu Lys Phe Lys Gly Lys Ala Thr Leu Thr Ser Asp Lys Ser
                85                  90                  95

Ser Ser Thr Ala Tyr Met Glu Leu Ser Ser Leu Thr Ser Glu Asp Ser
            100                 105                 110

Ala Val Tyr Tyr Cys Ala Arg Gly Thr Tyr Tyr Gly Ser Arg Val
        115                 120                 125
```

```
Phe Asp Tyr Trp Gly Gln Gly Thr Thr Leu Thr Val Ser Ser Gly Gly
    130                 135                 140

Gly Gly Ser Gly Gly Gly Ser Gly Gly Gly Ser Asp Ile Val
145                 150                 155                 160

Met Thr Gln Ala Ala Pro Ser Ile Pro Val Thr Pro Gly Glu Ser Val
                165                 170                 175

Ser Ile Ser Cys Arg Ser Ser Lys Ser Leu Leu Asn Ser Asn Gly Asn
                180                 185                 190

Gly Ser Gly Ser Gly Thr Ala Phe Thr Leu Arg Ile Ser Arg Val Glu
            195                 200                 205

Ala Glu Asp Val Gly Val Tyr Tyr Cys Met Gln His Leu Glu Tyr Pro
    210                 215                 220

Phe Thr Ala Gly Thr Lys Leu Glu Leu Lys Arg Ser Asp Pro Thr Thr
225                 230                 235                 240

Thr Pro Ala Pro Arg Pro Pro Thr Pro Ala Pro Thr Ile Ala Ser Gln
                245                 250                 255

Pro Leu Ser Leu Arg Pro Glu Ala Cys Arg Pro Ala Ala Gly Gly Ala
                260                 265                 270

Val His Thr Arg Gly Leu Asp Phe Ala Cys Asp Ile Tyr Ile Trp Ala
            275                 280                 285

Pro Leu Ala Gly Thr Cys Gly Val Leu Leu Leu Ser Leu Val Ile Thr
    290                 295                 300

Leu Tyr Cys Lys Arg Gly Arg Lys Lys Leu Leu Tyr Ile Phe Lys Gln
305                 310                 315                 320

Pro Phe Met Arg Pro Val Gln Thr Thr Gln Glu Glu Asp Gly Cys Ser
                325                 330                 335

Cys Arg Phe Pro Glu Glu Glu Glu Gly Gly Cys Glu Leu Arg Val Lys
                340                 345                 350

Phe Ser Arg Ser Ala Asp Ala Pro Ala Tyr Gln Gln Gly Gln Asn Gln
            355                 360                 365

Leu Tyr Asn Glu Leu Asn Leu Gly Arg Arg Glu Glu Tyr Asp Val Leu
    370                 375                 380

Asp Lys Arg Arg Gly Arg Asp Pro Glu Met Gly Gly Lys Pro Arg Arg
385                 390                 395                 400

Lys Asn Pro Gln Glu Gly Leu Tyr Asn Glu Leu Gln Lys Asp Lys Met
                405                 410                 415

Ala Glu Ala Tyr Ser Glu Ile Gly Met Lys Gly Glu Arg Arg Arg Gly
            420                 425                 430

Lys Gly His Asp Gly Leu Tyr Gln Gly Leu Ser Thr Ala Thr Lys Asp
    435                 440                 445

Thr Tyr Asp Ala Leu His Met Gln Ala Leu Pro Pro Arg
450                 455                 460

<210> SEQ ID NO 128
<211> LENGTH: 495
<212> TYPE: PRT
<213> ORGANISM: Artificial Sequence
<220> FEATURE:
<223> OTHER INFORMATION: Synthetic

<400> SEQUENCE: 128

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile
                20                  25                  30
```

-continued

Lys Pro Gly Ala Ser Val Lys Met Ser Cys Lys Ala Ser Gly Tyr Thr
            35                  40                  45

Phe Thr Ser Tyr Val Met His Trp Val Lys Gln Lys Pro Gly Gln Gly
 50                  55                  60

Leu Glu Trp Ile Gly Tyr Ile Asn Pro Tyr Asn Asp Gly Thr Lys Tyr
 65                  70                  75                  80

Asn Glu Lys Phe Lys Gly Lys Ala Thr Leu Thr Ser Asp Lys Ser Ser
                 85                  90                  95

Ser Thr Ala Tyr Met Glu Leu Ser Ser Leu Thr Ser Glu Asp Ser Ala
             100                 105                 110

Val Tyr Tyr Cys Ala Arg Gly Thr Tyr Tyr Gly Ser Arg Val Phe
             115                 120                 125

Asp Tyr Trp Gly Gln Gly Thr Thr Leu Thr Val Ser Ser Gly Gly Gly
     130                 135                 140

Gly Ser Gly Gly Gly Gly Ser Gly Gly Gly Gly Ser Asp Ile Val Met
145                 150                 155                 160

Thr Gln Ala Ala Pro Ser Ile Pro Val Thr Pro Gly Glu Ser Val Ser
                 165                 170                 175

Ile Ser Cys Arg Ser Ser Lys Ser Leu Leu Asn Ser Asn Gly Asn Thr
             180                 185                 190

Tyr Leu Tyr Trp Phe Leu Gln Arg Pro Gly Gln Ser Pro Gln Leu Leu
         195                 200                 205

Ile Tyr Arg Met Ser Asn Leu Ala Ser Gly Val Pro Asp Arg Phe Ser
         210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                 245                 250                 255

Phe Thr Phe Gly Ala Gly Thr Lys Leu Glu Leu Lys Arg Ser Asp Pro
         260                 265                 270

Thr Thr Thr Pro Ala Pro Arg Pro Pro Thr Pro Ala Pro Thr Ile Ala
         275                 280                 285

Ser Gln Pro Leu Ser Leu Arg Pro Glu Ala Cys Arg Pro Ala Ala Gly
     290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                 325                 330                 335

Ile Thr Leu Tyr Cys Lys Arg Gly Arg Lys Lys Leu Leu Tyr Ile Phe
             340                 345                 350

Lys Gln Pro Phe Met Arg Pro Val Gln Thr Thr Gln Glu Glu Asp Gly
             355                 360                 365

Cys Ser Cys Arg Phe Pro Glu Glu Glu Glu Gly Gly Cys Glu Leu Arg
     370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
             405                 410                 415

Val Leu Asp Lys Arg Arg Gly Arg Asp Pro Glu Met Gly Gly Lys Pro
             420                 425                 430

Arg Arg Lys Asn Pro Gln Glu Gly Leu Tyr Asn Glu Leu Gln Lys Asp
             435                 440                 445

Lys Met Ala Glu Ala Tyr Ser Glu Ile Gly Met Lys Gly Glu Arg Arg

```
            450                 455                 460
Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 129
<211> LENGTH: 432
<212> TYPE: PRT
<213> ORGANISM: Artificial Sequence
<220> FEATURE:
<223> OTHER INFORMATION: Synthetic

<400> SEQUENCE: 129

Met Ala Leu Pro Val Thr Ala Leu Leu Leu Pro Leu Ala Leu Leu Leu
1               5                   10                  15

His Ala Ala Arg Pro Glu Val Lys Leu Leu Glu Ser Gly Gly Gly Leu
                20                  25                  30

Val Gln Pro Gly Gly Ser Leu Lys Leu Ser Cys Ala Ala Ser Gly Phe
            35                  40                  45

Asp Phe Ser Arg Tyr Trp Met Ser Trp Val Arg Gln Ala Pro Gly Lys
        50                  55                  60

Gly Leu Glu Trp Ile Gly Glu Ile Asn Pro Asp Ser Ser Thr Ile Asn
65                  70                  75                  80

Tyr Thr Pro Ser Leu Lys Asp Lys Phe Ile Ile Ser Arg Asp Asn Ala
                85                  90                  95

Lys Asn Thr Leu Tyr Leu Gln Met Ser Lys Val Arg Ser Glu Asp Thr
            100                 105                 110

Ala Leu Tyr Tyr Cys Ala Arg Pro Asp Gly Asn Tyr Trp Tyr Phe Asp
        115                 120                 125

Val Trp Gly Ala Gly Thr Thr Val Thr Val Ser Ser Gly Gly Gly Gly
130                 135                 140

Ser Gly Gly Gly Gly Ser Gly Gly Gly Gly Ser Asp Ile Val Met Thr
145                 150                 155                 160

Gln Ser His Lys Phe Met Ser Thr Ser Val Gly Asp Arg Val Ser Ile
                165                 170                 175

Thr Cys Lys Ala Ser Gln Asp Val Gly Ile Ala Val Ala Trp Tyr Gln
            180                 185                 190

Gln Lys Pro Gly Gln Ser Pro Lys Leu Leu Ile Tyr Trp Ala Ser Thr
        195                 200                 205

Arg His Thr Gly Val Pro Asp Arg Phe Thr Gly Ser Gly Ser Gly Thr
    210                 215                 220

Asp Phe Thr Leu Thr Ile Ser Asn Val Gln Ser Glu Asp Leu Ala Asp
225                 230                 235                 240

Tyr Phe Cys Gln Gln Tyr Ser Ser Tyr Pro Tyr Thr Phe Gly Gly Gly
                245                 250                 255

Thr Lys Leu Glu Ile Lys Gly Leu Ala Val Ser Thr Ile Ser Ser Phe
            260                 265                 270

Phe Pro Pro Gly Tyr Gln Lys Arg Gly Arg Lys Lys Leu Leu Tyr Ile
        275                 280                 285

Phe Lys Gln Pro Phe Met Arg Pro Val Gln Thr Thr Gln Glu Glu Asp
    290                 295                 300

Gly Cys Ser Cys Arg Phe Pro Glu Glu Glu Glu Gly Gly Cys Glu Leu
305                 310                 315                 320

Arg Val Lys Phe Ser Arg Ser Ala Asp Ala Pro Ala Tyr Gln Gln Gly
```

```
                        325                 330                 335
Gln Asn Gln Leu Tyr Asn Glu Leu Asn Leu Gly Arg Arg Glu Glu Tyr
                340                 345                 350
Asp Val Leu Asp Lys Arg Arg Gly Arg Asp Pro Glu Met Gly Gly Lys
            355                 360                 365
Pro Arg Arg Lys Asn Pro Gln Glu Gly Leu Tyr Asn Glu Leu Gln Lys
        370                 375                 380
Asp Lys Met Ala Glu Ala Tyr Ser Glu Ile Gly Met Lys Gly Glu Arg
385                 390                 395                 400
Arg Arg Gly Lys Gly His Asp Gly Leu Tyr Gln Gly Leu Ser Thr Ala
                405                 410                 415
Thr Lys Asp Thr Tyr Asp Ala Leu His Met Gln Ala Leu Pro Pro Arg
            420                 425                 430

<210> SEQ ID NO 130
<211> LENGTH: 485
<212> TYPE: PRT
<213> ORGANISM: Artificial Sequence
<220> FEATURE:
<223> OTHER INFORMATION: Synthetic

<400> SEQUENCE: 130

Met Ala Leu Pro Val Thr Ala Leu Leu Leu Pro Leu Ala Leu Leu Leu
1               5                   10                  15
His Ala Ala Arg Pro Glu Val Lys Leu Glu Ser Gly Gly Gly Leu
            20                  25                  30
Val Gln Pro Gly Gly Ser Leu Lys Leu Ser Cys Ala Ala Ser Gly Phe
        35                  40                  45
Asp Phe Ser Arg Tyr Trp Met Ser Trp Val Arg Gln Ala Pro Gly Lys
    50                  55                  60
Gly Leu Glu Trp Ile Gly Glu Ile Asn Pro Asp Ser Ser Thr Ile Asn
65                  70                  75                  80
Tyr Thr Pro Ser Leu Lys Asp Lys Phe Ile Ile Ser Arg Asp Asn Ala
                85                  90                  95
Lys Asn Thr Leu Tyr Leu Gln Met Ser Lys Val Arg Ser Glu Asp Thr
            100                 105                 110
Ala Leu Tyr Tyr Cys Ala Arg Pro Asp Gly Asn Tyr Trp Tyr Phe Asp
        115                 120                 125
Val Trp Gly Ala Gly Thr Thr Val Thr Val Ser Ser Gly Gly Gly Gly
    130                 135                 140
Ser Gly Gly Gly Gly Ser Gly Gly Gly Gly Ser Asp Ile Val Met Thr
145                 150                 155                 160
Gln Ser His Lys Phe Met Ser Thr Ser Val Gly Asp Arg Val Ser Ile
                165                 170                 175
Thr Cys Lys Ala Ser Gln Asp Val Gly Ile Ala Val Ala Trp Tyr Gln
            180                 185                 190
Gln Lys Pro Gly Gln Ser Pro Lys Leu Leu Ile Tyr Trp Ala Ser Thr
        195                 200                 205
Arg His Thr Gly Val Pro Asp Arg Phe Thr Gly Ser Gly Ser Gly Thr
    210                 215                 220
Asp Phe Thr Leu Thr Ile Ser Asn Val Gln Ser Glu Asp Leu Ala Asp
225                 230                 235                 240
Tyr Phe Cys Gln Gln Tyr Ser Ser Tyr Pro Tyr Thr Phe Gly Gly Gly
                245                 250                 255
Thr Lys Leu Glu Ile Lys Thr Thr Thr Pro Ala Pro Arg Pro Pro Thr
```

```
            260                 265                 270
Pro Ala Pro Thr Ile Ala Ser Gln Pro Leu Ser Leu Arg Pro Glu Ala
            275                 280                 285
Cys Arg Pro Ala Ala Gly Gly Ala Val His Thr Arg Gly Leu Asp Phe
            290                 295                 300
Ala Cys Asp Ile Tyr Ile Trp Ala Pro Leu Ala Gly Thr Cys Gly Val
305                 310                 315                 320
Leu Leu Leu Ser Leu Val Ile Thr Leu Tyr Cys Lys Arg Gly Arg Lys
                    325                 330                 335
Lys Leu Leu Tyr Ile Phe Lys Gln Pro Phe Met Arg Pro Val Gln Thr
                340                 345                 350
Thr Gln Glu Glu Asp Gly Cys Ser Cys Arg Phe Pro Glu Glu Glu Glu
            355                 360                 365
Gly Gly Cys Glu Leu Arg Val Lys Phe Ser Arg Ser Ala Asp Ala Pro
            370                 375                 380
Ala Tyr Gln Gln Gly Gln Asn Gln Leu Tyr Asn Glu Leu Asn Leu Gly
385                 390                 395                 400
Arg Arg Glu Glu Tyr Asp Val Leu Asp Lys Arg Arg Gly Arg Asp Pro
                405                 410                 415
Glu Met Gly Gly Lys Pro Arg Arg Lys Asn Pro Gln Glu Gly Leu Tyr
                420                 425                 430
Asn Glu Leu Gln Lys Asp Lys Met Ala Glu Ala Tyr Ser Glu Ile Gly
            435                 440                 445
Met Lys Gly Glu Arg Arg Arg Gly Lys Gly His Asp Gly Leu Tyr Gln
        450                 455                 460
Gly Leu Ser Thr Ala Thr Lys Asp Thr Tyr Asp Ala Leu His Met Gln
465                 470                 475                 480
Ala Leu Pro Pro Arg
            485

<210> SEQ ID NO 131
<211> LENGTH: 647
<212> TYPE: PRT
<213> ORGANISM: Artificial Sequence
<220> FEATURE:
<223> OTHER INFORMATION: Synthetic

<400> SEQUENCE: 131

Met Ala Leu Pro Val Thr Ala Leu Leu Leu Pro Leu Ala Leu Leu Leu
1               5                   10                  15
His Ala Arg Pro Glu Val Lys Leu Leu Glu Ser Gly Gly Gly Leu
            20                  25                  30
Val Gln Pro Gly Gly Ser Leu Lys Leu Ser Cys Ala Ala Ser Gly Phe
        35                  40                  45
Asp Phe Ser Arg Tyr Trp Met Ser Trp Val Arg Gln Ala Pro Gly Lys
    50                  55                  60
Gly Leu Glu Trp Ile Gly Glu Ile Asn Pro Asp Ser Ser Thr Ile Asn
65                  70                  75                  80
Tyr Thr Pro Ser Leu Lys Asp Lys Phe Ile Ile Ser Arg Asp Asn Ala
                85                  90                  95
Lys Asn Thr Leu Tyr Leu Gln Met Ser Lys Val Arg Ser Glu Asp Thr
            100                 105                 110
Ala Leu Tyr Tyr Cys Ala Arg Pro Asp Gly Asn Tyr Trp Tyr Phe Asp
        115                 120                 125
Val Trp Gly Ala Gly Thr Thr Val Thr Val Ser Ser Gly Gly Gly Gly
```

```
            130                 135                 140
Ser Gly Gly Gly Ser Gly Gly Gly Ser Asp Ile Val Met Thr
145                 150                 155                 160

Gln Ser His Lys Phe Met Ser Thr Ser Val Gly Asp Arg Val Ser Ile
                165                 170                 175

Thr Cys Lys Ala Ser Gln Asp Val Gly Ile Ala Val Ala Trp Tyr Gln
                180                 185                 190

Gln Lys Pro Gly Gln Ser Pro Lys Leu Leu Ile Tyr Trp Ala Ser Thr
                195                 200                 205

Arg His Thr Gly Val Pro Asp Arg Phe Thr Gly Ser Gly Ser Gly Thr
210                 215                 220

Asp Phe Thr Leu Thr Ile Ser Asn Val Gln Ser Glu Asp Leu Ala Asp
225                 230                 235                 240

Tyr Phe Cys Gln Gln Tyr Ser Ser Tyr Pro Tyr Thr Phe Gly Gly Gly
                245                 250                 255

Thr Lys Leu Glu Ile Lys Glu Pro Lys Ser Pro Asp Lys Thr His Thr
                260                 265                 270

Cys Pro Pro Cys Pro Ala Pro Pro Val Ala Gly Pro Ser Val Phe Leu
                275                 280                 285

Phe Pro Pro Lys Pro Lys Asp Thr Leu Met Ile Ala Arg Thr Pro Glu
                290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
                340                 345                 350

Thr Val Leu His Gln Asp Trp Leu Asn Gly Lys Glu Tyr Lys Cys Lys
                355                 360                 365

Val Ser Asn Lys Ala Leu Pro Ala Pro Ile Glu Lys Thr Ile Ser Lys
                370                 375                 380

Ala Lys Gly Gln Pro Arg Glu Pro Gln Val Tyr Thr Leu Pro Pro Ser
385                 390                 395                 400

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
                420                 425                 430

Pro Glu Asn Asn Tyr Lys Thr Thr Pro Pro Val Leu Asp Ser Asp Gly
                435                 440                 445

Ser Phe Phe Leu Tyr Ser Lys Leu Thr Val Asp Lys Ser Arg Trp Gln
450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys Lys Arg Gly
                485                 490                 495

Arg Lys Lys Leu Leu Tyr Ile Phe Lys Gln Pro Phe Met Arg Pro Val
                500                 505                 510

Gln Thr Thr Gln Glu Glu Asp Gly Cys Ser Cys Arg Phe Pro Glu Glu
                515                 520                 525

Glu Glu Gly Gly Cys Glu Leu Arg Val Lys Phe Ser Arg Ser Ala Asp
                530                 535                 540

Ala Pro Ala Tyr Gln Gln Gly Gln Asn Gln Leu Tyr Asn Glu Leu Asn
545                 550                 555                 560
```

Leu Gly Arg Arg Glu Glu Tyr Asp Val Leu Asp Lys Arg Gly Arg
            565                 570                 575

Asp Pro Glu Met Gly Gly Lys Pro Arg Arg Lys Asn Pro Gln Glu Gly
            580                 585                 590

Leu Tyr Asn Glu Leu Gln Lys Asp Lys Met Ala Glu Ala Tyr Ser Glu
            595                 600                 605

Ile Gly Met Lys Gly Glu Arg Arg Arg Gly Lys Gly His Asp Gly Leu
            610                 615                 620

Tyr Gln Gly Leu Ser Thr Ala Thr Lys Asp Thr Tyr Asp Ala Leu His
625                 630                 635                 640

Met Gln Ala Leu Pro Pro Arg
            645

<210> SEQ ID NO 132
<211> LENGTH: 433
<212> TYPE: PRT
<213> ORGANISM: Artificial Sequence
<220> FEATURE:
<223> OTHER INFORMATION: Synthetic

<400> SEQUENCE: 132

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Arg Pro Gly Ala Ser Val Lys Leu Ser Cys Lys Ala Ser Gly Tyr
        35                  40                  45

Ser Phe Thr Thr Tyr Trp Met Asn Trp Val Lys Gln Arg Pro Gly Gln
    50                  55                  60

Gly Leu Glu Trp Ile Gly Met Ile His Pro Ser Asp Ser Glu Thr Arg
65                  70                  75                  80

Leu Asn Gln Lys Phe Lys Asp Lys Ala Thr Leu Thr Val Asp Lys Ser
                85                  90                  95

Ser Ser Thr Ala Tyr Met Gln Leu Ser Ser Pro Thr Ser Glu Asp Ser
            100                 105                 110

Ala Val Tyr Tyr Cys Ala Arg Ser Thr Met Ile Ala Thr Arg Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Gln Lys Ser Met Ser Thr Ser Val Gly Asp Arg Val Ser
                165                 170                 175

Ile Thr Cys Lys Ala Ser Gln Asp Val Ile Thr Gly Val Ala Trp Tyr
            180                 185                 190

Gln Gln Lys Pro Gly Gln Ser Pro Lys Leu Leu Ile Tyr Ser Ala Ser
        195                 200                 205

Tyr Arg Tyr Thr Gly Val Pro Asp Arg Phe Thr Gly Ser Gly Ser Gly
    210                 215                 220

Thr Asp Phe Thr Phe Thr Ile Ser Asn Val Gln Ala Glu Asp Leu Ala
225                 230                 235                 240

Val Tyr Tyr Cys Gln Gln His Tyr Ser Thr Pro Leu Thr Phe Gly Ala
                245                 250                 255

Gly Thr Lys Leu Glu Leu Lys Gly Leu Ala Val Ser Thr Ile Ser Ser
            260                 265                 270

```
Phe Phe Pro Pro Gly Tyr Gln Lys Arg Gly Lys Lys Leu Leu Tyr
        275                 280                 285

Ile Phe Lys Gln Pro Phe Met Arg Pro Val Gln Thr Thr Gln Glu Glu
        290                 295                 300

Asp Gly Cys Ser Cys Arg Phe Pro Glu Glu Glu Gly Gly Cys Glu
305                 310                 315                 320

Leu Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
                340                 345                 350

Tyr Asp Val Leu Asp Lys Arg Gly Arg Asp Pro Glu Met Gly Gly
                355                 360                 365

Lys Pro Arg Arg Lys Asn Pro Gln Glu Gly Leu Tyr Asn Glu Leu Gln
370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
                420                 425                 430

Arg

<210> SEQ ID NO 133
<211> LENGTH: 486
<212> TYPE: PRT
<213> ORGANISM: Artificial Sequence
<220> FEATURE:
<223> OTHER INFORMATION: Synthetic

<400> SEQUENCE: 133

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
                20                  25                  30

Val Arg Pro Gly Ala Ser Val Lys Leu Ser Cys Lys Ala Ser Gly Tyr
            35                  40                  45

Ser Phe Thr Thr Tyr Trp Met Asn Trp Val Lys Gln Arg Pro Gly Gln
    50                  55                  60

Gly Leu Glu Trp Ile Gly Met Ile His Pro Ser Asp Ser Glu Thr Arg
65                  70                  75                  80

Leu Asn Gln Lys Phe Lys Asp Lys Ala Thr Leu Thr Val Asp Lys Ser
                85                  90                  95

Ser Ser Thr Ala Tyr Met Gln Leu Ser Ser Pro Thr Ser Glu Asp Ser
                100                 105                 110

Ala Val Tyr Tyr Cys Ala Arg Ser Thr Met Ile Ala Thr Arg Ala Met
            115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Gln Lys Ser Met Ser Thr Ser Val Gly Asp Arg Val Ser
                165                 170                 175

Ile Thr Cys Lys Ala Ser Gln Asp Val Ile Thr Gly Val Ala Trp Tyr
            180                 185                 190
```

```
Gln Gln Lys Pro Gly Gln Ser Pro Lys Leu Leu Ile Tyr Ser Ala Ser
            195                 200                 205

Tyr Arg Tyr Thr Gly Val Pro Asp Arg Phe Thr Gly Ser Gly Ser Gly
    210                 215                 220

Thr Asp Phe Thr Phe Thr Ile Ser Asn Val Gln Ala Glu Asp Leu Ala
225                 230                 235                 240

Val Tyr Tyr Cys Gln Gln His Tyr Ser Thr Pro Leu Thr Phe Gly Ala
                245                 250                 255

Gly Thr Lys Leu Glu Leu Lys Thr Thr Pro Ala Pro Arg Pro Pro
            260                 265                 270

Thr Pro Ala Pro Thr Ile Ala Ser Gln Pro Leu Ser Leu Arg Pro Glu
        275                 280                 285

Ala Cys Arg Pro Ala Ala Gly Gly Ala Val His Thr Arg Gly Leu Asp
    290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
            485

<210> SEQ ID NO 134
<211> LENGTH: 648
<212> TYPE: PRT
<213> ORGANISM: Artificial Sequence
<220> FEATURE:
<223> OTHER INFORMATION: Synthetic

<400> SEQUENCE: 134

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Arg Pro Gly Ala Ser Val Lys Leu Ser Cys Lys Ala Ser Gly Tyr
        35                  40                  45

Ser Phe Thr Thr Tyr Trp Met Asn Trp Val Lys Gln Arg Pro Gly Gln
    50                  55                  60
```

```
Gly Leu Glu Trp Ile Gly Met Ile His Pro Ser Asp Ser Glu Thr Arg
 65                  70                  75                  80

Leu Asn Gln Lys Phe Lys Asp Lys Ala Thr Leu Thr Val Asp Lys Ser
                 85                  90                  95

Ser Ser Thr Ala Tyr Met Gln Leu Ser Ser Pro Thr Ser Glu Asp Ser
            100                 105                 110

Ala Val Tyr Tyr Cys Ala Arg Ser Thr Met Ile Ala Thr Arg Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Gln Lys Ser Met Ser Thr Ser Val Gly Asp Arg Val Ser
                165                 170                 175

Ile Thr Cys Lys Ala Ser Gln Asp Val Ile Thr Gly Val Ala Trp Tyr
            180                 185                 190

Gln Gln Lys Pro Gly Gln Ser Pro Lys Leu Leu Ile Tyr Ser Ala Ser
        195                 200                 205

Tyr Arg Tyr Thr Gly Val Pro Asp Arg Phe Thr Gly Ser Gly Ser Gly
    210                 215                 220

Thr Asp Phe Thr Phe Thr Ile Ser Asn Val Gln Ala Glu Asp Leu Ala
225                 230                 235                 240

Val Tyr Tyr Cys Gln Gln His Tyr Ser Thr Pro Leu Thr Phe Gly Ala
                245                 250                 255

Gly Thr Lys Leu Glu Leu Lys Glu Pro Lys Ser Pro Asp Lys Thr His
            260                 265                 270

Thr Cys Pro Pro Cys Pro Ala Pro Pro Val Ala Gly Pro Ser Val Phe
        275                 280                 285

Leu Phe Pro Pro Lys Pro Lys Asp Thr Leu Met Ile Ala Arg Thr Pro
    290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
    450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys Lys Arg
```

```
                485                 490                 495
Gly Arg Lys Lys Leu Leu Tyr Ile Phe Lys Gln Pro Phe Met Arg Pro
            500                 505                 510

Val Gln Thr Thr Gln Glu Glu Asp Gly Cys Ser Cys Arg Phe Pro Glu
            515                 520                 525

Glu Glu Glu Gly Gly Cys Glu Leu Arg Val Lys Phe Ser Arg Ser Ala
            530                 535                 540

Asp Ala Pro Ala Tyr Gln Gln Gly Gln Asn Gln Leu Tyr Asn Glu Leu
545                 550                 555                 560

Asn Leu Gly Arg Arg Glu Glu Tyr Asp Val Leu Asp Lys Arg Arg Gly
                565                 570                 575

Arg Asp Pro Glu Met Gly Gly Lys Pro Arg Arg Lys Asn Pro Gln Glu
            580                 585                 590

Gly Leu Tyr Asn Glu Leu Gln Lys Asp Lys Met Ala Glu Ala Tyr Ser
            595                 600                 605

Glu Ile Gly Met Lys Gly Glu Arg Arg Arg Gly Lys Gly His Asp Gly
            610                 615                 620

Leu Tyr Gln Gly Leu Ser Thr Ala Thr Lys Asp Thr Tyr Asp Ala Leu
625                 630                 635                 640

His Met Gln Ala Leu Pro Pro Arg
                645

<210> SEQ ID NO 135
<211> LENGTH: 434
<212> TYPE: PRT
<213> ORGANISM: Artificial Sequence
<220> FEATURE:
<223> OTHER INFORMATION: Synthetic

<400> SEQUENCE: 135

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Ala Arg Pro Gly Ala Ser Val Lys Leu Ser Cys Lys Ala Ser Gly Tyr
        35                  40                  45

Thr Phe Thr Ser Tyr Trp Met Gln Trp Val Lys Gln Arg Pro Gly Gln
    50                  55                  60

Gly Leu Glu Trp Ile Gly Ala Ile Tyr Pro Gly Asp Gly Asp Thr Arg
65                  70                  75                  80

Tyr Thr Gln Lys Phe Lys Gly Lys Ala Thr Leu Thr Ala Asp Lys Ser
                85                  90                  95

Ser Ser Thr Ala Tyr Met Gln Leu Ser Ser Leu Ala Ser Glu Asp Ser
            100                 105                 110

Ala Val Tyr Tyr Cys Ala Arg Gly Lys Val Tyr Tyr Gly Ser Asn Pro
        115                 120                 125

Phe Ala Tyr Trp Gly Gln Gly Thr Leu Val Thr Val Ser Ala Gly Gly
    130                 135                 140

Gly Gly Ser Gly Gly Gly Gly Ser Gly Gly Gly Gly Ser Asp Ile Gln
145                 150                 155                 160

Met Thr Gln Ser Ser Ser Tyr Leu Ser Val Ser Leu Gly Gly Arg Val
                165                 170                 175

Thr Ile Thr Cys Lys Ala Ser Asp His Ile Asn Asn Trp Leu Ala Trp
            180                 185                 190

Tyr Gln Gln Lys Pro Gly Asn Ala Pro Arg Leu Leu Ile Ser Gly Ala
```

```
            195                 200                 205
Thr Ser Leu Glu Thr Gly Val Pro Ser Arg Phe Ser Gly Ser Gly Ser
210                 215                 220

Gly Lys Asp Tyr Thr Leu Ser Ile Thr Ser Leu Gln Thr Glu Asp Val
225                 230                 235                 240

Ala Thr Tyr Tyr Cys Gln Gln Tyr Trp Ser Thr Pro Trp Thr Phe Gly
                245                 250                 255

Gly Gly Thr Lys Leu Glu Ile Lys Gly Leu Ala Val Ser Thr Ile Ser
            260                 265                 270

Ser Phe Phe Pro Pro Gly Tyr Gln Lys Arg Gly Arg Lys Lys Leu Leu
        275                 280                 285

Tyr Ile Phe Lys Gln Pro Phe Met Arg Pro Val Gln Thr Thr Gln Glu
    290                 295                 300

Glu Asp Gly Cys Ser Cys Arg Phe Pro Glu Glu Glu Glu Gly Gly Cys
305                 310                 315                 320

Glu Leu Arg Val Lys Phe Ser Arg Ser Ala Asp Ala Pro Ala Tyr Gln
                325                 330                 335

Gln Gly Gln Asn Gln Leu Tyr Asn Glu Leu Asn Leu Gly Arg Arg Glu
            340                 345                 350

Glu Tyr Asp Val Leu Asp Lys Arg Arg Gly Arg Asp Pro Glu Met Gly
        355                 360                 365

Gly Lys Pro Arg Arg Lys Asn Pro Gln Glu Gly Leu Tyr Asn Glu Leu
    370                 375                 380

Gln Lys Asp Lys Met Ala Glu Ala Tyr Ser Glu Ile Gly Met Lys Gly
385                 390                 395                 400

Glu Arg Arg Arg Gly Lys Gly His Asp Gly Leu Tyr Gln Gly Leu Ser
                405                 410                 415

Thr Ala Thr Lys Asp Thr Tyr Asp Ala Leu His Met Gln Ala Leu Pro
            420                 425                 430

Pro Arg

<210> SEQ ID NO 136
<211> LENGTH: 487
<212> TYPE: PRT
<213> ORGANISM: Artificial Sequence
<220> FEATURE:
<223> OTHER INFORMATION: Synthetic

<400> SEQUENCE: 136

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Ala Arg Pro Gly Ala Ser Val Lys Leu Ser Cys Lys Ala Ser Gly Tyr
        35                  40                  45

Thr Phe Thr Ser Tyr Trp Met Gln Trp Val Lys Gln Arg Pro Gly Gln
    50                  55                  60

Gly Leu Glu Trp Ile Gly Ala Ile Tyr Pro Gly Asp Gly Asp Thr Arg
65                  70                  75                  80

Tyr Thr Gln Lys Phe Lys Gly Lys Ala Thr Leu Thr Ala Asp Lys Ser
                85                  90                  95

Ser Ser Thr Ala Tyr Met Gln Leu Ser Ser Leu Ala Ser Glu Asp Ser
            100                 105                 110

Ala Val Tyr Tyr Cys Ala Arg Gly Lys Val Tyr Tyr Gly Ser Asn Pro
        115                 120                 125
```

Phe Ala Tyr Trp Gly Gln Gly Thr Leu Val Thr Val Ser Ala Gly Gly
130                 135                 140

Gly Gly Ser Gly Gly Gly Gly Ser Gly Gly Gly Gly Ser Asp Ile Gln
145                 150                 155                 160

Met Thr Gln Ser Ser Ser Tyr Leu Ser Val Ser Leu Gly Gly Arg Val
                165                 170                 175

Thr Ile Thr Cys Lys Ala Ser Asp His Ile Asn Asn Trp Leu Ala Trp
            180                 185                 190

Tyr Gln Gln Lys Pro Gly Asn Ala Pro Arg Leu Leu Ile Ser Gly Ala
        195                 200                 205

Thr Ser Leu Glu Thr Gly Val Pro Ser Arg Phe Ser Gly Ser Gly Ser
210                 215                 220

Gly Lys Asp Tyr Thr Leu Ser Ile Thr Ser Leu Gln Thr Glu Asp Val
225                 230                 235                 240

Ala Thr Tyr Tyr Cys Gln Gln Tyr Trp Ser Thr Pro Trp Thr Phe Gly
                245                 250                 255

Gly Gly Thr Lys Leu Glu Ile Lys Thr Thr Pro Ala Pro Arg Pro
                260                 265                 270

Pro Thr Pro Ala Pro Thr Ile Ala Ser Gln Pro Leu Ser Leu Arg Pro
            275                 280                 285

Glu Ala Cys Arg Pro Ala Ala Gly Gly Ala Val His Thr Arg Gly Leu
290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 137
<211> LENGTH: 649
<212> TYPE: PRT
<213> ORGANISM: Artificial Sequence
<220> FEATURE:
<223> OTHER INFORMATION: Synthetic

<400> SEQUENCE: 137

```
Met Ala Leu Pro Val Thr Ala Leu Leu Leu Pro Leu Ala Leu Leu
1               5                   10                  15

His Ala Ala Arg Pro Gln Val Gln Leu Gln Gln Ser Gly Ala Glu Leu
                20                  25                  30

Ala Arg Pro Gly Ala Ser Val Lys Leu Ser Cys Lys Ala Ser Gly Tyr
            35                  40                  45

Thr Phe Thr Ser Tyr Trp Met Gln Trp Val Lys Gln Arg Pro Gly Gln
        50                  55                  60

Gly Leu Glu Trp Ile Gly Ala Ile Tyr Pro Gly Asp Gly Asp Thr Arg
65                  70                  75                  80

Tyr Thr Gln Lys Phe Lys Gly Lys Ala Thr Leu Thr Ala Asp Lys Ser
                85                  90                  95

Ser Ser Thr Ala Tyr Met Gln Leu Ser Ser Leu Ala Ser Glu Asp Ser
            100                 105                 110

Ala Val Tyr Tyr Cys Ala Arg Gly Lys Val Tyr Tyr Gly Ser Asn Pro
        115                 120                 125

Phe Ala Tyr Trp Gly Gln Gly Thr Leu Val Thr Val Ser Ala Gly Gly
    130                 135                 140

Gly Gly Ser Gly Gly Gly Gly Ser Gly Gly Gly Gly Ser Asp Ile Gln
145                 150                 155                 160

Met Thr Gln Ser Ser Ser Tyr Leu Ser Val Ser Leu Gly Gly Arg Val
                165                 170                 175

Thr Ile Thr Cys Lys Ala Ser Asp His Ile Asn Asn Trp Leu Ala Trp
            180                 185                 190

Tyr Gln Gln Lys Pro Gly Asn Ala Pro Arg Leu Leu Ile Ser Gly Ala
        195                 200                 205

Thr Ser Leu Glu Thr Gly Val Pro Ser Arg Phe Ser Gly Ser Gly Ser
210                 215                 220

Gly Lys Asp Tyr Thr Leu Ser Ile Thr Ser Leu Gln Thr Glu Asp Val
225                 230                 235                 240

Ala Thr Tyr Tyr Cys Gln Gln Tyr Trp Ser Thr Pro Trp Thr Phe Gly
            245                 250                 255

Gly Gly Thr Lys Leu Glu Ile Lys Glu Pro Lys Ser Pro Asp Lys Thr
        260                 265                 270

His Thr Cys Pro Pro Cys Pro Ala Pro Pro Val Ala Gly Pro Ser Val
    275                 280                 285

Phe Leu Phe Pro Pro Lys Pro Lys Asp Thr Leu Met Ile Ala Arg Thr
    290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Ala Leu Pro Ala Pro Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                405                 410                 415
```

```
Val Lys Gly Phe Tyr Pro Ser Asp Ile Ala Val Glu Trp Glu Ser Asn
                420                 425                 430

Gly Gln Pro Glu Asn Asn Tyr Lys Thr Thr Pro Pro Val Leu Asp Ser
            435                 440                 445

Asp Gly Ser Phe Phe Leu Tyr Ser Lys Leu Thr Val Asp Lys Ser Arg
        450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys Lys
                485                 490                 495

Arg Gly Arg Lys Lys Leu Leu Tyr Ile Phe Lys Gln Pro Phe Met Arg
            500                 505                 510

Pro Val Gln Thr Thr Gln Glu Glu Asp Gly Cys Ser Cys Arg Phe Pro
        515                 520                 525

Glu Glu Glu Glu Gly Gly Cys Glu Leu Arg Val Lys Phe Ser Arg Ser
530                 535                 540

Ala Asp Ala Pro Ala Tyr Gln Gln Gly Gln Asn Gln Leu Tyr Asn Glu
545                 550                 555                 560

Leu Asn Leu Gly Arg Arg Glu Glu Tyr Asp Val Leu Asp Lys Arg Arg
                565                 570                 575

Gly Arg Asp Pro Glu Met Gly Gly Lys Pro Arg Arg Lys Asn Pro Gln
            580                 585                 590

Glu Gly Leu Tyr Asn Glu Leu Gln Lys Asp Lys Met Ala Glu Ala Tyr
        595                 600                 605

Ser Glu Ile Gly Met Lys Gly Glu Arg Arg Gly Lys Gly His Asp
610                 615                 620

Gly Leu Tyr Gln Gly Leu Ser Thr Ala Thr Lys Asp Thr Tyr Asp Ala
625                 630                 635                 640

Leu His Met Gln Ala Leu Pro Pro Arg
                645

<210> SEQ ID NO 138
<211> LENGTH: 433
<212> TYPE: PRT
<213> ORGANISM: Artificial Sequence
<220> FEATURE:
<223> OTHER INFORMATION: Synthetic

<400> SEQUENCE: 138

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
                20                  25                  30

Val Lys Pro Gly Ala Ser Val Lys Ile Ser Cys Lys Ala Ser Gly Tyr
            35                  40                  45

Ala Phe Ser Ser Ser Trp Met Asn Trp Val Lys Gln Arg Pro Gly Gln
        50                  55                  60

Gly Leu Glu Trp Ile Gly Arg Ile Tyr Pro Gly Asp Gly Asp Thr Lys
65                  70                  75                  80

Tyr Asn Gly Lys Phe Lys Gly Lys Ala Thr Leu Thr Ala Asp Lys Ser
                85                  90                  95

Ser Ser Thr Ala Tyr Met Gln Leu Ser Ser Leu Thr Ser Val Asp Ser
            100                 105                 110

Ala Val Tyr Phe Cys Ala Arg Ser Thr Met Ile Ala Thr Gly Ala Met
        115                 120                 125
```

Asp Tyr Trp Gly Gln Gly Thr Ser Val Thr Val Ser Ser Gly Gly Gly
            130                 135                 140

Gly Ser Gly Gly Gly Ser Gly Gly Gly Ser Glu Thr Thr Val
145                 150                 155                 160

Thr Gln Ser Pro Ala Ser Leu Ser Met Ala Ile Gly Glu Lys Val Thr
                165                 170                 175

Ile Arg Cys Ile Thr Ser Thr Asp Ile Asp Asp Met Asn Trp Tyr
            180                 185                 190

Gln Gln Lys Pro Gly Glu Pro Pro Lys Leu Leu Ile Ser Glu Gly Asn
                195                 200                 205

Thr Leu Arg Pro Gly Val Pro Ser Arg Phe Ser Ser Ser Gly Tyr Gly
        210                 215                 220

Thr Asp Phe Val Phe Thr Ile Glu Asn Met Leu Ser Glu Asp Val Ala
225                 230                 235                 240

Asp Tyr Tyr Cys Leu Gln Ser Asp Asn Leu Pro Leu Thr Phe Gly Gly
                245                 250                 255

Gly Thr Lys Leu Glu Ile Lys Gly Leu Ala Val Ser Thr Ile Ser Ser
            260                 265                 270

Phe Phe Pro Pro Gly Tyr Gln Lys Arg Gly Arg Lys Lys Leu Leu Tyr
        275                 280                 285

Ile Phe Lys Gln Pro Phe Met Arg Pro Val Gln Thr Thr Gln Glu Glu
        290                 295                 300

Asp Gly Cys Ser Cys Arg Phe Pro Glu Glu Glu Gly Gly Cys Glu
305                 310                 315                 320

Leu Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
            340                 345                 350

Tyr Asp Val Leu Asp Lys Arg Gly Arg Asp Pro Glu Met Gly Gly
        355                 360                 365

Lys Pro Arg Arg Lys Asn Pro Gln Glu Gly Leu Tyr Asn Glu Leu Gln
        370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
            420                 425                 430

Arg

<210> SEQ ID NO 139
<211> LENGTH: 486
<212> TYPE: PRT
<213> ORGANISM: Artificial Sequence
<220> FEATURE:
<223> OTHER INFORMATION: Synthetic

<400> SEQUENCE: 139

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Ala Arg Pro Gly Ala Ser Val Lys Leu Ser Cys Lys Ala Ser Gly Tyr
        35                  40                  45

Thr Phe Thr Ser Tyr Trp Met Gln Trp Val Lys Gln Arg Pro Gly Gln

```
                50                  55                  60
Gly Leu Glu Trp Ile Gly Ala Ile Tyr Pro Gly Asp Gly Asp Thr Arg
 65                  70                  75                  80

Tyr Thr Gln Lys Phe Lys Gly Lys Ala Thr Leu Thr Ala Asp Lys Ser
                 85                  90                  95

Ser Ser Thr Ala Tyr Met Gln Leu Ser Ser Leu Ala Ser Glu Asp Ser
                100                 105                 110

Ala Val Tyr Tyr Cys Ala Arg Gly Lys Val Tyr Tyr Gly Ser Asn Pro
                115                 120                 125

Phe Ala Tyr Trp Gly Gln Gly Thr Leu Val Thr Val Ser Ala Gly Gly
                130                 135                 140

Gly Gly Ser Gly Gly Gly Ser Gly Gly Gly Ser Asp Ile Gln
145                 150                 155                 160

Met Thr Gln Ser Ser Ser Tyr Leu Ser Val Ser Leu Gly Gly Arg Val
                165                 170                 175

Thr Ile Thr Cys Lys Ala Ser Asp His Ile Asn Asn Trp Leu Ala Trp
                180                 185                 190

Tyr Gln Gln Lys Pro Gly Asn Ala Pro Arg Leu Leu Ile Ser Gly Ala
                195                 200                 205

Thr Ser Leu Glu Thr Gly Val Pro Ser Arg Phe Ser Gly Ser Gly Ser
                210                 215                 220

Gly Lys Asp Tyr Thr Leu Ser Ile Thr Ser Leu Gln Thr Glu Asp Val
225                 230                 235                 240

Ala Thr Tyr Tyr Cys Gln Gln Tyr Trp Ser Thr Pro Trp Thr Phe Gly
                245                 250                 255

Gly Gly Thr Lys Leu Glu Ile Lys Thr Thr Thr Pro Ala Pro Arg Pro
                260                 265                 270

Pro Thr Pro Ala Pro Thr Ile Ala Ser Gln Pro Leu Ser Leu Arg Pro
                275                 280                 285

Glu Ala Cys Arg Pro Ala Ala Gly Gly Ala Val His Thr Arg Gly Leu
                290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
                340                 345                 350

Gln Thr Thr Gln Glu Glu Asp Gly Cys Ser Cys Arg Phe Pro Glu Glu
                355                 360                 365

Glu Glu Gly Gly Cys Glu Leu Arg Val Lys Phe Ser Arg Ser Ala Asp
                370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
                450                 455                 460

Gln Gly Leu Ser Thr Ala Thr Lys Asp Thr Tyr Asp Ala Leu His Met
465                 470                 475                 480
```

Gln Ala Leu Pro Pro Arg
            485

<210> SEQ ID NO 140
<211> LENGTH: 647
<212> TYPE: PRT
<213> ORGANISM: Artificial Sequence
<220> FEATURE:
<223> OTHER INFORMATION: Synthetic

<400> SEQUENCE: 140

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ala Phe Ser Ser Ser Trp Met Asn Trp Val Lys Gln Arg Pro Gly Gln
    50                  55                  60

Gly Leu Glu Trp Ile Gly Arg Ile Tyr Pro Gly Asp Gly Asp Thr Lys
65                  70                  75                  80

Tyr Asn Gly Lys Phe Lys Gly Lys Ala Thr Leu Thr Ala Asp Lys Ser
                85                  90                  95

Ser Ser Thr Ala Tyr Met Gln Leu Ser Ser Leu Thr Ser Val Asp Ser
            100                 105                 110

Ala Val Tyr Phe Cys Ala Arg Ser Thr Met Ile Ala Thr Gly Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Glu Thr Thr Val
145                 150                 155                 160

Thr Gln Ser Pro Ala Ser Leu Ser Met Ala Ile Gly Glu Lys Val Thr
                165                 170                 175

Ile Arg Cys Ile Thr Ser Thr Asp Ile Asp Asp Asp Met Asn Trp Tyr
            180                 185                 190

Gln Gln Lys Pro Gly Glu Pro Pro Lys Leu Leu Ile Ser Glu Gly Asn
        195                 200                 205

Thr Leu Arg Pro Gly Val Pro Ser Arg Phe Ser Ser Ser Gly Tyr Gly
    210                 215                 220

Thr Asp Phe Val Phe Thr Ile Glu Asn Met Leu Ser Glu Asp Val Ala
225                 230                 235                 240

Asp Tyr Tyr Cys Leu Gln Ser Asp Asn Leu Pro Leu Thr Phe Gly Gly
                245                 250                 255

Gly Thr Lys Leu Glu Ile Lys Glu Pro Lys Ser Pro Asp Lys Thr His
            260                 265                 270

Thr Cys Pro Pro Cys Pro Ala Pro Pro Val Ala Gly Pro Ser Val Phe
        275                 280                 285

Leu Phe Pro Pro Lys Pro Lys Asp Thr Leu Met Ile Ala Arg Thr Pro
    290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

Lys Pro Arg Glu Glu Gln Tyr Asn Ser Thr Tyr Arg Val Val Ser Val
            340                 345                 350

```
Leu Thr Val Leu His Gln Asp Trp Leu Asn Gly Lys Glu Tyr Lys Cys
            355                 360                 365

Lys Val Ser Asn Lys Ala Leu Pro Ala Pro Ile Glu Lys Thr Ile Ser
        370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
                435                 440                 445

Gly Ser Phe Phe Leu Tyr Ser Lys Leu Thr Val Asp Lys Ser Arg Trp
            450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys Lys Arg
                485                 490                 495

Gly Arg Lys Lys Leu Leu Tyr Ile Phe Lys Gln Pro Phe Met Arg Pro
            500                 505                 510

Val Gln Thr Thr Gln Glu Glu Asp Gly Cys Ser Cys Arg Phe Pro Glu
        515                 520                 525

Glu Glu Glu Gly Gly Cys Glu Leu Arg Val Lys Phe Ser Arg Ser Ala
        530                 535                 540

Asp Ala Pro Ala Tyr Gln Gln Gly Gln Asn Gln Leu Tyr Asn Glu Leu
545                 550                 555                 560

Asn Leu Gly Arg Arg Glu Glu Tyr Asp Val Leu Asp Lys Arg Arg Gly
                565                 570                 575

Arg Asp Pro Glu Met Gly Gly Lys Pro Arg Arg Lys Asn Pro Gln Glu
            580                 585                 590

Gly Leu Tyr Asn Glu Leu Gln Lys Asp Lys Met Ala Glu Ala Tyr Ser
        595                 600                 605

Glu Ile Gly Met Lys Gly Glu Arg Arg Gly Lys Gly His Asp Gly Leu
    610                 615                 620

Tyr Gln Gly Leu Ser Thr Ala Thr Lys Asp Thr Tyr Asp Ala Leu His
625                 630                 635                 640

Met Gln Ala Leu Pro Pro Arg
                645

<210> SEQ ID NO 141
<211> LENGTH: 432
<212> TYPE: PRT
<213> ORGANISM: Artificial Sequence
<220> FEATURE:
<223> OTHER INFORMATION: Synthetic

<400> SEQUENCE: 141

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ala Phe Ser Ser Ser Trp Met Asn Trp Val Lys Gln Arg Pro Gly Gln
    50                  55                  60
```

```
Gly Leu Glu Trp Ile Gly Arg Ile Tyr Pro Gly Asp Gly Asp Thr Lys
 65                  70                  75                  80

Tyr Asn Gly Lys Phe Lys Gly Lys Ala Thr Leu Thr Ala Asp Lys Ser
                 85                  90                  95

Ser Ser Thr Ala Tyr Met Gln Leu Ser Ser Leu Thr Ser Val Asp Ser
            100                 105                 110

Ala Val Tyr Phe Cys Ala Arg Ser Thr Met Ile Ala Thr Gly Ala Met
            115                 120                 125

Asp Tyr Trp Gly Gln Gly Thr Ser Val Thr Val Ser Ser Gly Gly Gly
            130                 135                 140

Gly Ser Gly Gly Gly Ser Gly Gly Ser Asp Ile Val Met Thr
145                 150                 155                 160

Gln Ser His Lys Phe Met Ser Thr Ser Val Gly Asp Arg Val Ser Ile
                165                 170                 175

Thr Cys Lys Ala Ser Gln Asp Val Ser Thr Ala Val Ala Trp Tyr Gln
            180                 185                 190

Gln Lys Pro Gly Gln Ser Pro Lys Leu Leu Ile Tyr Ser Ala Ser Tyr
            195                 200                 205

Arg Tyr Thr Gly Val Pro Asp Arg Phe Thr Gly Ser Gly Ser Gly Thr
            210                 215                 220

Asp Phe Thr Phe Thr Ile Ser Ser Val Gln Ala Glu Asp Leu Ala Val
225                 230                 235                 240

Tyr Tyr Cys Gln Gln His Tyr Ser Thr Pro Pro Tyr Thr Phe Gly Gly
                245                 250                 255

Gly Thr Lys Leu Glu Ile Lys Gly Leu Ala Val Ser Thr Ile Ser Ser
            260                 265                 270

Phe Phe Pro Pro Gly Tyr Gln Lys Arg Gly Arg Lys Lys Leu Leu Tyr
            275                 280                 285

Ile Phe Lys Gln Pro Phe Met Arg Pro Val Gln Thr Thr Gln Glu Glu
            290                 295                 300

Asp Gly Cys Cys Arg Phe Pro Glu Glu Glu Gly Cys Glu Leu
305                 310                 315                 320

Arg Val Lys Phe Ser Arg Ser Ala Asp Ala Pro Ala Tyr Gln Gln Gly
                325                 330                 335

Gln Asn Gln Leu Tyr Asn Glu Leu Asn Leu Gly Arg Arg Glu Glu Tyr
            340                 345                 350

Asp Val Leu Asp Lys Arg Arg Gly Arg Asp Pro Glu Met Gly Gly Lys
            355                 360                 365

Pro Arg Arg Lys Asn Pro Gln Glu Gly Leu Tyr Asn Glu Leu Gln Lys
            370                 375                 380

Asp Lys Met Ala Glu Ala Tyr Ser Glu Ile Gly Met Lys Gly Glu Arg
385                 390                 395                 400

Arg Arg Gly Lys Gly His Asp Gly Leu Tyr Gln Gly Leu Ser Thr Ala
                405                 410                 415

Thr Lys Asp Thr Tyr Asp Ala Leu His Met Gln Ala Leu Pro Pro Arg
            420                 425                 430
```

<210> SEQ ID NO 142
<211> LENGTH: 486
<212> TYPE: PRT
<213> ORGANISM: Artificial Sequence
<220> FEATURE:
<223> OTHER INFORMATION: Synthetic

<400> SEQUENCE: 142

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
                20                  25                  30

Val Lys Pro Gly Ala Ser Val Lys Ile Ser Cys Lys Ala Ser Gly Tyr
        35                  40                  45

Ala Phe Ser Ser Ser Trp Met Asn Trp Val Lys Gln Arg Pro Gly Gln
        50                  55                  60

Gly Leu Glu Trp Ile Gly Arg Ile Tyr Pro Gly Asp Gly Asp Thr Lys
65                  70                  75                  80

Tyr Asn Gly Lys Phe Lys Gly Lys Ala Thr Leu Thr Ala Asp Lys Ser
                85                  90                  95

Ser Ser Thr Ala Tyr Met Gln Leu Ser Ser Leu Thr Ser Val Asp Ser
            100                 105                 110

Ala Val Tyr Phe Cys Ala Arg Ser Thr Met Ile Ala Thr Gly Ala Met
            115                 120                 125

Asp Tyr Trp Gly Gln Gly Thr Ser Val Thr Val Ser Ser Gly Gly Gly
        130                 135                 140

Gly Ser Gly Gly Gly Gly Ser Gly Gly Gly Gly Ser Asp Ile Val Met
145                 150                 155                 160

Thr Gln Ser His Lys Phe Met Ser Thr Ser Val Gly Asp Arg Val Ser
                165                 170                 175

Ile Thr Cys Lys Ala Ser Gln Asp Val Ser Thr Ala Val Ala Trp Tyr
            180                 185                 190

Gln Gln Lys Pro Gly Gln Ser Pro Lys Leu Leu Ile Tyr Ser Ala Ser
        195                 200                 205

Tyr Arg Tyr Thr Gly Val Pro Asp Arg Phe Thr Gly Ser Gly Ser Gly
210                 215                 220

Thr Asp Phe Thr Phe Thr Ile Ser Ser Val Gln Ala Glu Asp Leu Ala
225                 230                 235                 240

Val Tyr Tyr Cys Gln Gln His Tyr Ser Thr Pro Pro Tyr Thr Phe Gly
                245                 250                 255

Gly Gly Thr Lys Leu Glu Ile Lys Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
290                 295                 300

Asp Phe Ala Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

```
Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 143
<211> LENGTH: 648
<212> TYPE: PRT
<213> ORGANISM: Artificial Sequence
<220> FEATURE:
<223> OTHER INFORMATION: Synthetic

<400> SEQUENCE: 143

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ala Phe Ser Ser Ser Trp Met Asn Trp Val Lys Gln Arg Pro Gly Gln
    50                  55                  60

Gly Leu Glu Trp Ile Gly Arg Ile Tyr Pro Gly Asp Gly Asp Thr Lys
65                  70                  75                  80

Tyr Asn Gly Lys Phe Lys Gly Lys Ala Thr Leu Thr Ala Asp Lys Ser
                85                  90                  95

Ser Ser Thr Ala Tyr Met Gln Leu Ser Ser Leu Thr Ser Val Asp Ser
            100                 105                 110

Ala Val Tyr Phe Cys Ala Arg Ser Thr Met Ile Ala Thr Gly Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser His Lys Phe Met Ser Thr Ser Val Gly Asp Arg Val Ser
                165                 170                 175

Ile Thr Cys Lys Ala Ser Gln Asp Val Ser Thr Ala Val Ala Trp Tyr
            180                 185                 190

Gln Gln Lys Pro Gly Gln Ser Pro Lys Leu Leu Ile Tyr Ser Ala Ser
        195                 200                 205

Tyr Arg Tyr Thr Gly Val Pro Asp Arg Phe Thr Gly Ser Gly Ser Gly
    210                 215                 220

Thr Asp Phe Thr Phe Thr Ile Ser Ser Val Gln Ala Glu Asp Leu Ala
225                 230                 235                 240

Val Tyr Tyr Cys Gln Gln His Tyr Ser Thr Pro Pro Tyr Thr Phe Gly
                245                 250                 255

Gly Gly Thr Lys Leu Glu Ile Lys Glu Pro Lys Ser Pro Asp Lys Thr
            260                 265                 270

His Thr Cys Pro Pro Cys Pro Ala Pro Pro Val Ala Gly Pro Ser Val
        275                 280                 285
```

```
Phe Leu Phe Pro Pro Lys Pro Lys Asp Thr Leu Met Ile Ala Arg Thr
290                 295                 300
Pro Glu Val Cys Val Val Val Asp Val Ser His Glu Asp Pro Glu Val
305                 310                 315                 320
Lys Phe Asn Trp Tyr Val Asp Gly Val Glu Val His Asn Ala Lys Thr
                325                 330                 335
Lys Pro Arg Glu Glu Gln Tyr Asn Ser Thr Tyr Arg Val Val Ser Val
            340                 345                 350
Leu Thr Val Leu His Gln Asp Trp Leu Asn Gly Lys Glu Tyr Lys Cys
        355                 360                 365
Lys Val Ser Asn Lys Ala Leu Pro Ala Pro Ile Glu Lys Thr Ile Ser
370                 375                 380
Lys Ala Lys Gly Gln Pro Arg Glu Pro Gln Val Tyr Thr Leu Pro Pro
385                 390                 395                 400
Ser Arg Asp Glu Leu Thr Lys Asn Gln Val Ser Leu Thr Cys Leu Val
                405                 410                 415
Lys Gly Phe Tyr Pro Ser Asp Ile Ala Val Glu Trp Glu Ser Asn Gly
            420                 425                 430
Gln Pro Glu Asn Asn Tyr Lys Thr Thr Pro Pro Val Leu Asp Ser Asp
        435                 440                 445
Gly Ser Phe Phe Leu Tyr Ser Lys Leu Thr Val Asp Lys Ser Arg Trp
450                 455                 460
Gln Gln Gly Asn Val Phe Ser Cys Ser Val Met His Glu Ala Leu His
465                 470                 475                 480
Asn His Tyr Thr Gln Lys Ser Leu Ser Leu Ser Pro Gly Lys Lys Arg
                485                 490                 495
Gly Arg Lys Lys Leu Leu Tyr Ile Phe Lys Gln Pro Phe Met Arg Pro
            500                 505                 510
Val Gln Thr Thr Gln Glu Glu Asp Gly Cys Ser Cys Arg Phe Pro Glu
        515                 520                 525
Glu Glu Glu Gly Gly Cys Glu Leu Arg Val Lys Phe Ser Arg Ser Ala
530                 535                 540
Asp Ala Pro Ala Tyr Gln Gln Gly Gln Asn Gln Leu Tyr Asn Glu Leu
545                 550                 555                 560
Asn Leu Gly Arg Arg Glu Glu Tyr Asp Val Leu Asp Lys Arg Arg Gly
                565                 570                 575
Arg Asp Pro Glu Met Gly Gly Lys Pro Arg Arg Lys Asn Pro Gln Glu
            580                 585                 590
Gly Leu Tyr Asn Glu Leu Gln Lys Asp Lys Met Ala Glu Ala Tyr Ser
        595                 600                 605
Glu Ile Gly Met Lys Gly Glu Arg Arg Arg Gly Lys Gly His Asp Gly
610                 615                 620
Leu Tyr Gln Gly Leu Ser Thr Ala Thr Lys Asp Thr Tyr Asp Ala Leu
625                 630                 635                 640
His Met Gln Ala Leu Pro Pro Arg
                645

<210> SEQ ID NO 144
<211> LENGTH: 156
<212> TYPE: PRT
<213> ORGANISM: Artificial Sequence
<220> FEATURE:
<223> OTHER INFORMATION: Synthetic

<400> SEQUENCE: 144
```

Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Ser Pro Ala Pro Pro
65                  70                  75                  80

Thr Pro Ala Pro Thr Ile Ala Ser Gln Pro Leu Ser Leu Arg Pro Glu
                85                  90                  95

Ala Cys Arg Pro Ala Ala Gly Gly Ala Val His Thr Arg Gly Leu Asp
                100                 105                 110

Phe Ala Cys Asp Ile Tyr Ile Trp Ala Pro Leu Ala Gly Thr Cys Gly
            115                 120                 125

Val Leu Leu Leu Ser Leu Val Ile Thr Leu Tyr Cys Asn His Arg Asn
    130                 135                 140

Arg Arg Arg Val Cys Lys Cys Pro Arg Pro Val Val
145                 150                 155

<210> SEQ ID NO 145
<211> LENGTH: 55
<212> TYPE: PRT
<213> ORGANISM: Artificial Sequence
<220> FEATURE:
<223> OTHER INFORMATION: Synthetic

<400> SEQUENCE: 145

Ala Cys Pro Tyr Ser Asn Pro Ser Leu Cys Ser Gly Gly Gly Ser
1               5                   10                  15

Glu Leu Pro Thr Gln Gly Thr Phe Ser Asn Val Ser Thr Asn Val Ser
                20                  25                  30

Pro Ala Lys Pro Thr Thr Thr Ala Cys Pro Tyr Ser Asn Pro Ser Leu
            35                  40                  45

Cys Ser Gly Gly Gly Ser
    50                  55

<210> SEQ ID NO 146
<211> LENGTH: 20
<212> TYPE: DNA
<213> ORGANISM: Homo Sapiens

<400> SEQUENCE: 146
tgacgttacc tcgtgcggcc                                              20

<210> SEQ ID NO 147
<211> LENGTH: 20
<212> TYPE: DNA
<213> ORGANISM: Homo Sapiens

<400> SEQUENCE: 147
cacgaagctc tccgatgtgt                                              20

<210> SEQ ID NO 148
<211> LENGTH: 20
<212> TYPE: DNA
<213> ORGANISM: Homo Sapiens

<400> SEQUENCE: 148
gcgtgacttc cacatgagcg                                                     20

<210> SEQ ID NO 149
<211> LENGTH: 20
<212> TYPE: DNA
<213> ORGANISM: Homo Sapiens

<400> SEQUENCE: 149
ttggaactgg ccggctggcc                                                     20

<210> SEQ ID NO 150
<211> LENGTH: 20
<212> TYPE: DNA
<213> ORGANISM: Homo Sapiens

<400> SEQUENCE: 150
gtggcatact ccgtctgctc                                                     20

<210> SEQ ID NO 151
<211> LENGTH: 20
<212> TYPE: DNA
<213> ORGANISM: Homo Sapiens

<400> SEQUENCE: 151
gatgaggtgc ccattccgct                                                     20

<210> SEQ ID NO 152
<211> LENGTH: 20
<212> TYPE: DNA
<213> ORGANISM: Homo Sapiens

<400> SEQUENCE: 152
taccgctgca tgatcagcta                                                     20

<210> SEQ ID NO 153
<211> LENGTH: 20
<212> TYPE: DNA
<213> ORGANISM: Homo Sapiens

<400> SEQUENCE: 153
agctactatg ctgaaccttc                                                     20

<210> SEQ ID NO 154
<211> LENGTH: 20
<212> TYPE: DNA
<213> ORGANISM: Homo Sapiens

<400> SEQUENCE: 154
ggatgaccaa ttcagctgta                                                     20

<210> SEQ ID NO 155
<211> LENGTH: 20
<212> TYPE: DNA
<213> ORGANISM: Homo Sapiens

<400> SEQUENCE: 155
accccaaggc cgaagtcatc                                                     20

<210> SEQ ID NO 156
<211> LENGTH: 20
<212> TYPE: DNA
<213> ORGANISM: Homo Sapiens

```
<400> SEQUENCE: 156
tctttatatt catgacctac                                               20

<210> SEQ ID NO 157
<211> LENGTH: 20
<212> TYPE: DNA
<213> ORGANISM: Homo Sapiens

<400> SEQUENCE: 157
accgttcagc aaatgccagt                                               20

<210> SEQ ID NO 158
<211> LENGTH: 20
<212> TYPE: DNA
<213> ORGANISM: Homo Sapiens

<400> SEQUENCE: 158
gtacccaccg ccatactacc                                               20

<210> SEQ ID NO 159
<211> LENGTH: 20
<212> TYPE: DNA
<213> ORGANISM: Homo Sapiens

<400> SEQUENCE: 159
ttgcctatgc ccaggtagta                                               20

<210> SEQ ID NO 160
<211> LENGTH: 20
<212> TYPE: DNA
<213> ORGANISM: Homo Sapiens

<400> SEQUENCE: 160
ccttgtgccg ctgaaatcca                                               20

<210> SEQ ID NO 161
<211> LENGTH: 20
<212> TYPE: DNA
<213> ORGANISM: Homo Sapiens

<400> SEQUENCE: 161
accccgaact aactgctgca                                               20

<210> SEQ ID NO 162
<211> LENGTH: 20
<212> TYPE: DNA
<213> ORGANISM: Homo Sapiens

<400> SEQUENCE: 162
acatagaccc ctgttgtaag                                               20

<210> SEQ ID NO 163
<211> LENGTH: 20
<212> TYPE: DNA
<213> ORGANISM: Homo Sapiens

<400> SEQUENCE: 163
atccttgcag cagttagttc                                               20

<210> SEQ ID NO 164
<211> LENGTH: 20
<212> TYPE: DNA
<213> ORGANISM: Homo Sapiens
```

```
<400> SEQUENCE: 164
acatcgaacc tcttgcacgt                                                 20

<210> SEQ ID NO 165
<211> LENGTH: 20
<212> TYPE: DNA
<213> ORGANISM: Homo Sapiens

<400> SEQUENCE: 165
tacagctcac cttctcgcag                                                 20

<210> SEQ ID NO 166
<211> LENGTH: 20
<212> TYPE: DNA
<213> ORGANISM: Homo Sapiens

<400> SEQUENCE: 166
ggtatatctc ctcgaggagc                                                 20

<210> SEQ ID NO 167
<211> LENGTH: 20
<212> TYPE: DNA
<213> ORGANISM: Homo Sapiens

<400> SEQUENCE: 167
tacactgctt gtagctctta                                                 20

<210> SEQ ID NO 168
<211> LENGTH: 20
<212> TYPE: DNA
<213> ORGANISM: Homo Sapiens

<400> SEQUENCE: 168
gagctctaga caccaacgtg                                                 20

<210> SEQ ID NO 169
<211> LENGTH: 20
<212> TYPE: DNA
<213> ORGANISM: Homo Sapiens

<400> SEQUENCE: 169
caagcagctg tccgagtccc                                                 20

<210> SEQ ID NO 170
<211> LENGTH: 20
<212> TYPE: DNA
<213> ORGANISM: Homo Sapiens

<400> SEQUENCE: 170
aatgtgtagc cagcaccacg                                                 20

<210> SEQ ID NO 171
<211> LENGTH: 20
<212> TYPE: DNA
<213> ORGANISM: Homo Sapiens

<400> SEQUENCE: 171
gaacttcctg taaacgatcc                                                 20

<210> SEQ ID NO 172
<211> LENGTH: 20
<212> TYPE: DNA
```

```
<213> ORGANISM: Homo Sapiens

<400> SEQUENCE: 172
tacatacctc cattacaagc                                          20

<210> SEQ ID NO 173
<211> LENGTH: 20
<212> TYPE: DNA
<213> ORGANISM: Homo Sapiens

<400> SEQUENCE: 173
ccatctacta aagctgtaag                                          20

<210> SEQ ID NO 174
<211> LENGTH: 20
<212> TYPE: DNA
<213> ORGANISM: Homo Sapiens

<400> SEQUENCE: 174
ctcaatattg taatgcgttc                                          20

<210> SEQ ID NO 175
<211> LENGTH: 20
<212> TYPE: DNA
<213> ORGANISM: Homo Sapiens

<400> SEQUENCE: 175
ctctccatcc atagacacac                                          20

<210> SEQ ID NO 176
<211> LENGTH: 20
<212> TYPE: DNA
<213> ORGANISM: Homo Sapiens

<400> SEQUENCE: 176
taagacctac atcgccagcc                                          20

<210> SEQ ID NO 177
<211> LENGTH: 20
<212> TYPE: DNA
<213> ORGANISM: Homo Sapiens

<400> SEQUENCE: 177
gaagaacttg caccagcgtc                                          20

<210> SEQ ID NO 178
<211> LENGTH: 20
<212> TYPE: DNA
<213> ORGANISM: Homo Sapiens

<400> SEQUENCE: 178
gtcagccgca ttcaccctcg                                          20

<210> SEQ ID NO 179
<211> LENGTH: 20
<212> TYPE: DNA
<213> ORGANISM: Homo Sapiens

<400> SEQUENCE: 179
ctgccagaag tcattgaccg                                          20

<210> SEQ ID NO 180
<211> LENGTH: 20
```

-continued

```
<212> TYPE: DNA
<213> ORGANISM: Homo Sapiens

<400> SEQUENCE: 180
cccagccgta ctatgccacg                                               20

<210> SEQ ID NO 181
<211> LENGTH: 20
<212> TYPE: DNA
<213> ORGANISM: Homo Sapiens

<400> SEQUENCE: 181
gccgctgccc ttccagacgc                                               20

<210> SEQ ID NO 182
<211> LENGTH: 20
<212> TYPE: DNA
<213> ORGANISM: Homo Sapiens

<400> SEQUENCE: 182
gtagctggaa tcctcatcag                                               20

<210> SEQ ID NO 183
<211> LENGTH: 20
<212> TYPE: DNA
<213> ORGANISM: Homo Sapiens

<400> SEQUENCE: 183
caaaacctat cctacaactg                                               20

<210> SEQ ID NO 184
<211> LENGTH: 20
<212> TYPE: DNA
<213> ORGANISM: Homo Sapiens

<400> SEQUENCE: 184
ttagggagtt tatggaccca                                               20

<210> SEQ ID NO 185
<211> LENGTH: 20
<212> TYPE: DNA
<213> ORGANISM: Homo Sapiens

<400> SEQUENCE: 185
ctcagccaca gttgtaggat                                               20

<210> SEQ ID NO 186
<211> LENGTH: 20
<212> TYPE: DNA
<213> ORGANISM: Homo Sapiens

<400> SEQUENCE: 186
tcactgtacc ttaatgaagt                                               20

<210> SEQ ID NO 187
<211> LENGTH: 20
<212> TYPE: DNA
<213> ORGANISM: Homo Sapiens

<400> SEQUENCE: 187
tcctttatct acaaccctcc                                               20

<210> SEQ ID NO 188
```

-continued

```
<211> LENGTH: 20
<212> TYPE: DNA
<213> ORGANISM: Homo Sapiens

<400> SEQUENCE: 188
tccataggtg cccaacgctc                                               20

<210> SEQ ID NO 189
<211> LENGTH: 20
<212> TYPE: DNA
<213> ORGANISM: Homo Sapiens

<400> SEQUENCE: 189
gttccggaac caatgcacag                                               20

<210> SEQ ID NO 190
<211> LENGTH: 20
<212> TYPE: DNA
<213> ORGANISM: Homo Sapiens

<400> SEQUENCE: 190
gcgagaagtc cccgcgctgc                                               20

<210> SEQ ID NO 191
<211> LENGTH: 20
<212> TYPE: DNA
<213> ORGANISM: Homo Sapiens

<400> SEQUENCE: 191
tgacccctgc tcttcgcaga                                               20

<210> SEQ ID NO 192
<211> LENGTH: 20
<212> TYPE: DNA
<213> ORGANISM: Homo Sapiens

<400> SEQUENCE: 192
cgccggcgag taccgcgccg                                               20

<210> SEQ ID NO 193
<211> LENGTH: 20
<212> TYPE: DNA
<213> ORGANISM: Homo Sapiens

<400> SEQUENCE: 193
tgggcggtca gggcggctga                                               20

<210> SEQ ID NO 194
<211> LENGTH: 20
<212> TYPE: DNA
<213> ORGANISM: Homo Sapiens

<400> SEQUENCE: 194
ctaaatgggg atttccgcaa                                               20

<210> SEQ ID NO 195
<211> LENGTH: 20
<212> TYPE: DNA
<213> ORGANISM: Homo Sapiens

<400> SEQUENCE: 195
atccccattt agccagtatc                                               20
```

```
<210> SEQ ID NO 196
<211> LENGTH: 20
<212> TYPE: DNA
<213> ORGANISM: Homo Sapiens

<400> SEQUENCE: 196
gtgaagtctc tctgccgagt                                               20

<210> SEQ ID NO 197
<211> LENGTH: 20
<212> TYPE: DNA
<213> ORGANISM: Homo Sapiens

<400> SEQUENCE: 197
aggtcacccc tgcaccgact                                               20

<210> SEQ ID NO 198
<211> LENGTH: 20
<212> TYPE: DNA
<213> ORGANISM: Homo Sapiens

<400> SEQUENCE: 198
cttactgtta gatttatatc                                               20

<210> SEQ ID NO 199
<211> LENGTH: 20
<212> TYPE: DNA
<213> ORGANISM: Homo Sapiens

<400> SEQUENCE: 199
tatagcagag acacagacac                                               20

<210> SEQ ID NO 200
<211> LENGTH: 20
<212> TYPE: DNA
<213> ORGANISM: Homo Sapiens

<400> SEQUENCE: 200
gtgacttggt gcaagctcaa                                               20

<210> SEQ ID NO 201
<211> LENGTH: 20
<212> TYPE: DNA
<213> ORGANISM: Homo Sapiens

<400> SEQUENCE: 201
tctgcttgcc atttcgtcct                                               20

<210> SEQ ID NO 202
<211> LENGTH: 20
<212> TYPE: DNA
<213> ORGANISM: Homo Sapiens

<400> SEQUENCE: 202
ctgttagcac agtatttcac                                               20

<210> SEQ ID NO 203
<211> LENGTH: 20
<212> TYPE: DNA
<213> ORGANISM: Homo Sapiens

<400> SEQUENCE: 203
ccaaaggaag taaacgatac                                               20
```

```
<210> SEQ ID NO 204
<211> LENGTH: 20
<212> TYPE: DNA
<213> ORGANISM: Homo Sapiens

<400> SEQUENCE: 204
atgttccaga tgtccagata                                              20

<210> SEQ ID NO 205
<211> LENGTH: 20
<212> TYPE: DNA
<213> ORGANISM: Homo Sapiens

<400> SEQUENCE: 205
cttcttctta atcccatatc                                              20

<210> SEQ ID NO 206
<211> LENGTH: 20
<212> TYPE: DNA
<213> ORGANISM: Homo Sapiens

<400> SEQUENCE: 206
agtttagtcg cgttccttcc                                              20

<210> SEQ ID NO 207
<211> LENGTH: 20
<212> TYPE: DNA
<213> ORGANISM: Homo Sapiens

<400> SEQUENCE: 207
cactgtgcaa cggtgtgact                                              20

<210> SEQ ID NO 208
<211> LENGTH: 20
<212> TYPE: DNA
<213> ORGANISM: Homo Sapiens

<400> SEQUENCE: 208
ggatgtccac aattgccagc                                              20

<210> SEQ ID NO 209
<211> LENGTH: 20
<212> TYPE: DNA
<213> ORGANISM: Homo Sapiens

<400> SEQUENCE: 209
aactgagagt gccttcatta                                              20

<210> SEQ ID NO 210
<211> LENGTH: 20
<212> TYPE: DNA
<213> ORGANISM: Homo Sapiens

<400> SEQUENCE: 210
gacagggaac tacacagtga                                              20

<210> SEQ ID NO 211
<211> LENGTH: 965
<212> TYPE: PRT
<213> ORGANISM: Artificial Sequence
<220> FEATURE:
<223> OTHER INFORMATION: Synthetic

<400> SEQUENCE: 211
```

-continued

```
Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
            35                  40                  45

Thr Asn Val Ser Pro Ala Lys Pro Thr Thr Ala Cys Pro Tyr Ser
    50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
                100                 105                 110

Asp Phe Ala Cys Asp Ile Tyr Ile Trp Ala Pro Leu Ala Gly Thr Cys
            115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val Arg Ser Gly
145                 150                 155                 160

Ser Gly Gln Cys Thr Asn Tyr Ala Leu Leu Lys Leu Ala Gly Asp Val
                165                 170                 175

Glu Ser Asn Pro Gly Pro Pro Thr Gly Met Val Cys Leu Lys Leu Pro
            180                 185                 190

Gly Gly Ser Cys Met Thr Ala Leu Thr Val Thr Leu Met Val Leu Ser
            195                 200                 205

Ser Pro Leu Ala Leu Ala Ser Asp Glu Asn Pro Val Val His Phe Phe
    210                 215                 220

Lys Asn Ile Val Thr Pro Arg Thr Pro Gly Gly Gly Ser Gly
225                 230                 235                 240

Gly Gly Gly Ser Gly Gly Ser Gly Asp Thr Arg Pro Arg Phe Leu Trp
                245                 250                 255

Gln Pro Lys Arg Glu Cys His Phe Phe Asn Gly Thr Glu Arg Val Arg
                260                 265                 270

Phe Leu Asp Arg Tyr Phe Tyr Asn Gln Glu Glu Ser Val Arg Phe Asp
    275                 280                 285

Ser Asp Val Gly Glu Phe Arg Ala Val Thr Glu Leu Gly Arg Pro Asp
    290                 295                 300

Ala Glu Tyr Trp Asn Ser Gln Lys Asp Ile Leu Glu Gln Ala Arg Ala
305                 310                 315                 320

Ala Val Asp Thr Tyr Cys Arg His Asn Tyr Gly Val Val Glu Ser Phe
                325                 330                 335

Thr Val Gln Arg Arg Val Gln Pro Lys Val Thr Val Tyr Pro Ser Lys
                340                 345                 350

Thr Gln Pro Leu Gln His His Asn Leu Leu Val Cys Ser Val Ser Gly
            355                 360                 365

Phe Tyr Pro Gly Ser Ile Glu Val Arg Trp Phe Leu Asn Gly Gln Glu
    370                 375                 380

Glu Lys Ala Gly Met Val Ser Thr Gly Leu Ile Gln Asn Gly Asp Trp
385                 390                 395                 400

Thr Phe Gln Thr Leu Val Met Leu Glu Thr Val Pro Arg Ser Gly Glu
            405                 410                 415
```

-continued

```
Val Tyr Thr Cys Gln Val Glu His Pro Ser Val Thr Ser Pro Leu Thr
            420                 425                 430

Val Glu Trp Arg Ala Arg Ser Glu Ser Ala Gln Ser Lys Met Leu Ser
        435                 440                 445

Gly Val Gly Gly Phe Val Leu Gly Leu Leu Phe Leu Gly Ala Gly Leu
    450                 455                 460

Phe Ile Tyr Phe Arg Asn Gln Thr Ser Arg Val Lys Phe Ser Arg Ser
465                 470                 475                 480

Ala Asp Ala Pro Ala Tyr Gln Gln Gly Gln Asn Gln Leu Tyr Asn Glu
                485                 490                 495

Leu Asn Leu Gly Arg Arg Glu Glu Tyr Asp Val Leu Asp Lys Arg Arg
            500                 505                 510

Gly Arg Asp Pro Glu Met Gly Gly Lys Pro Arg Arg Lys Asn Pro Gln
        515                 520                 525

Glu Gly Leu Tyr Asn Glu Leu Gln Lys Asp Lys Met Ala Glu Ala Tyr
    530                 535                 540

Ser Glu Ile Gly Met Lys Gly Glu Arg Arg Arg Gly Lys Gly His Asp
545                 550                 555                 560

Gly Leu Tyr Gln Gly Leu Ser Thr Ala Thr Lys Asp Thr Tyr Asp Ala
                565                 570                 575

Leu His Met Gln Ala Leu Pro Pro Arg Gly Ser Ser Gly Ser Gly Glu
            580                 585                 590

Gly Arg Gly Ser Leu Leu Thr Cys Gly Asp Val Glu Glu Asn Pro Gly
        595                 600                 605

Pro Met Ala Ile Ser Gly Val Pro Val Leu Gly Phe Phe Ile Ile Ala
    610                 615                 620

Val Leu Met Ser Ala Gln Glu Ser Trp Ala Ile Lys Glu Glu His Val
625                 630                 635                 640

Ile Ile Gln Ala Glu Phe Tyr Leu Asn Pro Asp Gln Ser Gly Glu Phe
                645                 650                 655

Met Phe Asp Phe Asp Gly Asp Glu Ile Phe His Val Asp Met Ala Lys
            660                 665                 670

Lys Glu Thr Val Trp Arg Leu Glu Glu Phe Gly Arg Phe Ala Ser Phe
        675                 680                 685

Glu Ala Gln Gly Ala Leu Ala Asn Ile Ala Val Asp Lys Ala Asn Leu
    690                 695                 700

Glu Ile Met Thr Lys Arg Ser Asn Tyr Thr Pro Ile Thr Asn Val Pro
705                 710                 715                 720

Pro Glu Val Thr Val Leu Thr Asn Ser Pro Val Glu Leu Arg Glu Pro
                725                 730                 735

Asn Val Leu Ile Cys Phe Ile Asp Lys Phe Thr Pro Pro Val Val Asn
            740                 745                 750

Val Thr Trp Leu Arg Asn Gly Lys Pro Val Thr Thr Gly Val Ser Glu
        755                 760                 765

Thr Val Phe Leu Pro Arg Glu Asp His Leu Phe Arg Lys Phe His Tyr
    770                 775                 780

Leu Pro Phe Leu Pro Ser Thr Glu Asp Val Tyr Asp Cys Arg Val Glu
785                 790                 795                 800

His Trp Gly Leu Asp Glu Pro Leu Leu Lys His Trp Glu Phe Asp Ala
                805                 810                 815

Pro Ser Pro Leu Pro Glu Thr Thr Glu Asn Val Val Cys Ala Leu Gly
            820                 825                 830

Leu Thr Val Gly Leu Val Gly Ile Ile Ile Gly Thr Ile Phe Ile Ile
```

```
            835                 840                 845
Lys Gly Leu Thr Ser Arg Val Lys Phe Ser Arg Ser Ala Asp Ala Pro
            850                 855                 860

Ala Tyr Gln Gln Gly Gln Asn Gln Leu Tyr Asn Glu Leu Asn Leu Gly
865                 870                 875                 880

Arg Arg Glu Glu Tyr Asp Val Leu Asp Lys Arg Gly Arg Asp Pro
                885                 890                 895

Glu Met Gly Gly Lys Pro Arg Arg Lys Asn Pro Gln Glu Gly Leu Tyr
            900                 905                 910

Asn Glu Leu Gln Lys Asp Lys Met Ala Glu Ala Tyr Ser Glu Ile Gly
                915                 920                 925

Met Lys Gly Glu Arg Arg Gly Lys Gly His Asp Gly Leu Tyr Gln
            930                 935                 940

Gly Leu Ser Thr Ala Thr Lys Asp Thr Tyr Asp Ala Leu His Met Gln
945                 950                 955                 960

Ala Leu Pro Pro Arg
            965

<210> SEQ ID NO 212
<211> LENGTH: 20
<212> TYPE: DNA
<213> ORGANISM: Homo Sapiens

<400> SEQUENCE: 212
attgtggaca tccagtctgg                                              20

<210> SEQ ID NO 213
<211> LENGTH: 20
<212> TYPE: DNA
<213> ORGANISM: Homo Sapiens

<400> SEQUENCE: 213
tcgctgaccg tgaacgatac                                              20

<210> SEQ ID NO 214
<211> LENGTH: 20
<212> TYPE: DNA
<213> ORGANISM: Homo Sapiens

<400> SEQUENCE: 214
tggggccact cgatccttga                                              20

<210> SEQ ID NO 215
<211> LENGTH: 20
<212> TYPE: DNA
<213> ORGANISM: Homo Sapiens

<400> SEQUENCE: 215
gcagatgacc accagcgtcg                                              20

<210> SEQ ID NO 216
<211> LENGTH: 20
<212> TYPE: DNA
<213> ORGANISM: Homo Sapiens

<400> SEQUENCE: 216
tcaggcctta cctgaggcga                                              20

<210> SEQ ID NO 217
<211> LENGTH: 20
```

```
<212> TYPE: DNA
<213> ORGANISM: Homo Sapiens

<400> SEQUENCE: 217
catctgcaca gcagtcatcg                                         20

<210> SEQ ID NO 218
<211> LENGTH: 20
<212> TYPE: DNA
<213> ORGANISM: Homo Sapiens

<400> SEQUENCE: 218
attgaagtag tcatgcagct                                         20

<210> SEQ ID NO 219
<211> LENGTH: 20
<212> TYPE: DNA
<213> ORGANISM: Homo Sapiens

<400> SEQUENCE: 219
aggcacagta gaagccgtat                                         20

<210> SEQ ID NO 220
<211> LENGTH: 20
<212> TYPE: DNA
<213> ORGANISM: Homo Sapiens

<400> SEQUENCE: 220
gctgtctatc atccccaata                                         20

<210> SEQ ID NO 221
<211> LENGTH: 20
<212> TYPE: DNA
<213> ORGANISM: Homo Sapiens

<400> SEQUENCE: 221
acttaccacc gaccatgcat                                         20

<210> SEQ ID NO 222
<211> LENGTH: 20
<212> TYPE: DNA
<213> ORGANISM: Homo Sapiens

<400> SEQUENCE: 222
cacactttag agtgagcgtc                                         20

<210> SEQ ID NO 223
<211> LENGTH: 20
<212> TYPE: DNA
<213> ORGANISM: Homo Sapiens

<400> SEQUENCE: 223
ctccagtggc tgacccctc                                          20

<210> SEQ ID NO 224
<211> LENGTH: 20
<212> TYPE: DNA
<213> ORGANISM: Homo Sapiens

<400> SEQUENCE: 224
ccacagcagc ccaccagtac                                         20

<210> SEQ ID NO 225
```

```
<211> LENGTH: 20
<212> TYPE: DNA
<213> ORGANISM: Homo Sapiens

<400> SEQUENCE: 225
ttataataga tgcagcgata                                                 20

<210> SEQ ID NO 226
<211> LENGTH: 20
<212> TYPE: DNA
<213> ORGANISM: Homo Sapiens

<400> SEQUENCE: 226
tcattgtgac tgttgtccga                                                 20

<210> SEQ ID NO 227
<211> LENGTH: 20
<212> TYPE: DNA
<213> ORGANISM: Homo Sapiens

<400> SEQUENCE: 227
gccaggcacc gtgatccccc                                                 20

<210> SEQ ID NO 228
<211> LENGTH: 20
<212> TYPE: DNA
<213> ORGANISM: Homo Sapiens

<400> SEQUENCE: 228
catccttatc cccggtaccc                                                 20

<210> SEQ ID NO 229
<211> LENGTH: 20
<212> TYPE: DNA
<213> ORGANISM: Homo Sapiens

<400> SEQUENCE: 229
cagagagttc tgagctcgac                                                 20

<210> SEQ ID NO 230
<211> LENGTH: 20
<212> TYPE: DNA
<213> ORGANISM: Homo Sapiens

<400> SEQUENCE: 230
agtgttgctg ggggcggtcg                                                 20

<210> SEQ ID NO 231
<211> LENGTH: 20
<212> TYPE: DNA
<213> ORGANISM: Homo Sapiens

<400> SEQUENCE: 231
gacgatgcag agttccgtga                                                 20

<210> SEQ ID NO 232
<211> LENGTH: 20
<212> TYPE: DNA
<213> ORGANISM: Homo Sapiens

<400> SEQUENCE: 232
actcacagga cacgttgaga                                                 20
```

```
<210> SEQ ID NO 233
<211> LENGTH: 20
<212> TYPE: DNA
<213> ORGANISM: Homo Sapiens

<400> SEQUENCE: 233
taccctggcc cagtagttca                                              20

<210> SEQ ID NO 234
<211> LENGTH: 20
<212> TYPE: DNA
<213> ORGANISM: Homo Sapiens

<400> SEQUENCE: 234
accttcgtct gtatgctgtt                                              20

<210> SEQ ID NO 235
<211> LENGTH: 20
<212> TYPE: DNA
<213> ORGANISM: Homo Sapiens

<400> SEQUENCE: 235
accaaacagc atacagacga                                              20

<210> SEQ ID NO 236
<211> LENGTH: 20
<212> TYPE: DNA
<213> ORGANISM: Homo Sapiens

<400> SEQUENCE: 236
ctactctatg atccagtccc                                              20

<210> SEQ ID NO 237
<211> LENGTH: 20
<212> TYPE: DNA
<213> ORGANISM: Homo Sapiens

<400> SEQUENCE: 237
actccgtcag ctcgttagaa                                              20

<210> SEQ ID NO 238
<211> LENGTH: 20
<212> TYPE: DNA
<213> ORGANISM: Homo Sapiens

<400> SEQUENCE: 238
gttcatactc tcttcgtcat                                              20

<210> SEQ ID NO 239
<211> LENGTH: 20
<212> TYPE: DNA
<213> ORGANISM: Homo Sapiens

<400> SEQUENCE: 239
agagtagcag ctcacataac                                              20

<210> SEQ ID NO 240
<211> LENGTH: 20
<212> TYPE: DNA
<213> ORGANISM: Homo Sapiens

<400> SEQUENCE: 240
ttccagagct cacaacgacc                                              20
```

```
<210> SEQ ID NO 241
<211> LENGTH: 20
<212> TYPE: DNA
<213> ORGANISM: Homo Sapiens

<400> SEQUENCE: 241
atagtcctgt ccatatttgc                                               20

<210> SEQ ID NO 242
<211> LENGTH: 20
<212> TYPE: DNA
<213> ORGANISM: Homo Sapiens

<400> SEQUENCE: 242
agatactcac gatctcattg                                               20

<210> SEQ ID NO 243
<211> LENGTH: 20
<212> TYPE: DNA
<213> ORGANISM: Homo Sapiens

<400> SEQUENCE: 243
aggtcaagga ttgtacgccc                                               20

<210> SEQ ID NO 244
<211> LENGTH: 20
<212> TYPE: DNA
<213> ORGANISM: Homo Sapiens

<400> SEQUENCE: 244
gaagtccctg caccacgacc                                               20

<210> SEQ ID NO 245
<211> LENGTH: 20
<212> TYPE: DNA
<213> ORGANISM: Homo Sapiens

<400> SEQUENCE: 245
tttggttgtt ccgttgctgt                                               20

<210> SEQ ID NO 246
<211> LENGTH: 20
<212> TYPE: DNA
<213> ORGANISM: Homo Sapiens

<400> SEQUENCE: 246
tgatcgaccc tccgccagaa                                               20

<210> SEQ ID NO 247
<211> LENGTH: 20
<212> TYPE: DNA
<213> ORGANISM: Homo Sapiens

<400> SEQUENCE: 247
gggtcgatca tctattaata                                               20

<210> SEQ ID NO 248
<211> LENGTH: 20
<212> TYPE: DNA
<213> ORGANISM: Homo Sapiens

<400> SEQUENCE: 248
tcctttgcgg aatgtagtcc                                               20
```

```
<210> SEQ ID NO 249
<211> LENGTH: 20
<212> TYPE: DNA
<213> ORGANISM: Homo Sapiens

<400> SEQUENCE: 249
ctatgtatcc tttcggcatg                                              20

<210> SEQ ID NO 250
<211> LENGTH: 20
<212> TYPE: DNA
<213> ORGANISM: Homo Sapiens

<400> SEQUENCE: 250
tcttctgccg tatgatatag                                              20

<210> SEQ ID NO 251
<211> LENGTH: 20
<212> TYPE: DNA
<213> ORGANISM: Homo Sapiens

<400> SEQUENCE: 251
gtgagacatg atctcccgaa                                              20

<210> SEQ ID NO 252
<211> LENGTH: 20
<212> TYPE: DNA
<213> ORGANISM: Homo Sapiens

<400> SEQUENCE: 252
atgtcgatgc agcaaacctc                                              20

<210> SEQ ID NO 253
<211> LENGTH: 20
<212> TYPE: DNA
<213> ORGANISM: Homo Sapiens

<400> SEQUENCE: 253
attatacata aacccatctc                                              20

<210> SEQ ID NO 254
<211> LENGTH: 20
<212> TYPE: DNA
<213> ORGANISM: Homo Sapiens

<400> SEQUENCE: 254
aatggactct ggaatatccc                                              20

<210> SEQ ID NO 255
<211> LENGTH: 20
<212> TYPE: DNA
<213> ORGANISM: Homo Sapiens

<400> SEQUENCE: 255
atagagacaa tcttacccgc                                              20

<210> SEQ ID NO 256
<211> LENGTH: 20
<212> TYPE: DNA
<213> ORGANISM: Homo Sapiens

<400> SEQUENCE: 256
```
aagattgtct ctatctgcgc                                              20

<210> SEQ ID NO 257
<211> LENGTH: 20
<212> TYPE: DNA
<213> ORGANISM: Homo Sapiens

<400> SEQUENCE: 257
aaatgtgatt gccttcgcca                                              20

<210> SEQ ID NO 258
<211> LENGTH: 20
<212> TYPE: DNA
<213> ORGANISM: Homo Sapiens

<400> SEQUENCE: 258
cgtttgtacc gtccctcttc                                              20

<210> SEQ ID NO 259
<211> LENGTH: 20
<212> TYPE: DNA
<213> ORGANISM: Homo Sapiens

<400> SEQUENCE: 259
tgcgatccat caagaccacc                                              20

<210> SEQ ID NO 260
<211> LENGTH: 20
<212> TYPE: DNA
<213> ORGANISM: Homo Sapiens

<400> SEQUENCE: 260
ttgatattta ggcttgccga                                              20

<210> SEQ ID NO 261
<211> LENGTH: 20
<212> TYPE: DNA
<213> ORGANISM: Homo Sapiens

<400> SEQUENCE: 261
agtcgtcgac gcgccgcagc                                              20

<210> SEQ ID NO 262
<211> LENGTH: 20
<212> TYPE: DNA
<213> ORGANISM: Homo Sapiens

<400> SEQUENCE: 262
agcggcccat caggacgctt                                              20

<210> SEQ ID NO 263
<211> LENGTH: 20
<212> TYPE: DNA
<213> ORGANISM: Homo Sapiens

<400> SEQUENCE: 263
gcggcgcgtc gacgacttcg                                              20

<210> SEQ ID NO 264
<211> LENGTH: 20
<212> TYPE: DNA
<213> ORGANISM: Homo Sapiens

<400> SEQUENCE: 264
gtgtaacata cctggaggac                                       20

<210> SEQ ID NO 265
<211> LENGTH: 20
<212> TYPE: DNA
<213> ORGANISM: Homo Sapiens

<400> SEQUENCE: 265
tacatctgca cttggtattc                                       20

<210> SEQ ID NO 266
<211> LENGTH: 20
<212> TYPE: DNA
<213> ORGANISM: Homo Sapiens

<400> SEQUENCE: 266
ctaaaactta cttggtgcaa                                       20

<210> SEQ ID NO 267
<211> LENGTH: 20
<212> TYPE: DNA
<213> ORGANISM: Homo Sapiens

<400> SEQUENCE: 267
tctcaactct ttctcgaagc                                       20

<210> SEQ ID NO 268
<211> LENGTH: 20
<212> TYPE: DNA
<213> ORGANISM: Homo Sapiens

<400> SEQUENCE: 268
ctgcctgatc tcatagagtc                                       20

<210> SEQ ID NO 269
<211> LENGTH: 20
<212> TYPE: DNA
<213> ORGANISM: Homo Sapiens

<400> SEQUENCE: 269
cagatactta ctcataagtc                                       20

<210> SEQ ID NO 270
<211> LENGTH: 20
<212> TYPE: DNA
<213> ORGANISM: Homo Sapiens

<400> SEQUENCE: 270
cgctgagaaa tgactgcacg                                       20

<210> SEQ ID NO 271
<211> LENGTH: 20
<212> TYPE: DNA
<213> ORGANISM: Homo Sapiens

<400> SEQUENCE: 271
catatacttc ttcaccagtt                                       20

<210> SEQ ID NO 272
<211> LENGTH: 20
<212> TYPE: DNA
<213> ORGANISM: Homo Sapiens

<400> SEQUENCE: 272
atgtactcac acatctggat                                              20

<210> SEQ ID NO 273
<211> LENGTH: 20
<212> TYPE: DNA
<213> ORGANISM: Homo Sapiens

<400> SEQUENCE: 273
accgaatgtc ccgcgtgcaa                                              20

<210> SEQ ID NO 274
<211> LENGTH: 20
<212> TYPE: DNA
<213> ORGANISM: Homo Sapiens

<400> SEQUENCE: 274
gcctttgcac gcgggacatt                                              20

<210> SEQ ID NO 275
<211> LENGTH: 20
<212> TYPE: DNA
<213> ORGANISM: Homo Sapiens

<400> SEQUENCE: 275
ggggaccctg aaagaatacg                                              20

<210> SEQ ID NO 276
<211> LENGTH: 20
<212> TYPE: DNA
<213> ORGANISM: Homo Sapiens

<400> SEQUENCE: 276
cctgcgctgg agaaactatt                                              20

<210> SEQ ID NO 277
<211> LENGTH: 20
<212> TYPE: DNA
<213> ORGANISM: Homo Sapiens

<400> SEQUENCE: 277
ccttgtagta actgcccagc                                              20

<210> SEQ ID NO 278
<211> LENGTH: 20
<212> TYPE: DNA
<213> ORGANISM: Homo Sapiens

<400> SEQUENCE: 278
catagtagcc actctgttgc                                              20

<210> SEQ ID NO 279
<211> LENGTH: 20
<212> TYPE: DNA
<213> ORGANISM: Homo Sapiens

<400> SEQUENCE: 279
caatatcaac gtaatagttc                                              20

<210> SEQ ID NO 280
<211> LENGTH: 20
<212> TYPE: DNA
<213> ORGANISM: Homo Sapiens

```
<400> SEQUENCE: 280
gacttagtgc aatgcaagac                                              20

<210> SEQ ID NO 281
<211> LENGTH: 20
<212> TYPE: DNA
<213> ORGANISM: Homo Sapiens

<400> SEQUENCE: 281
gatattgctg attaagtccc                                              20

<210> SEQ ID NO 282
<211> LENGTH: 20
<212> TYPE: DNA
<213> ORGANISM: Homo Sapiens

<400> SEQUENCE: 282
gcgggccgac cgcatttggg                                              20

<210> SEQ ID NO 283
<211> LENGTH: 20
<212> TYPE: DNA
<213> ORGANISM: Homo Sapiens

<400> SEQUENCE: 283
catattacat cggatatctg                                              20

<210> SEQ ID NO 284
<211> LENGTH: 20
<212> TYPE: DNA
<213> ORGANISM: Homo Sapiens

<400> SEQUENCE: 284
actcttctgc cggacacttg                                              20

<210> SEQ ID NO 285
<211> LENGTH: 20
<212> TYPE: DNA
<213> ORGANISM: Homo Sapiens

<400> SEQUENCE: 285
ttatagagga accctactaa                                              20

<210> SEQ ID NO 286
<211> LENGTH: 20
<212> TYPE: DNA
<213> ORGANISM: Homo Sapiens

<400> SEQUENCE: 286
ttgtgggcac cttactgagt                                              20

<210> SEQ ID NO 287
<211> LENGTH: 20
<212> TYPE: DNA
<213> ORGANISM: Homo Sapiens

<400> SEQUENCE: 287
cgaacacatc gctgacaact                                              20

<210> SEQ ID NO 288
<211> LENGTH: 20
<212> TYPE: DNA
```

```
<213> ORGANISM: Homo Sapiens

<400> SEQUENCE: 288
gttaacgttt ccactttacc                                               20

<210> SEQ ID NO 289
<211> LENGTH: 20
<212> TYPE: DNA
<213> ORGANISM: Homo Sapiens

<400> SEQUENCE: 289
ttcccgctga gcctcgtcca                                               20

<210> SEQ ID NO 290
<211> LENGTH: 20
<212> TYPE: DNA
<213> ORGANISM: Homo Sapiens

<400> SEQUENCE: 290
tatctaattt atcgtcttcc                                               20

<210> SEQ ID NO 291
<211> LENGTH: 20
<212> TYPE: DNA
<213> ORGANISM: Homo Sapiens

<400> SEQUENCE: 291
ttcggagcat cagtcgttga                                               20

<210> SEQ ID NO 292
<211> LENGTH: 20
<212> TYPE: DNA
<213> ORGANISM: Homo Sapiens

<400> SEQUENCE: 292
ttcaacgact gatgctccga                                               20

<210> SEQ ID NO 293
<211> LENGTH: 20
<212> TYPE: DNA
<213> ORGANISM: Homo Sapiens

<400> SEQUENCE: 293
catgcactct gtttgcgaag                                               20

<210> SEQ ID NO 294
<211> LENGTH: 19
<212> TYPE: DNA
<213> ORGANISM: Homo Sapiens

<400> SEQUENCE: 294
ttctcccaga accaaacga                                                19

<210> SEQ ID NO 295
<211> LENGTH: 20
<212> TYPE: DNA
<213> ORGANISM: Homo Sapiens

<400> SEQUENCE: 295
gatgatgtct gcctcgcgcc                                               20

<210> SEQ ID NO 296
<211> LENGTH: 20
```

```
<212> TYPE: DNA
<213> ORGANISM: Homo Sapiens

<400> SEQUENCE: 296
atgccccatc ttcaattgtc                                               20

<210> SEQ ID NO 297
<211> LENGTH: 20
<212> TYPE: DNA
<213> ORGANISM: Homo Sapiens

<400> SEQUENCE: 297
tattcggcca tcaaaggagc                                               20

<210> SEQ ID NO 298
<211> LENGTH: 20
<212> TYPE: DNA
<213> ORGANISM: Homo Sapiens

<400> SEQUENCE: 298
gactaagcct caactccaac                                               20

<210> SEQ ID NO 299
<211> LENGTH: 20
<212> TYPE: DNA
<213> ORGANISM: Homo Sapiens

<400> SEQUENCE: 299
tatacaagct attagctgcg                                               20

<210> SEQ ID NO 300
<211> LENGTH: 20
<212> TYPE: DNA
<213> ORGANISM: Homo Sapiens

<400> SEQUENCE: 300
gaactacatc gctgagcttc                                               20

<210> SEQ ID NO 301
<211> LENGTH: 20
<212> TYPE: DNA
<213> ORGANISM: Homo Sapiens

<400> SEQUENCE: 301
gccatcctat tgtgagtttc                                               20

<210> SEQ ID NO 302
<211> LENGTH: 20
<212> TYPE: DNA
<213> ORGANISM: Homo Sapiens

<400> SEQUENCE: 302
tgtctccaat ttaactaacg                                               20

<210> SEQ ID NO 303
<211> LENGTH: 20
<212> TYPE: DNA
<213> ORGANISM: Homo Sapiens

<400> SEQUENCE: 303
aaggaatagt cacctccgta                                               20

<210> SEQ ID NO 304
```

```
<211> LENGTH: 20
<212> TYPE: DNA
<213> ORGANISM: Homo Sapiens

<400> SEQUENCE: 304
aatggggcat tataacaacg                                              20

<210> SEQ ID NO 305
<211> LENGTH: 20
<212> TYPE: DNA
<213> ORGANISM: Homo Sapiens

<400> SEQUENCE: 305
ggtgaggttc gtggtgttcg                                              20

<210> SEQ ID NO 306
<211> LENGTH: 20
<212> TYPE: DNA
<213> ORGANISM: Homo Sapiens

<400> SEQUENCE: 306
gtgcagcaat cgtcgactac                                              20

<210> SEQ ID NO 307
<211> LENGTH: 20
<212> TYPE: DNA
<213> ORGANISM: Homo Sapiens

<400> SEQUENCE: 307
aatcccggta tacaatcaaa                                              20

<210> SEQ ID NO 308
<211> LENGTH: 20
<212> TYPE: DNA
<213> ORGANISM: Homo Sapiens

<400> SEQUENCE: 308
ctcgagttgc ttgacttacg                                              20

<210> SEQ ID NO 309
<211> LENGTH: 20
<212> TYPE: DNA
<213> ORGANISM: Homo Sapiens

<400> SEQUENCE: 309
ggctcacggc tattcggccg                                              20

<210> SEQ ID NO 310
<211> LENGTH: 20
<212> TYPE: DNA
<213> ORGANISM: Homo Sapiens

<400> SEQUENCE: 310
gcgtctccgt gacaattacc                                              20

<210> SEQ ID NO 311
<211> LENGTH: 20
<212> TYPE: DNA
<213> ORGANISM: Homo Sapiens

<400> SEQUENCE: 311
ccgacaggtc cacgtagcgc                                              20
```

```
<210> SEQ ID NO 312
<211> LENGTH: 20
<212> TYPE: DNA
<213> ORGANISM: Homo Sapiens

<400> SEQUENCE: 312
cccacattta cgcctatcct                                               20

<210> SEQ ID NO 313
<211> LENGTH: 20
<212> TYPE: DNA
<213> ORGANISM: Homo Sapiens

<400> SEQUENCE: 313
taacattaat agcagctcga                                               20

<210> SEQ ID NO 314
<211> LENGTH: 20
<212> TYPE: DNA
<213> ORGANISM: Homo Sapiens

<400> SEQUENCE: 314
gaccccagcc acaacgacac                                               20

<210> SEQ ID NO 315
<211> LENGTH: 20
<212> TYPE: DNA
<213> ORGANISM: Homo Sapiens

<400> SEQUENCE: 315
ccccaccaaa tttgtccaat                                               20

<210> SEQ ID NO 316
<211> LENGTH: 20
<212> TYPE: DNA
<213> ORGANISM: Homo Sapiens

<400> SEQUENCE: 316
gaggccctat tggacaaatt                                               20

<210> SEQ ID NO 317
<211> LENGTH: 20
<212> TYPE: DNA
<213> ORGANISM: Homo Sapiens

<400> SEQUENCE: 317
gttgctccgt gccacatctg                                               20

<210> SEQ ID NO 318
<211> LENGTH: 20
<212> TYPE: DNA
<213> ORGANISM: Homo Sapiens

<400> SEQUENCE: 318
ccatacttac tccgcagagc                                               20

<210> SEQ ID NO 319
<211> LENGTH: 20
<212> TYPE: DNA
<213> ORGANISM: Homo Sapiens

<400> SEQUENCE: 319
tatggtgcgt tctacagcga                                               20
```

```
<210> SEQ ID NO 320
<211> LENGTH: 20
<212> TYPE: DNA
<213> ORGANISM: Homo Sapiens

<400> SEQUENCE: 320
cccgacggct ctgcagttaa                                           20

<210> SEQ ID NO 321
<211> LENGTH: 20
<212> TYPE: DNA
<213> ORGANISM: Homo Sapiens

<400> SEQUENCE: 321
tcggtgcagc tccacgactc                                           20

<210> SEQ ID NO 322
<211> LENGTH: 20
<212> TYPE: DNA
<213> ORGANISM: Homo Sapiens

<400> SEQUENCE: 322
aactattcat gctaccgggc                                           20

<210> SEQ ID NO 323
<211> LENGTH: 20
<212> TYPE: DNA
<213> ORGANISM: Homo Sapiens

<400> SEQUENCE: 323
cgtggtgcag cttcgtgccc                                           20

<210> SEQ ID NO 324
<211> LENGTH: 20
<212> TYPE: DNA
<213> ORGANISM: Homo Sapiens

<400> SEQUENCE: 324
agatgcctca acttggagcc                                           20

<210> SEQ ID NO 325
<211> LENGTH: 20
<212> TYPE: DNA
<213> ORGANISM: Homo Sapiens

<400> SEQUENCE: 325
tttgagttgc attgtgaacg                                           20

<210> SEQ ID NO 326
<211> LENGTH: 20
<212> TYPE: DNA
<213> ORGANISM: Homo Sapiens

<400> SEQUENCE: 326
attcgctgta tgaaggaaga                                           20

<210> SEQ ID NO 327
<211> LENGTH: 20
<212> TYPE: DNA
<213> ORGANISM: Homo Sapiens

<400> SEQUENCE: 327
ttcctacaca atgcgttgcc                                           20
```

<210> SEQ ID NO 328
<211> LENGTH: 20
<212> TYPE: DNA
<213> ORGANISM: Homo Sapiens

<400> SEQUENCE: 328
gatattggca taagcctccc          20

<210> SEQ ID NO 329
<211> LENGTH: 20
<212> TYPE: DNA
<213> ORGANISM: Homo Sapiens

<400> SEQUENCE: 329
tcaactgcga ccagttcagc          20

<210> SEQ ID NO 330
<211> LENGTH: 20
<212> TYPE: DNA
<213> ORGANISM: Homo Sapiens

<400> SEQUENCE: 330
tcgtatgtgc cctcgtcaga          20

<210> SEQ ID NO 331
<211> LENGTH: 20
<212> TYPE: DNA
<213> ORGANISM: Homo Sapiens

<400> SEQUENCE: 331
gagtgaatca gaccttcaac          20

<210> SEQ ID NO 332
<211> LENGTH: 20
<212> TYPE: DNA
<213> ORGANISM: Homo Sapiens

<400> SEQUENCE: 332
tatggcccga gtacaagaac          20

<210> SEQ ID NO 333
<211> LENGTH: 20
<212> TYPE: DNA
<213> ORGANISM: Homo Sapiens

<400> SEQUENCE: 333
gtaaccgtgt atagatgagc          20

<210> SEQ ID NO 334
<211> LENGTH: 20
<212> TYPE: DNA
<213> ORGANISM: Homo Sapiens

<400> SEQUENCE: 334
atactcgata gttgaattct          20

<210> SEQ ID NO 335
<211> LENGTH: 20
<212> TYPE: DNA
<213> ORGANISM: Homo Sapiens

<400> SEQUENCE: 335

```
catcagatct ttcaggtata                                                    20

<210> SEQ ID NO 336
<211> LENGTH: 20
<212> TYPE: DNA
<213> ORGANISM: Homo Sapiens

<400> SEQUENCE: 336
actcacgctg gatagcctcc                                                    20

<210> SEQ ID NO 337
<211> LENGTH: 20
<212> TYPE: DNA
<213> ORGANISM: Homo Sapiens

<400> SEQUENCE: 337
gagtagcgcg agcacagcta                                                    20

<210> SEQ ID NO 338
<211> LENGTH: 20
<212> TYPE: DNA
<213> ORGANISM: Homo Sapiens

<400> SEQUENCE: 338
cagtaagtca acttcaatgt                                                    20

<210> SEQ ID NO 339
<211> LENGTH: 20
<212> TYPE: DNA
<213> ORGANISM: Homo Sapiens

<400> SEQUENCE: 339
ggttgttgca agattgaccc                                                    20

<210> SEQ ID NO 340
<211> LENGTH: 20
<212> TYPE: DNA
<213> ORGANISM: Homo Sapiens

<400> SEQUENCE: 340
gaggaactct aagtatcccc                                                    20

<210> SEQ ID NO 341
<211> LENGTH: 20
<212> TYPE: DNA
<213> ORGANISM: Homo Sapiens

<400> SEQUENCE: 341
tctggttgcc ttggtaggat                                                    20

<210> SEQ ID NO 342
<211> LENGTH: 20
<212> TYPE: DNA
<213> ORGANISM: Homo Sapiens

<400> SEQUENCE: 342
cgcagccaca agttcgtgcc                                                    20

<210> SEQ ID NO 343
<211> LENGTH: 20
<212> TYPE: DNA
<213> ORGANISM: Homo Sapiens

<400> SEQUENCE: 343
```
ggagctgggt ggccgcatat                                                    20

<210> SEQ ID NO 344
<211> LENGTH: 20
<212> TYPE: DNA
<213> ORGANISM: Homo Sapiens

<400> SEQUENCE: 344
cccgaacagc aggtcgttaa                                                    20

<210> SEQ ID NO 345
<211> LENGTH: 20
<212> TYPE: DNA
<213> ORGANISM: Homo Sapiens

<400> SEQUENCE: 345
ctcttacctg taccataacc                                                    20

<210> SEQ ID NO 346
<211> LENGTH: 20
<212> TYPE: DNA
<213> ORGANISM: Homo Sapiens

<400> SEQUENCE: 346
aatgcctccg cttatgttgc                                                    20

<210> SEQ ID NO 347
<211> LENGTH: 20
<212> TYPE: DNA
<213> ORGANISM: Homo Sapiens

<400> SEQUENCE: 347
tggcattggc cacgaagaaa                                                    20

<210> SEQ ID NO 348
<211> LENGTH: 20
<212> TYPE: DNA
<213> ORGANISM: Homo Sapiens

<400> SEQUENCE: 348
cgactacttc ggtagtatgc                                                    20

<210> SEQ ID NO 349
<211> LENGTH: 20
<212> TYPE: DNA
<213> ORGANISM: Homo Sapiens

<400> SEQUENCE: 349
cagcatacta ccgaagtagt                                                    20

<210> SEQ ID NO 350
<211> LENGTH: 20
<212> TYPE: DNA
<213> ORGANISM: Homo Sapiens

<400> SEQUENCE: 350
gtgtttgtgt acatcaactc                                                    20

<210> SEQ ID NO 351
<211> LENGTH: 43
<212> TYPE: DNA
<213> ORGANISM: Homo Sapiens

```
<400> SEQUENCE: 351
tgacttccag agagcaatat ggctggttcc ccaacatgcc tca                              43

<210> SEQ ID NO 352
<211> LENGTH: 17
<212> TYPE: DNA
<213> ORGANISM: Homo Sapiens

<400> SEQUENCE: 352
tgacttccag agagcaa                                                           17

<210> SEQ ID NO 353
<211> LENGTH: 969
<212> TYPE: PRT
<213> ORGANISM: Homo Sapiens

<400> SEQUENCE: 353
```

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65              70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Asn Gly Gly Lys
            180                 185                 190

Gln Ala Leu Glu Thr Val Gln Arg Leu Leu Pro Val Leu Cys Gln Ala
        195                 200                 205

His Gly Leu Thr Pro Glu Gln Val Val Ala Ile Ala Ser Asn Ile Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Glu Gln Val Val Ala Ile Ala Ser His
                245                 250                 255

Asp Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
        275                 280                 285

Ser Asn Gly Gly Gly Lys Gln Ala Leu Glu Thr Val Gln Arg Leu Leu
    290                 295                 300

```
Pro Val Leu Cys Gln Ala His Gly Leu Thr Pro Glu Gln Val Val Ala
305                 310                 315                 320

Ile Ala Ser Asn Gly Gly Lys Gln Ala Leu Glu Thr Val Gln Arg
            325                 330                 335

Leu Leu Pro Val Leu Cys Gln Ala His Gly Leu Thr Pro Glu Gln Val
                340                 345                 350

Val Ala Ile Ala Ser His Asp Gly Gly Lys Gln Ala Leu Glu Thr Val
            355                 360                 365

Gln Arg Leu Leu Pro Val Leu Cys Gln Ala His Gly Leu Thr Pro Glu
    370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser Asn Ile Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Asn Gly Gly Lys
450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Ile Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser Asn
                515                 520                 525

Asn Gly Gly Lys Gln Ala Leu Glu Thr Val Gln Arg Leu Leu Pro Val
        530                 535                 540

Leu Cys Gln Ala His Gly Leu Thr Pro Glu Gln Val Val Ala Ile Ala
545                 550                 555                 560

Ser Asn Ile Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
            580                 585                 590

Ile Ala Ser Asn Asn Gly Gly Lys Gln Ala Leu Glu Thr Val Gln Arg
        595                 600                 605

Leu Leu Pro Val Leu Cys Gln Ala His Gly Leu Thr Pro Glu Gln Val
    610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser Asn Ile Gly Gly Lys Gln Ala Leu Glu
            660                 665                 670

Thr Val Gln Arg Leu Leu Pro Val Leu Cys Gln Ala His Gly Leu Thr
        675                 680                 685

Pro Glu Gln Val Val Ala Ile Ala Ser Asn Ile Gly Gly Arg Pro Ala
690                 695                 700

Leu Glu Ser Ile Val Ala Gln Leu Ser Arg Pro Asp Pro Ala Leu Ala
    705                 710                 715                 720

Ala Leu Thr Asn Asp His Leu Val Ala Leu Ala Cys Leu Gly Gly Arg
```

```
                        725                 730                 735

Pro Ala Leu Asp Ala Val Lys Lys Gly Leu Pro His Ala Pro Ala Leu
                740                 745                 750

Ile Lys Arg Thr Asn Arg Ile Pro Glu Arg Thr Ser His Arg Val
            755                 760                 765

Ala Gly Ser Gln Leu Val Lys Ser Glu Leu Glu Lys Lys Ser Glu
        770                 775                 780

Leu Arg His Lys Leu Lys Tyr Val Pro His Glu Tyr Ile Glu Leu Ile
785                 790                 795                 800

Glu Ile Ala Arg Asn Ser Thr Gln Asp Arg Ile Leu Glu Met Lys Val
                805                 810                 815

Met Glu Phe Phe Met Lys Val Tyr Gly Tyr Arg Gly Lys His Leu Gly
                820                 825                 830

Gly Ser Arg Lys Pro Asp Gly Ala Ile Tyr Thr Val Gly Ser Pro Ile
            835                 840                 845

Asp Tyr Gly Val Ile Val Asp Thr Lys Ala Tyr Ser Gly Gly Tyr Asn
        850                 855                 860

Leu Pro Ile Gly Gln Ala Asp Glu Met Gln Arg Tyr Val Glu Glu Asn
865                 870                 875                 880

Gln Thr Arg Asn Lys His Ile Asn Pro Asn Glu Trp Trp Lys Val Tyr
                885                 890                 895

Pro Ser Ser Val Thr Glu Phe Lys Phe Leu Phe Val Ser Gly His Phe
            900                 905                 910

Lys Gly Asn Tyr Lys Ala Gln Leu Thr Arg Leu Asn His Ile Thr Asn
        915                 920                 925

Cys Asn Gly Ala Val Leu Ser Val Glu Glu Leu Leu Ile Gly Gly Glu
    930                 935                 940

Met Ile Lys Ala Gly Thr Leu Thr Leu Glu Glu Val Arg Arg Lys Phe
945                 950                 955                 960

Asn Asn Gly Glu Ile Asn Phe Arg Ser
                965

<210> SEQ ID NO 354
<211> LENGTH: 17
<212> TYPE: DNA
<213> ORGANISM: Homo Sapiens

<400> SEQUENCE: 354
aacatgcctc accctca                                                        17

<210> SEQ ID NO 355
<211> LENGTH: 969
<212> TYPE: PRT
<213> ORGANISM: Homo Sapiens

<400> SEQUENCE: 355

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
                20                  25                  30

Gly Ile His Gly Val Pro Ala Ala Val Asp Leu Arg Thr Leu Gly Tyr
            35                  40                  45

Ser Gln Gln Gln Gln Glu Lys Ile Lys Pro Lys Val Arg Ser Thr Val
        50                  55                  60

Ala Gln His His Glu Ala Leu Val Gly His Gly Phe Thr His Ala His
65                  70                  75                  80
```

```
Ile Val Ala Leu Ser Gln His Pro Ala Ala Leu Gly Thr Val Ala Val
                85              90              95

Lys Tyr Gln Asp Met Ile Ala Ala Leu Pro Glu Ala Thr His Glu Ala
                100             105             110

Ile Val Gly Val Gly Lys Gln Trp Ser Gly Ala Arg Ala Leu Glu Ala
                115             120             125

Leu Leu Thr Val Ala Gly Glu Leu Arg Gly Pro Pro Leu Gln Leu Asp
            130             135             140

Thr Gly Gln Leu Leu Lys Ile Ala Lys Arg Gly Gly Val Thr Ala Val
145             150             155             160

Glu Ala Val His Ala Trp Arg Asn Ala Leu Thr Gly Ala Pro Leu Asn
                165             170             175

Leu Thr Pro Glu Gln Val Val Ala Ile Ala Ser Asn Asn Gly Gly Lys
                180             185             190

Gln Ala Leu Glu Thr Val Gln Arg Leu Leu Pro Val Leu Cys Gln Ala
                195             200             205

His Gly Leu Thr Pro Glu Gln Val Val Ala Ile Ala Ser Asn Ile Gly
                210             215             220

Gly Lys Gln Ala Leu Glu Thr Val Gln Arg Leu Leu Pro Val Leu Cys
225             230             235             240

Gln Ala His Gly Leu Thr Pro Glu Gln Val Val Ala Ile Ala Ser Asn
                245             250             255

Asn Gly Gly Lys Gln Ala Leu Glu Thr Val Gln Arg Leu Leu Pro Val
                260             265             270

Leu Cys Gln Ala His Gly Leu Thr Pro Glu Gln Val Val Ala Ile Ala
                275             280             285

Ser Asn Asn Gly Gly Lys Gln Ala Leu Glu Thr Val Gln Arg Leu Leu
                290             295             300

Pro Val Leu Cys Gln Ala His Gly Leu Thr Pro Glu Gln Val Val Ala
305             310             315             320

Ile Ala Ser Asn Asn Gly Gly Lys Gln Ala Leu Glu Thr Val Gln Arg
                325             330             335

Leu Leu Pro Val Leu Cys Gln Ala His Gly Leu Thr Pro Glu Gln Val
                340             345             350

Val Ala Ile Ala Ser Asn Gly Gly Gly Lys Gln Ala Leu Glu Thr Val
                355             360             365

Gln Arg Leu Leu Pro Val Leu Cys Gln Ala His Gly Leu Thr Pro Glu
370             375             380

Gln Val Val Ala Ile Ala Ser Asn Asn Gly Gly Lys Gln Ala Leu Glu
385             390             395             400

Thr Val Gln Arg Leu Leu Pro Val Leu Cys Gln Ala His Gly Leu Thr
                405             410             415

Pro Glu Gln Val Val Ala Ile Ala Ser Asn Ile Gly Gly Lys Gln Ala
                420             425             430

Leu Glu Thr Val Gln Arg Leu Leu Pro Val Leu Cys Gln Ala His Gly
                435             440             445

Leu Thr Pro Glu Gln Val Val Ala Ile Ala Ser Asn Asn Gly Gly Lys
                450             455             460

Gln Ala Leu Glu Thr Val Gln Arg Leu Leu Pro Val Leu Cys Gln Ala
465             470             475             480

His Gly Leu Thr Pro Glu Gln Val Val Ala Ile Ala Ser Asn Asn Gly
                485             490             495
```

```
Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser His
            515                 520                 525

Asp Gly Gly Lys Gln Ala Leu Glu Thr Val Gln Arg Leu Leu Pro Val
530                 535                 540

Leu Cys Gln Ala His Gly Leu Thr Pro Glu Gln Val Val Ala Ile Ala
545                 550                 555                 560

Ser Asn Ile Gly Gly Lys Gln Ala Leu Glu Thr Val Gln Arg Leu Leu
            565                 570                 575

Pro Val Leu Cys Gln Ala His Gly Leu Thr Pro Glu Gln Val Val Ala
            580                 585                 590

Ile Ala Ser Asn Gly Gly Lys Gln Ala Leu Glu Thr Val Gln Arg
            595                 600                 605

Leu Leu Pro Val Leu Cys Gln Ala His Gly Leu Thr Pro Glu Gln Val
            610                 615                 620

Val Ala Ile Ala Ser Asn Gly Gly Lys Gln Ala Leu Glu Thr Val
625                 630                 635                 640

Gln Arg Leu Leu Pro Val Leu Cys Gln Ala His Gly Leu Thr Pro Glu
            645                 650                 655

Gln Val Val Ala Ile Ala Ser Asn Gly Gly Lys Gln Ala Leu Glu
            660                 665                 670

Thr Val Gln Arg Leu Leu Pro Val Leu Cys Gln Ala His Gly Leu Thr
            675                 680                 685

Pro Glu Gln Val Val Ala Ile Ala Ser Asn Gly Gly Arg Pro Ala
            690                 695                 700

Leu Glu Ser Ile Val Ala Gln Leu Ser Arg Pro Asp Pro Ala Leu Ala
705                 710                 715                 720

Ala Leu Thr Asn Asp His Leu Val Ala Leu Ala Cys Leu Gly Gly Arg
            725                 730                 735

Pro Ala Leu Asp Ala Val Lys Lys Gly Leu Pro His Ala Pro Ala Leu
            740                 745                 750

Ile Lys Arg Thr Asn Arg Arg Ile Pro Glu Arg Thr Ser His Arg Val
            755                 760                 765

Ala Gly Ser Gln Leu Val Lys Ser Glu Leu Glu Glu Lys Lys Ser Glu
            770                 775                 780

Leu Arg His Lys Leu Lys Tyr Val Pro His Glu Tyr Ile Glu Leu Ile
785                 790                 795                 800

Glu Ile Ala Arg Asn Ser Thr Gln Asp Arg Ile Leu Glu Met Lys Val
            805                 810                 815

Met Glu Phe Phe Met Lys Val Tyr Gly Tyr Arg Gly Lys His Leu Gly
            820                 825                 830

Gly Ser Arg Lys Pro Asp Gly Ala Ile Tyr Thr Val Gly Ser Pro Ile
            835                 840                 845

Asp Tyr Gly Val Ile Val Asp Thr Lys Ala Tyr Ser Gly Gly Tyr Asn
850                 855                 860

Leu Pro Ile Gly Gln Ala Asp Glu Met Gln Arg Tyr Val Glu Glu Asn
865                 870                 875                 880

Gln Thr Arg Asn Lys His Ile Asn Pro Asn Glu Trp Trp Lys Val Tyr
            885                 890                 895

Pro Ser Ser Val Thr Glu Phe Lys Phe Leu Phe Val Ser Gly His Phe
            900                 905                 910

Lys Gly Asn Tyr Lys Ala Gln Leu Thr Arg Leu Asn His Ile Thr Asn
```

```
                915                 920                 925
Cys Asn Gly Ala Val Leu Ser Val Glu Glu Leu Leu Ile Gly Gly Glu
    930                 935                 940

Met Ile Lys Ala Gly Thr Leu Thr Leu Glu Glu Val Arg Arg Lys Phe
945                 950                 955                 960

Asn Asn Gly Glu Ile Asn Phe Arg Ser
                965
```

<210> SEQ ID NO 356
<211> LENGTH: 49
<212> TYPE: DNA
<213> ORGANISM: Homo Sapiens

<400> SEQUENCE: 356
ttccagagag caatatggct ggttccccaa catgcctcac cctcatcta                49

<210> SEQ ID NO 357
<211> LENGTH: 17
<212> TYPE: DNA
<213> ORGANISM: Homo Sapiens

<400> SEQUENCE: 357
ttccagagag caatatg                                                  17

<210> SEQ ID NO 358
<211> LENGTH: 969
<212> TYPE: PRT
<213> ORGANISM: Homo Sapiens

<400> SEQUENCE: 358

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
                20                  25                  30

Gly Ile His Gly Val Pro Ala Ala Val Asp Leu Arg Thr Leu Gly Tyr
                35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
                100                 105                 110

Ile Val Gly Val Gly Lys Gln Trp Ser Gly Ala Arg Ala Leu Glu Ala
                115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Gly Gly Gly Lys
                180                 185                 190

Gln Ala Leu Glu Thr Val Gln Arg Leu Leu Pro Val Leu Cys Gln Ala
                195                 200                 205

His Gly Leu Thr Pro Glu Gln Val Val Ala Ile Ala Ser His Asp Gly
```

```
            210                 215                 220
Gly Lys Gln Ala Leu Glu Thr Val Gln Arg Leu Leu Pro Val Leu Cys
225                 230                 235                 240

Gln Ala His Gly Leu Thr Pro Glu Gln Val Val Ala Ile Ala Ser His
                245                 250                 255

Asp Gly Gly Lys Gln Ala Leu Glu Thr Val Gln Arg Leu Leu Pro Val
                260                 265                 270

Leu Cys Gln Ala His Gly Leu Thr Pro Glu Gln Val Val Ala Ile Ala
                275                 280                 285

Ser Asn Ile Gly Gly Lys Gln Ala Leu Glu Thr Val Gln Arg Leu Leu
            290                 295                 300

Pro Val Leu Cys Gln Ala His Gly Leu Thr Pro Glu Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Glu Gln Val
                340                 345                 350

Val Ala Ile Ala Ser Asn Ile Gly Gly Lys Gln Ala Leu Glu Thr Val
                355                 360                 365

Gln Arg Leu Leu Pro Val Leu Cys Gln Ala His Gly Leu Thr Pro Glu
                370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser Asn Ile Gly Gly Lys Gln Ala
                420                 425                 430

Leu Glu Thr Val Gln Arg Leu Leu Pro Val Leu Cys Gln Ala His Gly
                435                 440                 445

Leu Thr Pro Glu Gln Val Val Ala Ile Ala Ser Asn Asn Gly Gly Lys
                450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser His Asp Gly
                485                 490                 495

Gly Lys Gln Ala Leu Glu Thr Val Gln Arg Leu Leu Pro Val Leu Cys
                500                 505                 510

Gln Ala His Gly Leu Thr Pro Glu Gln Val Val Ala Ile Ala Ser Asn
                515                 520                 525

Ile Gly Gly Lys Gln Ala Leu Glu Thr Val Gln Arg Leu Leu Pro Val
            530                 535                 540

Leu Cys Gln Ala His Gly Leu Thr Pro Glu Gln Val Val Ala Ile Ala
545                 550                 555                 560

Ser Asn Ile Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
                580                 585                 590

Ile Ala Ser Asn Gly Gly Gly Lys Gln Ala Leu Glu Thr Val Gln Arg
                595                 600                 605

Leu Leu Pro Val Leu Cys Gln Ala His Gly Leu Thr Pro Glu Gln Val
                610                 615                 620

Val Ala Ile Ala Ser Asn Ile Gly Gly Lys Gln Ala Leu Glu Thr Val
625                 630                 635                 640
```

```
Gln Arg Leu Leu Pro Val Leu Cys Gln Ala His Gly Leu Thr Pro Glu
            645                 650                 655
Gln Val Val Ala Ile Ala Ser Asn Gly Gly Lys Gln Ala Leu Glu
        660                 665                 670
Thr Val Gln Arg Leu Leu Pro Val Leu Cys Gln Ala His Gly Leu Thr
    675                 680                 685
Pro Glu Gln Val Val Ala Ile Ala Ser Asn Asn Gly Gly Arg Pro Ala
690                 695                 700
Leu Glu Ser Ile Val Ala Gln Leu Ser Arg Pro Asp Pro Ala Leu Ala
705                 710                 715                 720
Ala Leu Thr Asn Asp His Leu Val Ala Leu Ala Cys Leu Gly Gly Arg
                725                 730                 735
Pro Ala Leu Asp Ala Val Lys Lys Gly Leu Pro His Ala Pro Ala Leu
            740                 745                 750
Ile Lys Arg Thr Asn Arg Arg Ile Pro Glu Arg Thr Ser His Arg Val
        755                 760                 765
Ala Gly Ser Gln Leu Val Lys Ser Glu Leu Glu Glu Lys Lys Ser Glu
    770                 775                 780
Leu Arg His Lys Leu Lys Tyr Val Pro His Glu Tyr Ile Glu Leu Ile
785                 790                 795                 800
Glu Ile Ala Arg Asn Ser Thr Gln Asp Arg Ile Leu Glu Met Lys Val
                805                 810                 815
Met Glu Phe Phe Met Lys Val Tyr Gly Tyr Arg Gly Lys His Leu Gly
            820                 825                 830
Gly Ser Arg Lys Pro Asp Gly Ala Ile Tyr Thr Val Gly Ser Pro Ile
        835                 840                 845
Asp Tyr Gly Val Ile Val Asp Thr Lys Ala Tyr Ser Gly Gly Tyr Asn
    850                 855                 860
Leu Pro Ile Gly Gln Ala Asp Glu Met Gln Arg Tyr Val Glu Glu Asn
865                 870                 875                 880
Gln Thr Arg Asn Lys His Ile Asn Pro Asn Glu Trp Trp Lys Val Tyr
                885                 890                 895
Pro Ser Ser Val Thr Glu Phe Lys Phe Leu Phe Val Ser Gly His Phe
            900                 905                 910
Lys Gly Asn Tyr Lys Ala Gln Leu Thr Arg Leu Asn His Ile Thr Asn
        915                 920                 925
Cys Asn Gly Ala Val Leu Ser Val Glu Glu Leu Leu Ile Gly Gly Glu
    930                 935                 940
Met Ile Lys Ala Gly Thr Leu Thr Leu Glu Glu Val Arg Arg Lys Phe
945                 950                 955                 960
Asn Asn Gly Glu Ile Asn Phe Arg Ser
                965

<210> SEQ ID NO 359
<211> LENGTH: 17
<212> TYPE: DNA
<213> ORGANISM: Homo Sapiens

<400> SEQUENCE: 359
tgcctcaccc tcatcta                                                  17

<210> SEQ ID NO 360
<211> LENGTH: 969
<212> TYPE: PRT
<213> ORGANISM: Homo Sapiens
```

<400> SEQUENCE: 360

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Val Asp Leu Arg Thr Leu Gly Tyr
                35                  40                  45

Ser Gln Gln Gln Gln Glu Lys Ile Lys Pro Lys Val Arg Ser Thr Val
        50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
                115                 120                 125

Leu Leu Thr Val Ala Gly Glu Leu Arg Gly Pro Pro Leu Gln Leu Asp
130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190

Gln Ala Leu Glu Thr Val Gln Arg Leu Leu Pro Val Leu Cys Gln Ala
        195                 200                 205

His Gly Leu Thr Pro Glu Gln Val Val Ala Ile Ala Ser Asn Asn Gly
210                 215                 220

Gly Lys Gln Ala Leu Glu Thr Val Gln Arg Leu Leu Pro Val Leu Cys
225                 230                 235                 240

Gln Ala His Gly Leu Thr Pro Glu Gln Val Val Ala Ile Ala Ser Asn
                245                 250                 255

Ile Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
        275                 280                 285

Ser Asn Gly Gly Gly Lys Gln Ala Leu Glu Thr Val Gln Arg Leu Leu
    290                 295                 300

Pro Val Leu Cys Gln Ala His Gly Leu Thr Pro Glu Gln Val Val Ala
305                 310                 315                 320

Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser Asn Ile Gly Gly Lys Gln Ala Leu Glu Thr Val
        355                 360                 365

Gln Arg Leu Leu Pro Val Leu Cys Gln Ala His Gly Leu Thr Pro Glu
370                 375                 380

Gln Val Val Ala Ile Ala Ser Asn Asn Gly Gly Lys Gln Ala Leu Glu
385                 390                 395                 400

Thr Val Gln Arg Leu Leu Pro Val Leu Cys Gln Ala His Gly Leu Thr
```

-continued

```
                405                 410                 415
Pro Glu Gln Val Val Ala Ile Ala Ser Asn Asn Gly Gly Lys Gln Ala
                420                 425                 430

Leu Glu Thr Val Gln Arg Leu Leu Pro Val Leu Cys Gln Ala His Gly
                435                 440                 445

Leu Thr Pro Glu Gln Val Val Ala Ile Ala Ser Asn Asn Gly Gly Lys
                450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Gly Gly
                485                 490                 495

Gly Lys Gln Ala Leu Glu Thr Val Gln Arg Leu Leu Pro Val Leu Cys
                500                 505                 510

Gln Ala His Gly Leu Thr Pro Glu Gln Val Val Ala Ile Ala Ser Asn
                515                 520                 525

Asn Gly Gly Lys Gln Ala Leu Glu Thr Val Gln Arg Leu Leu Pro Val
530                 535                 540

Leu Cys Gln Ala His Gly Leu Thr Pro Glu Gln Val Val Ala Ile Ala
545                 550                 555                 560

Ser Asn Ile Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
                580                 585                 590

Ile Ala Ser Asn Asn Gly Gly Lys Gln Ala Leu Glu Thr Val Gln Arg
                595                 600                 605

Leu Leu Pro Val Leu Cys Gln Ala His Gly Leu Thr Pro Glu Gln Val
610                 615                 620

Val Ala Ile Ala Ser Asn Asn Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser His Asp Gly Gly Lys Gln Ala Leu Glu
                660                 665                 670

Thr Val Gln Arg Leu Leu Pro Val Leu Cys Gln Ala His Gly Leu Thr
                675                 680                 685

Pro Glu Gln Val Val Ala Ile Ala Ser Asn Ile Gly Gly Arg Pro Ala
                690                 695                 700

Leu Glu Ser Ile Val Ala Gln Leu Ser Arg Pro Asp Pro Ala Leu Ala
705                 710                 715                 720

Ala Leu Thr Asn Asp His Leu Val Ala Leu Ala Cys Leu Gly Gly Arg
                725                 730                 735

Pro Ala Leu Asp Ala Val Lys Lys Gly Leu Pro His Ala Pro Ala Leu
                740                 745                 750

Ile Lys Arg Thr Asn Arg Arg Ile Pro Glu Arg Thr Ser His Arg Val
                755                 760                 765

Ala Gly Ser Gln Leu Val Lys Ser Glu Leu Glu Glu Lys Lys Ser Glu
                770                 775                 780

Leu Arg His Lys Leu Lys Tyr Val Pro His Glu Tyr Ile Glu Leu Ile
785                 790                 795                 800

Glu Ile Ala Arg Asn Ser Thr Gln Asp Arg Ile Leu Glu Met Lys Val
                805                 810                 815

Met Glu Phe Phe Met Lys Val Tyr Gly Tyr Arg Gly Lys His Leu Gly
                820                 825                 830
```

```
Gly Ser Arg Lys Pro Asp Gly Ala Ile Tyr Thr Val Gly Ser Pro Ile
        835                 840                 845

Asp Tyr Gly Val Ile Val Asp Thr Lys Ala Tyr Ser Gly Gly Tyr Asn
    850                 855                 860

Leu Pro Ile Gly Gln Ala Asp Glu Met Gln Arg Tyr Val Glu Asn
865                 870                 875                 880

Gln Thr Arg Asn Lys His Ile Asn Pro Asn Glu Trp Trp Lys Val Tyr
                885                 890                 895

Pro Ser Ser Val Thr Glu Phe Lys Phe Leu Phe Val Ser Gly His Phe
                900                 905                 910

Lys Gly Asn Tyr Lys Ala Gln Leu Thr Arg Leu Asn His Ile Thr Asn
                915                 920                 925

Cys Asn Gly Ala Val Leu Ser Val Glu Glu Leu Leu Ile Gly Gly Glu
                930                 935                 940

Met Ile Lys Ala Gly Thr Leu Thr Leu Glu Glu Val Arg Arg Lys Phe
945                 950                 955                 960

Asn Asn Gly Glu Ile Asn Phe Arg Ser
                965

<210> SEQ ID NO 361
<211> LENGTH: 49
<212> TYPE: DNA
<213> ORGANISM: Homo Sapiens

<400> SEQUENCE: 361
ttgactctat tgtctggacc ttcaacacaa cccctcttgt caccataca           49

<210> SEQ ID NO 362
<211> LENGTH: 17
<212> TYPE: DNA
<213> ORGANISM: Homo Sapiens

<400> SEQUENCE: 362
ttgactctat tgtctgg                                              17

<210> SEQ ID NO 363
<211> LENGTH: 969
<212> TYPE: PRT
<213> ORGANISM: Homo Sapiens

<400> SEQUENCE: 363

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Val Asp Leu Arg Thr Leu Gly Tyr
            35                  40                  45

Ser Gln Gln Gln Gln Glu Lys Ile Lys Pro Lys Val Arg Ser Thr Val
        50                  55                  60

Ala Gln His His Glu Ala Leu Val Gly His Gly Phe Thr His Ala His
65              70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125
```

```
Leu Leu Thr Val Ala Gly Glu Leu Arg Gly Pro Leu Gln Leu Asp
            130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Gly Gly Gly Lys
            180                 185                 190

Gln Ala Leu Glu Thr Val Gln Arg Leu Leu Pro Val Leu Cys Gln Ala
        195                 200                 205

His Gly Leu Thr Pro Glu Gln Val Val Ala Ile Ala Ser Asn Asn Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Glu Gln Val Val Ala Ile Ala Ser Asn
                245                 250                 255

Ile Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Glu Gln Val Val Ala
305                 310                 315                 320

Ile Ala Ser Asn Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser His Asp Gly Gly Lys Gln Ala Leu Glu Thr Val
        355                 360                 365

Gln Arg Leu Leu Pro Val Leu Cys Gln Ala His Gly Leu Thr Pro Glu
    370                 375                 380

Gln Val Val Ala Ile Ala Ser Asn Gly Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser Asn Ile Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Gly Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser Asn
        515                 520                 525

Asn Gly Gly Lys Gln Ala Leu Glu Thr Val Gln Arg Leu Leu Pro Val
    530                 535                 540
```

```
Leu Cys Gln Ala His Gly Leu Thr Pro Glu Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
            580                 585                 590

Ile Ala Ser His Asp Gly Gly Lys Gln Ala Leu Glu Thr Val Gln Arg
        595                 600                 605

Leu Leu Pro Val Leu Cys Gln Ala His Gly Leu Thr Pro Glu Gln Val
    610                 615                 620

Val Ala Ile Ala Ser Asn Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser Asn Asn Gly Gly Lys Gln Ala Leu Glu
                660                 665                 670

Thr Val Gln Arg Leu Leu Pro Val Leu Cys Gln Ala His Gly Leu Thr
            675                 680                 685

Pro Glu Gln Val Val Ala Ile Ala Ser Asn Asn Gly Gly Arg Pro Ala
        690                 695                 700

Leu Glu Ser Ile Val Ala Gln Leu Ser Arg Pro Asp Pro Ala Leu Ala
705                 710                 715                 720

Ala Leu Thr Asn Asp His Leu Val Ala Leu Ala Cys Leu Gly Gly Arg
                725                 730                 735

Pro Ala Leu Asp Ala Val Lys Lys Gly Leu Pro His Ala Pro Ala Leu
                740                 745                 750

Ile Lys Arg Thr Asn Arg Arg Ile Pro Glu Arg Thr Ser His Arg Val
            755                 760                 765

Ala Gly Ser Gln Leu Val Lys Ser Glu Leu Glu Lys Lys Ser Glu
            770                 775                 780

Leu Arg His Lys Leu Lys Tyr Val Pro His Glu Tyr Ile Glu Leu Ile
785                 790                 795                 800

Glu Ile Ala Arg Asn Ser Thr Gln Asp Arg Ile Leu Glu Met Lys Val
                805                 810                 815

Met Glu Phe Phe Met Lys Val Tyr Gly Tyr Arg Gly Lys His Leu Gly
                820                 825                 830

Gly Ser Arg Lys Pro Asp Gly Ala Ile Tyr Thr Val Gly Ser Pro Ile
            835                 840                 845

Asp Tyr Gly Val Ile Val Asp Thr Lys Ala Tyr Ser Gly Gly Tyr Asn
850                 855                 860

Leu Pro Ile Gly Gln Ala Asp Glu Met Gln Arg Tyr Val Glu Glu Asn
865                 870                 875                 880

Gln Thr Arg Asn Lys His Ile Asn Pro Asn Glu Trp Trp Lys Val Tyr
                885                 890                 895

Pro Ser Ser Val Thr Glu Phe Lys Phe Leu Phe Val Ser Gly His Phe
            900                 905                 910

Lys Gly Asn Tyr Lys Ala Gln Leu Thr Arg Leu Asn His Ile Thr Asn
            915                 920                 925

Cys Asn Gly Ala Val Leu Ser Val Glu Glu Leu Leu Ile Gly Gly Glu
            930                 935                 940

Met Ile Lys Ala Gly Thr Leu Thr Leu Glu Glu Val Arg Arg Lys Phe
945                 950                 955                 960

Asn Asn Gly Glu Ile Asn Phe Arg Ser
```

965

<210> SEQ ID NO 364
<211> LENGTH: 17
<212> TYPE: DNA
<213> ORGANISM: Homo Sapiens

<400> SEQUENCE: 364
cctcttgtca ccataca                                                    17

<210> SEQ ID NO 365
<211> LENGTH: 969
<212> TYPE: PRT
<213> ORGANISM: Homo Sapiens

<400> SEQUENCE: 365

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Val Asp Leu Arg Thr Leu Gly Tyr
        35                  40                  45

Ser Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Asn Gly Gly Lys
            180                 185                 190

Gln Ala Leu Glu Thr Val Gln Arg Leu Leu Pro Val Leu Cys Gln Ala
        195                 200                 205

His Gly Leu Thr Pro Glu Gln Val Val Ala Ile Ala Ser Asn Gly Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Glu Gln Val Val Ala Ile Ala Ser Asn
                245                 250                 255

Ile Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
        275                 280                 285

Ser Asn Gly Gly Gly Lys Gln Ala Leu Glu Thr Val Gln Arg Leu Leu
    290                 295                 300

Pro Val Leu Cys Gln Ala His Gly Leu Thr Pro Glu Gln Val Val Ala
305                 310                 315                 320

```
Ile Ala Ser Asn Asn Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser Asn Asn Gly Gly Lys Gln Ala Leu Glu Thr Val
        355                 360                 365

Gln Arg Leu Leu Pro Val Leu Cys Gln Ala His Gly Leu Thr Pro Glu
    370                 375                 380

Gln Val Val Ala Ile Ala Ser Asn Gly Gly Lys Gln Ala Leu Glu
385                 390                 395                 400

Thr Val Gln Arg Leu Leu Pro Val Leu Cys Gln Ala His Gly Leu Thr
            405                 410                 415

Pro Glu Gln Val Val Ala Ile Ala Ser Asn Asn Gly Gly Lys Gln Ala
        420                 425                 430

Leu Glu Thr Val Gln Arg Leu Leu Pro Val Leu Cys Gln Ala His Gly
    435                 440                 445

Leu Thr Pro Glu Gln Val Val Ala Ile Ala Ser Asn Ile Gly Gly Lys
450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser His Asp Gly
            485                 490                 495

Gly Lys Gln Ala Leu Glu Thr Val Gln Arg Leu Leu Pro Val Leu Cys
        500                 505                 510

Gln Ala His Gly Leu Thr Pro Glu Gln Val Val Ala Ile Ala Ser Asn
    515                 520                 525

Ile Gly Gly Lys Gln Ala Leu Glu Thr Val Gln Arg Leu Leu Pro Val
530                 535                 540

Leu Cys Gln Ala His Gly Leu Thr Pro Glu Gln Val Val Ala Ile Ala
545                 550                 555                 560

Ser Asn Ile Gly Gly Lys Gln Ala Leu Glu Thr Val Gln Arg Leu Leu
            565                 570                 575

Pro Val Leu Cys Gln Ala His Gly Leu Thr Pro Glu Gln Val Val Ala
        580                 585                 590

Ile Ala Ser Asn Asn Gly Gly Lys Gln Ala Leu Glu Thr Val Gln Arg
    595                 600                 605

Leu Leu Pro Val Leu Cys Gln Ala His Gly Leu Thr Pro Glu Gln Val
610                 615                 620

Val Ala Ile Ala Ser Asn Ile Gly Gly Lys Gln Ala Leu Glu Thr Val
625                 630                 635                 640

Gln Arg Leu Leu Pro Val Leu Cys Gln Ala His Gly Leu Thr Pro Glu
            645                 650                 655

Gln Val Val Ala Ile Ala Ser Asn Asn Gly Gly Lys Gln Ala Leu Glu
        660                 665                 670

Thr Val Gln Arg Leu Leu Pro Val Leu Cys Gln Ala His Gly Leu Thr
    675                 680                 685

Pro Glu Gln Val Val Ala Ile Ala Ser Asn Asn Gly Gly Arg Pro Ala
690                 695                 700

Leu Glu Ser Ile Val Ala Gln Leu Ser Arg Pro Asp Pro Ala Leu Ala
705                 710                 715                 720

Ala Leu Thr Asn Asp His Leu Val Ala Leu Ala Cys Leu Gly Gly Arg
            725                 730                 735
```

```
Pro Ala Leu Asp Ala Val Lys Lys Gly Leu Pro His Ala Pro Ala Leu
            740                 745                 750

Ile Lys Arg Thr Asn Arg Ile Pro Glu Arg Thr Ser His Arg Val
        755                 760                 765

Ala Gly Ser Gln Leu Val Lys Ser Glu Leu Glu Glu Lys Lys Ser Glu
770                 775                 780

Leu Arg His Lys Leu Lys Tyr Val Pro His Glu Tyr Ile Glu Leu Ile
785                 790                 795                 800

Glu Ile Ala Arg Asn Ser Thr Gln Asp Arg Ile Leu Glu Met Lys Val
                805                 810                 815

Met Glu Phe Phe Met Lys Val Tyr Gly Tyr Arg Gly Lys His Leu Gly
            820                 825                 830

Gly Ser Arg Lys Pro Asp Gly Ala Ile Tyr Thr Val Gly Ser Pro Ile
        835                 840                 845

Asp Tyr Gly Val Ile Val Asp Thr Lys Ala Tyr Ser Gly Gly Tyr Asn
    850                 855                 860

Leu Pro Ile Gly Gln Ala Asp Glu Met Gln Arg Tyr Val Glu Glu Asn
865                 870                 875                 880

Gln Thr Arg Asn Lys His Ile Asn Pro Asn Glu Trp Trp Lys Val Tyr
                885                 890                 895

Pro Ser Ser Val Thr Glu Phe Lys Phe Leu Phe Val Ser Gly His Phe
            900                 905                 910

Lys Gly Asn Tyr Lys Ala Gln Leu Thr Arg Leu Asn His Ile Thr Asn
        915                 920                 925

Cys Asn Gly Ala Val Leu Ser Val Glu Glu Leu Leu Ile Gly Gly Glu
    930                 935                 940

Met Ile Lys Ala Gly Thr Leu Thr Leu Glu Glu Val Arg Arg Lys Phe
945                 950                 955                 960

Asn Asn Gly Glu Ile Asn Phe Arg Ser
                965

<210> SEQ ID NO 366
<211> LENGTH: 49
<212> TYPE: DNA
<213> ORGANISM: Homo Sapiens

<400> SEQUENCE: 366
ttccctccca ggcagctcac agtgtgccac catggagttg gggcccta                    49

<210> SEQ ID NO 367
<211> LENGTH: 18
<212> TYPE: DNA
<213> ORGANISM: Homo Sapiens

<400> SEQUENCE: 367
ttccctccca ggcagctc                                                      18

<210> SEQ ID NO 368
<211> LENGTH: 1003
<212> TYPE: PRT
<213> ORGANISM: Homo Sapiens

<400> SEQUENCE: 368

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30
```

```
Gly Ile His Gly Val Pro Ala Ala Val Asp Leu Arg Thr Leu Gly Tyr
            35                  40                  45

Ser Gln Gln Gln Gln Glu Lys Ile Lys Pro Lys Val Arg Ser Thr Val
 50                  55                  60

Ala Gln His His Glu Ala Leu Val Gly His Gly Phe Thr His Ala His
 65                  70                  75                  80

Ile Val Ala Leu Ser Gln His Pro Ala Ala Leu Gly Thr Val Ala Val
                 85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
            115                 120                 125

Leu Leu Thr Val Ala Gly Glu Leu Arg Gly Pro Pro Leu Gln Leu Asp
130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Gly Gly Gly Lys
            180                 185                 190

Gln Ala Leu Glu Thr Val Gln Arg Leu Leu Pro Val Leu Cys Gln Ala
            195                 200                 205

His Gly Leu Thr Pro Glu Gln Val Val Ala Ile Ala Ser His Asp Gly
            210                 215                 220

Gly Lys Gln Ala Leu Glu Thr Val Gln Arg Leu Leu Pro Val Leu Cys
225                 230                 235                 240

Gln Ala His Gly Leu Thr Pro Glu Gln Val Val Ala Ile Ala Ser His
                245                 250                 255

Asp Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
            275                 280                 285

Ser His Asp Gly Gly Lys Gln Ala Leu Glu Thr Val Gln Arg Leu Leu
            290                 295                 300

Pro Val Leu Cys Gln Ala His Gly Leu Thr Pro Glu Gln Val Val Ala
305                 310                 315                 320

Ile Ala Ser Asn Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser His Asp Gly Gly Lys Gln Ala Leu Glu Thr Val
            355                 360                 365

Gln Arg Leu Leu Pro Val Leu Cys Gln Ala His Gly Leu Thr Pro Glu
370                 375                 380

Gln Val Val Ala Ile Ala Ser His Asp Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser His Asp Gly Gly Lys Gln Ala
            420                 425                 430

Leu Glu Thr Val Gln Arg Leu Leu Pro Val Leu Cys Gln Ala His Gly
            435                 440                 445

Leu Thr Pro Glu Gln Val Val Ala Ile Ala Ser Asn Ile Gly Gly Lys
```

```
            450                 455                 460
Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Asn Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser Asn
        515                 520                 525

Asn Gly Gly Lys Gln Ala Leu Glu Thr Val Gln Arg Leu Leu Pro Val
    530                 535                 540

Leu Cys Gln Ala His Gly Leu Thr Pro Glu Gln Val Val Ala Ile Ala
545                 550                 555                 560

Ser His Asp Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
            580                 585                 590

Ile Ala Ser Asn Ile Gly Gly Lys Gln Ala Leu Glu Thr Val Gln Arg
        595                 600                 605

Leu Leu Pro Val Leu Cys Gln Ala His Gly Leu Thr Pro Glu Gln Val
    610                 615                 620

Val Ala Ile Ala Ser Asn Asn Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser His Asp Gly Gly Lys Gln Ala Leu Glu
            660                 665                 670

Thr Val Gln Arg Leu Leu Pro Val Leu Cys Gln Ala His Gly Leu Thr
        675                 680                 685

Pro Glu Gln Val Val Ala Ile Ala Ser Asn Gly Gly Gly Lys Gln Ala
    690                 695                 700

Leu Glu Thr Val Gln Arg Leu Leu Pro Val Leu Cys Gln Ala His Gly
705                 710                 715                 720

Leu Thr Pro Glu Gln Val Val Ala Ile Ala Ser His Asp Gly Gly Arg
                725                 730                 735

Pro Ala Leu Glu Ser Ile Val Ala Gln Leu Ser Arg Pro Asp Pro Ala
            740                 745                 750

Leu Ala Ala Leu Thr Asn Asp His Leu Val Ala Leu Ala Cys Leu Gly
        755                 760                 765

Gly Arg Pro Ala Leu Asp Ala Val Lys Lys Gly Leu Pro His Ala Pro
    770                 775                 780

Ala Leu Ile Lys Arg Thr Asn Arg Arg Ile Pro Glu Arg Thr Ser His
785                 790                 795                 800

Arg Val Ala Gly Ser Gln Leu Val Lys Ser Glu Leu Glu Glu Lys Lys
                805                 810                 815

Ser Glu Leu Arg His Lys Leu Lys Tyr Val Pro His Glu Tyr Ile Glu
            820                 825                 830

Leu Ile Glu Ile Ala Arg Asn Ser Thr Gln Asp Arg Ile Leu Glu Met
        835                 840                 845

Lys Val Met Glu Phe Phe Met Lys Val Tyr Gly Tyr Arg Gly Lys His
    850                 855                 860

Leu Gly Gly Ser Arg Lys Pro Asp Gly Ala Ile Tyr Thr Val Gly Ser
865                 870                 875                 880
```

```
Pro Ile Asp Tyr Gly Val Ile Val Asp Thr Lys Ala Tyr Ser Gly Gly
                885                 890                 895

Tyr Asn Leu Pro Ile Gly Gln Ala Asp Glu Met Gln Arg Tyr Val Glu
            900                 905                 910

Glu Asn Gln Thr Arg Asn Lys His Ile Asn Pro Asn Glu Trp Trp Lys
        915                 920                 925

Val Tyr Pro Ser Ser Val Thr Glu Phe Lys Phe Leu Phe Val Ser Gly
    930                 935                 940

His Phe Lys Gly Asn Tyr Lys Ala Gln Leu Thr Arg Leu Asn His Ile
945                 950                 955                 960

Thr Asn Cys Asn Gly Ala Val Leu Ser Val Glu Glu Leu Leu Ile Gly
                965                 970                 975

Gly Glu Met Ile Lys Ala Gly Thr Leu Thr Leu Glu Glu Val Arg Arg
            980                 985                 990

Lys Phe Asn Asn Gly Glu Ile Asn  Phe Arg Ser
        995                 1000
```

<210> SEQ ID NO 369
<211> LENGTH: 17
<212> TYPE: DNA
<213> ORGANISM: Homo Sapiens

<400> SEQUENCE: 369
tggagttggg gccccta                                                        17

<210> SEQ ID NO 370
<211> LENGTH: 969
<212> TYPE: PRT
<213> ORGANISM: Homo Sapiens

<400> SEQUENCE: 370

```
Met Asp Tyr Lys Asp His Asp Gly Asp Tyr Lys Asp His Asp Ile Asp
1               5                   10                  15

Tyr Lys Asp Asp Asp Lys Met Ala Pro Lys Lys Arg Lys Val
            20                  25                  30

Gly Ile His Gly Val Pro Ala Ala Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Ile Gly Gly Lys
            180                 185                 190
```

-continued

```
Gln Ala Leu Glu Thr Val Gln Arg Leu Leu Pro Val Leu Cys Gln Ala
            195                 200                 205
His Gly Leu Thr Pro Glu Gln Val Val Ala Ile Ala Ser Asn Asn Gly
            210                 215                 220
Gly Lys Gln Ala Leu Glu Thr Val Gln Arg Leu Leu Pro Val Leu Cys
225                 230                 235                 240
Gln Ala His Gly Leu Thr Pro Glu Gln Val Val Ala Ile Ala Ser Asn
                245                 250                 255
Asn Gly Gly Lys Gln Ala Leu Glu Thr Val Gln Arg Leu Leu Pro Val
            260                 265                 270
Leu Cys Gln Ala His Gly Leu Thr Pro Glu Gln Val Val Ala Ile Ala
            275                 280                 285
Ser Asn Asn Gly Gly Lys Gln Ala Leu Glu Thr Val Gln Arg Leu Leu
            290                 295                 300
Pro Val Leu Cys Gln Ala His Gly Leu Thr Pro Glu Gln Val Val Ala
305                 310                 315                 320
Ile Ala Ser Asn Asn Gly Gly Lys Gln Ala Leu Glu Thr Val Gln Arg
                325                 330                 335
Leu Leu Pro Val Leu Cys Gln Ala His Gly Leu Thr Pro Glu Gln Val
            340                 345                 350
Val Ala Ile Ala Ser His Asp Gly Gly Lys Gln Ala Leu Glu Thr Val
            355                 360                 365
Gln Arg Leu Leu Pro Val Leu Cys Gln Ala His Gly Leu Thr Pro Glu
            370                 375                 380
Gln Val Val Ala Ile Ala Ser His Asp Gly Gly Lys Gln Ala Leu Glu
385                 390                 395                 400
Thr Val Gln Arg Leu Leu Pro Val Leu Cys Gln Ala His Gly Leu Thr
                405                 410                 415
Pro Glu Gln Val Val Ala Ile Ala Ser His Asp Gly Gly Lys Gln Ala
            420                 425                 430
Leu Glu Thr Val Gln Arg Leu Leu Pro Val Leu Cys Gln Ala His Gly
            435                 440                 445
Leu Thr Pro Glu Gln Val Val Ala Ile Ala Ser His Asp Gly Gly Lys
            450                 455                 460
Gln Ala Leu Glu Thr Val Gln Arg Leu Leu Pro Val Leu Cys Gln Ala
465                 470                 475                 480
His Gly Leu Thr Pro Glu Gln Val Val Ala Ile Ala Ser Asn Ile Gly
                485                 490                 495
Gly Lys Gln Ala Leu Glu Thr Val Gln Arg Leu Leu Pro Val Leu Cys
            500                 505                 510
Gln Ala His Gly Leu Thr Pro Glu Gln Val Val Ala Ile Ala Ser Asn
            515                 520                 525
Ile Gly Gly Lys Gln Ala Leu Glu Thr Val Gln Arg Leu Leu Pro Val
            530                 535                 540
Leu Cys Gln Ala His Gly Leu Thr Pro Glu Gln Val Val Ala Ile Ala
545                 550                 555                 560
Ser His Asp Gly Gly Lys Gln Ala Leu Glu Thr Val Gln Arg Leu Leu
                565                 570                 575
Pro Val Leu Cys Gln Ala His Gly Leu Thr Pro Glu Gln Val Val Ala
            580                 585                 590
Ile Ala Ser Asn Gly Gly Gly Lys Gln Ala Leu Glu Thr Val Gln Arg
            595                 600                 605
Leu Leu Pro Val Leu Cys Gln Ala His Gly Leu Thr Pro Glu Gln Val
```

```
                610              615              620
   Val Ala Ile Ala Ser His Asp Gly Gly Lys Gln Ala Leu Glu Thr Val
   625              630              635              640

Gln Arg Leu Leu Pro Val Leu Cys Gln Ala His Gly Leu Thr Pro Glu
                   645              650              655

Gln Val Val Ala Ile Ala Ser His Asp Gly Gly Lys Gln Ala Leu Glu
                    660              665              670

Thr Val Gln Arg Leu Leu Pro Val Leu Cys Gln Ala His Gly Leu Thr
               675              680              685

Pro Glu Gln Val Val Ala Ile Ala Ser Asn Ile Gly Gly Arg Pro Ala
               690              695              700

Leu Glu Ser Ile Val Ala Gln Leu Ser Arg Pro Asp Pro Ala Leu Ala
   705              710              715              720

Ala Leu Thr Asn Asp His Leu Val Ala Leu Ala Cys Leu Gly Gly Arg
                   725              730              735

Pro Ala Leu Asp Ala Val Lys Lys Gly Leu Pro His Ala Pro Ala Leu
                   740              745              750

Ile Lys Arg Thr Asn Arg Arg Ile Pro Glu Arg Thr Ser His Arg Val
               755              760              765

Ala Gly Ser Gln Leu Val Lys Ser Glu Leu Glu Glu Lys Lys Ser Glu
               770              775              780

Leu Arg His Lys Leu Lys Tyr Val Pro His Glu Tyr Ile Glu Leu Ile
   785              790              795              800

Glu Ile Ala Arg Asn Ser Thr Gln Asp Arg Ile Leu Glu Met Lys Val
                   805              810              815

Met Glu Phe Phe Met Lys Val Tyr Gly Tyr Arg Gly Lys His Leu Gly
                   820              825              830

Gly Ser Arg Lys Pro Asp Gly Ala Ile Tyr Thr Val Gly Ser Pro Ile
               835              840              845

Asp Tyr Gly Val Ile Val Asp Thr Lys Ala Tyr Ser Gly Gly Tyr Asn
   850              855              860

Leu Pro Ile Gly Gln Ala Asp Glu Met Gln Arg Tyr Val Glu Glu Asn
   865              870              875              880

Gln Thr Arg Asn Lys His Ile Asn Pro Asn Glu Trp Trp Lys Val Tyr
                   885              890              895

Pro Ser Ser Val Thr Glu Phe Lys Phe Leu Phe Val Ser Gly His Phe
                   900              905              910

Lys Gly Asn Tyr Lys Ala Gln Leu Thr Arg Leu Asn His Ile Thr Asn
               915              920              925

Cys Asn Gly Ala Val Leu Ser Val Glu Glu Leu Leu Ile Gly Gly Glu
               930              935              940

Met Ile Lys Ala Gly Thr Leu Thr Leu Glu Glu Val Arg Arg Lys Phe
   945              950              955              960

Asn Asn Gly Glu Ile Asn Phe Arg Ser
                   965

<210> SEQ ID NO 371
<211> LENGTH: 49
<212> TYPE: DNA
<213> ORGANISM: Homo Sapiens

<400> SEQUENCE: 371
ttcctcctac tcaccatcag cctcctggtt atggtacagg taagagcaa           49
```

<210> SEQ ID NO 372
<211> LENGTH: 17
<212> TYPE: DNA
<213> ORGANISM: Homo Sapiens

<400> SEQUENCE: 372
ttcctcctac tcaccat                                                    17

<210> SEQ ID NO 373
<211> LENGTH: 969
<212> TYPE: PRT
<213> ORGANISM: Homo Sapiens

<400> SEQUENCE: 373

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Val Asp Leu Arg Thr Leu Gly Tyr
            35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
        115                 120                 125

Leu Leu Thr Val Ala Gly Glu Leu Arg Gly Pro Pro Leu Gln Leu Asp
    130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Gly Gly Gly Lys
            180                 185                 190

Gln Ala Leu Glu Thr Val Gln Arg Leu Leu Pro Val Leu Cys Gln Ala
        195                 200                 205

His Gly Leu Thr Pro Glu Gln Val Val Ala Ile Ala Ser His Asp Gly
    210                 215                 220

Gly Lys Gln Ala Leu Glu Thr Val Gln Arg Leu Leu Pro Val Leu Cys
225                 230                 235                 240

Gln Ala His Gly Leu Thr Pro Glu Gln Val Val Ala Ile Ala Ser His
                245                 250                 255

Asp Gly Gly Lys Gln Ala Leu Glu Thr Val Gln Arg Leu Leu Pro Val
            260                 265                 270

Leu Cys Gln Ala His Gly Leu Thr Pro Glu Gln Val Val Ala Ile Ala
        275                 280                 285

Ser Asn Gly Gly Gly Lys Gln Ala Leu Glu Thr Val Gln Arg Leu Leu
    290                 295                 300

Pro Val Leu Cys Gln Ala His Gly Leu Thr Pro Glu Gln Val Val Ala
305                 310                 315                 320

Ile Ala Ser His Asp Gly Gly Lys Gln Ala Leu Glu Thr Val Gln Arg
                325                 330                 335
```

```
Leu Leu Pro Val Leu Cys Gln Ala His Gly Leu Thr Pro Glu Gln Val
            340                 345                 350

Val Ala Ile Ala Ser His Asp Gly Lys Gln Ala Leu Glu Thr Val
        355                 360                 365

Gln Arg Leu Leu Pro Val Leu Cys Gln Ala His Gly Leu Thr Pro Glu
370                 375                 380

Gln Val Val Ala Ile Ala Ser Asn Gly Gly Lys Gln Ala Leu Glu
385                 390                 395                 400

Thr Val Gln Arg Leu Leu Pro Val Leu Cys Gln Ala His Gly Leu Thr
            405                 410                 415

Pro Glu Gln Val Val Ala Ile Ala Ser Asn Ile Gly Gly Lys Gln Ala
            420                 425                 430

Leu Glu Thr Val Gln Arg Leu Leu Pro Val Leu Cys Gln Ala His Gly
            435                 440                 445

Leu Thr Pro Glu Gln Val Val Ala Ile Ala Ser His Asp Gly Gly Lys
            450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Gly Gly
            485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser His
            515                 520                 525

Asp Gly Gly Lys Gln Ala Leu Glu Thr Val Gln Arg Leu Leu Pro Val
            530                 535                 540

Leu Cys Gln Ala His Gly Leu Thr Pro Glu Gln Val Val Ala Ile Ala
545                 550                 555                 560

Ser Asn Ile Gly Gly Lys Gln Ala Leu Glu Thr Val Gln Arg Leu Leu
            565                 570                 575

Pro Val Leu Cys Gln Ala His Gly Leu Thr Pro Glu Gln Val Val Ala
            580                 585                 590

Ile Ala Ser His Asp Gly Gly Lys Gln Ala Leu Glu Thr Val Gln Arg
            595                 600                 605

Leu Leu Pro Val Leu Cys Gln Ala His Gly Leu Thr Pro Glu Gln Val
            610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Ala His Gly Leu Thr Pro Glu
            645                 650                 655

Gln Val Val Ala Ile Ala Ser Asn Ile Gly Gly Lys Gln Ala Leu Glu
            660                 665                 670

Thr Val Gln Arg Leu Leu Pro Val Leu Cys Gln Ala His Gly Leu Thr
            675                 680                 685

Pro Glu Gln Val Val Ala Ile Ala Ser Asn Gly Gly Gly Arg Pro Ala
            690                 695                 700

Leu Glu Ser Ile Val Ala Gln Leu Ser Arg Pro Asp Pro Ala Leu Ala
705                 710                 715                 720

Ala Leu Thr Asn Asp His Leu Val Ala Leu Ala Cys Leu Gly Gly Arg
            725                 730                 735

Pro Ala Leu Asp Ala Val Lys Lys Gly Leu Pro His Ala Pro Ala Leu
            740                 745                 750
```

```
Ile Lys Arg Thr Asn Arg Arg Ile Pro Glu Arg Thr Ser His Arg Val
            755                 760                 765

Ala Gly Ser Gln Leu Val Lys Ser Glu Leu Glu Lys Lys Ser Glu
    770                 775                 780

Leu Arg His Lys Leu Lys Tyr Val Pro His Glu Tyr Ile Glu Leu Ile
785                 790                 795                 800

Glu Ile Ala Arg Asn Ser Thr Gln Asp Arg Ile Leu Glu Met Lys Val
                805                 810                 815

Met Glu Phe Phe Met Lys Val Tyr Gly Tyr Arg Gly Lys His Leu Gly
            820                 825                 830

Gly Ser Arg Lys Pro Asp Gly Ala Ile Tyr Thr Val Gly Ser Pro Ile
        835                 840                 845

Asp Tyr Gly Val Ile Val Asp Thr Lys Ala Tyr Ser Gly Gly Tyr Asn
    850                 855                 860

Leu Pro Ile Gly Gln Ala Asp Glu Met Gln Arg Tyr Val Glu Glu Asn
865                 870                 875                 880

Gln Thr Arg Asn Lys His Ile Asn Pro Asn Glu Trp Trp Lys Val Tyr
                885                 890                 895

Pro Ser Ser Val Thr Glu Phe Lys Phe Leu Phe Val Ser Gly His Phe
            900                 905                 910

Lys Gly Asn Tyr Lys Ala Gln Leu Thr Arg Leu Asn His Ile Thr Asn
        915                 920                 925

Cys Asn Gly Ala Val Leu Ser Val Glu Glu Leu Leu Ile Gly Gly Glu
    930                 935                 940

Met Ile Lys Ala Gly Thr Leu Thr Leu Glu Glu Val Arg Arg Lys Phe
945                 950                 955                 960

Asn Asn Gly Glu Ile Asn Phe Arg Ser
                965

<210> SEQ ID NO 374
<211> LENGTH: 17
<212> TYPE: DNA
<213> ORGANISM: Homo Sapiens

<400> SEQUENCE: 374
ggtacaggta agagcaa                                                    17

<210> SEQ ID NO 375
<211> LENGTH: 969
<212> TYPE: PRT
<213> ORGANISM: Homo Sapiens

<400> SEQUENCE: 375

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Lys Arg Lys Val
            20                  25                  30

Gly Ile His Gly Val Pro Ala Ala Val Asp Leu Arg Thr Leu Gly Tyr
        35                  40                  45

Ser Gln Gln Gln Gln Glu Lys Ile Lys Pro Lys Val Arg Ser Thr Val
    50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
```

```
                100             105                 110
        Ile Val Gly Val Gly Lys Gln Trp Ser Gly Ala Arg Ala Leu Glu Ala
                    115                 120                 125
        Leu Leu Thr Val Ala Gly Glu Leu Arg Gly Pro Leu Gln Leu Asp
                    130                 135                 140
        Thr Gly Gln Leu Leu Lys Ile Ala Lys Arg Gly Val Thr Ala Val
        145                 150                 155                 160
        Glu Ala Val His Ala Trp Arg Asn Ala Leu Thr Gly Ala Pro Leu Asn
                        165                 170                 175
        Leu Thr Pro Glu Gln Val Val Ala Ile Ala Ser Asn Gly Gly Lys
                    180                 185                 190
        Gln Ala Leu Glu Thr Val Gln Arg Leu Leu Pro Val Leu Cys Gln Ala
                    195                 200                 205
        His Gly Leu Thr Pro Glu Gln Val Val Ala Ile Ala Ser Asn Asn Gly
                    210                 215                 220
        Gly Lys Gln Ala Leu Glu Thr Val Gln Arg Leu Leu Pro Val Leu Cys
        225                 230                 235                 240
        Gln Ala His Gly Leu Thr Pro Glu Gln Val Val Ala Ile Ala Ser His
                        245                 250                 255
        Asp Gly Gly Lys Gln Ala Leu Glu Thr Val Gln Arg Leu Leu Pro Val
                    260                 265                 270
        Leu Cys Gln Ala His Gly Leu Thr Pro Glu Gln Val Val Ala Ile Ala
                    275                 280                 285
        Ser Asn Gly Gly Gly Lys Gln Ala Leu Glu Thr Val Gln Arg Leu Leu
                    290                 295                 300
        Pro Val Leu Cys Gln Ala His Gly Leu Thr Pro Glu Gln Val Val Ala
        305                 310                 315                 320
        Ile Ala Ser His Asp Gly Gly Lys Gln Ala Leu Glu Thr Val Gln Arg
                        325                 330                 335
        Leu Leu Pro Val Leu Cys Gln Ala His Gly Leu Thr Pro Glu Gln Val
                    340                 345                 350
        Val Ala Ile Ala Ser Asn Gly Gly Gly Lys Gln Ala Leu Glu Thr Val
                    355                 360                 365
        Gln Arg Leu Leu Pro Val Leu Cys Gln Ala His Gly Leu Thr Pro Glu
                    370                 375                 380
        Gln Val Val Ala Ile Ala Ser Asn Gly Gly Gly Lys Gln Ala Leu Glu
        385                 390                 395                 400
        Thr Val Gln Arg Leu Leu Pro Val Leu Cys Gln Ala His Gly Leu Thr
                        405                 410                 415
        Pro Glu Gln Val Val Ala Ile Ala Ser Asn Ile Gly Gly Lys Gln Ala
                    420                 425                 430
        Leu Glu Thr Val Gln Arg Leu Leu Pro Val Leu Cys Gln Ala His Gly
                    435                 440                 445
        Leu Thr Pro Glu Gln Val Val Ala Ile Ala Ser His Asp Gly Gly Lys
                    450                 455                 460
        Gln Ala Leu Glu Thr Val Gln Arg Leu Leu Pro Val Leu Cys Gln Ala
        465                 470                 475                 480
        His Gly Leu Thr Pro Glu Gln Val Val Ala Ile Ala Ser His Asp Gly
                        485                 490                 495
        Gly Lys Gln Ala Leu Glu Thr Val Gln Arg Leu Leu Pro Val Leu Cys
                    500                 505                 510
        Gln Ala His Gly Leu Thr Pro Glu Gln Val Val Ala Ile Ala Ser Asn
                    515                 520                 525
```

-continued

```
Gly Gly Gly Lys Gln Ala Leu Glu Thr Val Gln Arg Leu Leu Pro Val
        530                 535                 540
Leu Cys Gln Ala His Gly Leu Thr Pro Glu Gln Val Val Ala Ile Ala
545                 550                 555                 560
Ser Asn Asn Gly Gly Lys Gln Ala Leu Glu Thr Val Gln Arg Leu Leu
                565                 570                 575
Pro Val Leu Cys Gln Ala His Gly Leu Thr Pro Glu Gln Val Val Ala
            580                 585                 590
Ile Ala Ser Asn Gly Gly Lys Gln Ala Leu Glu Thr Val Gln Arg
        595                 600                 605
Leu Leu Pro Val Leu Cys Gln Ala His Gly Leu Thr Pro Glu Gln Val
610                 615                 620
Val Ala Ile Ala Ser Asn Ile Gly Gly Lys Gln Ala Leu Glu Thr Val
625                 630                 635                 640
Gln Arg Leu Leu Pro Val Leu Cys Gln Ala His Gly Leu Thr Pro Glu
                645                 650                 655
Gln Val Val Ala Ile Ala Ser His Asp Gly Gly Lys Gln Ala Leu Glu
            660                 665                 670
Thr Val Gln Arg Leu Leu Pro Val Leu Cys Gln Ala His Gly Leu Thr
        675                 680                 685
Pro Glu Gln Val Val Ala Ile Ala Ser His Asp Gly Gly Arg Pro Ala
690                 695                 700
Leu Glu Ser Ile Val Ala Gln Leu Ser Arg Pro Asp Pro Ala Leu Ala
705                 710                 715                 720
Ala Leu Thr Asn Asp His Leu Val Ala Leu Ala Cys Leu Gly Gly Arg
                725                 730                 735
Pro Ala Leu Asp Ala Val Lys Lys Gly Leu Pro His Ala Pro Ala Leu
            740                 745                 750
Ile Lys Arg Thr Asn Arg Arg Ile Pro Glu Arg Thr Ser His Arg Val
        755                 760                 765
Ala Gly Ser Gln Leu Val Lys Ser Glu Leu Glu Glu Lys Lys Ser Glu
770                 775                 780
Leu Arg His Lys Leu Lys Tyr Val Pro His Glu Tyr Ile Glu Leu Ile
785                 790                 795                 800
Glu Ile Ala Arg Asn Ser Thr Gln Asp Arg Ile Leu Glu Met Lys Val
                805                 810                 815
Met Glu Phe Phe Met Lys Val Tyr Gly Tyr Arg Gly Lys His Leu Gly
            820                 825                 830
Gly Ser Arg Lys Pro Asp Gly Ala Ile Tyr Thr Val Gly Ser Pro Ile
        835                 840                 845
Asp Tyr Gly Val Ile Val Asp Thr Lys Ala Tyr Ser Gly Gly Tyr Asn
850                 855                 860
Leu Pro Ile Gly Gln Ala Asp Glu Met Gln Arg Tyr Val Glu Glu Asn
865                 870                 875                 880
Gln Thr Arg Asn Lys His Ile Asn Pro Asn Glu Trp Trp Lys Val Tyr
                885                 890                 895
Pro Ser Ser Val Thr Glu Phe Lys Phe Leu Phe Val Ser Gly His Phe
            900                 905                 910
Lys Gly Asn Tyr Lys Ala Gln Leu Thr Arg Leu Asn His Ile Thr Asn
        915                 920                 925
Cys Asn Gly Ala Val Leu Ser Val Glu Glu Leu Leu Ile Gly Gly Glu
930                 935                 940
```

```
Met Ile Lys Ala Gly Thr Leu Thr Leu Glu Glu Val Arg Arg Lys Phe
945                 950                 955                 960

Asn Asn Gly Glu Ile Asn Phe Arg Ser
            965

<210> SEQ ID NO 376
<211> LENGTH: 49
<212> TYPE: DNA
<213> ORGANISM: Homo Sapiens

<400> SEQUENCE: 376
ttgtcccaca gatatccaga accctgaccc tgccgtgtac cagctgaga           49

<210> SEQ ID NO 377
<211> LENGTH: 17
<212> TYPE: DNA
<213> ORGANISM: Homo Sapiens

<400> SEQUENCE: 377
ttgtcccaca gatatcc                                              17

<210> SEQ ID NO 378
<211> LENGTH: 969
<212> TYPE: PRT
<213> ORGANISM: Homo Sapiens

<400> SEQUENCE: 378

Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30

Gly Ile His Gly Val Pro Ala Ala Val Asp Leu Arg Thr Leu Gly Tyr
            35                  40                  45

Ser Gln Gln Gln Gln Glu Lys Ile Lys Pro Lys Val Arg Ser Thr Val
50                  55                  60

Ala Gln His His Glu Ala Leu Val Gly His Gly Phe Thr His Ala His
65                  70                  75                  80

Ile Val Ala Leu Ser Gln His Pro Ala Ala Leu Gly Thr Val Ala Val
                85                  90                  95

Lys Tyr Gln Asp Met Ile Ala Ala Leu Pro Glu Ala Thr His Glu Ala
            100                 105                 110

Ile Val Gly Val Gly Lys Gln Trp Ser Gly Ala Arg Ala Leu Glu Ala
            115                 120                 125

Leu Leu Thr Val Ala Gly Glu Leu Arg Gly Pro Pro Leu Gln Leu Asp
130                 135                 140

Thr Gly Gln Leu Leu Lys Ile Ala Lys Arg Gly Gly Val Thr Ala Val
145                 150                 155                 160

Glu Ala Val His Ala Trp Arg Asn Ala Leu Thr Gly Ala Pro Leu Asn
                165                 170                 175

Leu Thr Pro Glu Gln Val Val Ala Ile Ala Ser Asn Gly Gly Gly Lys
            180                 185                 190

Gln Ala Leu Glu Thr Val Gln Arg Leu Leu Pro Val Leu Cys Gln Ala
            195                 200                 205

His Gly Leu Thr Pro Glu Gln Val Val Ala Ile Ala Ser Asn Asn Gly
210                 215                 220

Gly Lys Gln Ala Leu Glu Thr Val Gln Arg Leu Leu Pro Val Leu Cys
225                 230                 235                 240
```

-continued

Gln Ala His Gly Leu Thr Pro Glu Gln Val Ala Ile Ala Ser Asn
                245                 250                 255

Gly Gly Gly Lys Gln Ala Leu Glu Thr Val Gln Arg Leu Leu Pro Val
            260                 265                 270

Leu Cys Gln Ala His Gly Leu Thr Pro Glu Gln Val Ala Ile Ala
        275                 280                 285

Ser His Asp Gly Gly Lys Gln Ala Leu Glu Thr Val Gln Arg Leu Leu
    290                 295                 300

Pro Val Leu Cys Gln Ala His Gly Leu Thr Pro Glu Gln Val Val Ala
305                 310                 315                 320

Ile Ala Ser His Asp Gly Gly Lys Gln Ala Leu Glu Thr Val Gln Arg
                325                 330                 335

Leu Leu Pro Val Leu Cys Gln Ala His Gly Leu Thr Pro Glu Gln Val
            340                 345                 350

Val Ala Ile Ala Ser His Asp Gly Gly Lys Gln Ala Leu Glu Thr Val
        355                 360                 365

Gln Arg Leu Leu Pro Val Leu Cys Gln Ala His Gly Leu Thr Pro Glu
    370                 375                 380

Gln Val Val Ala Ile Ala Ser Asn Ile Gly Gly Lys Gln Ala Leu Glu
385                 390                 395                 400

Thr Val Gln Arg Leu Leu Pro Val Leu Cys Gln Ala His Gly Leu Thr
                405                 410                 415

Pro Glu Gln Val Val Ala Ile Ala Ser His Asp Gly Gly Lys Gln Ala
            420                 425                 430

Leu Glu Thr Val Gln Arg Leu Leu Pro Val Leu Cys Gln Ala His Gly
        435                 440                 445

Leu Thr Pro Glu Gln Val Val Ala Ile Ala Ser Asn Ile Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Asn Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser Asn
        515                 520                 525

Ile Gly Gly Lys Gln Ala Leu Glu Thr Val Gln Arg Leu Leu Pro Val
    530                 535                 540

Leu Cys Gln Ala His Gly Leu Thr Pro Glu Gln Val Val Ala Ile Ala
545                 550                 555                 560

Ser Asn Gly Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
            580                 585                 590

Ile Ala Ser Asn Ile Gly Gly Lys Gln Ala Leu Glu Thr Val Gln Arg
        595                 600                 605

Leu Leu Pro Val Leu Cys Gln Ala His Gly Leu Thr Pro Glu Gln Val
    610                 615                 620

Val Ala Ile Ala Ser Asn Gly Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser His Asp Gly Gly Lys Gln Ala Leu Glu

```
                  660             665             670
   Thr Val Gln Arg Leu Pro Val Leu Cys Gln Ala His Gly Leu Thr
                   675             680             685
   Pro Glu Gln Val Val Ala Ile Ala Ser His Asp Gly Gly Arg Pro Ala
               690             695             700
   Leu Glu Ser Ile Val Ala Gln Leu Ser Arg Pro Asp Pro Ala Leu Ala
   705             710             715             720
   Ala Leu Thr Asn Asp His Leu Val Ala Leu Ala Cys Leu Gly Gly Arg
                   725             730             735
   Pro Ala Leu Asp Ala Val Lys Lys Gly Leu Pro His Ala Pro Ala Leu
                   740             745             750
   Ile Lys Arg Thr Asn Arg Arg Ile Pro Glu Arg Thr Ser His Arg Val
                   755             760             765
   Ala Gly Ser Gln Leu Val Lys Ser Glu Leu Glu Lys Lys Ser Glu
                   770             775             780
   Leu Arg His Lys Leu Lys Tyr Val Pro His Glu Tyr Ile Glu Leu Ile
   785             790             795             800
   Glu Ile Ala Arg Asn Ser Thr Gln Asp Arg Ile Leu Glu Met Lys Val
                   805             810             815
   Met Glu Phe Phe Met Lys Val Tyr Gly Tyr Arg Gly Lys His Leu Gly
                   820             825             830
   Gly Ser Arg Lys Pro Asp Gly Ala Ile Tyr Thr Val Gly Ser Pro Ile
                   835             840             845
   Asp Tyr Gly Val Ile Val Asp Thr Lys Ala Tyr Ser Gly Gly Tyr Asn
                   850             855             860
   Leu Pro Ile Gly Gln Ala Asp Glu Met Gln Arg Tyr Val Glu Glu Asn
   865             870             875             880
   Gln Thr Arg Asn Lys His Ile Asn Pro Asn Glu Trp Trp Lys Val Tyr
                   885             890             895
   Pro Ser Ser Val Thr Glu Phe Lys Phe Leu Phe Val Ser Gly His Phe
                   900             905             910
   Lys Gly Asn Tyr Lys Ala Gln Leu Thr Arg Leu Asn His Ile Thr Asn
                   915             920             925
   Cys Asn Gly Ala Val Leu Ser Val Glu Glu Leu Leu Ile Gly Gly Glu
                   930             935             940
   Met Ile Lys Ala Gly Thr Leu Thr Leu Glu Glu Val Arg Arg Lys Phe
   945             950             955             960
   Asn Asn Gly Glu Ile Asn Phe Arg Ser
                   965

<210> SEQ ID NO 379
<211> LENGTH: 17
<212> TYPE: DNA
<213> ORGANISM: Homo Sapiens

<400> SEQUENCE: 379
ccgtgtacca gctgaga                                                 17

<210> SEQ ID NO 380
<211> LENGTH: 969
<212> TYPE: PRT
<213> ORGANISM: Homo Sapiens

<400> SEQUENCE: 380

Met Asp Tyr Lys Asp His Asp Gly Asp Tyr Lys Asp His Asp Ile Asp
1               5                   10                  15
```

```
Tyr Lys Asp Asp Asp Lys Met Ala Pro Lys Lys Arg Lys Val
         20              25              30

Gly Ile His Gly Val Pro Ala Ala Val Asp Leu Arg Thr Leu Gly Tyr
         35              40              45

Ser Gln Gln Gln Gln Glu Lys Ile Lys Pro Lys Val Arg Ser Thr Val
 50              55              60

Ala Gln His His Glu Ala Leu Val Gly His Gly Phe Thr His Ala His
 65              70              75              80

Ile Val Ala Leu Ser Gln His Pro Ala Ala Leu Gly Thr Val Ala Val
             85              90              95

Lys Tyr Gln Asp Met Ile Ala Ala Leu Pro Glu Ala Thr His Glu Ala
             100             105             110

Ile Val Gly Val Gly Lys Gln Trp Ser Gly Ala Arg Ala Leu Glu Ala
             115             120             125

Leu Leu Thr Val Ala Gly Glu Leu Arg Gly Pro Leu Gln Leu Asp
 130             135             140

Thr Gly Gln Leu Leu Lys Ile Ala Lys Arg Gly Gly Val Thr Ala Val
 145             150             155             160

Glu Ala Val His Ala Trp Arg Asn Ala Leu Thr Gly Ala Pro Leu Asn
                 165             170             175

Leu Thr Pro Glu Gln Val Val Ala Ile Ala Ser His Asp Gly Gly Lys
             180             185             190

Gln Ala Leu Glu Thr Val Gln Arg Leu Leu Pro Val Leu Cys Gln Ala
             195             200             205

His Gly Leu Thr Pro Glu Gln Val Val Ala Ile Ala Ser Asn Gly Gly
             210             215             220

Gly Lys Gln Ala Leu Glu Thr Val Gln Arg Leu Leu Pro Val Leu Cys
225             230             235             240

Gln Ala His Gly Leu Thr Pro Glu Gln Val Val Ala Ile Ala Ser His
             245             250             255

Asp Gly Gly Lys Gln Ala Leu Glu Thr Val Gln Arg Leu Leu Pro Val
             260             265             270

Leu Cys Gln Ala His Gly Leu Thr Pro Glu Gln Val Val Ala Ile Ala
             275             280             285

Ser Asn Ile Gly Gly Lys Gln Ala Leu Glu Thr Val Gln Arg Leu Leu
 290             295             300

Pro Val Leu Cys Gln Ala His Gly Leu Thr Pro Glu Gln Val Val Ala
305             310             315             320

Ile Ala Ser Asn Asn Gly Gly Lys Gln Ala Leu Glu Thr Val Gln Arg
             325             330             335

Leu Leu Pro Val Leu Cys Gln Ala His Gly Leu Thr Pro Glu Gln Val
             340             345             350

Val Ala Ile Ala Ser His Asp Gly Gly Lys Gln Ala Leu Glu Thr Val
             355             360             365

Gln Arg Leu Leu Pro Val Leu Cys Gln Ala His Gly Leu Thr Pro Glu
             370             375             380

Gln Val Val Ala Ile Ala Ser Asn Gly Gly Gly Lys Gln Ala Leu Glu
385             390             395             400

Thr Val Gln Arg Leu Leu Pro Val Leu Cys Gln Ala His Gly Leu Thr
             405             410             415

Pro Glu Gln Val Val Ala Ile Ala Ser Asn Asn Gly Gly Lys Gln Ala
             420             425             430
```

```
Leu Glu Thr Val Gln Arg Leu Leu Pro Val Leu Cys Gln Ala His Gly
            435                 440                 445

Leu Thr Pro Glu Gln Val Val Ala Ile Ala Ser Asn Asn Gly Gly Lys
    450                 455                 460

Gln Ala Leu Glu Thr Val Gln Arg Leu Leu Pro Val Leu Cys Gln Ala
465                 470                 475                 480

His Gly Leu Thr Pro Glu Gln Val Val Ala Ile Ala Ser Asn Gly Gly
                485                 490                 495

Gly Lys Gln Ala Leu Glu Thr Val Gln Arg Leu Leu Pro Val Leu Cys
            500                 505                 510

Gln Ala His Gly Leu Thr Pro Glu Gln Val Val Ala Ile Ala Ser Asn
        515                 520                 525

Ile Gly Gly Lys Gln Ala Leu Glu Thr Val Gln Arg Leu Leu Pro Val
    530                 535                 540

Leu Cys Gln Ala His Gly Leu Thr Pro Glu Gln Val Val Ala Ile Ala
545                 550                 555                 560

Ser His Asp Gly Gly Lys Gln Ala Leu Glu Thr Val Gln Arg Leu Leu
                565                 570                 575

Pro Val Leu Cys Gln Ala His Gly Leu Thr Pro Glu Gln Val Val Ala
            580                 585                 590

Ile Ala Ser Asn Ile Gly Gly Lys Gln Ala Leu Glu Thr Val Gln Arg
        595                 600                 605

Leu Leu Pro Val Leu Cys Gln Ala His Gly Leu Thr Pro Glu Gln Val
    610                 615                 620

Val Ala Ile Ala Ser His Asp Gly Gly Lys Gln Ala Leu Glu Thr Val
625                 630                 635                 640

Gln Arg Leu Leu Pro Val Leu Cys Gln Ala His Gly Leu Thr Pro Glu
                645                 650                 655

Gln Val Val Ala Ile Ala Ser Asn Asn Gly Gly Lys Gln Ala Leu Glu
            660                 665                 670

Thr Val Gln Arg Leu Leu Pro Val Leu Cys Gln Ala His Gly Leu Thr
        675                 680                 685

Pro Glu Gln Val Val Ala Ile Ala Ser Asn Asn Gly Gly Arg Pro Ala
    690                 695                 700

Leu Glu Ser Ile Val Ala Gln Leu Ser Arg Pro Asp Pro Ala Leu Ala
705                 710                 715                 720

Ala Leu Thr Asn Asp His Leu Val Ala Leu Ala Cys Leu Gly Gly Arg
                725                 730                 735

Pro Ala Leu Asp Ala Val Lys Lys Gly Leu Pro His Ala Pro Ala Leu
            740                 745                 750

Ile Lys Arg Thr Asn Arg Arg Ile Pro Glu Arg Thr Ser His Arg Val
        755                 760                 765

Ala Gly Ser Gln Leu Val Lys Ser Glu Leu Glu Glu Lys Lys Ser Glu
    770                 775                 780

Leu Arg His Lys Leu Lys Tyr Val Pro His Glu Tyr Ile Glu Leu Ile
785                 790                 795                 800

Glu Ile Ala Arg Asn Ser Thr Gln Asp Arg Ile Leu Glu Met Lys Val
                805                 810                 815

Met Glu Phe Phe Met Lys Val Tyr Gly Tyr Arg Gly Lys His Leu Gly
            820                 825                 830

Gly Ser Arg Lys Pro Asp Gly Ala Ile Tyr Thr Val Gly Ser Pro Ile
        835                 840                 845

Asp Tyr Gly Val Ile Val Asp Thr Lys Ala Tyr Ser Gly Gly Tyr Asn
```

```
                    850                 855                 860
Leu Pro Ile Gly Gln Ala Asp Glu Met Gln Arg Tyr Val Glu Asn
865                 870                 875                 880

Gln Thr Arg Asn Lys His Ile Asn Pro Asn Glu Trp Trp Lys Val Tyr
                885                 890                 895

Pro Ser Ser Val Thr Glu Phe Lys Phe Leu Phe Val Ser Gly His Phe
                900                 905                 910

Lys Gly Asn Tyr Lys Ala Gln Leu Thr Arg Leu Asn His Ile Thr Asn
                915                 920                 925

Cys Asn Gly Ala Val Leu Ser Val Glu Glu Leu Leu Ile Gly Gly Glu
                930                 935                 940

Met Ile Lys Ala Gly Thr Leu Thr Leu Glu Glu Val Arg Arg Lys Phe
945                 950                 955                 960

Asn Asn Gly Glu Ile Asn Phe Arg Ser
                965

<210> SEQ ID NO 381
<211> LENGTH: 49
<212> TYPE: DNA
<213> ORGANISM: Homo Sapiens

<400> SEQUENCE: 381
ttctccccag ccctgctcgt ggtgaccgaa ggggacaacg ccaccttca           49

<210> SEQ ID NO 382
<211> LENGTH: 936
<212> TYPE: PRT
<213> ORGANISM: Homo Sapiens

<400> SEQUENCE: 382

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
                20                  25                  30

Ser Gln Gln Gln Gln Glu Lys Ile Lys Pro Lys Val Arg Ser Thr Val
            35                  40                  45

Ala Gln His His Glu Ala Leu Val Gly His Gly Phe Thr His Ala His
        50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
                100                 105                 110

Leu Leu Thr Val Ala Gly Glu Leu Arg Gly Pro Pro Leu Gln Leu Asp
            115                 120                 125

Thr Gly Gln Leu Leu Lys Ile Ala Lys Arg Gly Gly Val Thr Ala Val
        130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Gly Gly Gly Lys
                165                 170                 175

Gln Ala Leu Glu Thr Val Gln Arg Leu Leu Pro Val Leu Cys Gln Ala
                180                 185                 190

His Gly Leu Thr Pro Glu Gln Val Val Ala Ile Ala Ser His Asp Gly
            195                 200                 205
```

```
Gly Lys Gln Ala Leu Glu Thr Val Gln Arg Leu Leu Pro Val Leu Cys
    210                 215                 220

Gln Ala His Gly Leu Thr Pro Gln Gln Val Val Ala Ile Ala Ser Asn
225                 230                 235                 240

Gly Gly Gly Lys Gln Ala Leu Glu Thr Val Gln Arg Leu Leu Pro Val
                245                 250                 255

Leu Cys Gln Ala His Gly Leu Thr Pro Glu Gln Val Val Ala Ile Ala
            260                 265                 270

Ser His Asp Gly Gly Lys Gln Ala Leu Glu Thr Val Gln Arg Leu Leu
        275                 280                 285

Pro Val Leu Cys Gln Ala His Gly Leu Thr Pro Glu Gln Val Val Ala
    290                 295                 300

Ile Ala Ser His Asp Gly Gly Lys Gln Ala Leu Glu Thr Val Gln Arg
305                 310                 315                 320

Leu Leu Pro Val Leu Cys Gln Ala His Gly Leu Thr Pro Glu Gln Val
                325                 330                 335

Val Ala Ile Ala Ser His Asp Gly Gly Lys Gln Ala Leu Glu Thr Val
            340                 345                 350

Gln Arg Leu Leu Pro Val Leu Cys Gln Ala His Gly Leu Thr Pro Glu
        355                 360                 365

Gln Val Val Ala Ile Ala Ser His Asp Gly Gly Lys Gln Ala Leu Glu
    370                 375                 380

Thr Val Gln Arg Leu Leu Pro Val Leu Cys Gln Ala His Gly Leu Thr
385                 390                 395                 400

Pro Glu Gln Val Val Ala Ile Ala Ser Asn Ile Gly Gly Lys Gln Ala
                405                 410                 415

Leu Glu Thr Val Gln Ala Leu Leu Pro Val Leu Cys Gln Ala His Gly
            420                 425                 430

Leu Thr Pro Gln Gln Val Val Ala Ile Ala Ser Asn Asn Gly Gly Lys
        435                 440                 445

Gln Ala Leu Glu Thr Val Gln Arg Leu Leu Pro Val Leu Cys Gln Ala
    450                 455                 460

His Gly Leu Thr Pro Glu Gln Val Val Ala Ile Ala Ser His Asp Gly
465                 470                 475                 480

Gly Lys Gln Ala Leu Glu Thr Val Gln Arg Leu Leu Pro Val Leu Cys
                485                 490                 495

Gln Ala His Gly Leu Thr Pro Glu Gln Val Val Ala Ile Ala Ser His
            500                 505                 510

Asp Gly Gly Lys Gln Ala Leu Glu Thr Val Gln Arg Leu Leu Pro Val
        515                 520                 525

Leu Cys Gln Ala His Gly Leu Thr Pro Glu Gln Val Val Ala Ile Ala
    530                 535                 540

Ser His Asp Gly Gly Lys Gln Ala Leu Glu Thr Val Gln Arg Leu Leu
545                 550                 555                 560

Pro Val Leu Cys Gln Ala His Gly Leu Thr Pro Gln Gln Val Val Ala
                565                 570                 575

Ile Ala Ser Asn Gly Gly Gly Lys Gln Ala Leu Glu Thr Val Gln Arg
            580                 585                 590

Leu Leu Pro Val Leu Cys Gln Ala His Gly Leu Thr Pro Gln Gln Val
        595                 600                 605

Val Ala Ile Ala Ser Asn Asn Gly Gly Lys Gln Ala Leu Glu Thr Val
    610                 615                 620
```

-continued

Gln Arg Leu Leu Pro Val Leu Cys Gln Ala His Gly Leu Thr Pro Glu
625                 630                 635                 640

Gln Val Val Ala Ile Ala Ser His Asp Gly Gly Lys Gln Ala Leu Glu
            645                 650                 655

Thr Val Gln Arg Leu Leu Pro Val Leu Cys Gln Ala His Gly Leu Thr
        660                 665                 670

Pro Gln Gln Val Val Ala Ile Ala Ser Asn Gly Gly Arg Pro Ala
    675                 680                 685

Leu Glu Ser Ile Val Ala Gln Leu Ser Arg Pro Asp Pro Ala Leu Ala
690                 695                 700

Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
                725                 730                 735

Ser Gln Leu Val Lys Ser Glu Leu Glu Glu Lys Lys Ser Glu Leu Arg
            740                 745                 750

His Lys Leu Lys Tyr Val Pro His Glu Tyr Ile Glu Leu Ile Glu Ile
        755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
        835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
        915                 920                 925

Gly Glu Ile Asn Phe Ala Ala Asp
930                 935

<210> SEQ ID NO 383
<211> LENGTH: 941
<212> TYPE: PRT
<213> ORGANISM: Homo Sapiens

<400> SEQUENCE: 383

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
            20                  25                  30

Leu Arg Thr Leu Gly Tyr Ser Gln Gln Gln Gln Glu Lys Ile Lys Pro
        35                  40                  45

Lys Val Arg Ser Thr Val Ala Gln His His Glu Ala Leu Val Gly His
    50                  55                  60

```
Gly Phe Thr His Ala His Ile Val Ala Leu Ser Gln His Pro Ala Ala
 65                  70                  75                  80

Leu Gly Thr Val Ala Val Lys Tyr Gln Asp Met Ile Ala Ala Leu Pro
                 85                  90                  95

Glu Ala Thr His Glu Ala Ile Val Gly Val Gly Lys Gln Trp Ser Gly
                100                 105                 110

Ala Arg Ala Leu Glu Ala Leu Leu Thr Val Ala Gly Glu Leu Arg Gly
            115                 120                 125

Pro Pro Leu Gln Leu Asp Thr Gly Gln Leu Leu Lys Ile Ala Lys Arg
130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Glu Gln Val Val Ala Ile Ala
                165                 170                 175

Ser His Asp Gly Gly Lys Gln Ala Leu Glu Thr Val Gln Arg Leu Leu
            180                 185                 190

Pro Val Leu Cys Gln Ala His Gly Leu Thr Pro Gln Gln Val Val Ala
            195                 200                 205

Ile Ala Ser Asn Gly Gly Gly Lys Gln Ala Leu Glu Thr Val Gln Arg
210                 215                 220

Leu Leu Pro Val Leu Cys Gln Ala His Gly Leu Thr Pro Glu Gln Val
225                 230                 235                 240

Val Ala Ile Ala Ser His Asp Gly Gly Lys Gln Ala Leu Glu Thr Val
                245                 250                 255

Gln Arg Leu Leu Pro Val Leu Cys Gln Ala His Gly Leu Thr Pro Gln
            260                 265                 270

Gln Val Val Ala Ile Ala Ser Asn Gly Gly Gly Lys Gln Ala Leu Glu
            275                 280                 285

Thr Val Gln Arg Leu Leu Pro Val Leu Cys Gln Ala His Gly Leu Thr
290                 295                 300

Pro Gln Gln Val Val Ala Ile Ala Ser Asn Gly Gly Gly Lys Gln Ala
305                 310                 315                 320

Leu Glu Thr Val Gln Arg Leu Leu Pro Val Leu Cys Gln Ala His Gly
                325                 330                 335

Leu Thr Pro Gln Gln Val Val Ala Ile Ala Ser Asn Gly Gly Gly Lys
            340                 345                 350

Gln Ala Leu Glu Thr Val Gln Arg Leu Leu Pro Val Leu Cys Gln Ala
            355                 360                 365

His Gly Leu Thr Pro Gln Gln Val Val Ala Ile Ala Ser Asn Asn Gly
            370                 375                 380

Gly Lys Gln Ala Leu Glu Thr Val Gln Arg Leu Leu Pro Val Leu Cys
385                 390                 395                 400

Gln Ala His Gly Leu Thr Pro Glu Gln Val Val Ala Ile Ala Ser Asn
                405                 410                 415

Ile Gly Gly Lys Gln Ala Leu Glu Thr Val Gln Ala Leu Leu Pro Val
            420                 425                 430

Leu Cys Gln Ala His Gly Leu Thr Pro Gln Gln Val Val Ala Ile Ala
            435                 440                 445

Ser Asn Gly Gly Gly Lys Gln Ala Leu Glu Thr Val Gln Arg Leu Leu
            450                 455                 460

Pro Val Leu Cys Gln Ala His Gly Leu Thr Pro Glu Gln Val Val Ala
465                 470                 475                 480
```

Ile Ala Ser His Asp Gly Gly Lys Gln Ala Leu Glu Thr Val Gln Arg
                485                 490                 495

Leu Leu Pro Val Leu Cys Gln Ala His Gly Leu Thr Pro Gln Gln Val
            500                 505                 510

Val Ala Ile Ala Ser Asn Gly Gly Lys Gln Ala Leu Glu Thr Val
        515                 520                 525

Gln Arg Leu Leu Pro Val Leu Cys Gln Ala His Gly Leu Thr Pro Gln
530                 535                 540

Gln Val Val Ala Ile Ala Ser Asn Gly Gly Lys Gln Ala Leu Glu
545                 550                 555                 560

Thr Val Gln Arg Leu Leu Pro Val Leu Cys Gln Ala His Gly Leu Thr
                565                 570                 575

Pro Glu Gln Val Val Ala Ile Ala Ser Asn Gly Gly Lys Gln Ala Leu
            580                 585                 590

Glu Thr Val Gln Arg Leu Leu Pro Val Leu Cys Gln Ala His Gly Leu
        595                 600                 605

Thr Pro Gln Gln Val Val Ala Ile Ala Ser Asn Asn Gly Gly Lys Gln
610                 615                 620

Ala Leu Glu Thr Val Gln Arg Leu Leu Pro Val Leu Cys Gln Ala His
625                 630                 635                 640

Gly Leu Thr Pro Glu Gln Val Val Ala Ile Ala Ser His Asp Gly Gly
                645                 650                 655

Lys Gln Ala Leu Glu Thr Val Gln Arg Leu Leu Pro Val Leu Cys Gln
            660                 665                 670

Ala His Gly Leu Thr Pro Gln Gln Val Val Ala Ile Ala Ser Asn Gly
        675                 680                 685

Gly Gly Arg Pro Ala Leu Glu Ser Ile Val Ala Gln Leu Ser Arg Pro
690                 695                 700

Asp Pro Ala Leu Ala Ala Leu Thr Asn Asp His Leu Val Ala Leu Ala
705                 710                 715                 720

Cys Leu Gly Gly Arg Pro Ala Leu Asp Ala Val Lys Lys Gly Leu Gly
                725                 730                 735

Asp Pro Ile Ser Arg Ser Gln Leu Val Lys Ser Glu Leu Glu Glu Lys
            740                 745                 750

Lys Ser Glu Leu Arg His Lys Leu Lys Tyr Val Pro His Glu Tyr Ile
        755                 760                 765

Glu Leu Ile Glu Ile Ala Arg Asn Ser Thr Gln Asp Arg Ile Leu Glu
770                 775                 780

Met Lys Val Met Glu Phe Phe Met Lys Val Tyr Gly Tyr Arg Gly Lys
785                 790                 795                 800

His Leu Gly Gly Ser Arg Lys Pro Asp Gly Ala Ile Tyr Thr Val Gly
                805                 810                 815

Ser Pro Ile Asp Tyr Gly Val Ile Val Asp Thr Lys Ala Tyr Ser Gly
            820                 825                 830

Gly Tyr Asn Leu Pro Ile Gly Gln Ala Asp Glu Met Gln Arg Tyr Val
        835                 840                 845

Glu Glu Asn Gln Thr Arg Asn Lys His Ile Asn Pro Asn Glu Trp Trp
850                 855                 860

Lys Val Tyr Pro Ser Ser Val Thr Glu Phe Lys Phe Leu Phe Val Ser
865                 870                 875                 880

Gly His Phe Lys Gly Asn Tyr Lys Ala Gln Leu Thr Arg Leu Asn His
                885                 890                 895

Ile Thr Asn Cys Asn Gly Ala Val Leu Ser Val Glu Glu Leu Leu Ile

```
               900             905             910
Gly Gly Glu Met Ile Lys Ala Gly Thr Leu Thr Leu Glu Glu Val Arg
            915             920             925

Arg Lys Phe Asn Asn Gly Glu Ile Asn Phe Ala Ala Asp
        930             935             940
```

<210> SEQ ID NO 384
<211> LENGTH: 100
<212> TYPE: RNA
<213> ORGANISM: Artificial Sequence
<220> FEATURE:
<223> OTHER INFORMATION: Synthetic

<400> SEQUENCE: 384

```
gagaaucaaa aucggugaau guuuuagagc uagaaauagc aaguuaaaau aaggcuaguc      60
cguuaucaac uugaaaaagu ggcaccgagu cggugcuuuu                           100
```

<210> SEQ ID NO 385
<211> LENGTH: 21
<212> TYPE: DNA
<213> ORGANISM: Artificial Sequence
<220> FEATURE:
<223> OTHER INFORMATION: Synthetic

<400> SEQUENCE: 385

```
agcgctctcg tacagagttg g                                                21
```

<210> SEQ ID NO 386
<211> LENGTH: 23
<212> TYPE: DNA
<213> ORGANISM: Artificial Sequence
<220> FEATURE:
<223> OTHER INFORMATION: Synthetic

<400> SEQUENCE: 386

```
aaaaaaagca ccgactcggt gcc                                              23
```

<210> SEQ ID NO 387
<211> LENGTH: 100
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: 2'OMe
<220> FEATURE:
<221> NAME/KEY: misc_feature
<222> LOCATION: (1)..(2)
<223> OTHER INFORMATION: phosphorothioate
<220> FEATURE:
<221> NAME/KEY: misc_feature
<222> LOCATION: (2)..(3)
<223> OTHER INFORMATION: phosphorothioate
<220> FEATURE:
<221> NAME/KEY: misc_feature
<222> LOCATION: (3)..(4)
<223> OTHER INFORMATION: phosphorothioate
<220> FEATURE:
<221> NAME/KEY: misc_feature
<222> LOCATION: (96)..(96)
<223> OTHER INFORMATION: 2'OMe
<220> FEATURE:
<221> NAME/KEY: misc_feature
<222> LOCATION: (97)..(98)
<223> OTHER INFORMATION: phosphorothioate
<220> FEATURE:
<221> NAME/KEY: misc_feature
<222> LOCATION: (98)..(99)
<223> OTHER INFORMATION: phosphorothioate
<220> FEATURE:
<221> NAME/KEY: misc_feature
<222> LOCATION: (99)..(100)
<223> OTHER INFORMATION: phosphorothioate

<400> SEQUENCE: 387
gagaaucaaa aucggugaau guuuuagagc uagaaauagc aaguuaaaau aaggcuaguc    60
cguuaucaac uugaaaaagu ggcaccgagu cggugcuuuu                          100

<210> SEQ ID NO 388
<211> LENGTH: 20
<212> TYPE: PRT
<213> ORGANISM: Artificial Sequence
<220> FEATURE:
<223> OTHER INFORMATION: Synthetic

<400> SEQUENCE: 388

Met Asp Pro Lys Gly Leu Leu Ser Leu Thr Phe Val Leu Phe Leu Ser
1               5                   10                  15

Leu Ala Phe Gly
            20

<210> SEQ ID NO 389
<211> LENGTH: 495
<212> TYPE: PRT
<213> ORGANISM: Artificial Sequence
<220> FEATURE:
<223> OTHER INFORMATION: Synthetic

<400> SEQUENCE: 389

Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile
            20                  25                  30

Lys Pro Gly Ala Ser Val Lys Met Ser Cys Lys Ala Ser Gly Tyr Thr
        35                  40                  45

Phe Thr Ser Tyr Val Met His Trp Val Lys Gln Lys Pro Gly Gln Gly
    50                  55                  60

Leu Glu Trp Ile Gly Tyr Ile Asn Pro Tyr Asn Asp Gly Thr Lys Tyr
65                  70                  75                  80

Asn Glu Lys Phe Lys Gly Lys Ala Thr Leu Thr Ser Asp Lys Ser Ser
                85                  90                  95

Ser Thr Ala Tyr Met Glu Leu Ser Ser Leu Thr Ser Glu Asp Ser Ala
            100                 105                 110

Val Tyr Tyr Cys Ala Arg Gly Thr Tyr Tyr Gly Ser Arg Val Phe
        115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ala Ala Pro Ser Ile Pro Val Thr Pro Gly Glu Ser Val Ser
                165                 170                 175

Ile Ser Cys Arg Ser Ser Lys Ser Leu Leu Asn Ser Asn Gly Asn Thr
            180                 185                 190

Tyr Leu Tyr Trp Phe Leu Gln Arg Pro Gly Gln Ser Pro Gln Leu Leu
        195                 200                 205

Ile Tyr Arg Met Ser Asn Leu Ala Ser Gly Val Pro Asp Arg Phe Ser

```
            210                 215                 220
Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                245                 250                 255

Phe Thr Phe Gly Ala Gly Thr Lys Leu Glu Leu Lys Arg Ser Asp Pro
            260                 265                 270

Thr Thr Thr Pro Ala Pro Arg Pro Thr Pro Ala Pro Thr Ile Ala
        275                 280                 285

Ser Gln Pro Leu Ser Leu Arg Pro Glu Ala Cys Arg Pro Ala Ala Gly
        290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
        370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg
                485                 490                 495

<210> SEQ ID NO 390
<211> LENGTH: 1485
<212> TYPE: DNA
<213> ORGANISM: Artificial Sequence
<220> FEATURE:
<223> OTHER INFORMATION: Synthetic

<400> SEQUENCE: 390
atggagacag acactcttct cctttgggtc ttgctgctgt gggttccgg aagcacagga      60 gaagtacagt tgcaacagtc tgggccagaa ctcatcaaac ccggagcttc tgtaaaaatg    120
tcatgcaaag ctagtggata tacatttact tcttacgtga tgcactgggt aaaacagaaa    180
cctggtcagg gccttgagtg gatcgggtac attaacccat ataatgacgg caccaaatat    240
aacgagaaat tcaagggaaa ggctacgctt acatcagata gtccagtag caccgcttat    300 atggaactta gcagccttac ttccgaagat tccgcggtgt attactgcgc gagagggact    360
tactactacg ggagtcgagt attcgattat tggggtcaag gcacgacgct cacggtgagc    420
tcaggtggtg gagggtctgg gggtggcggc agtggtgggg ggggctcaga catcgtgatg    480
```

```
acccaggcag caccttctat cccggtaacc ccaggcgagt ctgtatctat cagttgtcgg    540
tccagcaagt ctcttctcaa cagtaatggc aatacatatc tttactggtt cctccaaagg    600
cctgggcaaa gtcctcaact tcttatatat cggatgtcca atcttgcgag tggcgtaccc    660
gacaggtttt cagggtctgg gagcggaaca gcttttacgt tgagaatatc cagggtagaa    720
gctgaggacg tcggtgtata ttattgcatg caacatctcg aatacccctt taccttcggc    780
gctggtacaa agctcgaatt gaaacgcagc gatccaacca cgacgccagc gccacgacca    840
cctacgcccg ctccaactat tgcctcccag cccctgagtc ttcggccaga agcgtgtaga    900
cctgctgccg gcggggccgt tcatacgcgg ggccttgact ttgcatgtga tatctatata    960
tgggctcctt tggcgggaac ttgcggagtg cttcttttgt cactcgtgat aacgttgtat   1020
tgtaaaaggg gtcgaaagaa actcctctat atatttaagc agcccttat gaggcccgtg    1080 caaacaacac aagaagagga cggatgctct tgtcgattcc cggaagagga ggaggggggg   1140
tgtgagctta gggtcaagtt ttctcgctct gccgacgcgc cagcctatca acagggccaa   1200
aaccagctgt ataacgaact caacctcggg cgccgggaag agtatgacgt ccttgacaaa   1260
cggcgcggtc gcgaccctga aatgggtgga aaaccgaggc gaaagaaccc ccaggaggga   1320
ctttacaacg aattgcaaaa agacaagatg gccgaagcct attccgaaat tggaatgaaa   1380
ggcgagcgga gacgaggtaa ggggcatgac ggcctgtatc aagggctctc tacggccacg   1440
aaggatactt acgacgccct tcatatgcaa gctcttccac cacgg                   1485
```

<210> SEQ ID NO 391
<211> LENGTH: 374
<212> TYPE: PRT
<213> ORGANISM: Homo Sapiens

<400> SEQUENCE: 391

```
Met Ser Gly Glu Ser Met Asn Phe Ser Asp Val Phe Asp Ser Glu
1               5                   10                  15

Asp Tyr Phe Val Ser Val Asn Thr Ser Tyr Tyr Ser Val Asp Ser Glu
            20                  25                  30

Met Leu Leu Cys Ser Leu Gln Glu Val Arg Gln Phe Ser Arg Leu Phe
        35                  40                  45

Val Pro Ile Ala Tyr Ser Leu Ile Cys Val Phe Gly Leu Leu Gly Asn
    50                  55                  60

Ile Leu Val Val Ile Thr Phe Ala Phe Tyr Lys Lys Ala Arg Ser Met
65                  70                  75                  80

Thr Asp Val Tyr Leu Leu Asn Met Ala Ile Ala Asp Ile Leu Phe Val
                85                  90                  95

Leu Thr Leu Pro Phe Trp Ala Val Ser His Ala Thr Gly Ala Trp Val
            100                 105                 110

Phe Ser Asn Ala Thr Cys Lys Leu Leu Lys Gly Ile Tyr Ala Ile Asn
        115                 120                 125

Phe Asn Cys Gly Met Leu Leu Leu Thr Cys Ile Ser Met Asp Arg Tyr
    130                 135                 140

Ile Ala Ile Val Gln Ala Thr Lys Ser Phe Arg Leu Arg Ser Arg Thr
145                 150                 155                 160

Leu Pro Arg Ser Lys Ile Ile Cys Leu Val Val Trp Gly Leu Ser Val
                165                 170                 175

Ile Ile Ser Ser Ser Thr Phe Val Phe Asn Gln Lys Tyr Asn Thr Gln
            180                 185                 190

Gly Ser Asp Val Cys Glu Pro Lys Tyr Gln Thr Val Ser Glu Pro Ile
```

```
                    195                 200                 205
Arg Trp Lys Leu Leu Met Leu Gly Leu Glu Leu Leu Phe Gly Phe Phe
    210                 215                 220
Ile Pro Leu Met Phe Met Ile Phe Cys Tyr Thr Phe Ile Val Lys Thr
225                 230                 235                 240
Leu Val Gln Ala Gln Asn Ser Lys Arg His Lys Ala Ile Arg Val Ile
                245                 250                 255
Ile Ala Val Val Leu Val Phe Leu Ala Cys Gln Ile Pro His Asn Met
            260                 265                 270
Val Leu Leu Val Thr Ala Ala Asn Leu Gly Lys Met Asn Arg Ser Cys
        275                 280                 285
Gln Ser Glu Lys Leu Ile Gly Tyr Thr Lys Thr Val Thr Glu Val Leu
    290                 295                 300
Ala Phe Leu His Cys Cys Leu Asn Pro Val Leu Tyr Ala Phe Ile Gly
305                 310                 315                 320
Gln Lys Phe Arg Asn Tyr Phe Leu Lys Ile Leu Lys Asp Leu Trp Cys
                325                 330                 335
Val Arg Arg Lys Tyr Lys Ser Ser Gly Phe Ser Cys Ala Gly Arg Tyr
            340                 345                 350
Ser Glu Asn Ile Ser Arg Gln Thr Ser Glu Thr Ala Asp Asn Asp Asn
        355                 360                 365
Ala Ser Ser Phe Thr Met
    370
```

<210> SEQ ID NO 392
<211> LENGTH: 1122
<212> TYPE: DNA
<213> ORGANISM: Artificial Sequence
<220> FEATURE:
<223> OTHER INFORMATION: Synthetic

<400> SEQUENCE: 392

```
atgagtgggg aaagtatgaa cttcagcgat gtatttgact cctccgaaga ttactttgta      60
tctgtgaata cgagctatta ctccgtcgat agtgaaatgc tgctctgtag tctccaagaa     120
gtccgccaat tcagtcgcct cttcgttccc atcgcgtact cccttatttg tgttttggc      180
cttctgggta acatcctggt tgtaatcaca ttcgctttct ataaaaaagc tcggagtatg     240
actgatgttt accttcttaa catggctata gcggacattc ttttgtgct tactctccca      300
ttctgggctg tgagccatgc aacaggggcg tgggtttttt caaatgccac atgtaagctg     360
cttaaaggga tctatgcaat aaacttcaat tgcgggatgc tcctgctgac atgcatcagt     420
atggatcgat acatagctat agtacaggcg actaagtcct tccgcctgcg atcccgcaca     480
ctgcctagga gcaaaattat ttgcctcgtc gtatgggggc tctcagtgat catctcctcc     540
agtacgtttg tctttaacca gaaatataac acacagggtt ctgatgtatg tgaaccaaag     600
tatcagacag tgagtgaacc aatacggtgg aagttgctta tgttgggctt ggagctgctt     660
tttgggtttt tcatcccact gatgttcatg attttctgtt atacatttat tgttaagacc     720
ttggttcagg cgcaaaatag caagagacat aaggcaattc gagtcatcat tgccgtggtg     780
ttggtcttct tggcctgtca gatcccccat aatatggttc tgctcgtcac cgccgctaac     840
ttgggtaaga tgaatcgatc ttgtcagtcc gagaagttga tcggatacac caaaactgtg     900
acagaagtgc tggccttcct tcactgttgt ctgaacccag ttttgtatgc ttttatagga     960
cagaagtttc gaaattactt cttgaaaatc ctcaaggacc tctggtgtgt tcgaaggaag    1020
```

| | | |
|---|---|---|
| tacaagagct ctggctttag ttgcgctggg cgctacagtg agaatatatc ccggcagacc | 1080 | |
| tccgagactg ctgataatga caacgcaagt tccttcacta tg | 1122 | |

<210> SEQ ID NO 393
<211> LENGTH: 1122
<212> TYPE: DNA
<213> ORGANISM: Homo Sapiens

<400> SEQUENCE: 393

| | |
|---|---|
| atgagcgggg aatcaatgaa tttcagcgat gttttcgact ccagtgaaga ttattttgtg | 60 |
| tcagtcaata cttcatatta ctcagttgat tctgagatgt tactgtgctc cttgcaggag | 120 |
| gtcaggcagt tctccaggct atttgtaccg attgcctact ccttgatctg tgtctttggc | 180 |
| ctcctgggga atattctggt ggtgatcacc tttgcttttt ataagaaggc caggtctatg | 240 |
| acagacgtct atctcttgaa catggccatt gcagacatcc tctttgttct tactctccca | 300 |
| ttctgggcag tgagtcatgc cactggtgcg tgggttttca gcaatgccac gtgcaagttg | 360 |
| ctaaaaggca tctatgccat caactttaac tgcgggatgc tgctcctgac ttgcattagc | 420 |
| atggaccggt acatcgccat tgtacaggcg actaagtcat tccggctccg atccagaaca | 480 |
| ctaccgcgca cgaaaatcat ctgccttgtt gtgtggggc tgtcagtcat catctccagc | 540 |
| tcaacttttg tcttcaacca aaaatacaac acccaaggca gcgatgtctg tgaacccaag | 600 |
| taccagactg tctcggagcc catcaggtgg aagctgctga tgttggggct tgagctactc | 660 |
| tttggtttct ttatcccttt gatgttcatg atattttgtt acacgttcat tgtcaaaacc | 720 |
| ttggtgcaag ctcagaattc taaaaggcac aaagccatcc gtgtaatcat agctgtggtg | 780 |
| cttgtgtttc tggcttgtca gattcctcat aacatggtcc tgcttgtgac ggctgcaaat | 840 |
| ttgggtaaaa tgaaccgatc ctgccagagc gaaaagctaa ttggctatac gaaaactgtc | 900 |
| acagaagtcc tggctttcct gcactgctgc ctgaaccctg tgctctacgc ttttattggg | 960 |
| cagaagttca gaaactactt tctgaagatc ttgaaggacc tgtggtgtgt gagaaggaag | 1020 |
| tacaagtcct caggcttctc ctgtgccggg aggtactcag aaaacatttc tcggcagacc | 1080 |
| agtgagaccg cagataacga caatgcgtcg tccttcacta tg | 1122 |

<210> SEQ ID NO 394
<211> LENGTH: 157
<212> TYPE: PRT
<213> ORGANISM: Artificial Sequence
<220> FEATURE:
<223> OTHER INFORMATION: Synthetic

<400> SEQUENCE: 394

```
Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Gly Ala Val His Thr Arg Gly Leu
```

```
                    100                 105                 110
Asp Phe Ala Cys Asp Ile Tyr Ile Trp Ala Pro Leu Ala Gly Thr Cys
            115                 120                 125

Gly Val Leu Leu Leu Ser Leu Val Ile Thr Leu Tyr Cys Asn His Arg
        130                 135                 140

Asn Arg Arg Arg Val Cys Lys Cys Pro Arg Pro Val Val
145                 150                 155

<210> SEQ ID NO 395
<211> LENGTH: 471
<212> TYPE: DNA
<213> ORGANISM: Artificial Sequence
<220> FEATURE:
<223> OTHER INFORMATION: Synthetic

<400> SEQUENCE: 395
atgggtactt cactgttgtg ctggatggca ctttgtcttt tgggtgccga tcatgctgat     60
gcatgtccgt actccaatcc tagcctgtgc tccggggggg gagggagtga actccctaca    120
cagggaacct tctctaatgt ctccaccaac gtctcccctg caaaaccgac cacaacagct    180 tgccccctata gtaaccccttc cctctgtagt ggaggggggg gttcacctgc tccacgccct    240 cctaccccg cgccaacgat cgcgtcacaa ccgctcagtc ttaggccgga agcctgtagg    300
ccagcggctg gcggtgcggt tcatacgcgg ggattggatt ttgcctgcga catttacatt    360
tgggctccgc tggccggtac ttgtggggta ttgctgttgt ctcttgttat tacgctttat    420
tgcaatcaca ggaacaggcg acgagtatgc aaatgcccgc ggcccgtcgt g           471

<210> SEQ ID NO 396
<211> LENGTH: 28
<212> TYPE: PRT
<213> ORGANISM: Artificial Sequence
<220> FEATURE:
<223> OTHER INFORMATION: Synthetic

<400> SEQUENCE: 396

Met Val Cys Leu Lys Leu Pro Gly Gly Ser Cys Met Thr Ala Leu Thr
1               5                   10                  15

Val Thr Leu Met Val Leu Ser Ser Pro Leu Ala Leu
            20                  25

<210> SEQ ID NO 397
<211> LENGTH: 84
<212> TYPE: DNA
<213> ORGANISM: Artificial Sequence
<220> FEATURE:
<223> OTHER INFORMATION: Synthetic

<400> SEQUENCE: 397
atggtatgct tgaagctccc gggcgggtcc tgcatgaccg ctctcactgt tactcttatg     60
gtccttagtt caccgcttgc cctg                                            84

<210> SEQ ID NO 398
<211> LENGTH: 2
<212> TYPE: PRT
<213> ORGANISM: Artificial Sequence
<220> FEATURE:
<223> OTHER INFORMATION: Synthetic

<400> SEQUENCE: 398

Ala Ser
1
```

<210> SEQ ID NO 399
<211> LENGTH: 6
<212> TYPE: DNA
<213> ORGANISM: Artificial Sequence
<220> FEATURE:
<223> OTHER INFORMATION: Synthetic

<400> SEQUENCE: 399 gcatct							6

<210> SEQ ID NO 400
<211> LENGTH: 13
<212> TYPE: PRT
<213> ORGANISM: Artificial Sequence
<220> FEATURE:
<223> OTHER INFORMATION: Synthetic

<400> SEQUENCE: 400

Gly Gly Gly Gly Ser Gly Gly Gly Gly Ser Gly Gly Ser
1               5                   10

<210> SEQ ID NO 401
<211> LENGTH: 39
<212> TYPE: DNA
<213> ORGANISM: Artificial Sequence
<220> FEATURE:
<223> OTHER INFORMATION: Synthetic

<400> SEQUENCE: 401
gggggaggcg gatctggcgg aggcgggagt ggaggctca						39

<210> SEQ ID NO 402
<211> LENGTH: 555
<212> TYPE: DNA
<213> ORGANISM: Artificial Sequence
<220> FEATURE:
<223> OTHER INFORMATION: Synthetic

<400> SEQUENCE: 402
ggagacacaa gacccccgatt cttgtggcag cccaaaaggg agtgccattt tttcaatggg			60 acggaacgag ttcgcttcct tgatcggtac ttttacaacc aagaagagag tgtacggttc			120 gactcagatg tcggcgagtt ccgagcggtt acggaattgg ggcgacctga cgcggagtac			180 tggaactccc aaaaggatat tttggagcag gcacgagcag ctgtggacac ctattgtcga			240 cataattatg gtgtggtgga atcctttaca gttcagcggc gggtgcaacc taaagtgacc			300 gtgtatccat ctaaaacgca accccctccaa caccataacc tcctggtgtg ttccgtaagc			360 ggcttctatc ccgggtcaat tgaggtcagg tggttcctca acggtcagga ggagaaggcc			420 ggaatggtaa gtactggtct tatccagaac ggagactgga ccttccaaac tttggtaatg			480 ttggaaacgg tgccgcgatc cggggaggtg tatacatgcc aagttgaaca cccgagtgtt			540 acgagccccc tgacg									555

<210> SEQ ID NO 403
<211> LENGTH: 2895
<212> TYPE: DNA
<213> ORGANISM: Artificial Sequence
<220> FEATURE:
<223> OTHER INFORMATION: Synthetic

<400> SEQUENCE: 403
atgggtactt cactgttgtg ctggatggca ctttgtctttt tgggtgccga tcatgctgat			60

```
gcatgtccgt actccaatcc tagcctgtgc tccggggggg gagggagtga actccctaca      120
cagggaacct tctctaatgt ctccaccaac gtctccctg caaaaccgac cacaacagct       180
tgcccctata gtaacccttc cctctgtagt ggaggggggg gttcacctgc tccacgccct      240 cctaccccg cgccaacgat cgcgtcacaa ccgctcagtc ttaggccgga agcctgtagg       300
ccagcggctg gcggtgcggt tcatacgcgg ggattggatt ttgcctgcga catttacatt     360
tgggctccgc tggccggtac ttgtgggta ttgctgttgt ctcttgttat tacgctttat      420
tgcaatcaca ggaacaggcg acgagtatgc aaatgcccgc ggcccgtcgt gagatctggg     480
tccggccaat gtactaacta cgctttgttg aaactcgctg gcgatgttga aagtaacccc      540
ggtcctccaa caggtatggt atgcttgaag ctcccgggcg ggtcctgcat gaccgctctc     600
actgttactc ttatggtcct tagttcaccg cttgccctgg catctgatga gaatcccgtg      660 gttcatttt ttaagaacat cgtcacaccg cgcaccccac ctgggggagg cggatctggc     720
ggaggcggga gtggaggctc aggagacaca agaccccgat tcttgtggca gcccaaaagg     780
gagtgccatt ttttcaatgg gacggaacga gttcgcttcc ttgatcggta cttttacaac    840
caagaagaga gtgtacggtt cgactcagat gtcggcgagt tccgagcggt tacgaaattg    900
gggcgacctg acgcggagta ctggaactcc caaaaggata ttttggagca ggcacgagca    960
gctgtggaca cctattgtcg acataattat ggtgtggtgg aatcctttac agttcagcgg    1020
cgggtgcaac ctaaagtgac cgtgtatcca tctaaaacgc aaccctcca acaccataac      1080 ctcctggtgt gttccgtaag cggcttctat cccgggtcaa ttgaggtcag gtggttcctc    1140
aacggtcagg aggagaaggc cggaatggta agtactggtc ttatccagaa cggagactgg    1200
accttccaaa ctttggtaat gttggaaacg gtgccgcgat ccggggaggt gtatacatgc    1260
caagttgaac acccgagtgt tacgagcccc ctgacggttg agtggagggc gcggtcagag     1320
agcgcacaat ctaaaatgct gtcaggagta ggcggatttg tactcggact cctctttttg     1380
ggcgctgggt tgtttatcta ctttagaaac caaacaagta gagtaaagtt ttcccgaagt     1440
gcggacgctc ccgcgtatca gcaaggtcaa aaccagcttt acaacgaact gaacttggga    1500
cgacgcgaag agtacgatgt tcttgataag cggagagggc gcgatcccga aatgggggga    1560
aagcctcgga ggaagaaccc acaagaaggc ctttataatg aactgcagaa ggacaagatg     1620
gcggaggcgt attccgaaat aggcatgaag ggtgaacgga ggagaggaaa gggacatgac    1680
ggactttatc aaggattgtc taccgcaact aaagacacct atgacgcgtt gcacatgcag    1740
gctctcccct cgagagggttc gagcggcagt ggagagggca gaggaagtct gctaacatgc     1800
ggtgacgtcg aggagaatcc tggcccaatg gcaatatctg gtgttcctgt cctcgggttt    1860
tttatcatag ccgtactgat gtcagcacag gaatcatggg cgataaaaga agagcacgtg    1920
ataatacagg cggagtttta tttgaacccg gaccagagcg gtgagttcat gttcgatttt    1980
gatggcgaca agatatttca cgttgacatg gcaaaaaagg aaacggtgtg gagacttgag    2040
gagtttggac gattcgcatc atttgaggca caaggagcac tcgccaatat cgcggtggac    2100
aaggccaacc tggagatcat gacaaaacgc tccaattata cgcctatcac taatgtgccc    2160
cctgaggtta ctgtgctcac aaattctccc gtagaactta gggaacctaa cgtcctcata    2220
tgtttcatcg acaagttcac tcctccggtg gtcaatgtaa cgtggcttcg gaatggtaag    2280
ccggtcacca cgggtgtctc agagaccgta tttctgccca gagaagacca cctcttccgc    2340
aaatttcatt accttcccctt tcttccttca acggaagacg tttacgactg cagggtcgaa    2400
```

```
cattgggggc ttgacgagcc acttctcaag cattgggagt tcgacgcccc atcaccgctt    2460
ccagaaacga ctgaaaacgt tgtctgcgct cttggcctga cagtgggcct ggtaggcatt    2520
attatcggga ccatctttat catcaaaggt ttgacttccc gggtcaaatt tagcagatcc    2580
gctgacgcac cggcctacca gcagggccag aaccaactct acaacgagct gaatctcggc    2640
cgacgggaag agtatgacgt actcgacaag cggagaggtc gagaccctga gatgggcggt    2700
aaaccgagac ggaaaaatcc ccaagagggt ctttataatg aactccagaa ggataagatg    2760
gctgaagcct attctgagat agggatgaaa ggcgagcggc ggaggggtaa gggccatgat    2820
ggcctttacc agggactctc cacggcaacc aaagatactt acgacgccct tcacatgcaa    2880
gccctcccgc cacgc                                                    2895
```

<210> SEQ ID NO 404
<211> LENGTH: 39
<212> TYPE: DNA
<213> ORGANISM: Artificial Sequence
<220> FEATURE:
<223> OTHER INFORMATION: Synthetic

<400> SEQUENCE: 404

```
gttgagtgga gggcgcggtc agagagcgca caatctaaa                              39
```

<210> SEQ ID NO 405
<211> LENGTH: 1225
<212> TYPE: PRT
<213> ORGANISM: Artificial Sequence
<220> FEATURE:
<223> OTHER INFORMATION: Synthetic

<400> SEQUENCE: 405

```
Met Gly Thr Ser Leu Leu Cys Trp Met Ala Leu Cys Leu Leu Gly Ala
1               5                   10                  15

Asp His Ala Asp Ala Cys Pro Tyr Ser Asn Pro Ser Leu Cys Ser Gly
            20                  25                  30

Gly Gly Gly Ser Glu Leu Pro Thr Gln Gly Thr Phe Ser Asn Val Ser
        35                  40                  45

Thr Asn Val Ser Pro Ala Lys Pro Thr Thr Thr Ala Cys Pro Tyr Ser
    50                  55                  60

Asn Pro Ser Leu Cys Ser Gly Gly Gly Ser Pro Ala Pro Arg Pro
65                  70                  75                  80

Pro Thr Pro Ala Pro Thr Ile Ala Ser Gln Pro Leu Ser Leu Arg Pro
                85                  90                  95

Glu Ala Cys Arg Pro Ala Ala Gly Ala Val His Thr Arg Gly Leu
            100                 105                 110

Asp Phe Ala Cys Asp Ile Tyr Ile Trp Ala Pro Leu Ala Gly Thr Cys
        115                 120                 125

Gly Val Leu Leu Leu Ser Leu Val Ile Thr Leu Tyr Cys Asn His Arg
    130                 135                 140

Asn Arg Arg Arg Val Cys Lys Cys Pro Arg Pro Val Val Arg Ser Gly
145                 150                 155                 160

Ser Gly Gln Cys Thr Asn Tyr Ala Leu Leu Lys Leu Ala Gly Asp Val
                165                 170                 175

Glu Ser Asn Pro Gly Pro Pro Thr Gly Met Val Cys Leu Lys Leu Pro
            180                 185                 190

Gly Gly Ser Cys Met Thr Ala Leu Thr Val Thr Leu Met Val Leu Ser
        195                 200                 205
```

```
Ser Pro Leu Ala Leu Ala Ser Asp Glu Asn Pro Val His Phe Phe
    210                 215                 220

Lys Asn Ile Val Thr Pro Arg Thr Pro Gly Gly Gly Ser Gly
225                 230                 235                 240

Gly Gly Gly Ser Gly Gly Ser Gly Asp Thr Arg Pro Arg Phe Leu Trp
                245                 250                 255

Gln Pro Lys Arg Glu Cys His Phe Phe Asn Gly Thr Glu Arg Val Arg
                260                 265                 270

Phe Leu Asp Arg Tyr Phe Tyr Asn Gln Glu Glu Ser Val Arg Phe Asp
                275                 280                 285

Ser Asp Val Gly Glu Phe Arg Ala Val Thr Glu Leu Gly Arg Pro Asp
290                 295                 300

Ala Glu Tyr Trp Asn Ser Gln Lys Asp Ile Leu Glu Gln Ala Arg Ala
305                 310                 315                 320

Ala Val Asp Thr Tyr Cys Arg His Asn Tyr Gly Val Val Glu Ser Phe
                325                 330                 335

Thr Val Gln Arg Arg Val Gln Pro Lys Val Thr Val Tyr Pro Ser Lys
                340                 345                 350

Thr Gln Pro Leu Gln His His Asn Leu Leu Val Cys Ser Val Ser Gly
                355                 360                 365

Phe Tyr Pro Gly Ser Ile Glu Val Arg Trp Phe Leu Asn Gly Gln Glu
370                 375                 380

Glu Lys Ala Gly Met Val Ser Thr Gly Leu Ile Gln Asn Gly Asp Trp
385                 390                 395                 400

Thr Phe Gln Thr Leu Val Met Leu Glu Thr Val Pro Arg Ser Gly Glu
                405                 410                 415

Val Tyr Thr Cys Gln Val Glu His Pro Ser Val Thr Ser Pro Leu Thr
                420                 425                 430

Val Glu Trp Arg Ala Arg Ser Glu Ser Ala Gln Ser Lys Met Leu Ser
                435                 440                 445

Gly Val Gly Gly Phe Val Leu Gly Leu Leu Phe Leu Gly Ala Gly Leu
450                 455                 460

Phe Ile Tyr Phe Arg Asn Gln Thr Ser Arg Val Lys Phe Ser Arg Ser
465                 470                 475                 480

Ala Asp Ala Pro Ala Tyr Gln Gln Gly Gln Asn Gln Leu Tyr Asn Glu
                485                 490                 495

Leu Asn Leu Gly Arg Arg Glu Glu Tyr Asp Val Leu Asp Lys Arg Arg
                500                 505                 510

Gly Arg Asp Pro Glu Met Gly Gly Lys Pro Arg Arg Lys Asn Pro Gln
                515                 520                 525

Glu Gly Leu Tyr Asn Glu Leu Gln Lys Asp Lys Met Ala Glu Ala Tyr
530                 535                 540

Ser Glu Ile Gly Met Lys Gly Glu Arg Arg Arg Gly Lys Gly His Asp
545                 550                 555                 560

Gly Leu Tyr Gln Gly Leu Ser Thr Ala Thr Lys Asp Thr Tyr Asp Ala
                565                 570                 575

Leu His Met Gln Ala Leu Pro Pro Arg Gly Ser Gly Ser Gly Glu
                580                 585                 590

Gly Arg Gly Ser Leu Leu Thr Cys Gly Asp Val Glu Glu Asn Pro Gly
                595                 600                 605

Pro Met Ala Ile Ser Gly Val Pro Val Leu Gly Phe Phe Ile Ile Ala
610                 615                 620

Val Leu Met Ser Ala Gln Glu Ser Trp Ala Ile Lys Glu Glu His Val
```

```
              625                 630                 635                 640
        Ile Ile Gln Ala Glu Phe Tyr Leu Asn Pro Asp Gln Ser Gly Glu Phe
                        645                 650                 655

Met Phe Asp Phe Asp Gly Asp Glu Ile Phe His Val Asp Met Ala Lys
                        660                 665                 670

Lys Glu Thr Val Trp Arg Leu Glu Phe Gly Arg Phe Ala Ser Phe
                        675                 680                 685

Glu Ala Gln Gly Ala Leu Ala Asn Ile Ala Val Asp Lys Ala Asn Leu
                        690                 695                 700

Glu Ile Met Thr Lys Arg Ser Asn Tyr Thr Pro Ile Thr Asn Val Pro
        705                 710                 715                 720

Pro Glu Val Thr Val Leu Thr Asn Ser Pro Val Leu Arg Glu Pro
                        725                 730                 735

Asn Val Leu Ile Cys Phe Ile Asp Lys Phe Thr Pro Pro Val Val Asn
                        740                 745                 750

Val Thr Trp Leu Arg Asn Gly Lys Pro Val Thr Thr Gly Val Ser Glu
                        755                 760                 765

Thr Val Phe Leu Pro Arg Glu Asp His Leu Phe Arg Lys Phe His Tyr
                        770                 775                 780

Leu Pro Phe Leu Pro Ser Thr Glu Asp Val Tyr Asp Cys Arg Val Glu
        785                 790                 795                 800

His Trp Gly Leu Asp Glu Pro Leu Leu Lys His Trp Glu Phe Asp Ala
                        805                 810                 815

Pro Ser Pro Leu Pro Glu Thr Thr Glu Asn Val Val Cys Ala Leu Gly
                        820                 825                 830

Leu Thr Val Gly Leu Val Gly Ile Ile Gly Thr Ile Phe Ile Ile
                        835                 840                 845

Lys Gly Leu Thr Ser Arg Val Lys Phe Ser Arg Ser Ala Asp Ala Pro
                        850                 855                 860

Ala Tyr Gln Gln Gly Gln Asn Gln Leu Tyr Asn Glu Leu Asn Leu Gly
        865                 870                 875                 880

Arg Arg Glu Glu Tyr Asp Val Leu Asp Lys Arg Arg Gly Arg Asp Pro
                        885                 890                 895

Glu Met Gly Gly Lys Pro Arg Arg Lys Asn Pro Gln Glu Gly Leu Tyr
                        900                 905                 910

Asn Glu Leu Gln Lys Asp Lys Met Ala Glu Ala Tyr Ser Glu Ile Gly
                        915                 920                 925

Met Lys Gly Glu Arg Arg Arg Gly Lys Gly His Asp Gly Leu Tyr Gln
                        930                 935                 940

Gly Leu Ser Thr Ala Thr Lys Asp Thr Tyr Asp Ala Leu His Met Gln
        945                 950                 955                 960

Ala Leu Pro Pro Arg Gly Ser Gly Ala Thr Asn Phe Ser Leu Leu Lys
                        965                 970                 975

Gln Ala Gly Asp Val Glu Glu Asn Pro Gly Pro Val Ser Lys Gly Glu
                        980                 985                 990

Glu Leu Phe Thr Gly Val Val Pro Ile Leu Val Glu Leu Asp Gly Asp
                        995                 1000                1005

Val Asn Gly His Lys Phe Ser Val Ser Gly Glu Gly Glu Gly Asp
                        1010                1015                1020

Ala Thr Tyr Gly Lys Leu Thr Leu Lys Phe Ile Cys Thr Thr Gly
                        1025                1030                1035

Lys Leu Pro Val Pro Trp Pro Thr Leu Val Thr Thr Leu Thr Tyr
                        1040                1045                1050
```

| | | | | | | | | | | |
|---|---|---|---|---|---|---|---|---|---|---|
|Gly|Val|Gln|Cys|Phe|Ser|Arg|Tyr|Pro|Asp|His|Met|Lys|Gln|His|
| |1055| | | |1060| | | |1065| |

Asp Phe Phe Lys Ser Ala Met Pro Glu Gly Tyr Val Gln Glu Arg
    1070                1075                1080

Thr Ile Phe Phe Lys Asp Asp Gly Asn Tyr Lys Thr Arg Ala Glu
    1085                1090                1095

Val Lys Phe Glu Gly Asp Thr Leu Val Asn Arg Ile Glu Leu Lys
    1100                1105                1110

Gly Ile Asp Phe Lys Glu Asp Gly Asn Ile Leu Gly His Lys Leu
    1115                1120                1125

Glu Tyr Asn Tyr Asn Ser His Asn Val Tyr Ile Met Ala Asp Lys
    1130                1135                1140

Gln Lys Asn Gly Ile Lys Ala Asn Phe Lys Ile Arg His Asn Ile
    1145                1150                1155

Glu Asp Gly Ser Val Gln Leu Ala Asp His Tyr Gln Gln Asn Thr
    1160                1165                1170

Pro Ile Gly Asp Gly Pro Val Leu Leu Pro Asp Asn His Tyr Leu
    1175                1180                1185

Ser Thr Gln Ser Ala Leu Ser Lys Asp Pro Asn Glu Lys Arg Asp
    1190                1195                1200

His Met Val Leu Leu Glu Phe Val Thr Ala Ala Gly Ile Thr Leu
    1205                1210                1215

Gly Met Asp Glu Leu Tyr Lys
    1220                1225

<210> SEQ ID NO 406
<211> LENGTH: 78
<212> TYPE: DNA
<213> ORGANISM: Artificial Sequence
<220> FEATURE:
<223> OTHER INFORMATION: Synthetic

<400> SEQUENCE: 406
atgctgtcag gagtaggcgg atttgtactc ggactcctct ttttgggcgc tgggttgttt     60
atctacttta gaaaccaa                                                   78

<210> SEQ ID NO 407
<211> LENGTH: 2
<212> TYPE: PRT
<213> ORGANISM: Artificial Sequence
<220> FEATURE:
<223> OTHER INFORMATION: Synthetic

<400> SEQUENCE: 407

Thr Ala
1

<210> SEQ ID NO 408
<211> LENGTH: 6
<212> TYPE: DNA
<213> ORGANISM: Artificial Sequence
<220> FEATURE:
<223> OTHER INFORMATION: Synthetic

<400> SEQUENCE: 408 acaagt                                                                6

<210> SEQ ID NO 409
<211> LENGTH: 3678

<212> TYPE: DNA
<213> ORGANISM: Artificial Sequence
<220> FEATURE:
<223> OTHER INFORMATION: Synthetic

<400> SEQUENCE: 409

```
atgggtactt cactgttgtg ctggatggca ctttgtcttt tgggtgccga tcatgctgat      60
gcatgtccgt actccaatcc tagcctgtgc tccgggggg gagggagtga actccctaca     120
cagggaacct tctctaatgt ctccaccaac gtctcccctg caaaaccgac acaacagct     180
tgcccctata gtaacccttc cctctgtagt ggagggggg gttcacctgc tccacgccct     240
cctaccccg cgccaacgat cgcgtcacaa ccgctcagtc ttaggccgga agcctgtagg     300
ccagcggctg gcggtgcggt tcatacgcgg ggattggatt ttgcctgcga catttacatt     360
tgggctccgc tggccggtac ttgtgggta ttgctgttgt ctcttgttat tacgctttat     420
tgcaatcaca ggaacaggcg acgagtatgc aaatgcccgc ggcccgtcgt gagatctggg     480
tccggccaat gtactaacta cgctttgttg aaactcgctg gcgatgttga aagtaacccc     540
ggtcctccaa caggtatggt atgcttgaag ctcccgggcg ggtcctgcat gaccgctctc     600
actgttactc ttatggtcct tagttcaccg cttgccctgg catctgatga aatcccgtg     660
gttcattttt ttaagaacat cgtcacaccg cgcacccac ctgggggagg cggatctggc     720
ggaggcggga gtggaggctc aggagacaca agacccgat tcttgtggca gcccaaaagg     780
gagtgccatt ttttcaatgg gacggaacga gttcgcttcc ttgatcggta cttttacaac     840
caagaagaga gtgtacggtt cgactcagat gtcggcgagt tccgagcggt tacggaattg     900
gggcgacctg acgcggagta ctggaactcc caaaaggata ttttggagca ggcacgagca     960
gctgtggaca cctattgtcg acataattat ggtgtggtgg aatcctttac agttcagcgg    1020
cgggtgcaac ctaaagtgac cgtgtatcca tctaaaacgc aaccctcca acaccataac    1080
ctcctggtgt gttccgtaag cggcttctat cccgggtcaa ttgaggtcag gtggttcctc    1140
aacggtcagg aggagaaggc cggaatggta agtactggtc ttatccagaa cggagactgg    1200
accttccaaa ctttggtaat gttggaaacg gtgccgcgat ccggggaggt gtatacatgc    1260
caagttgaac acccgagtgt tacgagcccc ctgacggttg agtggagggc gcggtcagag    1320
agcgcacaat ctaaaatgct gtcaggagta ggcggattg tactcggact cctctttttg    1380
ggcgctgggt tgtttatcta cttagaaac caaacaagta gagtaaagtt tcccgaagt    1440
gcggacgctc ccgcgtatca gcaaggtcaa aaccagcttt acaacgaact gaacttggga    1500
cgacgcgaag agtacgatgt tcttgataag cggagagggc gcgatcccga atgggggga    1560
aagcctcgga ggaagaaccc acaagaaggc ctttataatg aactgcagaa ggacaagatg    1620
gcggaggcgt attccgaaat aggcatgaag ggtgaacgga ggagaggaaa gggacatgac    1680
ggactttatc aaggattgtc taccgcaact aaagacacct atgacgcgtt gcacatgcag    1740
gctctccctc cgagaggttc gagcggcagt ggagagggca gaggaagtct gctaacatgc    1800
ggtgacgtcg aggagaatcc tggcccaatg gcaatatctg tgttcctgt cctcgggttt    1860
tttatcatag ccgtactgat gtcagcacag gaatcatggg cgataaaaga agagcacgtg    1920
ataatacagg cggagtttta tttgaacccg gaccagagcg tgagttcat gttcgatttt    1980
gatggcgacg agatatttca cgttgacatg gcaaaaaagg aaacggtgtg gagacttgag    2040
gagtttggac gattcgcatc atttgaggca caaggagcac tcgccaatat cgcggtggac    2100
aaggccaacc tggagatcat gacaaaacgc tccaattata cgcctatcac taatgtgccc    2160
```

```
cctgaggtta ctgtgctcac aaattctccc gtagaactta gggaacctaa cgtcctcata    2220
tgtttcatcg acaagttcac tcctccggtg gtcaatgtaa cgtggcttcg gaatggtaag    2280
ccggtcacca cgggtgtctc agagaccgta tttctgccca gagaagacca cctcttccgc    2340
aaatttcatt accttccctt tcttccttca acggaagacg tttacgactg cagggtcgaa    2400 cattggggc ttgacgagcc acttctcaag cattgggagt tcgacgcccc atcaccgctt     2460
ccagaaacga ctgaaaacgt tgtctgcgct cttggcctga cagtgggcct ggtaggcatt    2520
attatcggga ccatctttat catcaaaggt ttgacttccc gggtcaaatt tagcagatcc    2580
gctgacgcac cggcctacca gcagggccag aaccaactct acaacgagct gaatctcggc    2640
cgacgggaag agtatgacgt actcgacaag cggagaggtc gagaccctga gatgggcggt    2700
aaaccgagac ggaaaaatcc ccaagagggt ctttataatg aactccagaa ggataagatg    2760
gctgaagcct attctgagat agggatgaaa ggcgagcggc ggaggggtaa gggccatgat    2820
ggcctttacc agggactctc cacggcaacc aaagatactt acgacgccct tcacatgcaa    2880
gccctcccgc cacgcggatc cggcgcaaca aacttctctc tgctgaaaca agccggagat    2940
gtcgaagaga atcctggacc ggtgagcaag ggcgaggagc tgttcaccgg ggtggtgccc    3000
atcctggtcg agctggacgg cgacgtaaac ggccacaagt tcagcgtgtc tggcgagggc    3060
gagggcgatg ccacctacgg caagctgacc ctgaagttca tctgcaccac cggcaagctg    3120
cccgtgccct ggcccaccct cgtgaccacc ctgacctacg gcgtgcagtg cttcagccgc    3180
taccccgacc acatgaagca gcacgacttc ttcaagtccg ccatgcccga aggctacgtc    3240
caggagcgca ccatcttctt caaggacgac ggcaactaca agacccgcgc cgaggtgaag    3300
ttcgagggcg acaccctggt gaaccgcatc gagctgaagg gcatcgactt caaggaggac    3360
ggcaacatcc tggggcacaa gctggagtac aactacaaca gccacaacgt ctatatcatg    3420
gccgacaagc agaagaacgg catcaaggcg aacttcaaga tccgccacaa catcgaggac    3480
ggcagcgtgc agctcgccga ccactaccag cagaacaccc ccatcggcga cggccccgtg    3540
ctgctgcccg acaaccacta cctgagcacc cagtccgccc tgagcaaaga ccccaacgag    3600
aagcgcgatc acatggtcct gctggagttc gtgaccgccg ccgggatcac tctcggcatg    3660
gacgagctgt acaagtaa                                                 3678
```

<210> SEQ ID NO 410
<211> LENGTH: 336
<212> TYPE: DNA
<213> ORGANISM: Artificial Sequence
<220> FEATURE:
<223> OTHER INFORMATION: Synthetic

<400> SEQUENCE: 410

```
agagtaaagt tttcccgaag tgcggacgct cccgcgtatc agcaaggtca aaaccagctt      60
tacaacgaac tgaacttggg acgacgcgaa gagtacgatg ttcttgataa gcggagaggg     120
cgcgatcccg aaatgggggg aaagcctcgg aggaagaacc cacaagaagg cctttataat     180
gaactgcaga aggacaagat ggcggaggcg tattccgaaa taggcatgaa gggtgaacgg     240
aggagaggaa agggacatga cggactttat caaggattgt ctaccgcaac taaagacacc     300
tatgacgcgt tgcacatgca ggctctccct ccgaga                              336
```

<210> SEQ ID NO 411
<211> LENGTH: 58
<212> TYPE: DNA
<213> ORGANISM: Artificial Sequence

```
<220> FEATURE:
<223> OTHER INFORMATION: Synthetic

<400> SEQUENCE: 411
gatgagaatc cgtggttca tttttttaag aacatcgtca caccgcgcac cccacctg    58

<210> SEQ ID NO 412
<211> LENGTH: 400
<212> TYPE: PRT
<213> ORGANISM: Artificial Sequence
<220> FEATURE:
<223> OTHER INFORMATION: Synthetic

<400> SEQUENCE: 412
```

Met Val Cys Leu Lys Leu Pro Gly Gly Ser Cys Met Thr Ala Leu Thr
1               5                   10                  15

Val Thr Leu Met Val Leu Ser Ser Pro Leu Ala Leu Ala Ser Asp Glu
            20                  25                  30

Asn Pro Val Val His Phe Phe Lys Asn Ile Val Thr Pro Arg Thr Pro
        35                  40                  45

Pro Gly Gly Gly Gly Ser Gly Gly Gly Gly Ser Gly Gly Ser Gly Asp
    50                  55                  60

Thr Arg Pro Arg Phe Leu Trp Gln Pro Lys Arg Glu Cys His Phe Phe
65                  70                  75                  80

Asn Gly Thr Glu Arg Val Arg Phe Leu Asp Arg Tyr Phe Tyr Asn Gln
                85                  90                  95

Glu Glu Ser Val Arg Phe Asp Ser Asp Val Gly Glu Phe Arg Ala Val
            100                 105                 110

Thr Glu Leu Gly Arg Pro Asp Ala Glu Tyr Trp Asn Ser Gln Lys Asp
        115                 120                 125

Ile Leu Glu Gln Ala Arg Ala Ala Val Asp Thr Tyr Cys Arg His Asn
    130                 135                 140

Tyr Gly Val Val Glu Ser Phe Thr Val Gln Arg Arg Val Gln Pro Lys
145                 150                 155                 160

Val Thr Val Tyr Pro Ser Lys Thr Gln Pro Leu Gln His His Asn Leu
                165                 170                 175

Leu Val Cys Ser Val Ser Gly Phe Tyr Pro Gly Ser Ile Glu Val Arg
            180                 185                 190

Trp Phe Leu Asn Gly Gln Glu Glu Lys Ala Gly Met Val Ser Thr Gly
        195                 200                 205

Leu Ile Gln Asn Gly Asp Trp Thr Phe Gln Thr Leu Val Met Leu Glu
    210                 215                 220

Thr Val Pro Arg Ser Gly Glu Val Tyr Thr Cys Gln Val Glu His Pro
225                 230                 235                 240

Ser Val Thr Ser Pro Leu Thr Val Glu Trp Arg Ala Arg Ser Glu Ser
                245                 250                 255

Ala Gln Ser Lys Met Leu Ser Gly Val Gly Gly Phe Val Leu Gly Leu
            260                 265                 270

Leu Phe Leu Gly Ala Gly Leu Phe Ile Tyr Phe Arg Asn Gln Thr Ser
        275                 280                 285

Arg Val Lys Phe Ser Arg Ser Ala Asp Ala Pro Ala Tyr Gln Gln Gly
    290                 295                 300

Gln Asn Gln Leu Tyr Asn Glu Leu Asn Leu Gly Arg Arg Glu Glu Tyr
305                 310                 315                 320

Asp Val Leu Asp Lys Arg Arg Gly Arg Asp Pro Glu Met Gly Gly Lys
                325                 330                 335

```
Pro Arg Arg Lys Asn Pro Gln Glu Gly Leu Tyr Asn Glu Leu Gln Lys
            340                 345                 350

Asp Lys Met Ala Glu Ala Tyr Ser Glu Ile Gly Met Lys Gly Glu Arg
        355                 360                 365

Arg Arg Gly Lys Gly His Asp Gly Leu Tyr Gln Gly Leu Ser Thr Ala
    370                 375                 380

Thr Lys Asp Thr Tyr Asp Ala Leu His Met Gln Ala Leu Pro Pro Arg
385                 390                 395                 400

<210> SEQ ID NO 413
<211> LENGTH: 1200
<212> TYPE: DNA
<213> ORGANISM: Artificial Sequence
<220> FEATURE:
<223> OTHER INFORMATION: Synthetic

<400> SEQUENCE: 413
atggtatgct tgaagctccc gggcgggtcc tgcatgaccg ctctcactgt tactcttatg      60
gtccttagtt caccgcttgc cctggcatct gatgagaatc ccgtggttca ttttttttaag    120 aacatcgtca caccgcgcac cccacctggg ggaggcggat ctggcggagg cgggagtgga    180
ggctcaggag acacaagacc ccgattcttg tggcagccca aagggagtg ccatttttc      240 aatgggacgg aacgagttcg cttccttgat cggtactttt acaaccaaga agagagtgta    300
cggttcgact cagatgtcgg cgagttccga gcggttacgg aattggggcg acctgacgcg    360
gagtactgga actcccaaaa ggatattttg gagcaggcac gagcagctgt ggacacctat    420
tgtcgacata attatggtgt ggtggaatcc tttacagttc agcggcgggt gcaacctaaa    480
gtgaccgtgt atccatctaa aacgcaaccc ctccaacacc ataacctcct ggtgtgttcc    540
gtaagcggct tctatcccgg gtcaattgag gtcaggtggt cctcaacgg tcaggaggag     600 aaggccggaa tggtaagtac tggtcttatc cagaacggag actggacctt ccaaactttg    660
gtaatgttgg aaacggtgcc gcgatccggg gaggtgtata catgccaagt tgaacacccg    720
agtgttacga gccccctgac ggttgagtgg agggcgcggt cagagagcgc acaatctaaa    780
atgctgtcag gagtaggcgg atttgtactc ggactcctct ttttgggcgc tgggttgttt    840
atctacttta gaaaccaaac aagtagagta agttttccc gaagtgcgga cgctcccgcg     900
tatcagcaag gtcaaaacca gctttacaac gaactgaact gggacgacg cgaagagtac     960 gatgttcttg ataagcggag agggcgcgat cccgaaatgg ggggaaagcc tcggaggaag    1020
aacccacaag aaggccttta taatgaactg cagaaggaca gatggcggga ggcgtattcc    1080
gaaataggca tgaagggtga acggaggaga ggaaagggac atgacggact ttatcaagga    1140
ttgtctaccg caactaaaga cacctatgac gcgttgcaca tgcaggctct ccctccgaga    1200

<210> SEQ ID NO 414
<211> LENGTH: 75
<212> TYPE: DNA
<213> ORGANISM: Artificial Sequence
<220> FEATURE:
<223> OTHER INFORMATION: Synthetic

<400> SEQUENCE: 414
atggcaatat ctggtgttcc tgtcctcggg tttttatca tagccgtact gatgtcagca      60
caggaatcat gggcg                                                      75

<210> SEQ ID NO 415
```

<211> LENGTH: 534
<212> TYPE: DNA
<213> ORGANISM: Artificial Sequence
<220> FEATURE:
<223> OTHER INFORMATION: Synthetic

<400> SEQUENCE: 415

```
ataaaagaag agcacgtgat aatacaggcg gagttttatt tgaacccgga ccagagcggt      60
gagttcatgt tcgattttga tggcgacgag atatttcacg ttgacatggc aaaaaaggaa     120
acggtgtgga gacttgagga gtttggacga ttcgcatcat ttgaggcaca aggagcactc     180
gccaatatcg cggtggacaa ggccaacctg gagatcatga caaaacgctc caattatacg     240
cctatcacta atgtgccccc tgaggttact gtgctcacaa attctcccgt agaacttagg     300
gaacctaacg tcctcatatg tttcatcgac aagttcactc ctccggtggt caatgtaacg     360
tggcttcgga atggtaagcc ggtcaccacg ggtgtctcag agaccgtatt tctgcccaga     420
gaagaccacc tcttccgcaa atttcattac cttcccttc ttccttcaac ggaagacgtt     480
tacgactgca gggtcgaaca ttgggggctt gacgagccac ttctcaagca ttgg           534
```

<210> SEQ ID NO 416
<211> LENGTH: 23
<212> TYPE: PRT
<213> ORGANISM: Artificial Sequence
<220> FEATURE:
<223> OTHER INFORMATION: Synthetic

<400> SEQUENCE: 416

Asn Val Val Cys Ala Leu Gly Leu Thr Val Gly Leu Val Gly Ile Ile
 1               5                  10                  15

Ile Gly Thr Ile Phe Ile Ile
            20

<210> SEQ ID NO 417
<211> LENGTH: 39
<212> TYPE: DNA
<213> ORGANISM: Artificial Sequence
<220> FEATURE:
<223> OTHER INFORMATION: Synthetic

<400> SEQUENCE: 417

```
gagttcgacg ccccatcacc gcttccagaa acgactgaa                             39
```

<210> SEQ ID NO 418
<211> LENGTH: 26
<212> TYPE: PRT
<213> ORGANISM: Artificial Sequence
<220> FEATURE:
<223> OTHER INFORMATION: Synthetic

<400> SEQUENCE: 418

Asn Val Val Cys Ala Leu Gly Leu Thr Val Gly Leu Val Gly Ile Ile
 1               5                  10                  15

Ile Gly Thr Ile Phe Ile Ile Lys Gly Leu
            20                  25

<210> SEQ ID NO 419
<211> LENGTH: 78
<212> TYPE: DNA
<213> ORGANISM: Artificial Sequence
<220> FEATURE:
<223> OTHER INFORMATION: Synthetic

<400> SEQUENCE: 419

-continued aacgttgtct gcgctcttgg cctgacagtg ggcctggtag gcattattat cgggaccatc    60
tttatcatca aaggtttg    78

<210> SEQ ID NO 420
<211> LENGTH: 2
<212> TYPE: PRT
<213> ORGANISM: Artificial Sequence
<220> FEATURE:
<223> OTHER INFORMATION: Synthetic

<400> SEQUENCE: 420

Thr Ser
1

<210> SEQ ID NO 421
<211> LENGTH: 6
<212> TYPE: DNA
<213> ORGANISM: Artificial Sequence
<220> FEATURE:
<223> OTHER INFORMATION: Synthetic

<400> SEQUENCE: 421 acttcc    6

<210> SEQ ID NO 422
<211> LENGTH: 336
<212> TYPE: DNA
<213> ORGANISM: Artificial Sequence
<220> FEATURE:
<223> OTHER INFORMATION: Synthetic

<400> SEQUENCE: 422
cgggtcaaat ttagcagatc cgctgacgca ccggcctacc agcagggcca gaaccaactc    60
tacaacgagc tgaatctcgg ccgacgggaa gagtatgacg tactcgacaa gcggagaggt   120
cgagaccctg agatgggcgg taaaccgaga cggaaaaatc cccaagaggg tctttataat   180
gaactccaga aggataagat ggctgaagcc tattctgaga tagggatgaa aggcgagcgg   240
cggaggggta agggccatga tggcctttac cagggactct ccacggcaac caaagatact   300
tacgacgccc ttcacatgca agccctcccg ccacgc    336

<210> SEQ ID NO 423
<211> LENGTH: 356
<212> TYPE: PRT
<213> ORGANISM: Artificial Sequence
<220> FEATURE:
<223> OTHER INFORMATION: Synthetic

<400> SEQUENCE: 423

Met Ala Ile Ser Gly Val Pro Val Leu Gly Phe Phe Ile Ile Ala Val
1               5                   10                  15

Leu Met Ser Ala Gln Glu Ser Trp Ala Ile Lys Glu Glu His Val Ile
                20                  25                  30

Ile Gln Ala Glu Phe Tyr Leu Asn Pro Asp Gln Ser Gly Glu Phe Met
            35                  40                  45

Phe Asp Phe Asp Gly Asp Glu Ile Phe His Val Asp Met Ala Lys Lys
        50                  55                  60

Glu Thr Val Trp Arg Leu Glu Glu Phe Gly Arg Phe Ala Ser Phe Glu
65                  70                  75                  80

Ala Gln Gly Ala Leu Ala Asn Ile Ala Val Asp Lys Ala Asn Leu Glu
                85                  90                  95

Ile Met Thr Lys Arg Ser Asn Tyr Thr Pro Ile Thr Asn Val Pro Pro
            100                 105                 110

Glu Val Thr Val Leu Thr Asn Ser Pro Val Glu Leu Arg Glu Pro Asn
            115                 120                 125

Val Leu Ile Cys Phe Ile Asp Lys Phe Thr Pro Val Val Asn Val
130                 135                 140

Thr Trp Leu Arg Asn Gly Lys Pro Val Thr Gly Val Ser Glu Thr
145                 150                 155                 160

Val Phe Leu Pro Arg Glu Asp His Leu Phe Arg Lys Phe His Tyr Leu
                165                 170                 175

Pro Phe Leu Pro Ser Thr Glu Asp Val Tyr Asp Cys Arg Val Glu His
            180                 185                 190

Trp Gly Leu Asp Glu Pro Leu Leu Lys His Trp Glu Phe Asp Ala Pro
            195                 200                 205

Ser Pro Leu Pro Glu Thr Thr Glu Asn Val Val Cys Ala Leu Gly Leu
            210                 215                 220

Thr Val Gly Leu Val Gly Ile Ile Ile Gly Thr Ile Phe Ile Ile Lys
225                 230                 235                 240

Gly Leu Thr Ser Arg Val Lys Phe Ser Arg Ser Ala Asp Ala Pro Ala
                245                 250                 255

Tyr Gln Gln Gly Gln Asn Gln Leu Tyr Asn Glu Leu Asn Leu Gly Arg
            260                 265                 270

Arg Glu Glu Tyr Asp Val Leu Asp Lys Arg Gly Arg Asp Pro Glu
            275                 280                 285

Met Gly Gly Lys Pro Arg Arg Lys Asn Pro Gln Glu Gly Leu Tyr Asn
    290                 295                 300

Glu Leu Gln Lys Asp Lys Met Ala Glu Ala Tyr Ser Glu Ile Gly Met
305                 310                 315                 320

Lys Gly Glu Arg Arg Arg Gly Lys Gly His Asp Gly Leu Tyr Gln Gly
                325                 330                 335

Leu Ser Thr Ala Thr Lys Asp Thr Tyr Asp Ala Leu His Met Gln Ala
            340                 345                 350

Leu Pro Pro Arg
        355

<210> SEQ ID NO 424
<211> LENGTH: 1068
<212> TYPE: DNA
<213> ORGANISM: Artificial Sequence
<220> FEATURE:
<223> OTHER INFORMATION: Synthetic

<400> SEQUENCE: 424
atggcaatat ctggtgttcc tgtcctcggg ttttttatca tagccgtact gatgtcagca      60
caggaatcat gggcgataaa agaagagcac gtgataatac aggcggagtt ttatttgaac     120
ccggaccaga gcggtgagtt catgttcgat tttgatggcg acgagatatt tcacgttgac     180
atggcaaaaa aggaaacggt gtggagactt gaggagtttg acgattcgc atcatttgag      240 gcacaaggag cactcgccaa tatcgcggtg gacaaggcca acctggagat catgacaaaa     300
cgctccaatt atacgcctat cactaatgtg cccctgagg ttactgtgct cacaaattct     360
cccgtagaac ttagggaacc taacgtcctc atatgtttca tcgacaagtt cactcctccg     420
gtggtcaatg taacgtggct tcggaatggt aagccggtca ccacgggtgt ctcagagacc     480
gtatttctgc ccagagaaga ccacctcttc cgcaaatttc attccttcc ctttcttcct     540

```
tcaacggaag acgtttacga ctgcagggtc gaacattggg ggcttgacga gccacttctc      600
aagcattggg agttcgacgc cccatcaccg cttccagaaa cgactgaaaa cgttgtctgc      660
gctcttggcc tgacagtggg cctggtaggc attattatcg ggaccatctt tatcatcaaa      720
ggtttgactt cccgggtcaa atttagcaga tccgctgacg caccggccta ccagcagggc      780
cagaaccaac tctacaacga gctgaatctc ggccgacggg aagagtatga cgtactcgac      840
aagcggagag gtcgagaccc tgagatgggc ggtaaaccga gacggaaaaa tccccaagag      900
ggtctttata atgaactcca gaaggataag atggctgaag cctattctga gatagggatg      960
aaaggcgagc ggcggagggg taagggccat gatggccttt accagggact ctccacggca     1020
accaaagata cttacgacgc ccttcacatg caagccctcc cgccacgc                  1068
```

<210> SEQ ID NO 425
<211> LENGTH: 893
<212> TYPE: PRT
<213> ORGANISM: Artificial Sequence
<220> FEATURE:
<223> OTHER INFORMATION: Synthetic

<400> SEQUENCE: 425

```
Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile
            20                  25                  30

Lys Pro Gly Ala Ser Val Lys Met Ser Cys Lys Ala Ser Gly Tyr Thr
        35                  40                  45

Phe Thr Ser Tyr Val Met His Trp Val Lys Gln Lys Pro Gly Gln Gly
    50                  55                  60

Leu Glu Trp Ile Gly Tyr Ile Asn Pro Tyr Asn Asp Gly Thr Lys Tyr
65                  70                  75                  80

Asn Glu Lys Phe Lys Gly Lys Ala Thr Leu Thr Ser Asp Lys Ser Ser
                85                  90                  95

Ser Thr Ala Tyr Met Glu Leu Ser Ser Leu Thr Ser Glu Asp Ser Ala
            100                 105                 110

Val Tyr Tyr Cys Ala Arg Gly Thr Tyr Tyr Gly Ser Arg Val Phe
        115                 120                 125

Asp Tyr Trp Gly Gln Gly Thr Thr Leu Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ala Ala Pro Ser Ile Pro Val Thr Pro Gly Glu Ser Val Ser
                165                 170                 175

Ile Ser Cys Arg Ser Ser Lys Ser Leu Leu Asn Ser Asn Gly Asn Thr
            180                 185                 190

Tyr Leu Tyr Trp Phe Leu Gln Arg Pro Gly Gln Ser Pro Gln Leu Leu
        195                 200                 205

Ile Tyr Arg Met Ser Asn Leu Ala Ser Gly Val Pro Asp Arg Phe Ser
    210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                245                 250                 255

Phe Thr Phe Gly Ala Gly Thr Lys Leu Glu Leu Lys Arg Ser Asp Pro
            260                 265                 270
```

```
Thr Thr Thr Pro Ala Pro Arg Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
            355                 360                 365

Cys Ser Cys Arg Phe Pro Glu Glu Glu Glu Gly Gly Cys Glu Leu Arg
        370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
            435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg Gly
                485                 490                 495

Ser Ser Gly Ser Gly Glu Gly Arg Gly Ser Leu Leu Thr Cys Gly Asp
                500                 505                 510

Val Glu Glu Asn Pro Gly Pro Met Ser Gly Glu Ser Met Asn Phe Ser
            515                 520                 525

Asp Val Phe Asp Ser Ser Glu Asp Tyr Phe Val Ser Val Asn Thr Ser
            530                 535                 540

Tyr Tyr Ser Val Asp Ser Glu Met Leu Leu Cys Ser Leu Gln Glu Val
545                 550                 555                 560

Arg Gln Phe Ser Arg Leu Phe Val Pro Ile Ala Tyr Ser Leu Ile Cys
                565                 570                 575

Val Phe Gly Leu Leu Gly Asn Ile Leu Val Val Ile Thr Phe Ala Phe
                580                 585                 590

Tyr Lys Lys Ala Arg Ser Met Thr Asp Val Tyr Leu Leu Asn Met Ala
            595                 600                 605

Ile Ala Asp Ile Leu Phe Val Leu Thr Leu Pro Phe Trp Ala Val Ser
            610                 615                 620

His Ala Thr Gly Ala Trp Val Phe Ser Asn Ala Thr Cys Lys Leu Leu
625                 630                 635                 640

Lys Gly Ile Tyr Ala Ile Asn Phe Asn Cys Gly Met Leu Leu Leu Thr
                645                 650                 655

Cys Ile Ser Met Asp Arg Tyr Ile Ala Ile Val Gln Ala Thr Lys Ser
                660                 665                 670

Phe Arg Leu Arg Ser Arg Thr Leu Pro Arg Ser Lys Ile Ile Cys Leu
            675                 680                 685
```

```
Val Val Trp Gly Leu Ser Val Ile Ile Ser Ser Thr Phe Val Phe
    690             695                 700

Asn Gln Lys Tyr Asn Thr Gln Gly Ser Asp Val Cys Glu Pro Lys Tyr
705                 710                 715                 720

Gln Thr Val Ser Glu Pro Ile Arg Trp Lys Leu Leu Met Leu Gly Leu
            725                 730                 735

Glu Leu Leu Phe Gly Phe Phe Ile Pro Leu Met Phe Met Ile Phe Cys
            740                 745                 750

Tyr Thr Phe Ile Val Lys Thr Leu Val Gln Ala Gln Asn Ser Lys Arg
            755                 760                 765

His Lys Ala Ile Arg Val Ile Ile Ala Val Val Leu Val Phe Leu Ala
        770                 775                 780

Cys Gln Ile Pro His Asn Met Val Leu Leu Val Thr Ala Ala Asn Leu
785                 790                 795                 800

Gly Lys Met Asn Arg Ser Cys Gln Ser Glu Lys Leu Ile Gly Tyr Thr
                805                 810                 815

Lys Thr Val Thr Glu Val Leu Ala Phe Leu His Cys Cys Leu Asn Pro
            820                 825                 830

Val Leu Tyr Ala Phe Ile Gly Gln Lys Phe Arg Asn Tyr Phe Leu Lys
            835                 840                 845

Ile Leu Lys Asp Leu Trp Cys Val Arg Arg Lys Tyr Lys Ser Ser Gly
850                 855                 860

Phe Ser Cys Ala Gly Arg Tyr Ser Glu Asn Ile Ser Arg Gln Thr Ser
865                 870                 875                 880

Glu Thr Ala Asp Asn Asp Asn Ala Ser Ser Phe Thr Met
                885                 890
```

<210> SEQ ID NO 426
<211> LENGTH: 2679
<212> TYPE: DNA
<213> ORGANISM: Artificial Sequence
<220> FEATURE:
<223> OTHER INFORMATION: Synthetic

<400> SEQUENCE: 426

```
atggagacag acactcttct cctttgggtc ttgctgctgt gggttcccgg aagcacagga     60
gaagtacagt tgcaacagtc tgggccagaa ctcatcaaac ccggagcttc tgtaaaaatg    120
tcatgcaaag ctagtggata tacatttact cttacgtga tgcactgggt aaaacagaaa    180
cctggtcagg gcttgagtg atcgggtac attaacccat ataatgacgg caccaaatat    240
aacgagaaat tcaagggaaa ggctacgctt acatcagata gtccagtag caccgcttat    300
atggaactta gcagccttac ttccgaagat tccgcggtgt attactgcgc gagagggact    360
tactactacg gagtcgagt attcgattat tggggtcaag caacgacgct cacggtgagc    420
tcaggtggtg agggtctgg gggtggcggc agtggtgggg gggctcaga catcgtgatg    480
acccaggcag caccttctat cccggtaacc ccaggcgagt ctgtatctat cagttgtcgg    540
tccagcaagt ctcttctcaa cagtaatggc aatacatatc tttactggtt cctccaaagg    600
cctgggcaaa gtcctcaact tcttatatat cggatgtcca atcttgcgag tggcgtaccc    660
gacaggtttt cagggtctgg gagcggaaca gcttttacgt tgagaatatc cagggtagaa    720
gctgaggacg tcggtgtata ttattgcatg caacatctcg aataccccctt taccttcggc    780
gctggtacaa agctcgaatt gaaacgcagc gatccaacca cgacgccagc gccacgacca    840
cctacgcccg ctccaactat tgcctcccag cccctgagtc ttcggccaga agcgtgtaga    900
```

```
cctgctgccg gcggggccgt tcatacgcgg ggccttgact ttgcatgtga tatctatata   960
tgggctcctt tggcgggaac ttgcggagtg cttcttttgt cactcgtgat aacgttgtat  1020
tgtaaaaggg gtcgaaagaa actcctctat atatttaagc agcccttat gaggcccgtg  1080
caaacaacac aagaagagga cggatgctct tgtcgattcc cggaagagga ggaggggggg  1140
tgtgagctta gggtcaagtt ttctcgctct gccgacgcgc cagcctatca cagggccaa   1200
aaccagctgt ataacgaact caacctcggg cgccgggaag agtatgacgt ccttgacaaa  1260
cggcgcggtc gcgaccctga aatgggtgga aaaccgaggc gaaagaaccc ccaggaggga  1320
ctttacaacg aattgcaaaa agacaagatg gccgaagcct attccgaaat tggaatgaaa  1380
ggcgagcgga gacgaggtaa ggggcatgac ggcctgtatc aagggctctc tacggccacg  1440
aaggatactt acgacgccct tcatatgcaa gctcttccac cacggggttc gagcggcagt  1500
ggagagggca gaggaagtct gctaacatgc ggtgacgtcg aggagaatcc tggcccaatg  1560
agtggggaaa gtatgaactt cagcgatgta tttgactcct ccgaagatta ctttgtatct  1620
gtgaatacga gctattactc cgtcgatagt gaaatgctgc tctgtagtct ccaagaagtc  1680
cgccaattca gtcgcctctt cgttcccatc gcgtactccc ttatttgtgt ttttggcctt  1740
ctgggtaaca tcctggttgt aatcacattc gctttctata aaaaagctcg gagtatgact  1800
gatgtttacc ttcttaacat ggctatagcg gacattcttt ttgtgcttac tctcccattc  1860
tgggctgtga gccatgcaac aggggcgtgg gttttttcaa atgccacatg taagctgctt  1920
aaagggatct atgcaataaa cttcaattgc gggatgctcc tgctgacatg catcagtatg  1980
gatcgataca tagctatagt acaggcgact aagtccttcc gcctgcgatc ccgcacactg  2040
cctaggagca aaattatttg cctcgtcgta tgggggctct cagtgatcat ctcctccagt  2100
acgtttgtct ttaaccagaa atataacaca cagggttctg atgtatgtga accaaagtat  2160
cagacagtga gtgaaccaat acggtggaag ttgcttatgt tgggcttgga gctgcttttt  2220
gggttttca tcccactgat gttcatgatt ttctgttata catttattgt taagaccttg  2280
gttcaggcgc aaaatagcaa gagacataag gcaattcgag tcatcattgc cgtggtgttg  2340
gtcttcttgg cctgtcagat cccccataat atggttctgc tcgtcaccgc cgctaacttg  2400
ggtaagatga atcgatcttg tcagtccgag aagttgatcg gatacaccaa aactgtgaca  2460
gaagtgctgg ccttccttca ctgttgtctg aacccagttt tgtatgcttt tataggacag  2520
aagtttcgaa attacttctt gaaaatcctc aaggacctct ggtgtgttcg aaggaagtac  2580
aagagctctg gctttagttg cgctgggcgc tacagtgaga atatatcccg gcagacctcc  2640
gagactgctg ataatgacaa cgcaagttcc ttcactatg                          2679
```

<210> SEQ ID NO 427
<211> LENGTH: 238
<212> TYPE: PRT
<213> ORGANISM: Artificial Sequence
<220> FEATURE:
<223> OTHER INFORMATION: Synthetic

<400> SEQUENCE: 427

```
Val Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45
```

```
Thr Thr Gly Lys Leu Pro Val Pro Trp Pro Thr Leu Val Thr Thr Leu
 50                  55                  60
Thr Tyr Gly Val Gln Cys Phe Ser Arg Tyr Pro Asp His Met Lys Gln
 65                  70                  75                  80
His Asp Phe Phe Lys Ser Ala Met Pro Glu Gly Tyr Val Gln Glu Arg
                 85                  90                  95
Thr Ile Phe Phe Lys Asp Asp Gly Asn Tyr Lys Thr Arg Ala Glu Val
             100                 105                 110
Lys Phe Glu Gly Asp Thr Leu Val Asn Arg Ile Glu Leu Lys Gly Ile
         115                 120                 125
Asp Phe Lys Glu Asp Gly Asn Ile Leu Gly His Lys Leu Glu Tyr Asn
 130                 135                 140
Tyr Asn Ser His Asn Val Tyr Ile Met Ala Asp Lys Gln Lys Asn Gly
145                 150                 155                 160
Ile Lys Ala Asn Phe Lys Ile Arg His Asn Ile Glu Asp Gly Ser Val
                165                 170                 175
Gln Leu Ala Asp His Tyr Gln Gln Asn Thr Pro Ile Gly Asp Gly Pro
            180                 185                 190
Val Leu Leu Pro Asp Asn His Tyr Leu Ser Thr Gln Ser Ala Leu Ser
        195                 200                 205
Lys Asp Pro Asn Glu Lys Arg Asp His Met Val Leu Leu Glu Phe Val
 210                 215                 220
Thr Ala Ala Gly Ile Thr Leu Gly Met Asp Glu Leu Tyr Lys
225                 230                 235

<210> SEQ ID NO 428
<211> LENGTH: 717
<212> TYPE: DNA
<213> ORGANISM: Artificial Sequence
<220> FEATURE:
<223> OTHER INFORMATION: Synthetic

<400> SEQUENCE: 428
gtgagcaagg gcgaggagct gttcaccggg gtggtgccca tcctggtcga gctggacggc      60
gacgtaaacg gccacaagtt cagcgtgtct ggcgagggcg agggcgatgc cacctacggc     120
aagctgaccc tgaagttcat ctgcaccacc ggcaagctgc ccgtgccctg gcccaccctc     180
gtgaccaccc tgacctacgg cgtgcagtgc ttcagccgct accccgacca catgaagcag     240
cacgacttct tcaagtccgc catgcccgaa ggctacgtcc aggagcgcac catcttcttc     300
aaggacgacg gcaactacaa gacccgcgcc gaggtgaagt tcgagggcga cacccctggtg    360 aaccgcatcg agctgaaggg catcgacttc aaggaggacg gcaacatcct ggggcacaag     420
ctggagtaca actacaacag ccacaacgtc tatatcatgg ccgacaagca gaagaacggc     480
atcaaggcga acttcaagat ccgccacaac atcgaggacg gcagcgtgca gctcgccgac     540
cactaccagc agaacacccc catcggcgac ggccccgtgc tgctgcccga caaccactac     600
ctgagcaccc agtccgccct gagcaaagac cccaacgaga agcgcgatca catggtcctg     660
ctggagttcg tgaccgccgc cgggatcact ctcggcatgg acgagctgta caagtaa        717

<210> SEQ ID NO 429
<211> LENGTH: 1153
<212> TYPE: PRT
<213> ORGANISM: Artificial Sequence
<220> FEATURE:
<223> OTHER INFORMATION: Synthetic

<400> SEQUENCE: 429
```

```
Met Glu Thr Asp Thr Leu Leu Leu Trp Val Leu Leu Leu Trp Val Pro
1               5                   10                  15

Gly Ser Thr Gly Glu Val Gln Leu Gln Gln Ser Gly Pro Glu Leu Ile
            20                  25                  30

Lys Pro Gly Ala Ser Val Lys Met Ser Cys Lys Ala Ser Gly Tyr Thr
            35                  40                  45

Phe Thr Ser Tyr Val Met His Trp Val Lys Gln Lys Pro Gly Gln Gly
    50                  55                  60

Leu Glu Trp Ile Gly Tyr Ile Asn Pro Tyr Asn Asp Gly Thr Lys Tyr
65                  70                  75                  80

Asn Glu Lys Phe Lys Gly Lys Ala Thr Leu Thr Ser Asp Lys Ser Ser
                85                  90                  95

Ser Thr Ala Tyr Met Glu Leu Ser Ser Leu Thr Ser Glu Asp Ser Ala
                100                 105                 110

Val Tyr Tyr Cys Ala Arg Gly Thr Tyr Tyr Gly Ser Arg Val Phe
            115                 120                 125

Asp Tyr Trp Gly Gln Gly Thr Thr Leu Thr Val Ser Ser Gly Gly Gly
            130                 135                 140

Gly Ser Gly Gly Gly Ser Gly Gly Gly Ser Asp Ile Val Met
145                 150                 155                 160

Thr Gln Ala Ala Pro Ser Ile Pro Val Thr Pro Gly Glu Ser Val Ser
                165                 170                 175

Ile Ser Cys Arg Ser Ser Lys Ser Leu Leu Asn Ser Asn Gly Asn Thr
            180                 185                 190

Tyr Leu Tyr Trp Phe Leu Gln Arg Pro Gly Gln Ser Pro Gln Leu Leu
        195                 200                 205

Ile Tyr Arg Met Ser Asn Leu Ala Ser Gly Val Pro Asp Arg Phe Ser
210                 215                 220

Gly Ser Gly Ser Gly Thr Ala Phe Thr Leu Arg Ile Ser Arg Val Glu
225                 230                 235                 240

Ala Glu Asp Val Gly Val Tyr Tyr Cys Met Gln His Leu Glu Tyr Pro
                245                 250                 255

Phe Thr Phe Gly Ala Gly Thr Lys Leu Glu Leu Lys Arg Ser Asp Pro
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
            325                 330                 335

Ile Thr Leu Tyr Cys Lys Arg Gly Arg Lys Lys Leu Leu Tyr Ile Phe
        340                 345                 350

Lys Gln Pro Phe Met Arg Pro Val Gln Thr Thr Gln Glu Glu Asp Gly
    355                 360                 365

Cys Ser Cys Arg Phe Pro Glu Glu Glu Glu Gly Gly Cys Glu Leu Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
            405                 410                 415
```

-continued

Val Leu Asp Lys Arg Arg Gly Arg Asp Pro Glu Met Gly Gly Lys Pro
        420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg Gly
                485                 490                 495

Ser Ser Gly Ser Gly Glu Gly Arg Gly Ser Leu Leu Thr Cys Gly Asp
        500                 505                 510

Val Glu Glu Asn Pro Gly Pro Met Ser Gly Glu Ser Met Asn Phe Ser
        515                 520                 525

Asp Val Phe Asp Ser Ser Glu Asp Tyr Phe Val Ser Val Asn Thr Ser
        530                 535                 540

Tyr Tyr Ser Val Asp Ser Glu Met Leu Leu Cys Ser Leu Gln Glu Val
545                 550                 555                 560

Arg Gln Phe Ser Arg Leu Phe Val Pro Ile Ala Tyr Ser Leu Ile Cys
                565                 570                 575

Val Phe Gly Leu Leu Gly Asn Ile Leu Val Val Ile Thr Phe Ala Phe
        580                 585                 590

Tyr Lys Lys Ala Arg Ser Met Thr Asp Val Tyr Leu Leu Asn Met Ala
        595                 600                 605

Ile Ala Asp Ile Leu Phe Val Leu Thr Leu Pro Phe Trp Ala Val Ser
610                 615                 620

His Ala Thr Gly Ala Trp Val Phe Ser Asn Ala Thr Cys Lys Leu Leu
625                 630                 635                 640

Lys Gly Ile Tyr Ala Ile Asn Phe Asn Cys Gly Met Leu Leu Leu Thr
                645                 650                 655

Cys Ile Ser Met Asp Arg Tyr Ile Ala Ile Val Gln Ala Thr Lys Ser
        660                 665                 670

Phe Arg Leu Arg Ser Arg Thr Leu Pro Arg Ser Lys Ile Ile Cys Leu
        675                 680                 685

Val Val Trp Gly Leu Ser Val Ile Ile Ser Ser Ser Thr Phe Val Phe
690                 695                 700

Asn Gln Lys Tyr Asn Thr Gln Gly Ser Asp Val Cys Glu Pro Lys Tyr
705                 710                 715                 720

Gln Thr Val Ser Glu Pro Ile Arg Trp Lys Leu Leu Met Leu Gly Leu
                725                 730                 735

Glu Leu Leu Phe Gly Phe Phe Ile Pro Leu Met Phe Met Ile Phe Cys
        740                 745                 750

Tyr Thr Phe Ile Val Lys Thr Leu Val Gln Ala Gln Asn Ser Lys Arg
        755                 760                 765

His Lys Ala Ile Arg Val Ile Ile Ala Val Val Leu Val Phe Leu Ala
770                 775                 780

Cys Gln Ile Pro His Asn Met Val Leu Leu Val Thr Ala Ala Asn Leu
785                 790                 795                 800

Gly Lys Met Asn Arg Ser Cys Gln Ser Glu Lys Leu Ile Gly Tyr Thr
                805                 810                 815

Lys Thr Val Thr Glu Val Leu Ala Phe Leu His Cys Cys Leu Asn Pro
        820                 825                 830

Val Leu Tyr Ala Phe Ile Gly Gln Lys Phe Arg Asn Tyr Phe Leu Lys

Ile Leu Lys Asp Leu Trp Cys Val Arg Arg Lys Tyr Lys Ser Ser Gly
835                 840                 845
                850                 855                 860

Phe Ser Cys Ala Gly Arg Tyr Ser Glu Asn Ile Ser Arg Gln Thr Ser
865                 870                 875                 880

Glu Thr Ala Asp Asn Asp Asn Ala Ser Ser Phe Thr Met Gly Ser Gly
                885                 890                 895

Ala Thr Asn Phe Ser Leu Leu Lys Gln Ala Gly Asp Val Glu Glu Asn
                900                 905                 910

Pro Gly Pro Val Ser Lys Gly Glu Glu Leu Phe Thr Gly Val Val Pro
                915                 920                 925

Ile Leu Val Glu Leu Asp Gly Asp Val Asn Gly His Lys Phe Ser Val
                930                 935                 940

Ser Gly Glu Gly Glu Gly Asp Ala Thr Tyr Gly Lys Leu Thr Leu Lys
945                 950                 955                 960

Phe Ile Cys Thr Thr Gly Lys Leu Pro Val Pro Trp Pro Thr Leu Val
                965                 970                 975

Thr Thr Leu Thr Tyr Gly Val Gln Cys Phe Ser Arg Tyr Pro Asp His
                980                 985                 990

Met Lys Gln His Asp Phe Phe Lys Ser Ala Met Pro Glu Gly Tyr Val
                995                 1000                1005

Gln Glu Arg Thr Ile Phe Phe Lys Asp Asp Gly Asn Tyr Lys Thr
1010                1015                1020

Arg Ala Glu Val Lys Phe Glu Gly Asp Thr Leu Val Asn Arg Ile
1025                1030                1035

Glu Leu Lys Gly Ile Asp Phe Lys Glu Asp Gly Asn Ile Leu Gly
1040                1045                1050

His Lys Leu Glu Tyr Asn Tyr Asn Ser His Asn Val Tyr Ile Met
1055                1060                1065

Ala Asp Lys Gln Lys Asn Gly Ile Lys Ala Asn Phe Lys Ile Arg
1070                1075                1080

His Asn Ile Glu Asp Gly Ser Val Gln Leu Ala Asp His Tyr Gln
1085                1090                1095

Gln Asn Thr Pro Ile Gly Asp Gly Pro Val Leu Leu Pro Asp Asn
1100                1105                1110

His Tyr Leu Ser Thr Gln Ser Ala Leu Ser Lys Asp Pro Asn Glu
1115                1120                1125

Lys Arg Asp His Met Val Leu Leu Glu Phe Val Thr Ala Ala Gly
1130                1135                1140

Ile Thr Leu Gly Met Asp Glu Leu Tyr Lys
1145                1150

<210> SEQ ID NO 430
<211> LENGTH: 3462
<212> TYPE: DNA
<213> ORGANISM: Artificial Sequence
<220> FEATURE:
<223> OTHER INFORMATION: Synthetic

<400> SEQUENCE: 430
atggagacag acactcttct cctttgggtc ttgctgctgt gggttcccgg aagcacagga      60
gaagtacagt tgcaacagtc tgggccagaa ctcatcaaac ccggagcttc tgtaaaaatg     120
tcatgcaaag ctagtggata tacattact tcttacgtga tgcactgggt aaaacagaaa     180
cctggtcagg ggcttgagtg gatcgggtac attaacccat ataatgacgg caccaaatat     240

```
aacgagaaat tcaagggaaa ggctacgctt acatcagata agtccagtag caccgcttat    300
atggaactta gcagccttac ttccgaagat tccgcggtgt attactgcgc gagagggact    360
tactactacg ggagtcgagt attcgattat tggggtcaag gcacgacgct cacggtgagc    420
tcaggtggtg gagggtctgg gggtggcggc agtggtgggg gggctcaga catcgtgatg    480 acccaggcag caccttctat cccggtaacc ccaggcgagt ctgtatctat cagttgtcgg    540
tccagcaagt ctcttctcaa cagtaatggc aatacatatc tttactggtt cctccaaagg    600
cctgggcaaa gtcctcaact tcttatatat cggatgtcca atcttgcgag tggcgtaccc    660
gacaggtttt cagggtctgg gagcggaaca gcttttacgt tgagaatatc cagggtagaa    720
gctgaggacg tcggtgtata ttattgcatg caacatctcg aatacccctt taccttcggc    780
gctggtacaa agctcgaatt gaaacgcagc gatccaacca cgacgccagc gccacgacca    840
cctacgcccg ctccaactat tgcctcccag ccctgagtc ttcggccaga agcgtgtaga    900
cctgctgccg gcggggccgt tcatacgcgg ggccttgact ttgcatgtga tatctatata    960
tgggctcctt tggcgggaac ttgcggagtg cttcttttgt cactcgtgat aacgttgtat   1020
tgtaaaaggg gtcgaaagaa actcctctat atatttaagc agccctttat gaggcccgtg   1080
caaacaacac aagaagagga cggatgctct tgtcgattcc cggaagagga ggaggggggg   1140
tgtgagctta gggtcaagtt ttctcgctct gccgacgcgc cagcctatca acagggccaa   1200
aaccagctgt ataacgaact caacctcggg cgccgggaag agtatgacgt ccttgacaaa   1260
cggcgcggtc gcgaccctga atgggtggga aaaccgaggc gaaagaaccc ccaggaggga   1320
ctttacaacg aattgcaaaa agacaagatg gccgaagcct attccgaaat tggaatgaaa   1380
ggcgagcgga gacgaggtaa ggggcatgac ggcctgtatc aagggctctc tacgccacg    1440 aaggatactt acgacgccct tcatatgcaa gctcttccac cacggggttc gagcggcagt   1500
ggagagggca gaggaagtct gctaacatgc ggtgacgtcg aggagaatcc tggcccaatg   1560
agtggggaaa gtatgaactt cagcgatgta tttgactcct ccgaagatta ctttgtatct   1620
gtgaatacga gctattactc cgtcgatagt gaaatgctgc tctgtagtct ccaagaagtc   1680
cgccaattca gtcgcctctt cgttcccatc gcgtactccc ttatttgtgt ttttggcctt   1740
ctgggtaaca tcctggttgt aatcacattc gctttctata aaaaagctcg gagtatgact   1800
gatgtttacc ttcttaacat ggctatagcg gacattcttt ttgtgcttac tctcccattc   1860
tgggctgtga gccatgcaac aggggcgtgg gtttttttcaa atgccacatg taagctgctt   1920
aaagggatct atgcaataaa cttcaattgc gggatgctcc tgctgacatg catcagtatg   1980
gatcgataca tagctatagt acaggcgact aagtccttcc gcctgcgatc ccgcacactg   2040
cctaggagca aaattatttg cctcgtcgta tgggggctct cagtgatcat ctcctccagt   2100
acgtttgtct ttaaccagaa atataacaca cagggttctg atgtatgtga accaaagtat   2160
cagacagtga gtgaaccaat acggtggaag ttgcttatgt tgggcttgga gctgcttttt   2220
gggtttttca tcccactgat gttcatgatt ttctgttata catttattgt taagaccttg   2280
gttcaggcgc aaaatagcaa agacataag gcaattcgag tcatcattgc cgtggtgttg   2340
gtcttcttgg cctgtcagat cccccataat atggttctgc tcgtcaccgc cgctaacttg   2400
ggtaagatga atcgatcttg tcagtccgag aagttgatcg gatacaccaa aactgtgaca   2460
gaagtgctgg cctttccttca ctgttgtctg aacccagttt tgtatgcttt tataggacag   2520
aagtttcgaa attacttctt gaaaatcctc aaggacctct ggtgtgttcg aaggaagtac   2580
```

-continued

```
aagagctctg gctttagttg cgctgggcgc tacagtgaga atatatcccg gcagacctcc    2640
gagactgctg ataatgacaa cgcaagttcc ttcactatgg gatccggcgc aacaaacttc    2700
tctctgctga acaagccgg agatgtcgaa gagaatcctg gaccggtgag caagggcgag    2760
gagctgttca ccggggtggt gcccatcctg gtcgagctgg acggcgacgt aaacggccac    2820
aagttcagcg tgtctggcga gggcgagggc gatgccacct acggcaagct gaccctgaag    2880
ttcatctgca ccaccggcaa gctgcccgtg ccctggccca ccctcgtgac cacccctgacc   2940 tacggcgtgc agtgcttcag ccgctacccc gaccacatga agcagcacga cttcttcaag    3000
tccgccatgc ccgaaggcta cgtccaggag cgcaccatct tcttcaagga cgacggcaac    3060
tacaagaccc gcgccgaggt gaagttcgag ggcgacaccc tggtgaaccg catcgagctg    3120
aagggcatcg acttcaagga ggacggcaac atcctggggc acaagctgga gtacaactac    3180
aacagccaca acgtctatat catggccgac aagcagaaga acggcatcaa ggcgaacttc    3240
aagatccgcc acaacatcga ggacggcagc gtgcagctcg ccgaccacta ccagcagaac    3300
acccccatcg gcgacggccc cgtgctgctg cccgacaacc actacctgag cacccagtcc    3360
gccctgagca agacccccaa cgagaagcgc gatcacatgg tcctgctgga gttcgtgacc    3420
gccgccggga tcactctcgg catggacgag ctgtacaagt aa                       3462
```

<210> SEQ ID NO 431
<211> LENGTH: 780
<212> TYPE: PRT
<213> ORGANISM: Artificial Sequence
<220> FEATURE:
<223> OTHER INFORMATION: Synthetic

<400> SEQUENCE: 431

```
Met Val Cys Leu Lys Leu Pro Gly Gly Ser Cys Met Thr Ala Leu Thr
1               5                   10                  15

Val Thr Leu Met Val Leu Ser Ser Pro Leu Ala Leu Ala Ser Asp Glu
            20                  25                  30

Asn Pro Val Val His Phe Phe Lys Asn Ile Val Thr Pro Arg Thr Pro
        35                  40                  45

Pro Gly Gly Gly Gly Ser Gly Gly Gly Gly Ser Gly Gly Ser Gly Asp
    50                  55                  60

Thr Arg Pro Arg Phe Leu Trp Gln Pro Lys Arg Glu Cys His Phe Phe
65                  70                  75                  80

Asn Gly Thr Glu Arg Val Arg Phe Leu Asp Arg Tyr Phe Tyr Asn Gln
                85                  90                  95

Glu Glu Ser Val Arg Phe Asp Ser Asp Val Gly Glu Phe Arg Ala Val
            100                 105                 110

Thr Glu Leu Gly Arg Pro Asp Ala Glu Tyr Trp Asn Ser Gln Lys Asp
        115                 120                 125

Ile Leu Glu Gln Ala Arg Ala Ala Val Asp Thr Tyr Cys Arg His Asn
    130                 135                 140

Tyr Gly Val Val Glu Ser Phe Thr Val Gln Arg Val Gln Pro Lys
145                 150                 155                 160

Val Thr Val Tyr Pro Ser Lys Thr Gln Pro Leu Gln His His Asn Leu
                165                 170                 175

Leu Val Cys Ser Val Ser Gly Phe Tyr Pro Gly Ser Ile Glu Val Arg
            180                 185                 190

Trp Phe Leu Asn Gly Gln Glu Glu Lys Ala Gly Met Val Ser Thr Gly
        195                 200                 205
```

```
Leu Ile Gln Asn Gly Asp Trp Thr Phe Gln Thr Leu Val Met Leu Glu
    210                 215                 220
Thr Val Pro Arg Ser Gly Glu Val Tyr Thr Cys Gln Val Glu His Pro
225                 230                 235                 240
Ser Val Thr Ser Pro Leu Thr Val Glu Trp Arg Ala Arg Ser Glu Ser
                245                 250                 255
Ala Gln Ser Lys Met Leu Ser Gly Val Gly Gly Phe Val Leu Gly Leu
            260                 265                 270
Leu Phe Leu Gly Ala Gly Leu Phe Ile Tyr Phe Arg Asn Gln Thr Ser
        275                 280                 285
Arg Val Lys Phe Ser Arg Ser Ala Asp Ala Pro Ala Tyr Gln Gln Gly
    290                 295                 300
Gln Asn Gln Leu Tyr Asn Glu Leu Asn Leu Gly Arg Arg Glu Glu Tyr
305                 310                 315                 320
Asp Val Leu Asp Lys Arg Arg Gly Arg Asp Pro Glu Met Gly Gly Lys
                325                 330                 335
Pro Arg Arg Lys Asn Pro Gln Glu Gly Leu Tyr Asn Glu Leu Gln Lys
            340                 345                 350
Asp Lys Met Ala Glu Ala Tyr Ser Glu Ile Gly Met Lys Gly Glu Arg
        355                 360                 365
Arg Arg Gly Lys Gly His Asp Gly Leu Tyr Gln Gly Leu Ser Thr Ala
    370                 375                 380
Thr Lys Asp Thr Tyr Asp Ala Leu His Met Gln Ala Leu Pro Pro Arg
385                 390                 395                 400
Gly Ser Ser Gly Ser Gly Glu Gly Arg Gly Ser Leu Leu Thr Cys Gly
                405                 410                 415
Asp Val Glu Glu Asn Pro Gly Pro Met Ala Ile Ser Gly Val Pro Val
            420                 425                 430
Leu Gly Phe Phe Ile Ile Ala Val Leu Met Ser Ala Gln Glu Ser Trp
        435                 440                 445
Ala Ile Lys Glu Glu His Val Ile Ile Gln Ala Glu Phe Tyr Leu Asn
    450                 455                 460
Pro Asp Gln Ser Gly Glu Phe Met Phe Asp Phe Asp Gly Asp Glu Ile
465                 470                 475                 480
Phe His Val Asp Met Ala Lys Lys Glu Thr Val Trp Arg Leu Glu Glu
                485                 490                 495
Phe Gly Arg Phe Ala Ser Phe Glu Ala Gln Gly Ala Leu Ala Asn Ile
            500                 505                 510
Ala Val Asp Lys Ala Asn Leu Glu Ile Met Thr Lys Arg Ser Asn Tyr
        515                 520                 525
Thr Pro Ile Thr Asn Val Pro Pro Glu Val Thr Val Leu Thr Asn Ser
    530                 535                 540
Pro Val Glu Leu Arg Glu Pro Asn Val Leu Ile Cys Phe Ile Asp Lys
545                 550                 555                 560
Phe Thr Pro Pro Val Val Asn Val Thr Trp Leu Arg Asn Gly Lys Pro
                565                 570                 575
Val Thr Thr Gly Val Ser Glu Thr Val Phe Leu Pro Arg Glu Asp His
            580                 585                 590
Leu Phe Arg Lys Phe His Tyr Leu Pro Phe Leu Pro Ser Thr Glu Asp
        595                 600                 605
Val Tyr Asp Cys Arg Val Glu His Trp Gly Leu Asp Glu Pro Leu Leu
    610                 615                 620
Lys His Trp Glu Phe Asp Ala Pro Ser Pro Leu Pro Glu Thr Thr Glu
```

```
625                 630                 635                 640
Asn Val Val Cys Ala Leu Gly Leu Thr Val Gly Leu Val Gly Ile Ile
                645                 650                 655

Ile Gly Thr Ile Phe Ile Ile Lys Gly Leu Thr Ser Arg Val Lys Phe
                660                 665                 670

Ser Arg Ser Ala Asp Ala Pro Ala Tyr Gln Gln Gly Gln Asn Gln Leu
            675                 680                 685

Tyr Asn Glu Leu Asn Leu Gly Arg Arg Glu Glu Tyr Asp Val Leu Asp
        690                 695                 700

Lys Arg Arg Gly Arg Asp Pro Glu Met Gly Gly Lys Pro Arg Arg Lys
705                 710                 715                 720

Asn Pro Gln Glu Gly Leu Tyr Asn Glu Leu Gln Lys Asp Lys Met Ala
                725                 730                 735

Glu Ala Tyr Ser Glu Ile Gly Met Lys Gly Glu Arg Arg Arg Gly Lys
            740                 745                 750

Gly His Asp Gly Leu Tyr Gln Gly Leu Ser Thr Ala Thr Lys Asp Thr
        755                 760                 765

Tyr Asp Ala Leu His Met Gln Ala Leu Pro Pro Arg
770                 775                 780
```

What is claimed is:

1. A major histocompatibility complex (MHC)-based chimeric receptor, comprising:
   (a) a first polypeptide, which comprises an extracellular domain of a first MHC class II, and
   (b) a second polypeptide, which comprises an extracellular domain of a beta chain of a second MHC class II,
   wherein an antigenic peptide is fused to either the first polypeptide or the second polypeptide, and
   wherein either the first polypeptide or the second polypeptide, but not both, further comprises a cytoplasmic signaling domain.

2. The MHC-based chimeric receptor of claim 1, which further comprises at least one co-stimulatory domain in the first polypeptide and/or the second polypeptide.

3. The MHC-based chimeric receptor of claim 2, wherein the at least one co-stimulatory domain is a co-stimulatory domain from 4-1BB (CD137), a co-stimulatory domain from CD28, or a combination thereof.

4. The MHC-based chimeric receptor of claim 1, which further comprises a hinge domain located between the antigenic peptide and the extracellular domain of the MHC Class II molecule fused to the antigenic peptide.

5. The MHC-based chimeric receptor of claim 1, which comprises a cytoplasmic signaling domain of CD3ζ.

6. The MHC-based chimeric receptor of claim 1, wherein the antigenic peptide is from myelin basic protein (MBP), myelin oligodendrocyte glycoprotein (MOG), proteolipid protein (PLP), insulin, or glutamate decarboxylase.

7. The MHC-based chimeric receptor of claim 1, wherein the first class II MHC, the second class II MHC, or both are human MHC II molecules.

8. The MHC-based chimeric receptor of claim 1, wherein the first MHC class II is human leukocyte antigen (HLA) DR alpha chain HLA-DRA*1010.

9. The MHC-based chimeric receptor of claim 1, wherein the second MHC class II is human leukocyte antigen (HLA) DR beta chain HLA-DRB1*1501.

* * * * *